US011271164B2

(12) United States Patent
Saito et al.

(10) Patent No.: US 11,271,164 B2
(45) Date of Patent: Mar. 8, 2022

(54) COMPOUND, COMPOSITION, ORGANIC ELECTROLUMINESCENT ELEMENT AND ELECTRONIC DEVICE

(71) Applicant: IDEMITSU KOSAN CO., LTD, Chiyoda-ku (JP)

(72) Inventors: Masatoshi Saito, Sodegaura (JP); Kei Yoshida, Sodegaura (JP); Yuichiro Kawamura, Sodegaura (JP); Toshinari Ogiwara, Sodegaura (JP); Kei Yoshizaki, Sodegaura (JP)

(73) Assignee: IDEMITSU KOSAN CO., LTD, Chiyoda-ku (JP)

(*) Notice: Subject to any disclaimer, the term of this patent is extended or adjusted under 35 U.S.C. 154(b) by 387 days.

(21) Appl. No.: 16/338,769

(22) PCT Filed: Oct. 3, 2017

(86) PCT No.: PCT/JP2017/035914
§ 371 (c)(1),
(2) Date: Apr. 2, 2019

(87) PCT Pub. No.: WO2018/066536
PCT Pub. Date: Apr. 12, 2018

(65) Prior Publication Data
US 2020/0358000 A1 Nov. 12, 2020

(30) Foreign Application Priority Data

Oct. 3, 2016 (JP) .............................. JP2016-196044
Feb. 24, 2017 (JP) .............................. JP2017-033745
Aug. 23, 2017 (JP) .............................. JP2017-160666

(51) Int. Cl.
C07C 13/62 (2006.01)
C07D 209/94 (2006.01)
(Continued)

(52) U.S. Cl.
CPC .......... *H01L 51/0056* (2013.01); *C07C 13/62* (2013.01); *C07D 209/94* (2013.01);
(Continued)

(58) Field of Classification Search
CPC .......................... C07C 13/62; H01L 51/0056
See application file for complete search history.

(56) References Cited

U.S. PATENT DOCUMENTS 9,005,778 B2 * 4/2015 Horikiri ................. C09K 11/06
428/690
2010/0270914 A1 10/2010 Kamatani et al.
(Continued)

FOREIGN PATENT DOCUMENTS

CN 102405200 4/2012
CN 104885249 9/2015
(Continued)

OTHER PUBLICATIONS

International Search Report dated Dec. 26, 2017 in PCT/JP2017/035914 filed on Oct. 3, 2017.
(Continued)

*Primary Examiner* — Vu A Nguyen
(74) *Attorney, Agent, or Firm* — Oblon, McClelland, Maier & Neustadt, L.L.P.

(57) ABSTRACT

A compound is represented by a formula (2) below. In the formula (2), at least one pair of a pair of $X_1$ and $X_2$, a pair of $X_2$ and $X_3$, a pair of $X_3$ and $X_4$, a pair of $X_4$ and $X_5$, a pair of $X_7$ and $X_8$, a pair of $X_8$ and $X_9$, a pair of $X_{10}$ and $X_{11}$, a pair of $X_{11}$ and $X_{12}$, a pair of $X_{12}$ and $X_{13}$, and a pair of $X_{16}$ and $X_1$ are carbon atoms to be bonded to a structure represented by as formula (2a) or (2b) below,
(Continued)

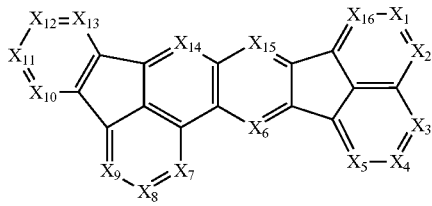

(2)

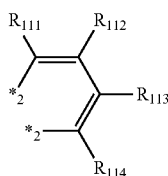

(2a)

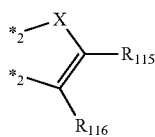

(2b)

34 Claims, 5 Drawing Sheets

(51) Int. Cl.

| | | |
|---|---|---|
| *C09K 11/06* | (2006.01) | |
| *H01L 51/00* | (2006.01) | |
| *H01L 51/50* | (2006.01) | |
| *C09K 11/02* | (2006.01) | |

(52) U.S. Cl.
CPC ............... *C09K 11/02* (2013.01); *C09K 11/06* (2013.01); *H01L 51/0072* (2013.01); *C07C 2603/54* (2017.05); *C09K 2211/1007* (2013.01); *C09K 2211/1018* (2013.01); *H01L 51/5016* (2013.01); *H01L 51/5056* (2013.01); *H01L 51/5072* (2013.01)

(56) References Cited

U.S. PATENT DOCUMENTS

| | | |
|---|---|---|
| 2011/0147732 A1 | 6/2011 | Mizuki |
| 2013/0038515 A1 | 2/2013 | Horikiri et al. |
| 2014/0103329 A1 | 4/2014 | Ogiwara et al. |
| 2016/0141506 A1 | 5/2016 | Miyashita et al. |

FOREIGN PATENT DOCUMENTS

| | | | |
|---|---|---|---|
| CN | 108701771 | | 10/2018 |
| JP | 2010-254610 | A | 11/2010 |
| JP | 2010-270103 | A | 12/2010 |
| JP | 2011-207829 | A | 10/2011 |
| JP | 2011-231086 | A | 11/2011 |
| JP | 2012-246258 | A | 12/2012 |
| JP | 2015-7011 | A | 1/2015 |
| JP | 2016-94373 | A | 5/2016 |
| WO | WO 2010/018842 | A1 | 2/2010 |
| WO | WO 2010/123153 | A1 | 10/2010 |
| WO | WO 2011/121935 | A1 | 10/2011 |
| WO | WO 2011/136155 | A1 | 11/2011 |
| WO | WO 2012/153780 | A1 | 11/2012 |
| WO | WO 2013/038650 | A1 | 3/2013 |
| WO | WO 2013/180241 | A1 | 12/2013 |
| WO | WO 2014/092083 | A1 | 6/2014 |
| WO | WO 2014/104346 | A1 | 7/2014 |
| WO | WO-2017146192 | A1 * | 8/2017 ........... C07C 255/50 |

OTHER PUBLICATIONS

Nakanotani, H. et al., "High-efficiency organic light-emitting diodes with fluorescent emitters", Nature Communications, May 30, 2014, pp. 1-7.
Nasu, K. et al., "A highly luminescent spiro-anthracenone-based organic light-emitting diode exhibiting thermally activated delayed fluorescence", Chemical Communication, vol. 49, The Royal Society of Chemistry, 2013, pp. 10385-10387.
Zhang, Q. et al., "Efficient blue organic light-emitting diodes employing thermally activated delayed fluorescence", Nature Photonics, 2014, pp. 326-332.
Lee, S. Y. et al., "High-efficiency organic light-emitting diodes utilizing thermally activated delayed fluorescence from triazine-based donor-acceptor hybrid molecules", Applied Physics Letters, vol. 101, 2012, 5 pages.
Japanese Office Action dated Apr. 13, 2021 in Japanese Patent Application No. 2018-543910, 3 pages.
Office Action as received in the corresponding patent application No. 201780060845.1 dated Aug. 20, 2021, 11 pages.

\* cited by examiner

COMPOUND, COMPOSITION, ORGANIC ELECTROLUMINESCENT ELEMENT AND ELECTRONIC DEVICE

TECHNICAL FIELD

The present invention relates to a compound, a composition, an organic electroluminescence device and an electronic device.

BACKGROUND ART

When a voltage is applied to an organic electroluminescence device (hereinafter, occasionally referred to as an "organic EL device"), holes are injected from an anode into an emitting layer and electrons are injected from a cathode into the emitting layer. The injected electrons and holes are recombined in the emitting layer to form excitons. According to the electron spin statistics theory, singlet excitons are generated at a ratio of 25% while triplet excitons are generated at a ratio of 75%.

A fluorescent organic EL device uses emission caused by singlet excitons and has been applied to a full-color display of a mobile phone, TV and the like. An internal quantum efficiency of the fluorescent organic EL device is believed to be 25% at the maximum. A fluorescent organic EL device is required to use triplet excitons in addition to singlet excitons to promote a further efficient emission from the organic EL device.

In view of the above, a highly efficient fluorescent organic EL device using delayed fluorescence has been proposed and studied.

For instance, a thermally activated delayed fluorescence (TADF) mechanism has been studied. The TADF mechanism uses such a phenomenon that inverse intersystem crossing from triplet excitons to singlet excitons thermally occurs when a material having a small energy difference (AST) between singlet energy level and triplet energy level is used. As for thermally activated delayed fluorescence, refer to, for instance, ADACHI, Chihaya, ed. "Yuki Handotai no Debaisu Bussei (Device Physics of Organic Semiconductors)", Kodansha Ltd., published on Apr. 1, 2012, pp. 261-262. An organic EL device using the TADF mechanism is disclosed in, for instance, non-Patent Literature 1.

An organic EL device disclosed in non-Patent Literature 1 includes an emitting layer containing a TADF compound as an assist dopant, a perylene derivative (TBPe; 2,5,8,11-tetra-tert-butylperylene) as a luminescent material, and DPEPO(bis-(2-(diphenylphosphino)phenyl)ether oxide) as a host material. This emitting layer exhibits a blue emission.

Also in a typical fluorescent organic EL device, a luminescent material used for a blue emitting device has been studied. Patent Literatures 1 to 4 disclose an acenaphtho[1,2-k]benzo[e]acephenanthrene derivative as an organic compound used for a blue emitting device.

Moreover, Patent Literature 5 shows study of a luminescent material used for a green emitting device in a typical fluorescent organic EL device. Patent Literature 5 discloses an acenaphtho[1,2-k]benzo[e]acephenanthrene derivative as an organic compound used for a green emitting device.

The organic compounds of Patent Literatures 1, 2, 3, 4 and 5 each have been used as a luminescent material in a typical fluorescent organic EL device. The organic EL devices of Patent Literatures 1, 2, 3, 4 and 5 do not use the TADF mechanism.

CITATION LIST

Patent Literature(S)
Patent Literature 1: JP 2012-246258 A
Patent Literature 2: JP 2010-270103 A
Patent Literature 3: JP 2010-254610 A
Patent Literature 4: JP 2011-231086 A
Patent Literature 5: JP 2011-207829 A Non-Patent Literature Non-Patent Literature 1: Hajime Nakanotani et al, "High-efficiency organic light-emitting diodes with fluorescent emitters", NATURE COMMUNICATIONS, 5, 4016, 2014

SUMMARY OF THE INVENTION

Problems to be Solved by the Invention

An organic electroluminescence device described in a non Patent Literature 1 contains a TADF compound as a host material and a perylene derivative (compound TBPe) as a luminescent material, thereby exhibiting a blue emission, however, at an insufficient luminous efficiency.

Also in Patent Literatures 1 to 5, a luminous efficiency of the light emission device containing an acenaphtho[1,2-k]benzo[e]acephenanthrene derivative is insufficient.

For this reason, an organic electroluminescence device emittable at a high efficiency has been desired.

An object of the invention is to provide a compound and a composition capable of improving a luminous efficiency of an organic EL device, to provide an organic electroluminescence device containing the compound, and to provide an electronic device including the organic electroluminescence device.

Means for Solving the Problems

An aspect of the invention provides a compound represented by a formula (2) below.

[Formula 1]

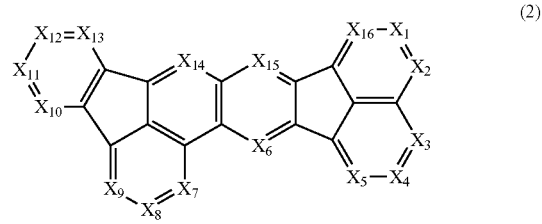

(2)

In the formula (2), $X_1$ to $X_5$, $X_7$ to $X_{13}$, and $X_{16}$ each independently represent $CR_x$ or a carbon atom to be bonded to a structure represented by a formula (2a) or (2b) below.

$X_6$, $X_{14}$, and $X_{15}$ each independently represent $CR_x$.

$R_x$ each independently represents a hydrogen atom or a substituent.

$R_x$ as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of $R_x$ are mutually the same or different.

When a plurality of ones of $X_1$ to $X_{16}$ are $CR_x$ and $R_x$ is a substituent, a plurality of $R_x$ as the substituents are bonded to each other to form a ring or are not bonded.

At least one pair of a pair of $X_1$ and $X_2$, a pair of $X_2$ and $X_3$, a pair of $X_3$ and $X_4$, a pair of $X_4$ and $X_5$, a pair of $X_7$ and $X_8$, a pair of $X_8$ and $X_9$, a pair of $X_{10}$ and $X_{11}$, a pair of $X_{11}$ and $X_{12}$, a pair of $X_{12}$ and $X_{13}$, and a pair of $X_{16}$ and $X_1$ are carbon atoms to be bonded to the structure represented by the formula (2a) or (2b) below.

[Formula 2]

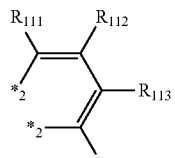
(2a)

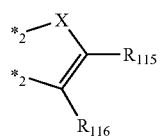
(2b)

In the formula (2a): *2 represent bonding positions to carbon atoms at one pair of the pair of $X_1$ and $X_2$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_1$ and $X_1$ in the formula (2).

$R_{111}$ to $R_{114}$ each independently represent a hydrogen atom or a substituent.

$R_{111}$ to $R_{114}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

At least one pair of a pair of $R_{111}$ and $R_{112}$, a pair of $R_{112}$ and $R_{113}$, and a pair of $R_{113}$ and $R_{114}$ are substituents, and the substituents are bonded to each other to form a ring.

In the formula (2b): *2 represent bonding positions to carbon atoms at one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_1$ and $X_{11}$, the pair of $X_{11}$ and $X_{12}$, the pair of $X_{12}$ and $X_{13}$, and the pair of $X_{16}$ and $X_1$ in the formula (2).

$R_{115}$ and $R_{116}$ each independently represent a hydrogen atom or a substituent.

$R_{115}$ and $R_{116}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{115}$ and $R_{116}$ as the substituents are bonded to each other to further form a ring, or are not bonded to each other.

X is selected from the group consisting of an oxygen atom, a sulfur atom, $CR_{117}R_{118}$, $SiR_{119}R_{120}$ and $NR_{121}$.

$R_{117}$ to $R_{121}$ each independently represent a hydrogen atom or a substituent.

$R_{117}$ to $R_{121}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{117}$ and $R_{118}$ as the substituents are bonded to each other to further form a ring, or are not bonded to each other.

$R_{119}$ and $R_{120}$ as the substituents are bonded to each other to further form a ring, or are not bonded to each other.

Another aspect of the invention provides a composition containing a plurality of compounds each represented by a formula (2) below.

[Formula 3]

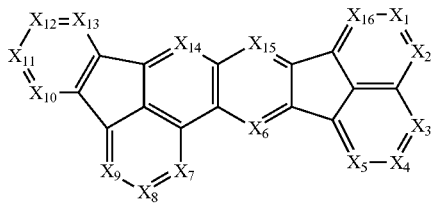

(2)

In the formula (2), $X_1$ to $X_5$, $X_7$ to $X_{13}$, and $X_{16}$ each independently represent $CR_x$ or a carbon atom to be bonded to a structure represented by a formula (2a) or (2b) below.

$X_6$, $X_{14}$, and $X_{15}$ each independently represent $CR_x$.

$R_x$ each independently represents a hydrogen atom or a substituent.

$R_x$ as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of $R_x$ are mutually the same or different.

When a plurality of ones of $X_1$ to $X_{16}$ are $CR_x$ and $R_x$ is a substituent, a plurality of $R_x$ as the substituents are bonded to each other to form a ring or are not bonded.

At least one pair of a pair of $X_1$ and $X_2$, a pair of $X_2$ and $X_3$, a pair of $X_3$ and $X_4$, a pair of $X_4$ and $X_5$, a pair of $X_7$ and $X_8$, a pair of $X_8$ and $X_9$, a pair of $X_1$ and $X_{11}$, a pair of $X_{11}$ and $X_{12}$, a pair of $X_{12}$ and $X_{13}$, and a pair of $X_4$ and $X_5$ are carbon atoms to be bonded to the structure represented by the formula (2a) or (2b) below.

[Formula 4]

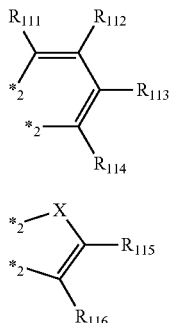

(2a)

(2b)

In the formula (2a): *2 represent bonding positions to carbon atoms at one pair of the pair of $X_1$ and $X_2$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2).

$R_{111}$ to $R_{114}$ each independently represent a hydrogen atom or a substituent.

$R_{111}$ to $R_{114}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

At least one pair of a pair of $R_{111}$ and $R_{112}$, a pair of $R_{112}$ and $R_{113}$, and a pair of $R_{113}$ and $R_{114}$ are substituents, and the substituents are bonded to each other to form a ring.

In the formula (2b): *2 represent bonding positions to carbon atoms at one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2).

$R_{11}$ and $R_{116}$ each independently represent a hydrogen atom or a substituent.

$R_{115}$ and $R_{116}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{115}$ and $R_{116}$ as the substituents are bonded to each other to further form a ring, or are not bonded to each other.

X is selected from the group consisting of an oxygen atom, a sulfur atom, $CR_{117}R_{11}$, $SiR_{119}R_{120}$ and $NR_{121}$.

$R_{117}$ to $R_{121}$ each independently represent a hydrogen atom or a substituent.

$R_{117}$ to $R_{121}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{117}$ and $R_{118}$ as the substituents are bonded to each other to further form a ring, or are not bonded to each other.

$R_{119}$ and $R_{120}$ as the substituents are bonded to each other to further form a ring, or are not bonded to each other.

Still another aspect of the invention provides an organic electroluminescence device including: an anode; an emitting layer; and a cathode, in which the emitting layer contains a first compound and a second compound, the second compound being the compound according to the above aspect of the invention.

A further aspect of the invention provides an electronic device including the organic electroluminescence device according to the above aspect of the invention.

The above aspects of the invention enable to provide a compound and a composition capable of improving a luminous efficiency of an organic EL device, to provide an organic electroluminescence device containing the compound, and to provide an electronic device including the organic electroluminescence device.

DESCRIPTION OF EMBODIMENT(S)

First Exemplary Embodiment

Compound

Figure 1:
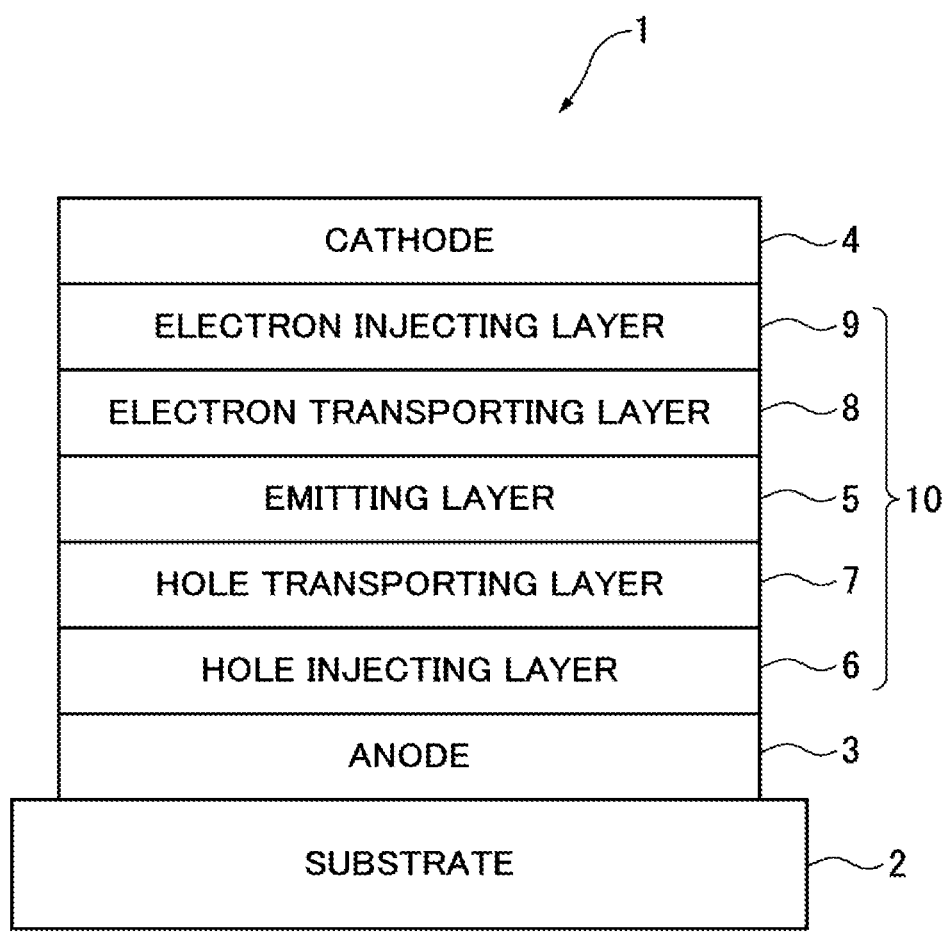
FIG. 1 schematically shows an exemplary arrangement of an organic EL device according to a first exemplary embodiment of the invention.

A compound of a first exemplary embodiment is represented by a formula (2) below.

[Formula 5]

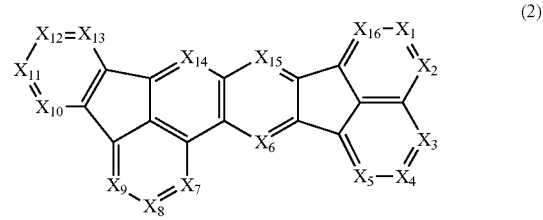

(2)

In the formula (2): $X_1$ to $X_5$, $X_7$ to $X_{13}$, and $X_{16}$ each independently represent $CR_x$ or a carbon atom to be bonded to a structure represented by a formula (2a) or (2b) below.

$X_6$, $X_{14}$, and $X_{15}$ each independently represent $CR_x$.

$R_x$ each independently represents a hydrogen atom or a substituent.

$R_x$ as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of $R_x$ are mutually the same or different.

When a plurality of ones of $X_1$ to $X_{16}$ are $CR_x$ and $R_x$ is a substituent, a plurality of $R_x$ as the substituents are bonded to each other to form a ring or are not bonded.

At least one pair of a pair of $X_1$ and $X_2$, a pair of $X_2$ and $X_3$, a pair of $X_3$ and $X_4$, a pair of $X_4$ and $X_5$, a pair of $X_7$ and $X_8$, a pair of $X_8$ and $X_9$, a pair of $X_{10}$ and $X_{11}$, a pair of $X_{11}$ and $X_{12}$, a pair of $X_{12}$ and $X_{13}$, and a pair of $X_{16}$ and $X_1$ are carbon atoms to be bonded to the structure represented by the formula (2a) or (2b) below.

[Formula 6]

(2a)

(2b)

In the formula (2a), *2 represent bonding positions to carbon atoms at one pair of the pair of $X_1$ and $X_2$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_1$ and $X_1$ in the formula (2).

$R_{111}$ to $R_{114}$ each independently represent a hydrogen atom or a substituent.

$R_{111}$ to $R_{114}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

At least one pair of a pair of $R_{111}$ and $R_{112}$, a pair of $R_{112}$ and $R_{113}$, and a pair of $R_{113}$ and $R_{114}$ are substituents. The substituents are bonded to each other to form a ring.

In the formula (2b), *2 represent bonding positions to carbon atoms at one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2).

$R_{115}$ and $R_{116}$ each independently represent a hydrogen atom or a substituent.

$R_{115}$ and $R_{116}$ as the substituent are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{115}$ and $R_{116}$ as the substituents are bonded to each other to further form a ring, or are not bonded to each other.

X is selected from the group consisting of an oxygen atom, a sulfur atom, $CR_{117}R_{118}$, $SiR_{119}R_{120}$ and $NR_{121}$.

$R_{117}$ to $R_{121}$ each independently represent a hydrogen atom or a substituent.

$R_{117}$ to $R_{121}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{117}$ and $R_{118}$ as the substituents are bonded to each other to form a ring, or are not bonded to each other.

$R_{119}$ and $R_{120}$ as the substituents are bonded to each other to further form a ring, or are not bonded to each other.

In the exemplary embodiment, $R_x$ in the formula (2) is each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, $R_{111}$ to $R_{114}$ in the formula (2a) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, $R_{115}$ to $R_{121}$ in the formula (2b) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the formula (2) representing the compound of the exemplary embodiment, at least one pair of the pair of $X_1$ and $X_2$ and the pair of $X_3$ and $X_4$ are preferably carbon atoms to be bonded to the structure represented by the formula (2a).

In the compound of the exemplary embodiment, the structure represented by the formula (2a) is preferably a structure represented by a formula (2a-1) below.

[Formula 7]

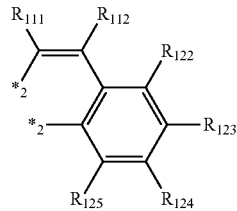

(2a-1)

In the formula (2a-1), *2 represents the same as *2 of the formula (2a).

$R_{111}$, $R_{112}$ and $R_{122}$ to $R_{125}$ each independently represent a hydrogen atom or a substituent.

$R_{111}$, $R_{112}$ and $R_{122}$ to $R_{125}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{111}$, $R_{112}$ and $R_{122}$ to $R_{125}$ as the substituents are bonded to each other to further form a ring, or are not bonded to each other.

In the exemplary embodiment, $R_{111}$, $R_{112}$ and $R_{122}$ to $R_{125}$ in the formula (2a-1) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is preferably represented by a formula (21A) below.

[Formula 8]

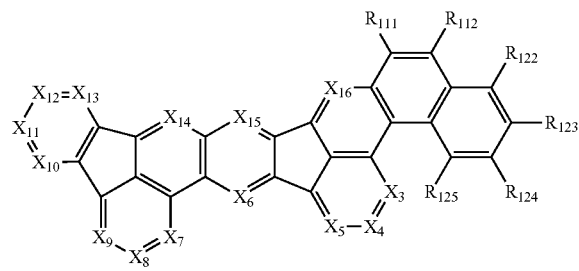

(21A)

In the formula (21A), $X_3$ to $X_{16}$ and $R_x$ respectively represent the same as $X_3$ to $X_{16}$ and $R_x$ in the formula (2), and $R_{111}$, $R_{112}$ and $R_{122}$ to $R_{125}$ respectively represent the same as $R_{111}$, $R_{112}$ and $R_{122}$ to $R_{125}$ in the formula (2a-1).

In the exemplary embodiment, when adjacent ones of the substituents of $R_{111}$, $R_{112}$ and $R_{122}$ to $R_{125}$ in the formula (21A) are bonded to each other to further form a ring, a pair of $R_{111}$ and $R_{112}$ or a pair of $R_{122}$ and $R_{123}$ are preferably bonded to each other to further form a ring.

In the exemplary embodiment, the compound represented by the formula (2) is also preferably represented by a formula (21B) below.

[Formula 9]

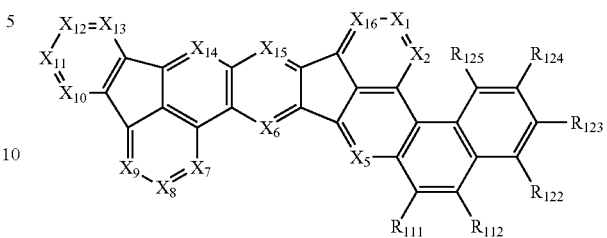

(21B)

In the formula (21B), $X_1$, $X_2$, $X_5$ to $X_{16}$ and $R_x$ respectively represent the same as $X_1$, $X_2$, $X_5$ to $X_{16}$ and $R_x$ in the formula (2), and $R_{111}$, $R_{112}$ and $R_{122}$ to $R_{125}$ respectively represent the same as $R_{111}$, $R_{112}$ and $R_{122}$ to $R_{125}$ in the formula (2a-1).

In the exemplary embodiment, when adjacent ones of the substituents of $R_{111}$, $R_{112}$ and $R_{122}$ to $R_{125}$ in the formula (21B) are bonded to each other to further form a ring, a pair of $R_{111}$ and $R_{112}$ or a pair of $R_{122}$ and $R_{123}$ are preferably bonded to each other to further form a ring.

In the compound of the exemplary embodiment, the structure represented by the formula (2a) is also preferably a structure represented by a formula (2a-2) below.

[Formula 10]

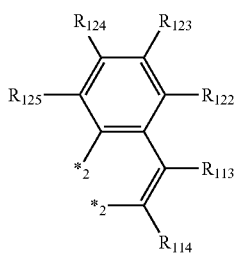

(2a-2)

In the formula (2a-2), *2 represents the same as *2 of the formula (2a).

$R_{113}$, $R_{114}$ and $R_{122}$ to $R_{125}$ each independently represent a hydrogen atom or a substituent.

$R_{113}$, $R_{114}$ and $R_{122}$ to $R_{125}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{113}$, $R_{114}$ and $R_{122}$ to $R_{125}$ as the substituents are bonded to each other to further form a ring, or are not bonded to each other.

In the exemplary embodiment, $R_{111}$, $R_{112}$ and $R_{122}$ to $R_{125}$ in the formula (2a-2) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (22A) below.

[Formula 11]

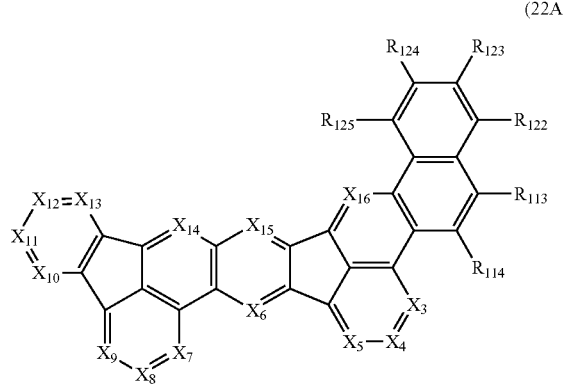

(22A)

In the formula (22A), $X_3$ to $X_{16}$ and $R_x$ respectively represent the same as $X_3$ to $X_{16}$ and $R_x$ in the formula (2), and $R_{113}$, $R_{114}$ and $R_{122}$ to $R_{125}$ respectively represent the same as $R_{113}$, $R_{114}$ and $R_{122}$ to $R_{125}$ in the formula (2a-2).

In the exemplary embodiment, when adjacent ones of the substituents of $R_{113}$, $R_{114}$ and $R_{122}$ to $R_{125}$ in the formula (22A) are bonded to each other to further form a ring, a pair of $R_{113}$ and $R_{114}$ or a pair of $R_{122}$ and $R_{123}$ are preferably bonded to each other to further form a ring.

In the exemplary embodiment, the compound represented by the formula (2) is also preferably represented by a formula (22B) below.

[Formula 12]

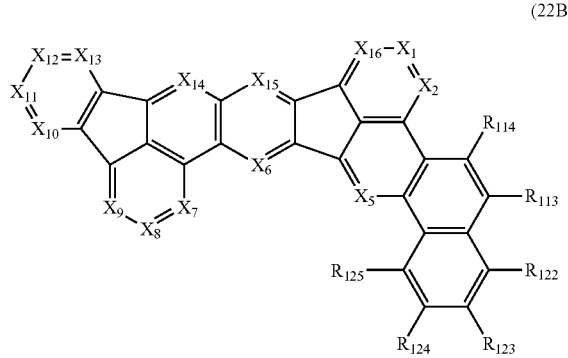

(22B)

In the formula (22B), $X_1$, $X_2$, $X_5$ to $X_{16}$ and $R_x$ respectively represent the same as $X_1$, $X_2$, $X_5$ to $X_{16}$ and $R_x$ in the formula (2), and $R_{113}$, $R_{114}$ and $R_{122}$ to $R_{125}$ respectively represent the same as $R_{113}$, $R_{114}$ and $R_{122}$ to $R_{125}$ in the formula (2a-2).

In the exemplary embodiment, when adjacent ones of the substituents of $R_{113}$, $R_{114}$ and $R_{122}$ to $R_{125}$ in the formula (22B) are bonded to each other to further form a ring, a pair of $R_{113}$ and $R_{114}$ or a pair of $R_{122}$ and $R_{123}$ are preferably bonded to each other to further form a ring.

In the exemplary embodiment, at least one pair of the pair of $X_1$ and $X_2$, the pair of $X_2$ and $X_3$ and the pair of $X_3$ and $X_4$ in the formula (2) are also preferably carbon atoms to be bonded to the structure represented by the formula (2b).

In the exemplary embodiment, the compound in which at least one pair of the pair of $X_1$ and $X_2$, the pair of $X_2$ and $X_3$ and the pair of $X_3$ and $X_4$ in the formula (2) are carbon atoms to be bonded to the structure represented by the formula (2b) is exemplified by a compound represented by a formula (23A), a compound represented by a formula (23B), a compound represented by a formula (24A), and a compound represented by a formula (24B).

[Formula 13]

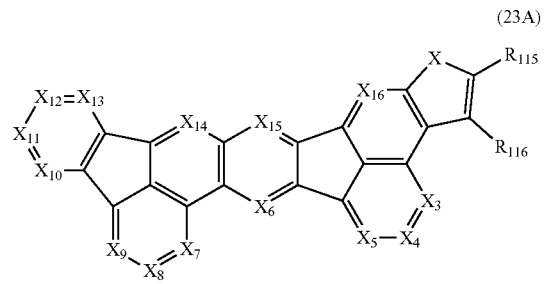

(23A)

[Formula 14]

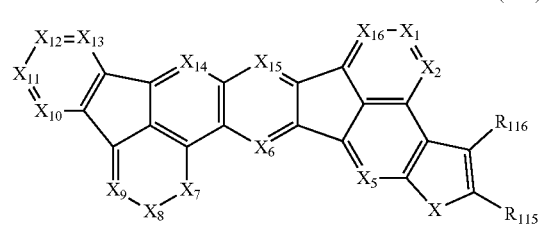

(23B)

[Formula 15]

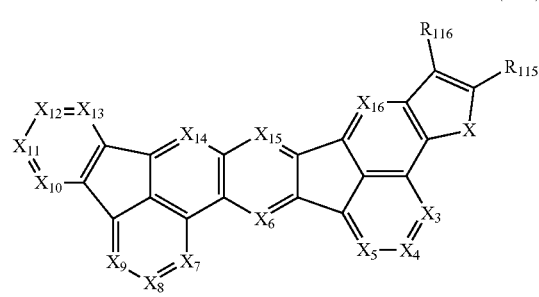

(24A)

[Formula 16]

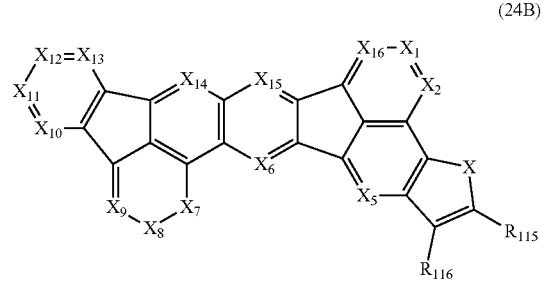

(24B)

In the formula (23A), $X_3$ to $X_{16}$ and $R_x$ respectively represent the same as $X_3$ to $X_{16}$ and $R_x$ of the formula (2).

In the formula (23B), $X_1$, $X_2$, $X_5$ to $X_{16}$ and $R_x$ respectively represent the same as $X_1$, $X_2$, $X_5$ to $X_{16}$ and $R_x$ of the formula (2).

In the formula (24A), $X_3$ to $X_{16}$ and $R_x$ respectively represent the same as $X_3$ to $X_{16}$ and $R_x$ of the formula (2).

In the formula (24B), $X_1$, $X_2$, $X_5$ to $X_{16}$ and $R_x$ respectively represent the same as $X_1$, $X_2$, $X_5$ to $X_{16}$ and $R_x$ of the formula (2).

In the formulae (23A), (23B), (24A) and (24B), $R_{115}$, $R_{116}$ and X respectively represent the same as $R_{115}$, $R_{116}$ and X of the formula (2b).

In the formulae (23A), (23B), (24A) and (24B), preferably, both of $R_{115}$ and $R_{116}$ are substituents and $R_{115}$ and $R_{116}$ as the substituents are bonded to each other to further form a ring.

In the exemplary embodiment, the compound represented by the formula (2) is also preferably represented by a formula (25A) below.

[Formula 17]

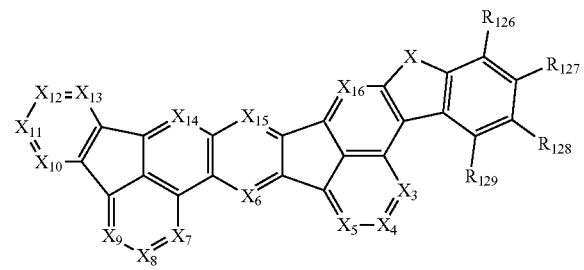

(25A)

In the formula (25A), $X_3$ to $X_{16}$ and $R_x$ respectively represent the same as $X_3$ to $X_{16}$ and $R_x$ of the formula (2), and X represents the same as X of the formula (2b).

$R_{126}$ to $R_{129}$ each independently represent a hydrogen atom or a substituent.

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{126}$ to $R_{129}$ as the substituents are bonded to each other to further form a ring, or are not bonded to each other.

In the exemplary embodiment, $R_{126}$ to $R_{129}$ in the formula (25A) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (25B) below.

[Formula 18]

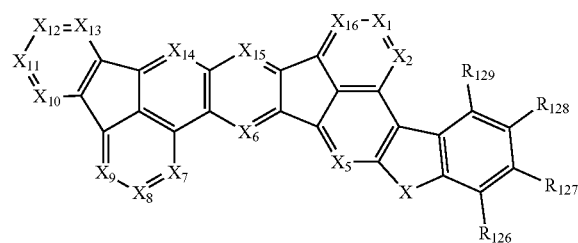

(25B)

In the formula (25B), $X_1$, $X_2$, $X_5$ to $X_{16}$ and $R_x$ respectively represent the same as $X_1$, $X_2$, $X_5$ to $X_{16}$ and $R_x$ of the formula (2), and X represents the same as X of the formula (2b).

$R_{126}$ to $R_{129}$ each independently represent a hydrogen atom or a substituent.

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{126}$ to $R_{129}$ as the substituents are bonded to each other to further form a ring, or are not bonded to each other.

In the exemplary embodiment, $R_{126}$ to $R_{129}$ in the formula (25B) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (26A) below.

[Formula 19]

(26A)

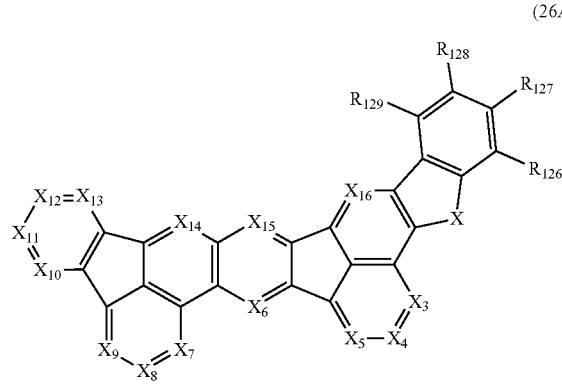

[Formula 20]

(26B)

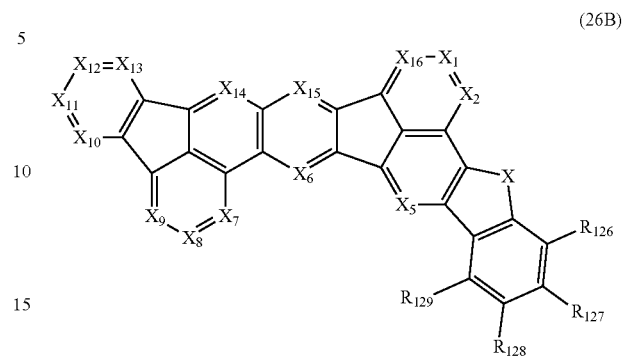

In the formula (26A), $X_3$ to $X_{16}$ and $R_x$ respectively represent the same as $X_3$ to $X_{16}$ and $R_x$ of the formula (2), and X represents the same as X of the formula (2b).

$R_{126}$ to $R_{129}$ each independently represent a hydrogen atom or a substituent.

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{126}$ to $R_{129}$ as the substituents are bonded to each other to further form a ring, or are not bonded to each other.

In the exemplary embodiment, $R_{126}$ to $R_{129}$ in the formula (26A) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (26B) below.

In the formula (26B), $X_1$, $X_2$, $X_5$ to $X_{16}$ and $R_x$ respectively represent the same as $X_1$, $X_2$, $X_5$ to $X_{16}$ and $R_x$ of the formula (2), and X represents the same as X of the formula (2b).

$R_{126}$ to $R_{129}$ each independently represent a hydrogen atom or a substituent.

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{126}$ to $R_{129}$ as the substituents are bonded to each other to further form a ring, or are not bonded to each other.

In the exemplary embodiment, $R_{126}$ to $R_{129}$ in the formula (26B) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (27A) below.

[Formula 21]

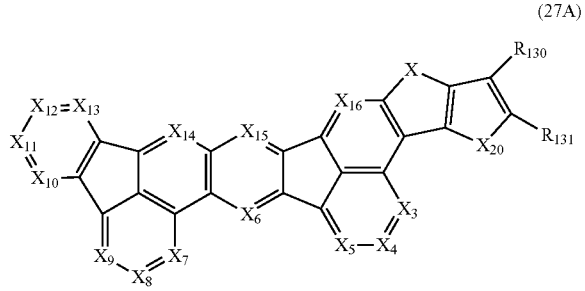

(27A)

In the formula (27A), $X_3$ to $X_{16}$ and $R_x$ respectively represent the same as $X_3$ to $X_{16}$ and $R_x$ of the formula (2), and X represents the same as X of the formula (2b).

$R_{130}$ and $R_{131}$ each independently represent a hydrogen atom or a substituent.

$R_{130}$ and $R_{131}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$X_{20}$ is selected from the group consisting of an oxygen atom, a sulfur atom, $CR_{132}R_{133}$, $SiR_{134}R_{135}$ and $NR_{136}$.

$R_{132}$ to $R_{136}$ each independently represent a hydrogen atom or a substituent.

$R_{132}$ to $R_{136}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{130}$ to $R_{136}$ as the substituents are bonded to each other to further form a ring, or are not bonded to each other.

In the exemplary embodiment, $R_{130}$ to $R_{136}$ in the formula (27A) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (27B) below.

[Formula 22]

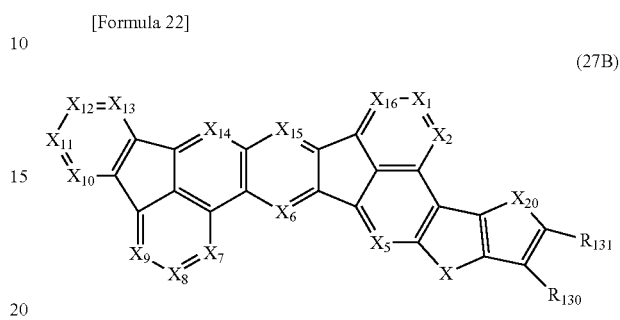

(27B)

In the formula (27B), $X_1$, $X_2$, $X_5$ to $X_{16}$ and $R_x$ respectively represent the same as $X_1$, $X_2$, $X_5$ to $X_{16}$ and $R_x$ of the formula (2), and X represents the same as X of the formula (2b).

$R_{130}$ and $R_{131}$ each independently represent a hydrogen atom or a substituent.

$R_{130}$ and $R_{131}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$X_{20}$ is selected from the group consisting of an oxygen atom, a sulfur atom, $CR_{132}R_{133}$, $SiR_{134}R_{135}$ and $NR_{136}$.

$R_{132}$ to $R_{136}$ each independently represent a hydrogen atom or a substituent.

$R_{132}$ to $R_{136}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{130}$ to $R_{136}$ as the substituents are bonded to each other to further form a ring, or are not bonded to each other.

In the exemplary embodiment, $R_{130}$ to $R_{136}$ in the formula (27B) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (28A) below.

[Formula 23]

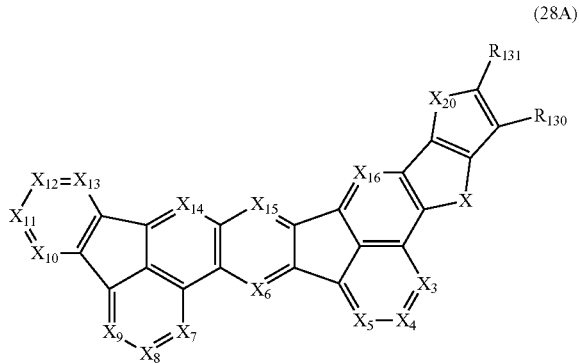

(28A)

In the formula (28A), $X_3$ to $X_{16}$ and $R_x$ respectively represent the same as $X_3$ to $X_{16}$ and $R_x$ of the formula (2), and X represents the same as X of the formula (2b).

$R_{130}$ and $R_{131}$ each independently represent a hydrogen atom or a substituent.

$R_{130}$ to $R_{131}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$X_{20}$ is selected from the group consisting of an oxygen atom, a sulfur atom, $CR_{132}R_{133}$, $SiR_{134}R_{135}$ and $NR_{136}$.

$R_{132}$ to $R_{136}$ each independently represent a hydrogen atom or a substituent.

$R_{132}$ to $R_{136}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{130}$ to $R_{136}$ as the substituents are bonded to each other to further form a ring, or are not bonded to each other.

In the exemplary embodiment, $R_{130}$ to $R_{136}$ in the formula (28A) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, the compound represented by the formula (2) is also preferably represented by a formula (28B) below.

[Formula 24]

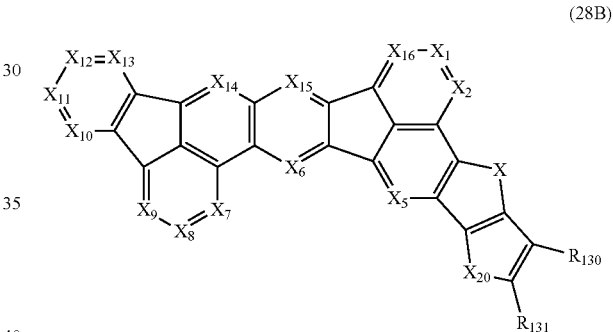

(28B)

In the formula (28B), $X_1$, $X_2$, $X_5$ to $X_{16}$ and $R_x$ respectively represent the same as $X_1$, $X_2$, $X_5$ to $X_{16}$ and $R_x$ of the formula (2), and X represents the same as X of the formula (2b).

$R_{130}$ and $R_{131}$ each independently represent a hydrogen atom or a substituent.

$R_{130}$ and $R_{131}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$X_{20}$ is selected from the group consisting of an oxygen atom, a sulfur atom, $CR_{132}R_{133}$, $SiR_{134}R_{135}$ and $NR_{136}$.

$R_{132}$ to $R_{136}$ each independently represent a hydrogen atom or a substituent.

$R_{132}$ to $R_{136}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{130}$ to $R_{136}$ as the substituents are bonded to each other to further form a ring, or are not bonded to each other.

In the exemplary embodiment, $R_{130}$ to $R_{136}$ in the formula (28B) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the formula (2) representing the compound of the exemplary embodiment, $X_6$ is preferably $CR_6$, $X_{15}$ is preferably $CR_{15}$, and $R_6$ and $R_{15}$ are each independently preferably a substituted or unsubstituted aryl group having 6 to 30 ring carbon atoms, more preferably a substituted or unsubstituted phenyl group.

In the formula (2) representing the compound of the exemplary embodiment, preferably, $X_5$ is $CR_5$, $X_6$ is $CR_6$, $X_7$ is $CR_7$, $X_8$ is $CR_8$, $X_9$ is $CR_9$, $X_{10}$ is $CR_{10}$, $X_{11}$ is $CR_{11}$, $X_{12}$ is $CR_{12}$, $X_{13}$ is $CR_{13}$, $X_{14}$ is $CR_{14}$, $X_{15}$ is $CR_{15}$, $X_{16}$ is $CR_{16}$, $R_6$ and $R_{15}$ are each independently a substituted or unsubstituted phenyl group, and $R_5$, $R_7$ to $R_{14}$, and $R_{16}$ are hydrogen atoms.

The compound of the exemplary embodiment can improve a luminous efficiency of an organic EL device.

This is considered to be attributed to the above-described particular structure of the compound of the exemplary embodiment. At least one of the structures represented by the formulae (2a) and (2b) is bonded to the structure represented by the formula (2). Conjugation is thus added to an acenaphtho[1,2-k]benzo[e]acephenanthrene skeleton, thereby allowing an increase in a molar absorbance coefficient and a decrease in Stokes shift. Accordingly, it is considered that, by using the compound of the exemplary embodiment as the luminescent material (a dopant) of the organic EL device, the compound can sufficiently absorb transfer energy from a host to the dopant, thereby improving the luminous efficiency.

In order to improve the luminous efficiency of the organic EL device in a blue wavelength region, conjugate addition to the acenaphtho[1,2-k]benzo[e]acephenanthrene skeleton is preferably performed by increasing the number of the fused ring by addition of a structure such as the structure represented by the formula (2a-1) or by increasing the number of the fused ring so as to form the structure represented by the formula (25A), (25B), (26A) or (26B). More preferably, conjugate addition is performed by increasing the number of the fused ring so as to form the structure represented by the formula (21A), (21B), (25A) or (25B). Conjugate addition by such an increase in the number of the fused ring avoids an excessively small singlet energy and a shift of an emission peak toward a long wavelength. Accordingly, it is expected that the luminous efficiency is improvable while the emission peak is kept in the blue emission region.

Manufacturing Method of Compound

The compound according to the exemplary embodiment can be manufactured by, for instance, a method described in Examples described below. The compound of the exemplary embodiment can be manufactured by application of known substitution reactions and/or materials depending on a target compound according to reactions described later in Examples.

Examples of the compound according to the exemplary embodiment are given below. It should be understood that examples of the compound according to the exemplary embodiment are merely illustrative and are not intended to limit the scope of the invention.

[Formula 25]

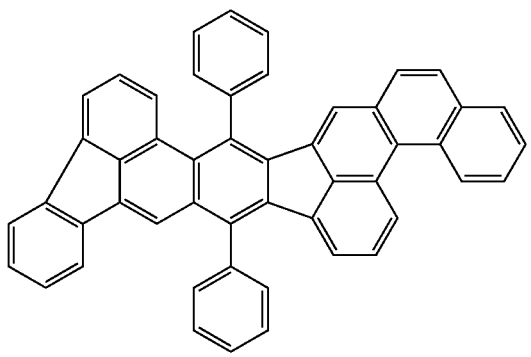

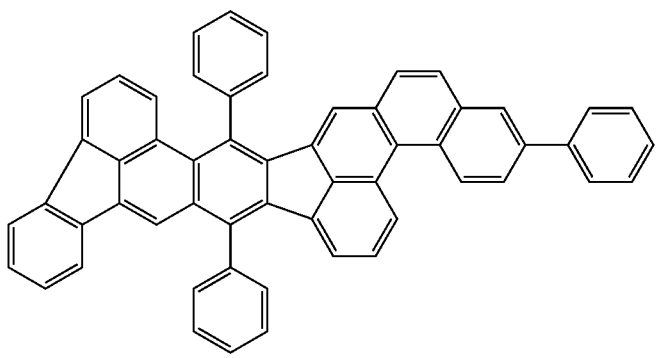
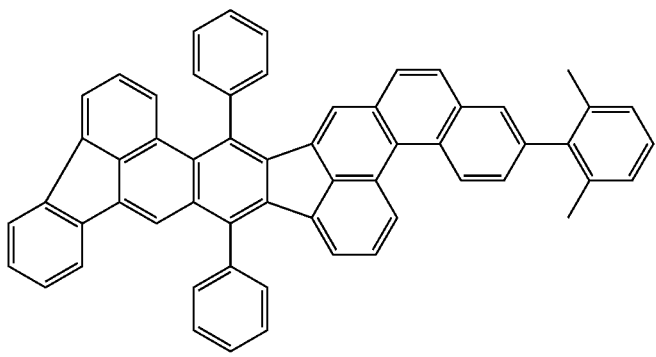
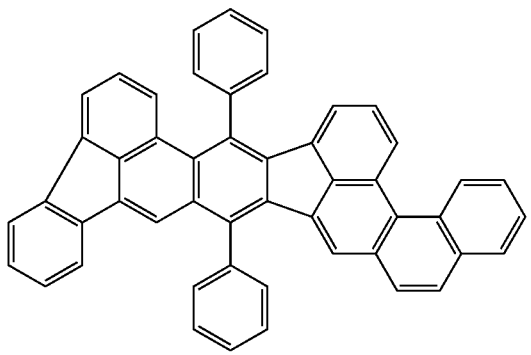
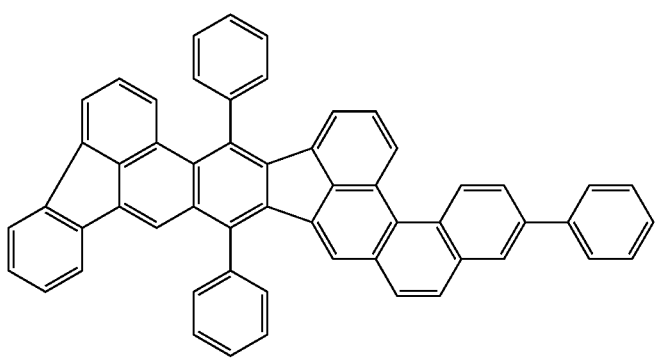

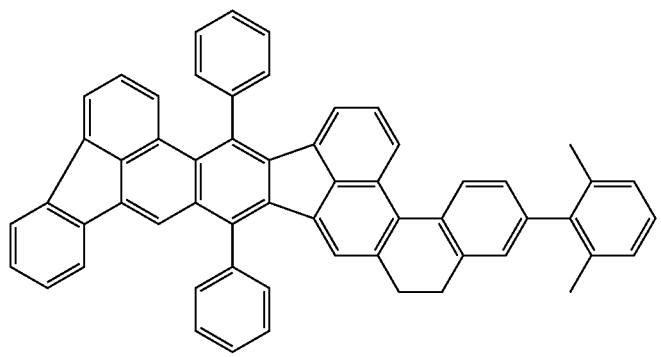
[Formula 26]
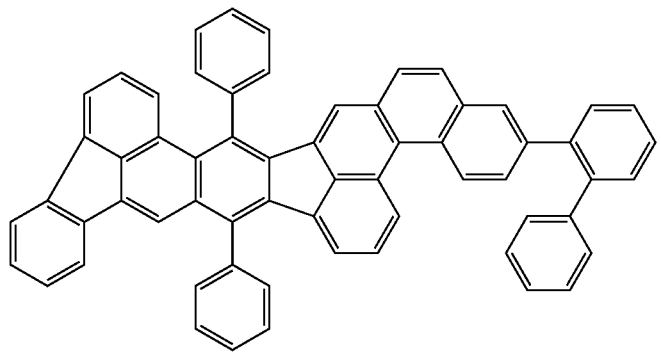
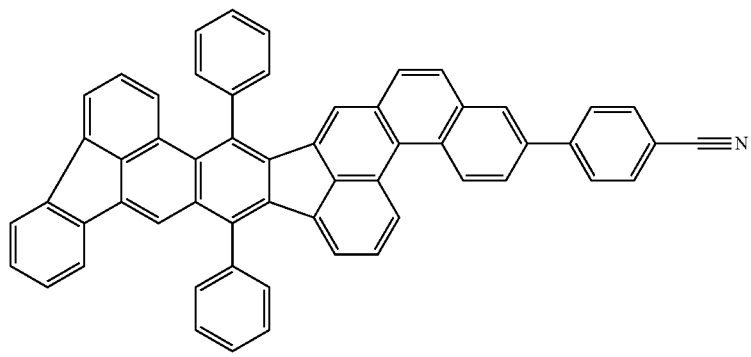
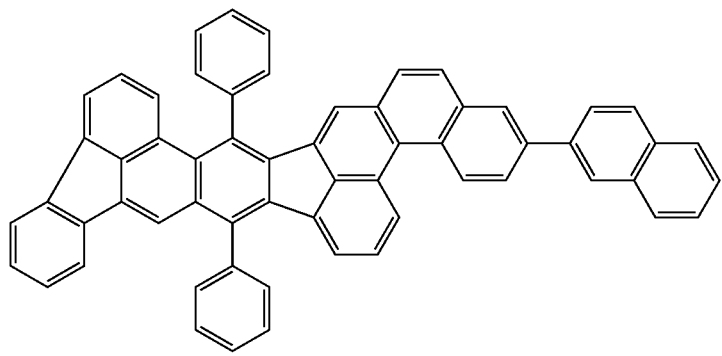

-continued
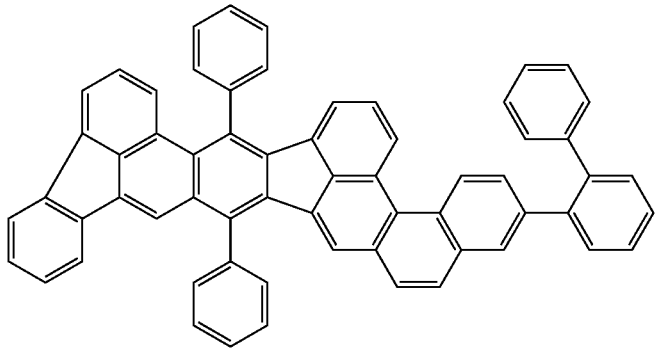
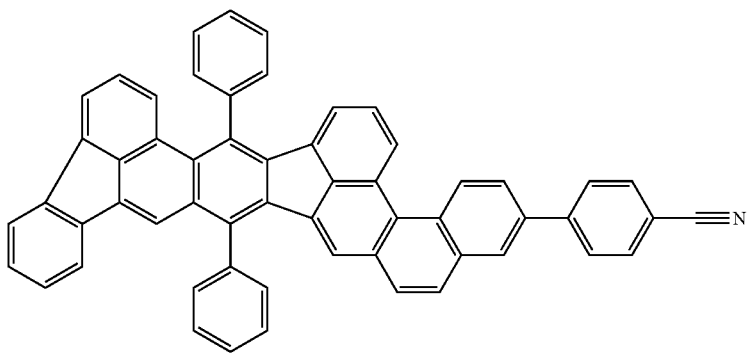
[Formula 27]
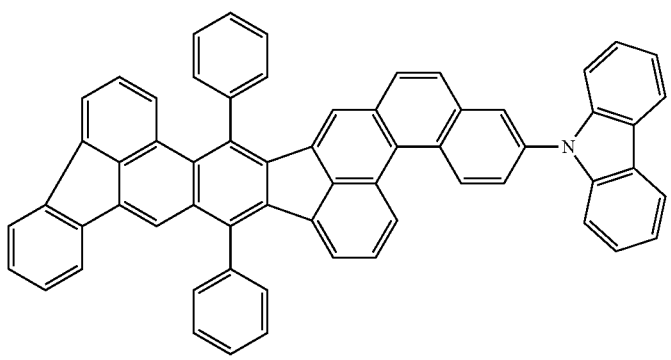

-continued
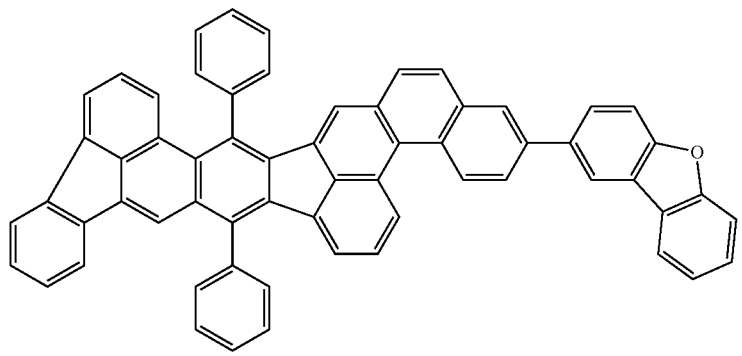
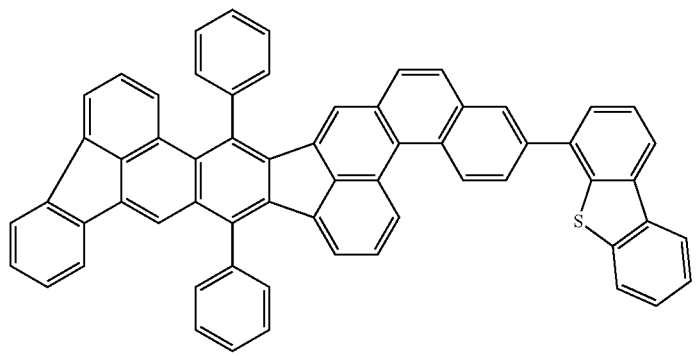
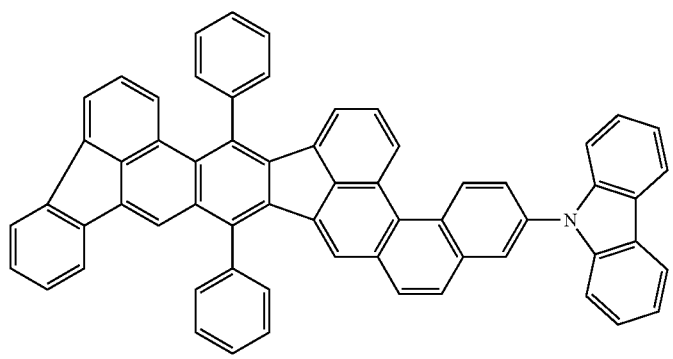
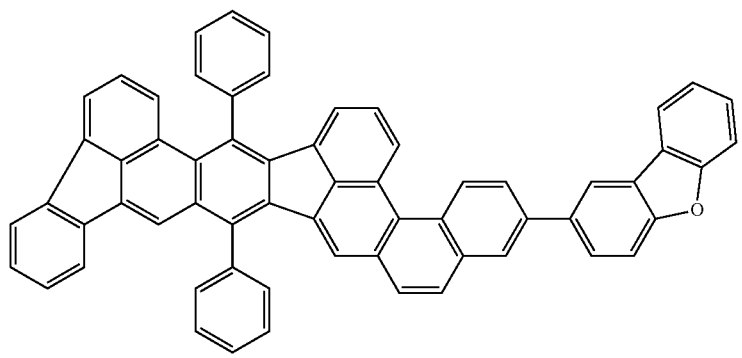

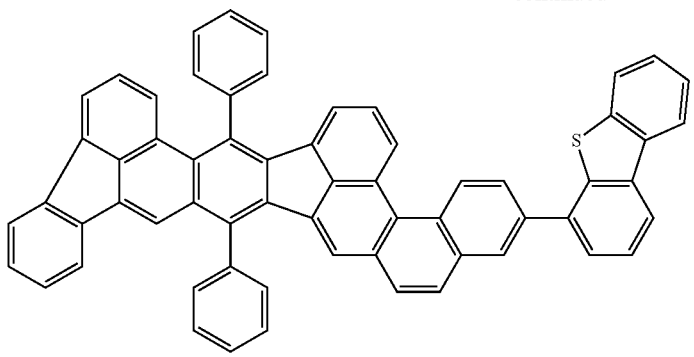
[Formula 28]
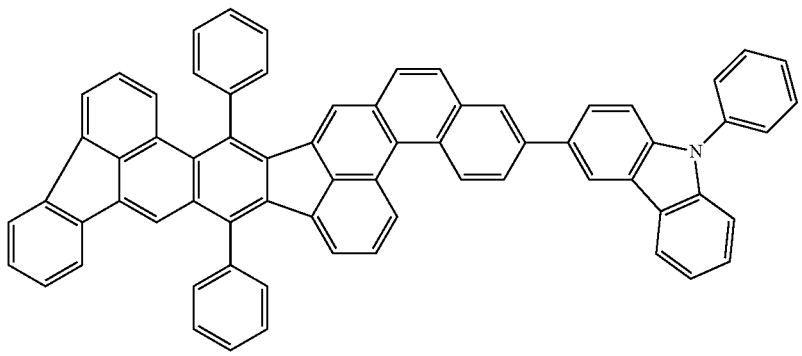
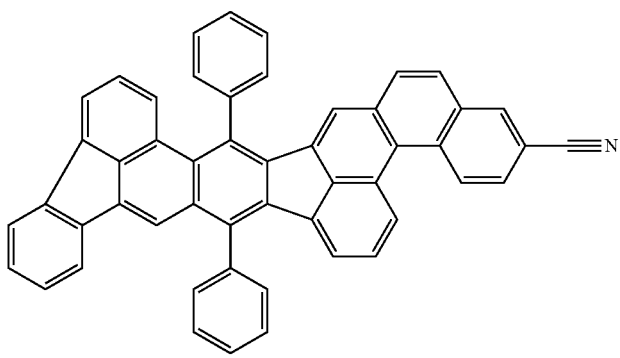
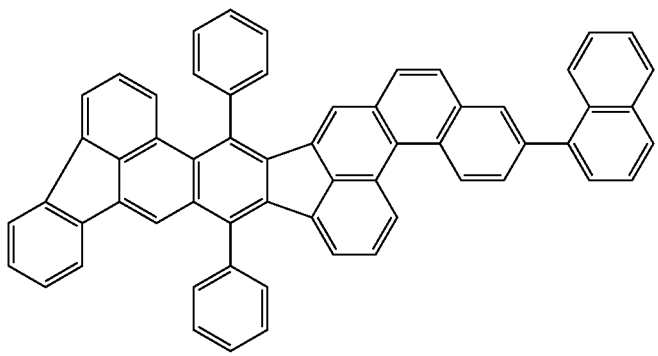

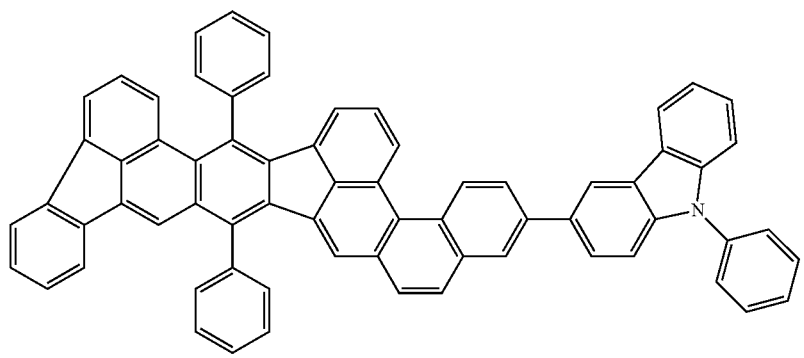
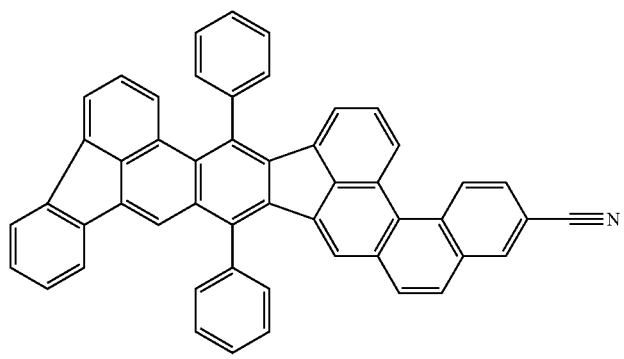
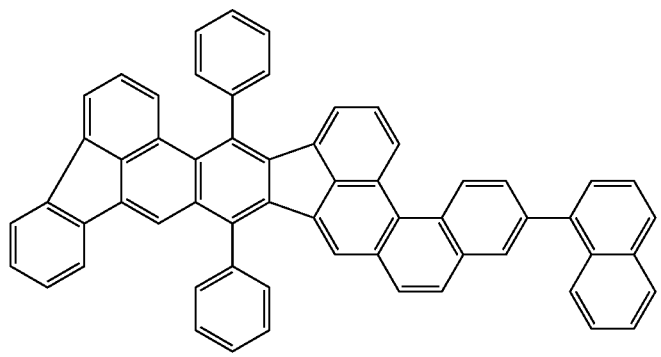
[Formula 29]
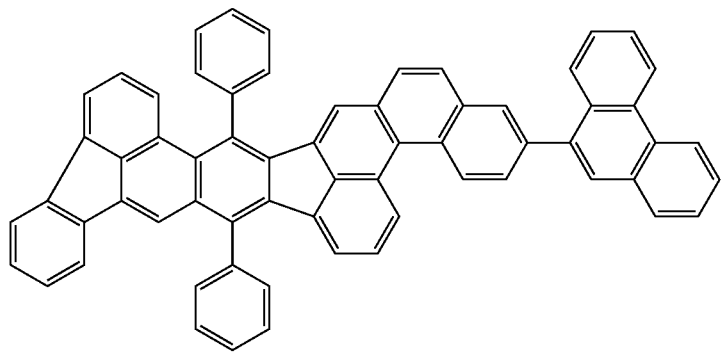

-continued
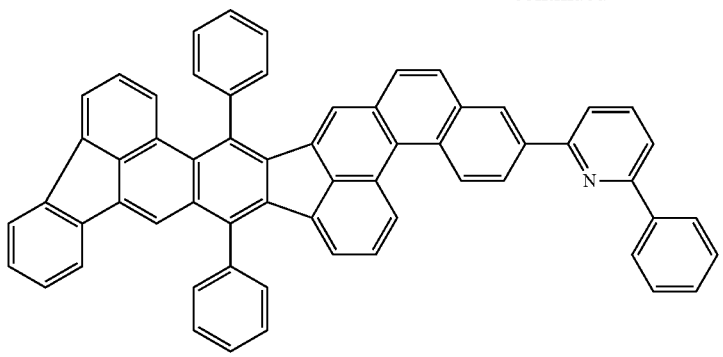
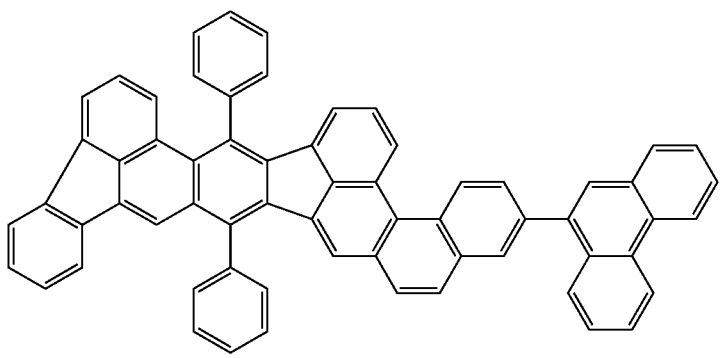
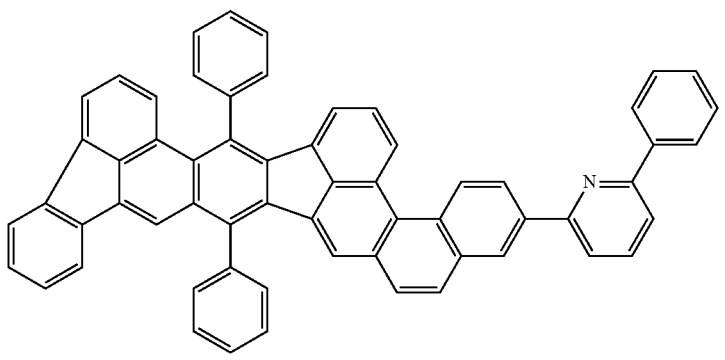
[Formula 30]
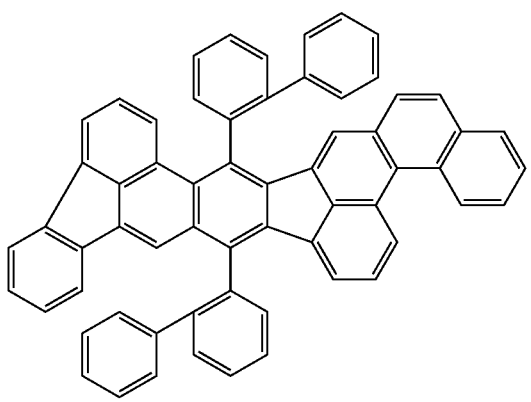

-continued
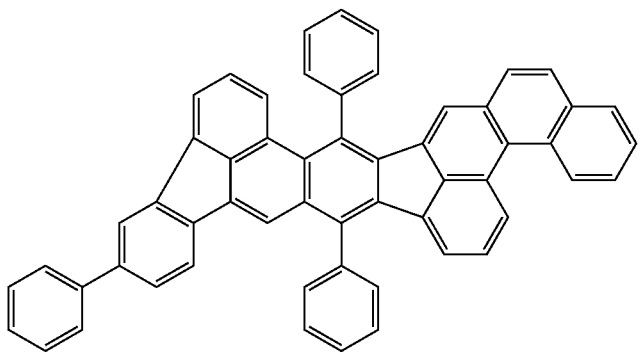
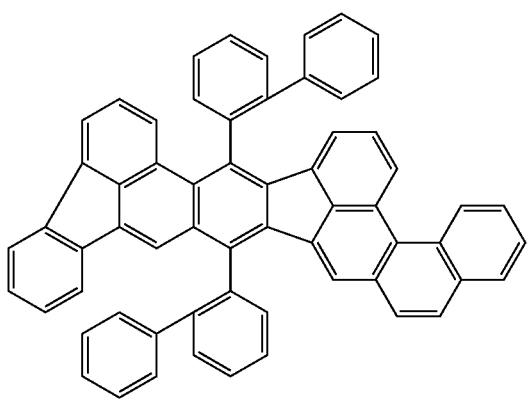
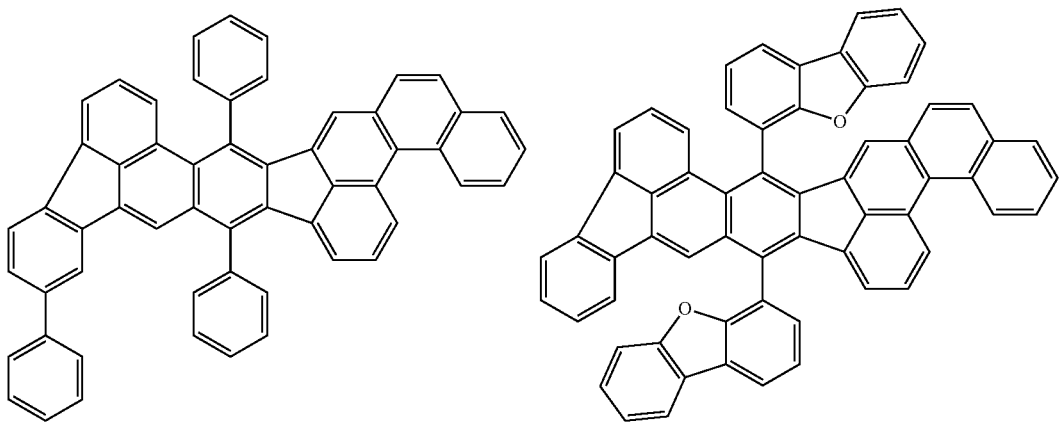
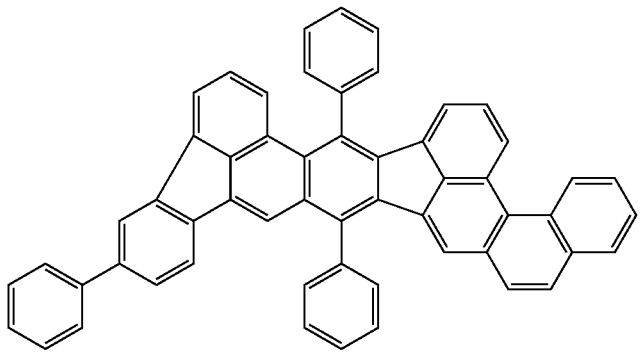

41 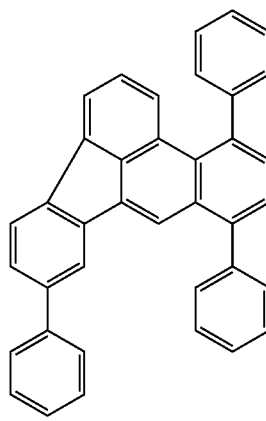
42 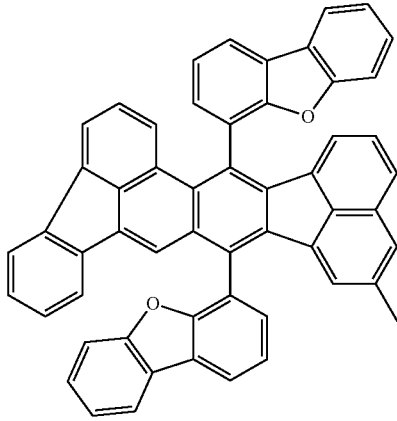
[Formula 31]
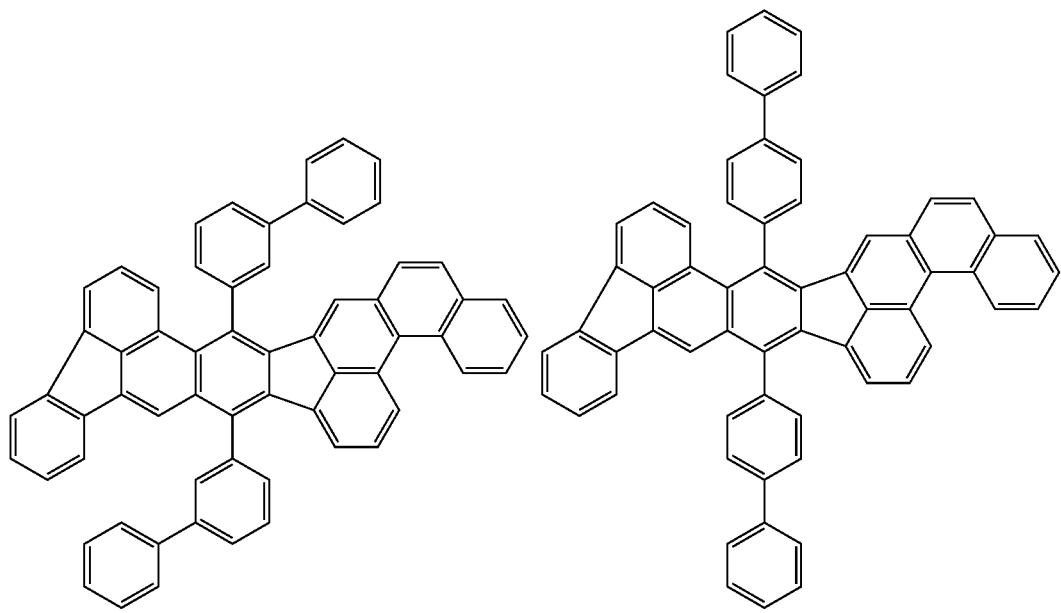
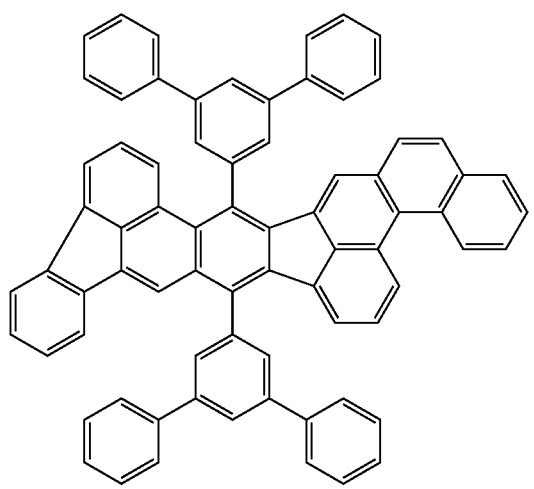
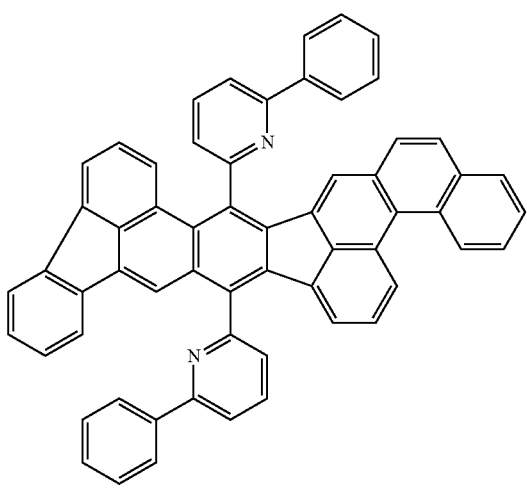

[Formula 32]
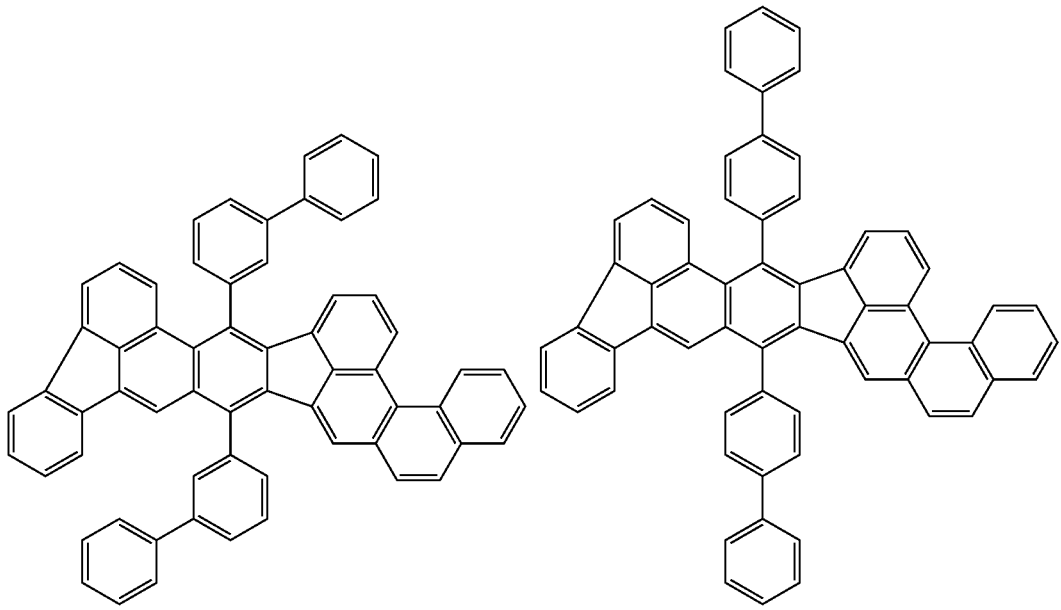
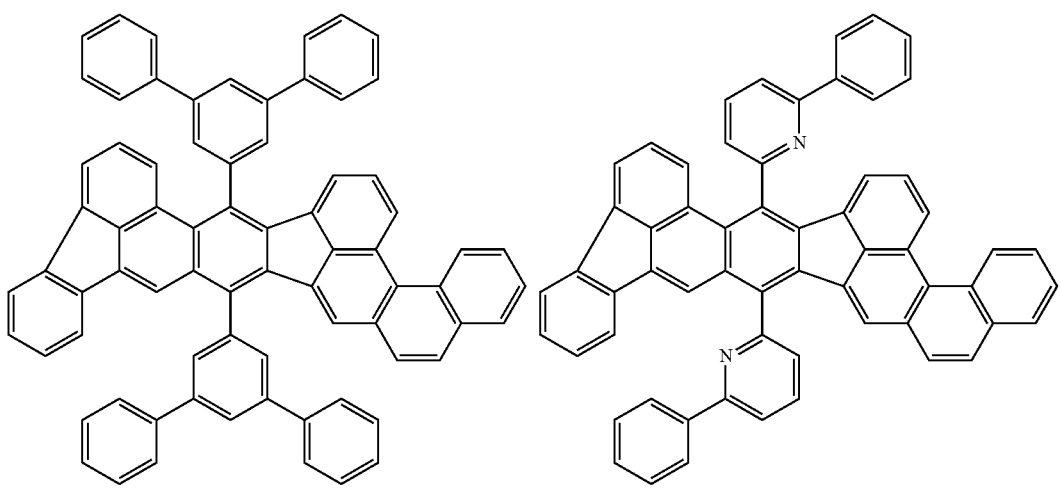
[Formula 33]
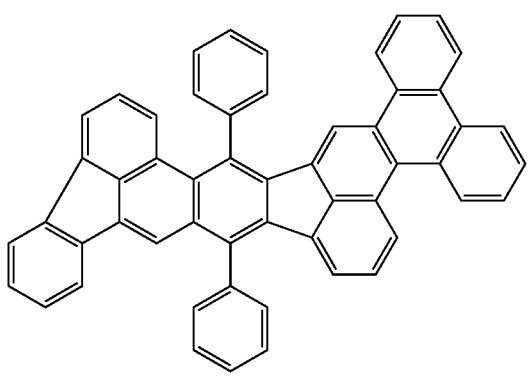

-continued
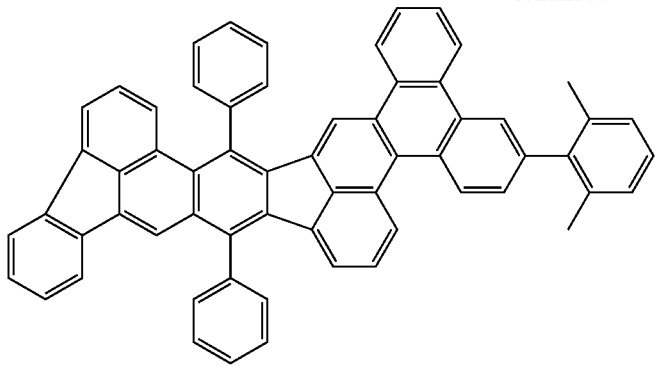
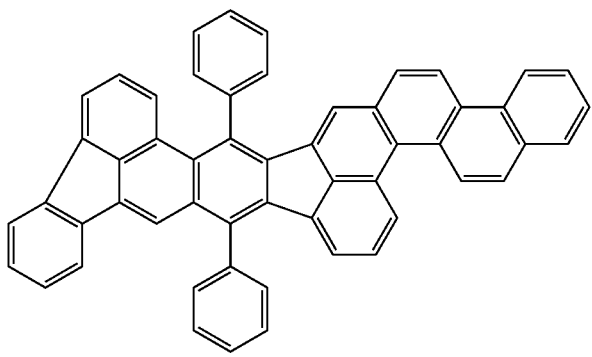
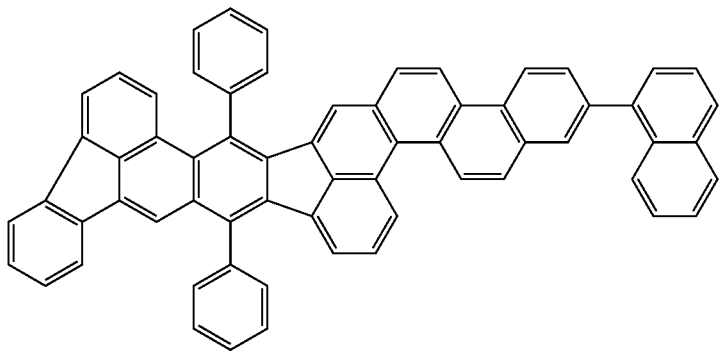
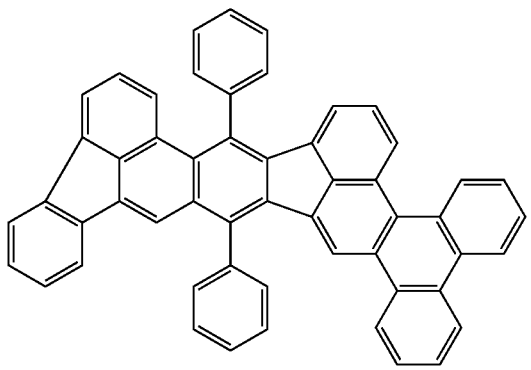

-continued
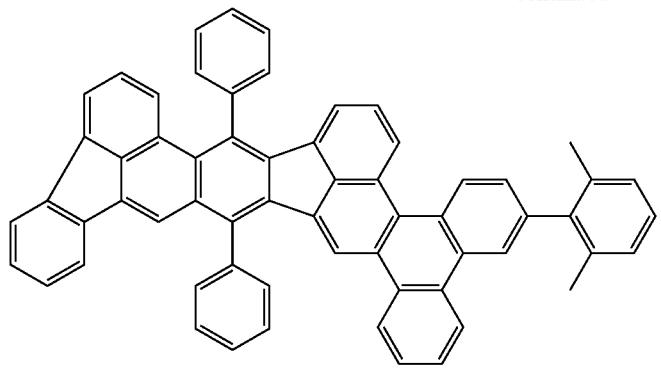
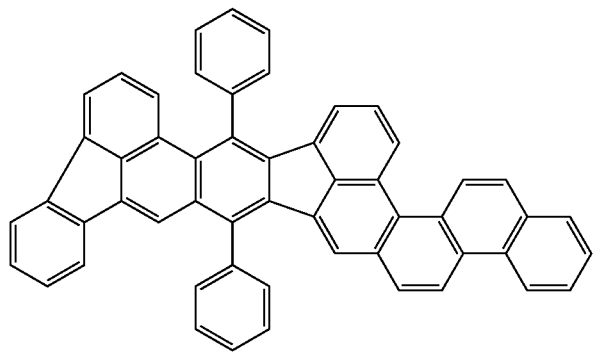
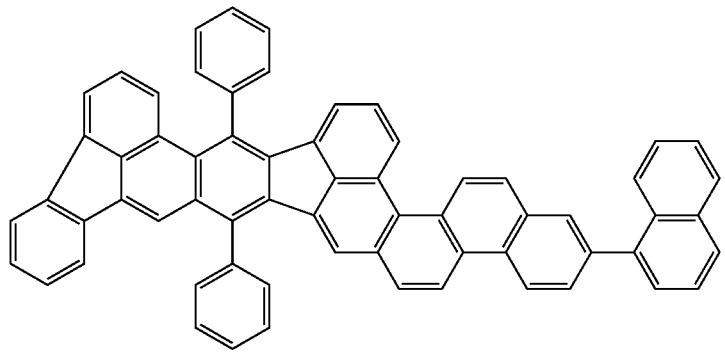
[Formula 34]
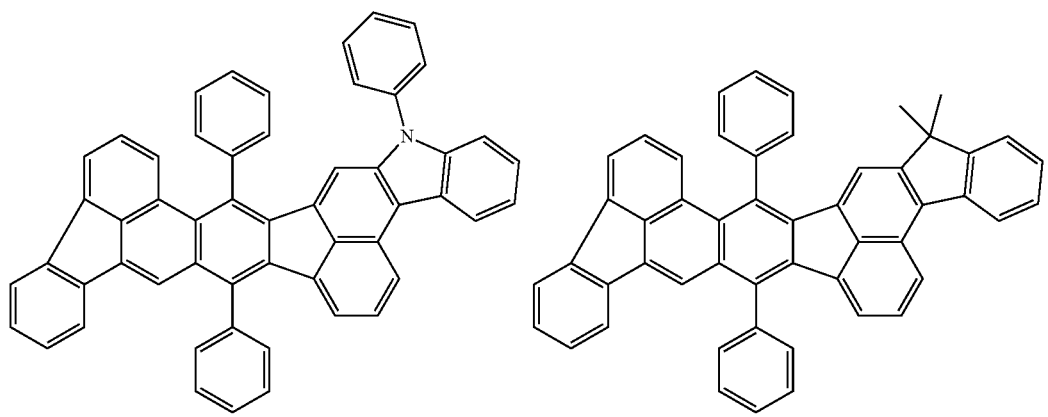

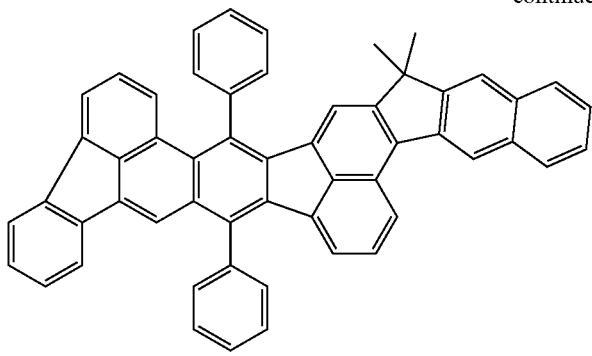
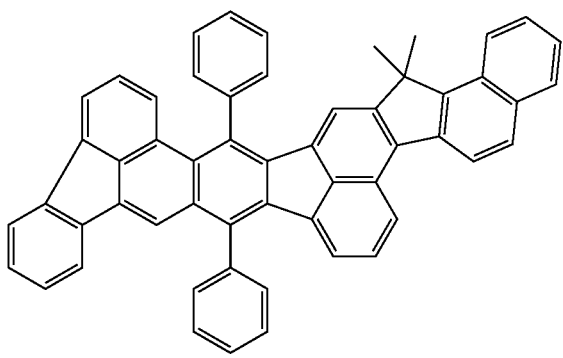
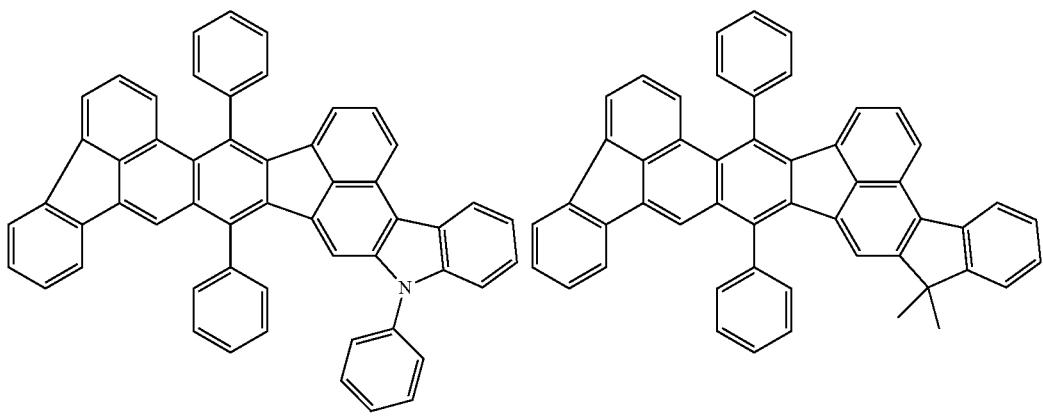
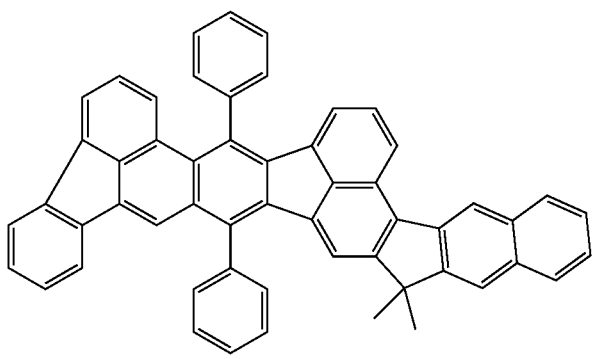

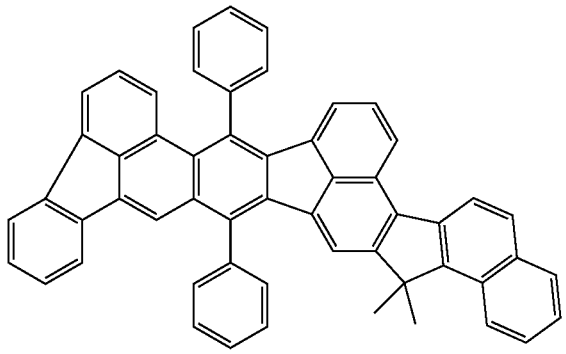
[Formula 35]
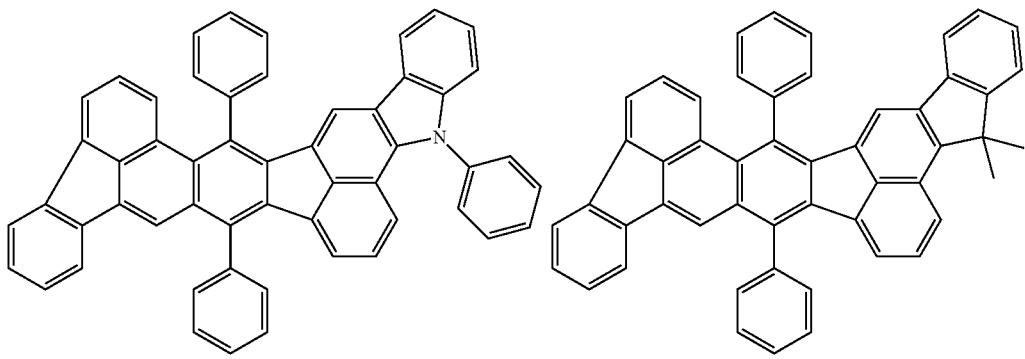
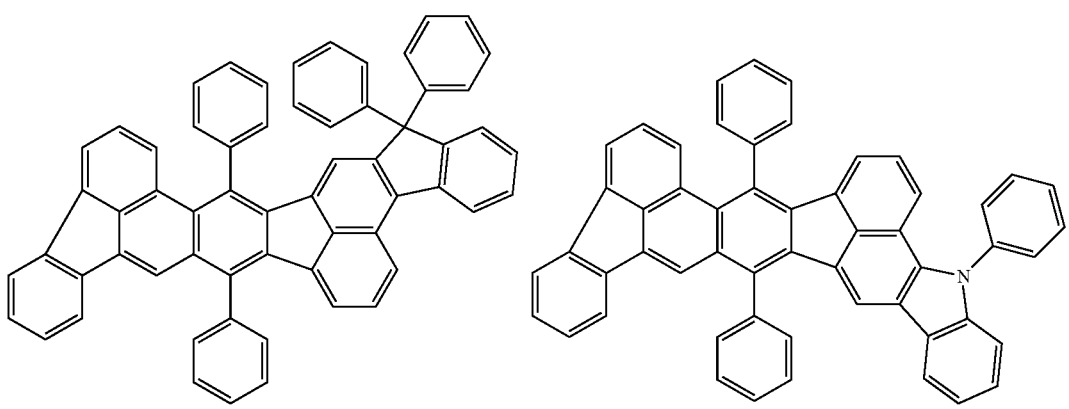
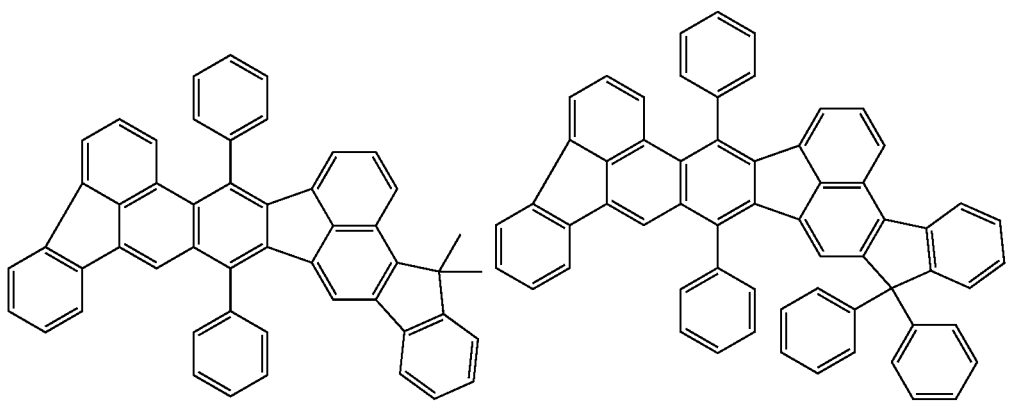

-continued
[Formula 36]
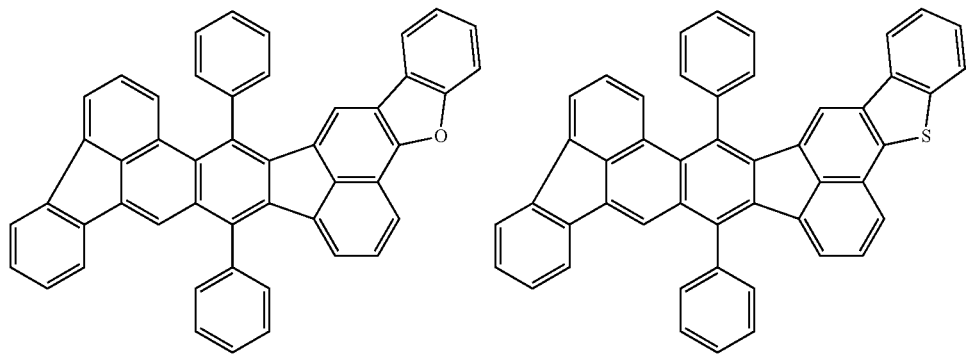
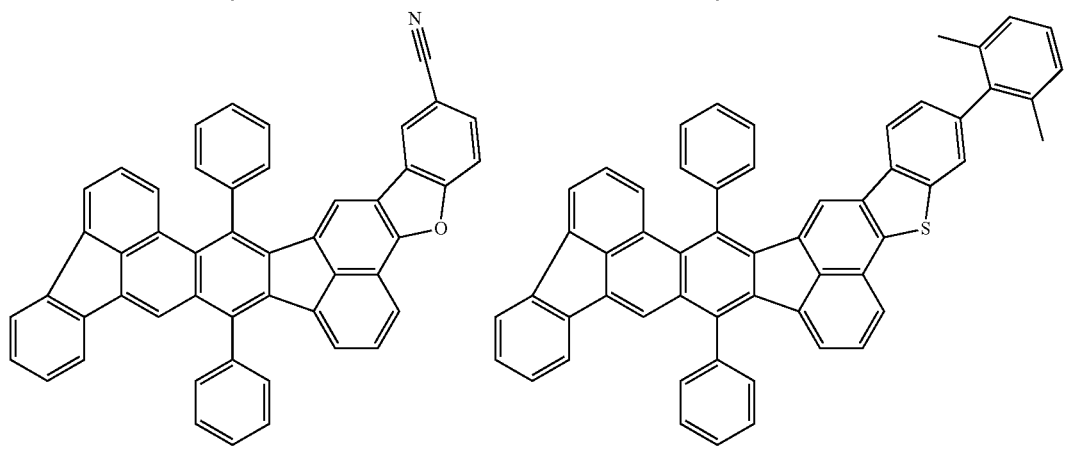
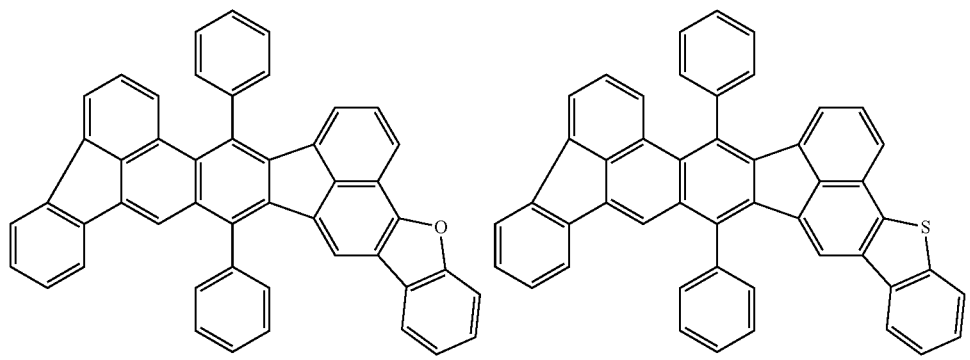
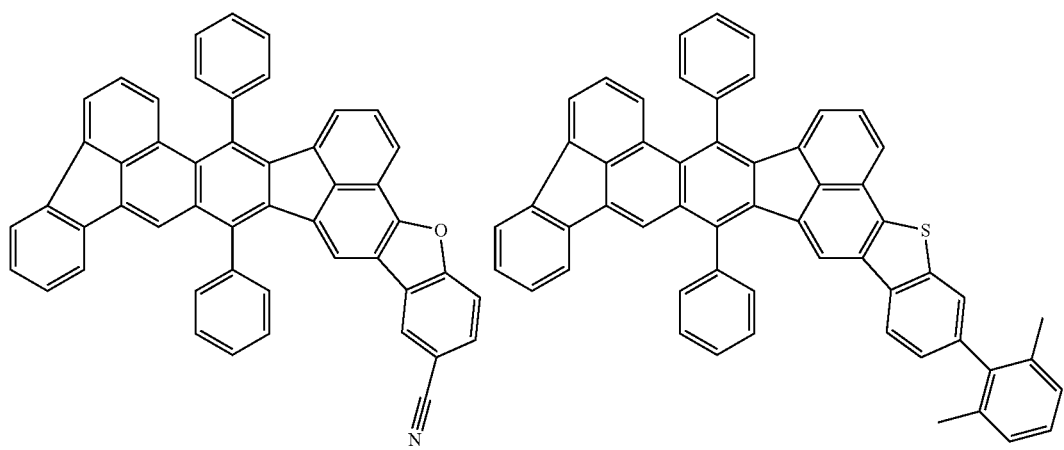

-continued
[Formula 37]
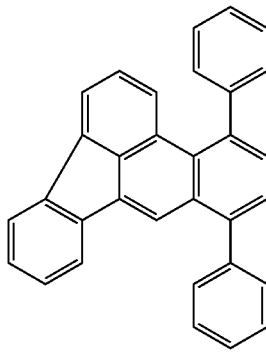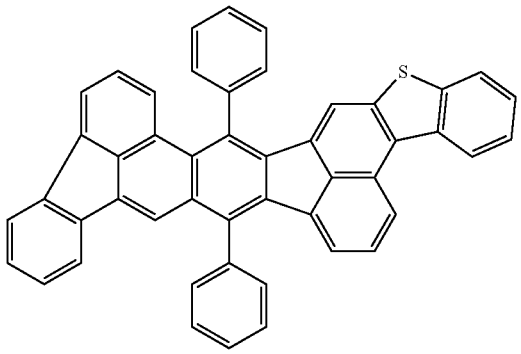
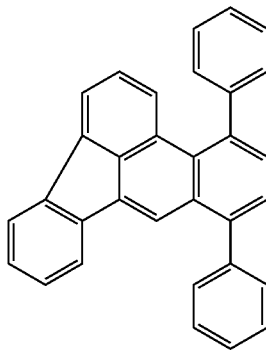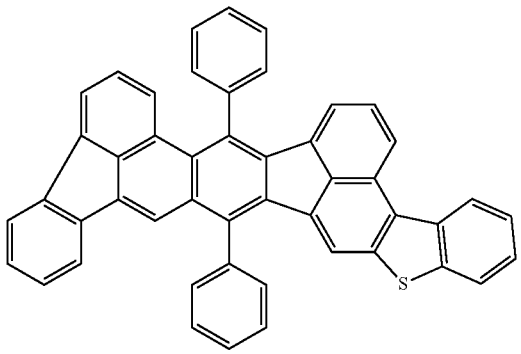
[Formula 38]
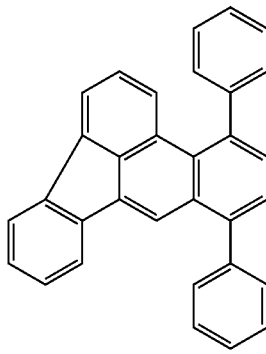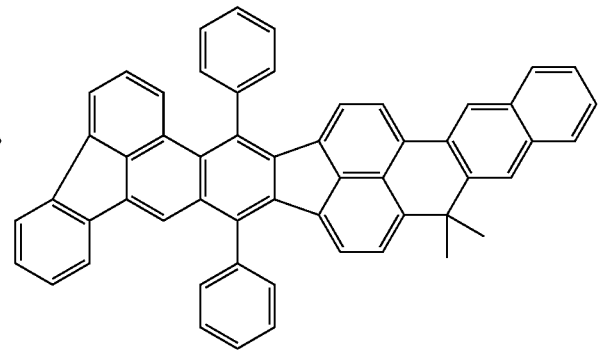
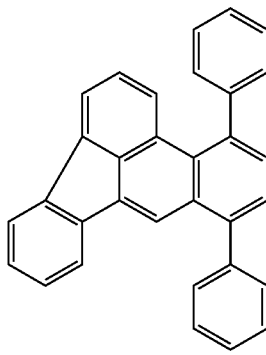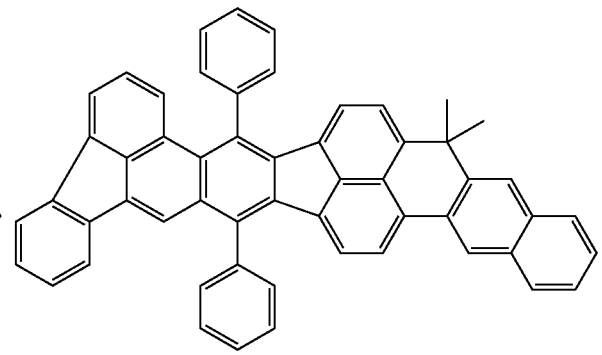

[Formula 39]
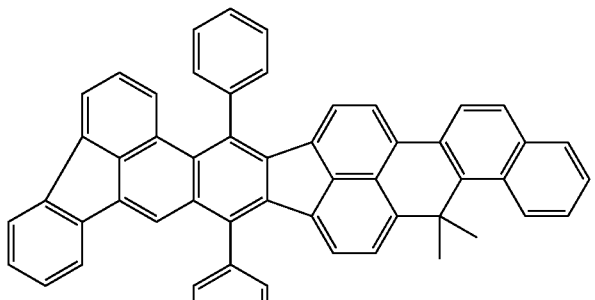
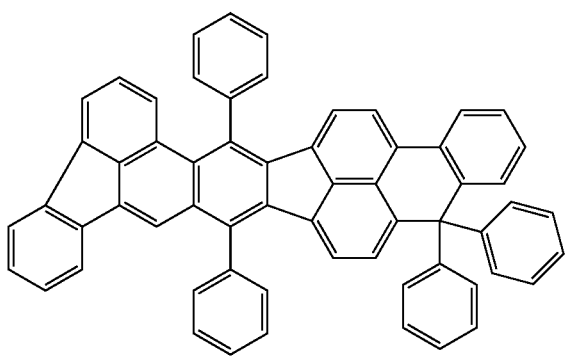
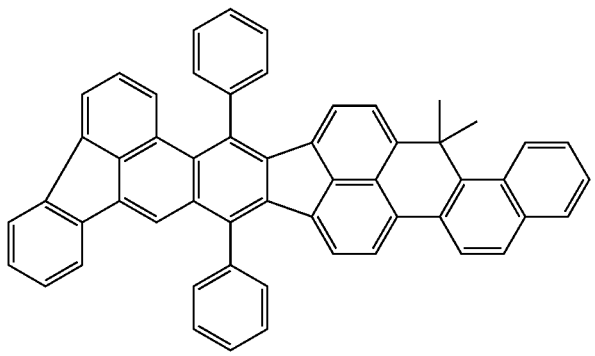
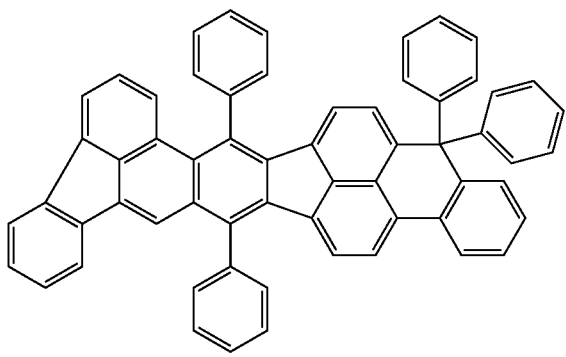

[Formula 40]
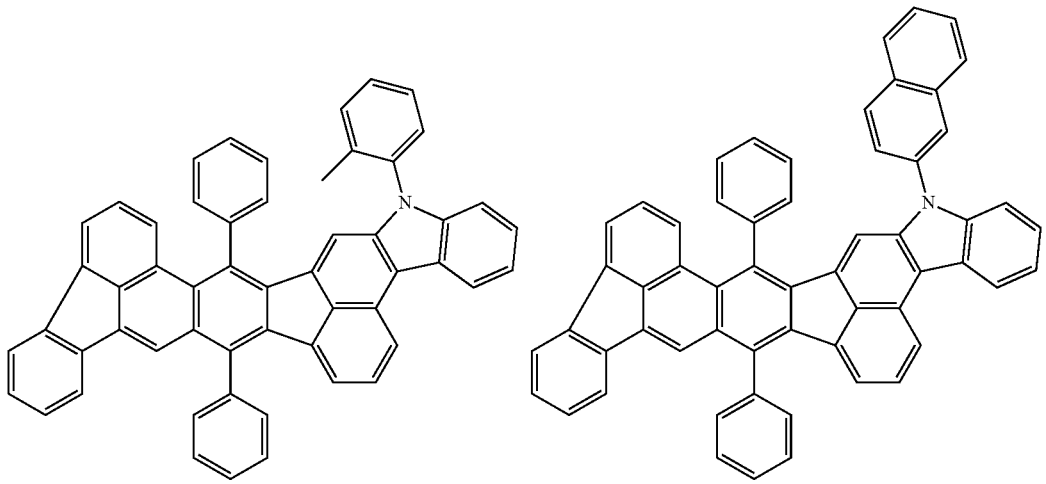
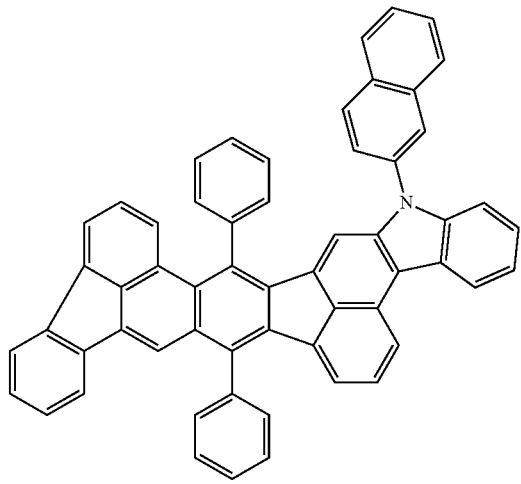
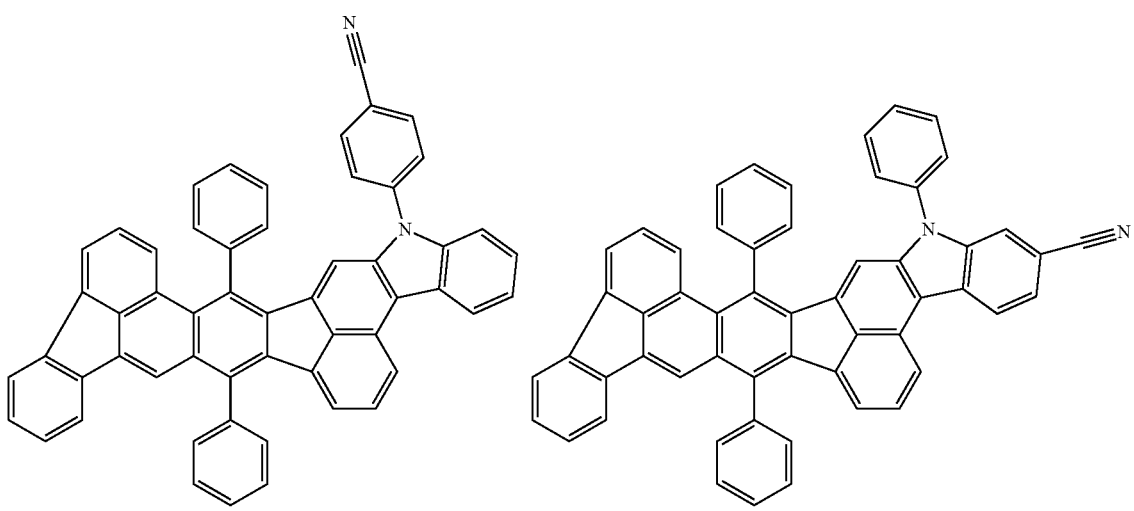
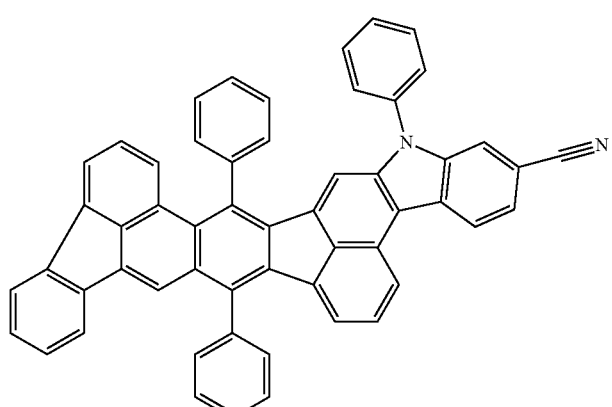
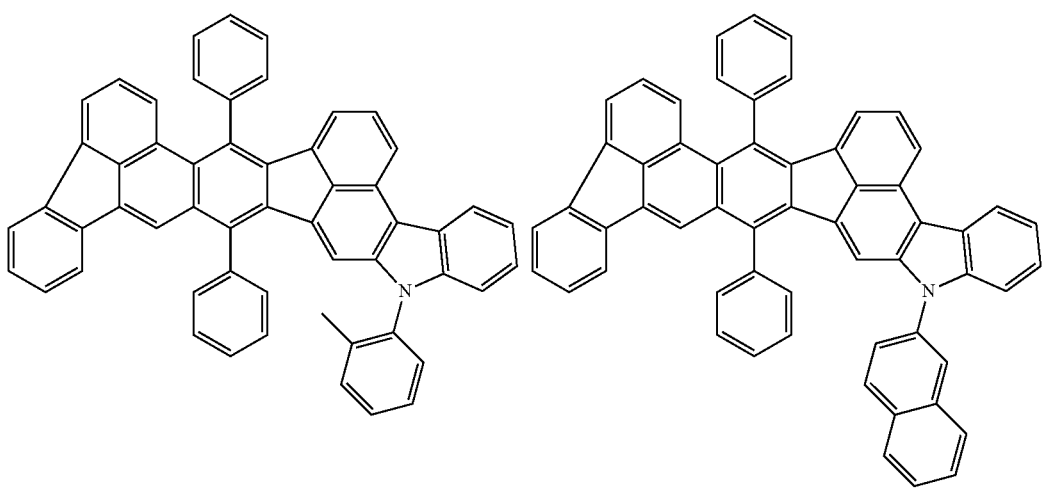
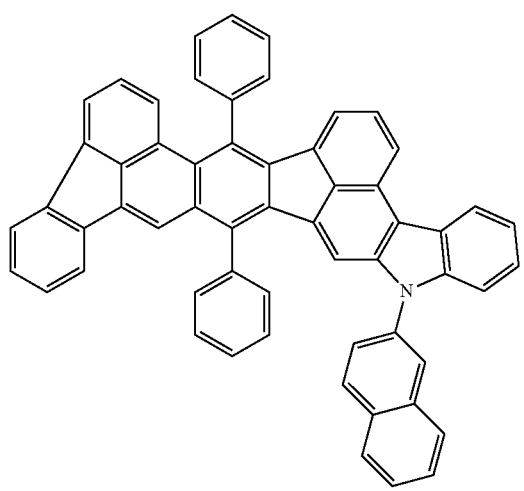

61
62
-continued
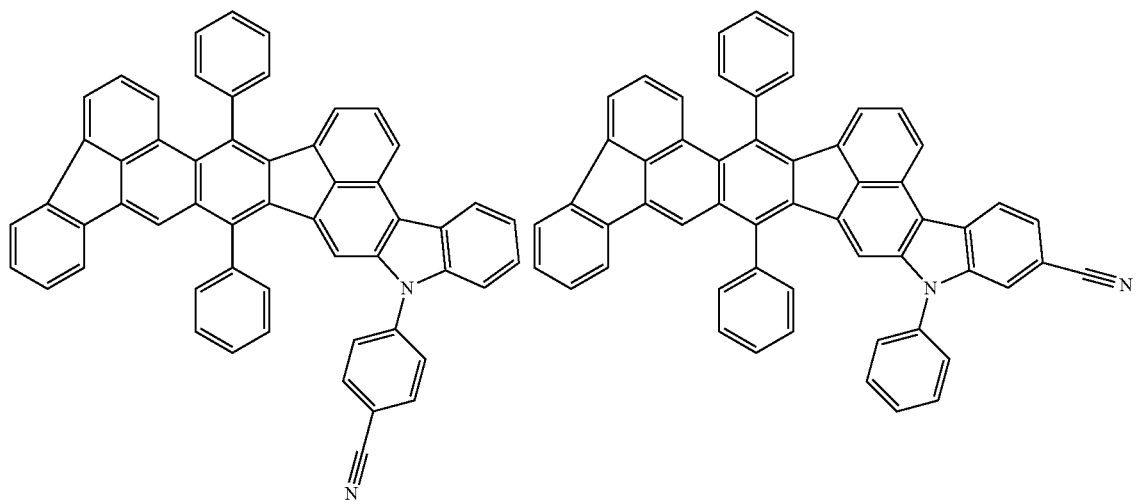
[Formula 41]
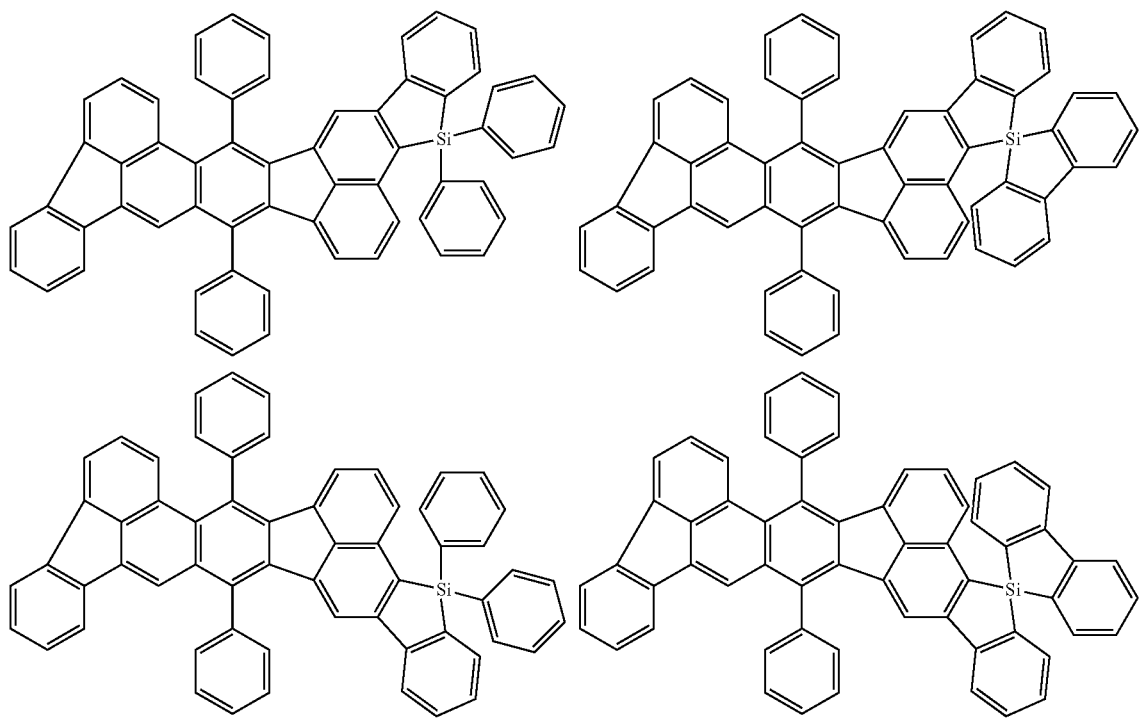
[Formula 42]
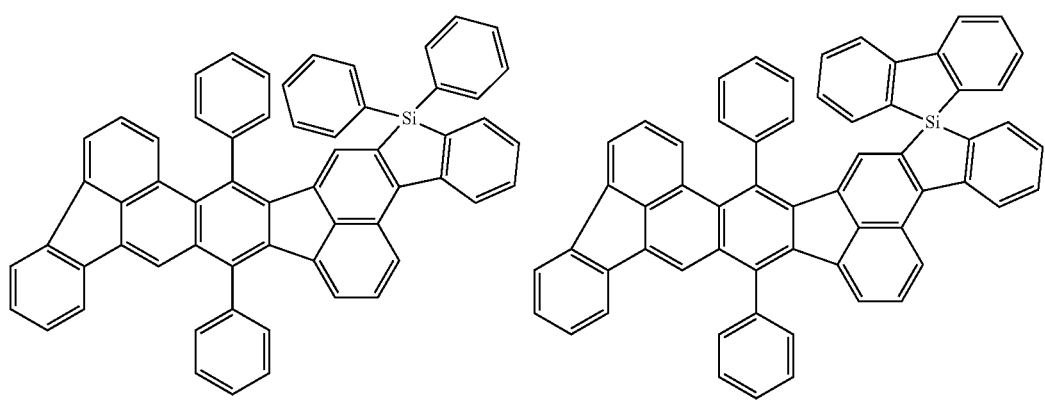

-continued

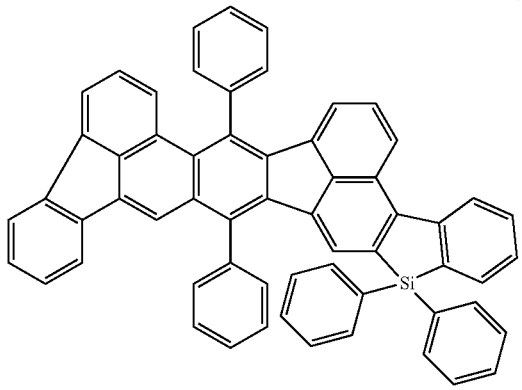
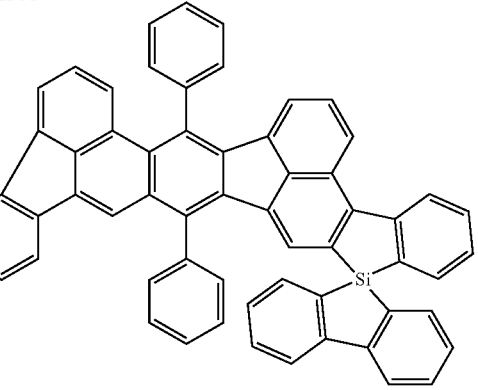

Composition

A composition of the exemplary embodiment contains a plurality of compounds each represented by the formula (2) below.

[Formula 43]

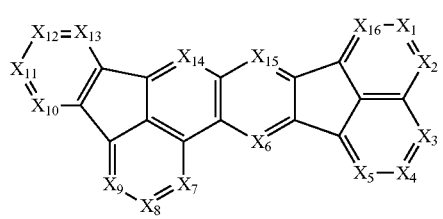

(2)

in the formula (2): $X_1$ to $X_5$, $X_7$ to $X_{13}$, and $X_{16}$ each independently represent $CR_x$ or a carbon atom to be bonded to the structure represented by the formula (2a) or (2b) below.

$X_6$, $X_{14}$, and $X_{15}$ each independently represent CRx.

$R_x$ each independently represents a hydrogen atom or a substituent.

$R_x$ as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of $R_x$ are mutually the same or different.

When a plurality of ones of $X_1$ to $X_{16}$ are $CR_x$ and $R_x$ is a substituent, a plurality of $R_x$ as the substituents are bonded to each other to form a ring or are not bonded.

At least one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ are carbon atoms to be bonded to the structure represented by the formula (2a) or (2b) below.

[Formula 44]

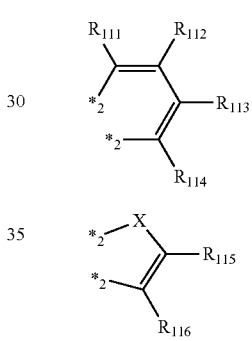

(2a)

(2b)

In the formula (2a), *2 represent bonding positions to carbon atoms at one pair of the pair of $X_1$ and $X_2$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2).

$R_{111}$ to $R_{114}$ each independently represent a hydrogen atom or a substituent.

$R_{111}$ to $R_{114}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

At least one pair of the pair of $R_{111}$ and $R_{112}$, the pair of $R_{112}$ and $R_{113}$, and the pair of $R_{113}$ and $R_{114}$ are substituents. The substituents are bonded to each other to form a ring.

In the formula (2b), *2 represent bonding positions to carbon atoms at one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_1$ and $X_{11}$, the pair of $X_{11}$ and $X_{12}$, the pair of $X_{12}$ and $X_{13}$, and the pair of $X_{16}$ and $X_1$ in the formula (2).

$R_{115}$ and $R_{116}$ each independently represent a hydrogen atom or a substituent.

$R_{115}$ and $R_{116}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{115}$ and $R_{116}$ as the substituents are bonded to each other to further form a ring, or are not bonded to each other.

X is selected from the group consisting of an oxygen atom, a sulfur atom, $CR_{117}R_{118}$, $SiR_{119}R_{120}$ and $NR_{121}$.

$R_{117}$ to $R_{121}$ each independently represent a hydrogen atom or a substituent.

$R_{117}$ to $R_{121}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

$R_{117}$ and $R_{118}$ as the substituents are bonded to each other to further form a ring, or are not bonded to each other.

$R_{119}$ and $R_{120}$ as the substituents are bonded to each other to further form a ring, or are not bonded to each other.

In the exemplary embodiment, $R_x$ in the formula (2) is each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, $R_{111}$ to $R_{114}$ in the formula (2a) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, $R_{115}$ to $R_{121}$ in the formula (2b) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the formula (2) representing the composition of the exemplary embodiment, at least one pair of the pair of $X_1$ and $X_2$ and the pair of $X_3$ and $X_4$ are preferably carbon atoms to be bonded to the structure represented by the formula (2a).

In the composition of the exemplary embodiment, the structure represented by the formula (2a) is preferably the structure represented by the formula (2a-1) below.

[Formula 45]

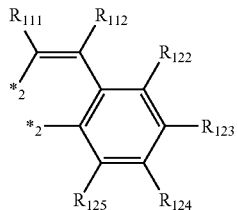

(2a-1)

In the formula (2a-1), *2 represents the same as *2 of the formula (2a).

$R_{111}$, $R_{112}$ and $R_{122}$ to $R_{125}$ each independently represent a hydrogen atom or a substituent.

$R_{111}$, $R_{112}$ and $R_{122}$ to $R_{125}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{111}$, $R_{112}$ and $R_{122}$ to $R_{125}$ as the substituents are bonded to each other to further form a ring, or are not bonded to each other.

In the exemplary embodiment, $R_{111}$, $R_{112}$ and $R_{122}$ to $R_{125}$ in the formula (2a-1) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

The composition of the exemplary embodiment preferably contains the compound represented by the formula (21A) below and the compound represented by the formula (21B) below as the compounds each represented by the formula (2).

[Formula 46]

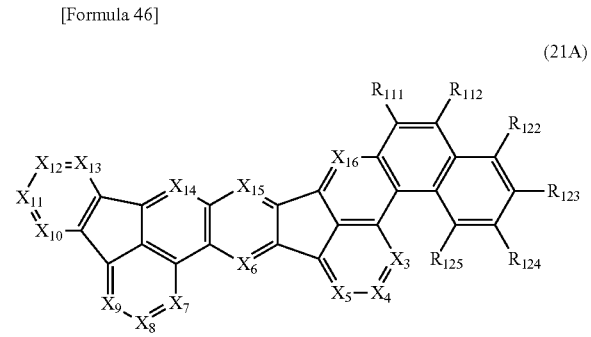

(21A)

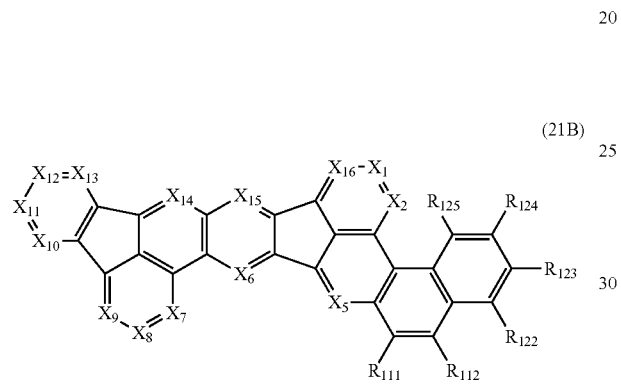

(21B)

[Formula 47]

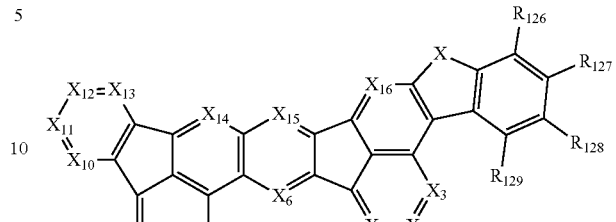

(25A)

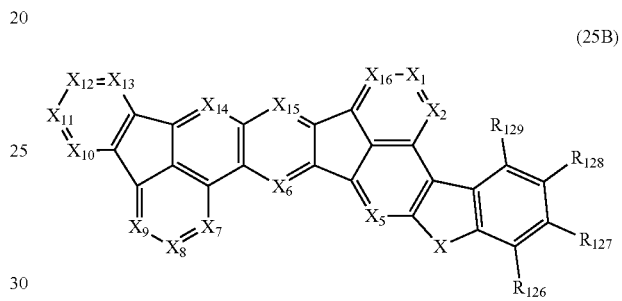

(25B)

In the formula (21A), $X_3$ to $X_{16}$ and $R_x$ respectively represent the same as $X_3$ to $X_{16}$ and $R_x$ of the formula (2).

In the formula (21B), $X_1$, $X_2$, $X_5$ to $X_{16}$ and $R_x$ respectively represent the same as $X_1$, $X_2$, $X_5$ to $X_{16}$ and $R_x$ of the formula (2).

In the formulae (21A) and (21B), $R_{111}$, $R_{112}$ and $R_{122}$ to $R_{125}$ respectively represent the same as $R_{111}$, $R_{112}$ and $R_{122}$ to $R_{125}$ of the formula (2a-1).

In the exemplary embodiment, when adjacent ones of the substituents of $R_{111}$, $R_{112}$ and $R_{122}$ to $R_{125}$ in the formula (21A) are bonded to each other to further form a ring, a pair of $R_{111}$ and $R_{112}$ or a pair of $R_{122}$ and $R_{123}$ are preferably bonded to each other to further form a ring.

In the exemplary embodiment, when adjacent ones of the substituents of $R_{111}$, $R_{112}$ and $R_{122}$ to $R_{125}$ in the formula (21B) are bonded to each other to further form a ring, a pair of $R_{111}$ and $R_{112}$ or a pair of $R_{122}$ and $R_{123}$ are preferably bonded to each other to further form a ring.

In the formula (2) representing the composition of the exemplary embodiment, at least one pair of the pair of $X_1$ and $X_2$, the pair of $X_2$ and $X_3$ and the pair of $X_3$ and $X_4$ are also preferably carbon atoms to be bonded to the structure represented by the formula (2b).

The composition of the exemplary embodiment also preferably contains the compound represented by the formula (25A) below and the compound represented by the formula (25B) below as the compound represented by the formula (2).

In the formula (25A), $X_3$ to $X_{16}$ and $R_x$ respectively represent the same as $X_3$ to $X_{16}$ and $R_x$ of the formula (2).

In the formula (25B), $X_1$, $X_2$, $X_5$ to $X_{16}$ and $R_x$ respectively represent the same as $X_1$, $X_2$, $X_5$ to $X_{16}$ and $R_x$ of the formula (2).

In the formulae (25A) and (25B), X represents the same as X of the formula (2b).

$R_{126}$ to $R_{129}$ each independently represent a hydrogen atom or a substituent.

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{126}$ to $R_{129}$ as the substituents are bonded to each other to further form a ring, or are not bonded to each other.

In the exemplary embodiment, $R_{126}$ to $R_{129}$ in the formula (25A) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, $R_{126}$ to $R_{129}$ in the formula (25B) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

The composition of the exemplary embodiment also preferably contains the compound represented by the formula (26A) below and the compound represented by the formula (26B) below as the compound represented by the formula (2).

[Formula 48]

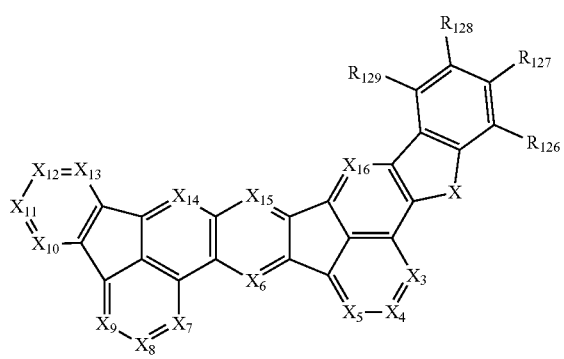

(26A)

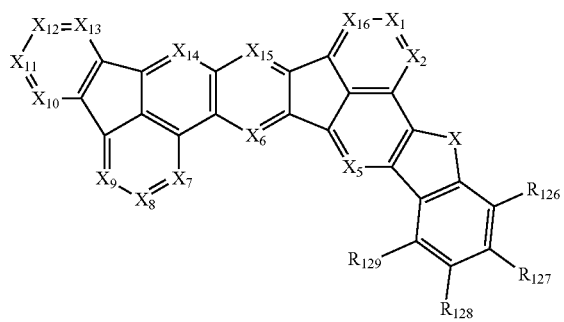

(26B)

In the formula (26A), $X_3$ to $X_{16}$ and $R_x$ respectively represent the same as $X_3$ to $X_{16}$ and $R_x$ of the formula (2).

In the formula (26B), $X_1$, $X_2$, $X_5$ to $X_{16}$ and $R_x$ respectively represent the same as $X_1$, $X_2$, $X_5$ to $X_{16}$ and $R_x$ of the formula (2).

In the formulae (26A) and (26B), X represents the same as X of the formula (2b).

$R_{126}$ to $R_{129}$ each independently represent a hydrogen atom or a substituent.

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

Adjacent ones of $R_{126}$ to $R_{129}$ as the substituents are bonded to each other to further form a ring, or are not bonded to each other.

In the exemplary embodiment, $R_{126}$ to $R_{129}$ in the formula (26A) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

In the exemplary embodiment, $R_{126}$ to $R_{129}$ in the formula (26B) are each independently preferably a hydrogen atom, or a group selected from the group consisting of an aryl group having 6 to 30 ring carbon atoms, a heteroaryl group having 5 to 30 ring atoms, an alkyl group having 1 to 30 carbon atoms (a linear or branched alkyl group), a halogen atom, and a cyano group.

A specific structure and a preferable form of the compound represented by the formula (2) contained in the composition of the exemplary embodiment are exemplified by the structures represented by the formulae of the compound for the composition in the exemplary embodiment, and the structures represented by the formulae and preferable forms of the compound in the description of the compound in the above exemplary embodiment.

Specific examples ([1] to [51]) of a combination of the compounds contained in the composition of the exemplary embodiment are shown below. It should be understood that examples of the composition of the exemplary embodiment are merely illustrative and are not intended to limit the scope of the invention.

[Formula 49]
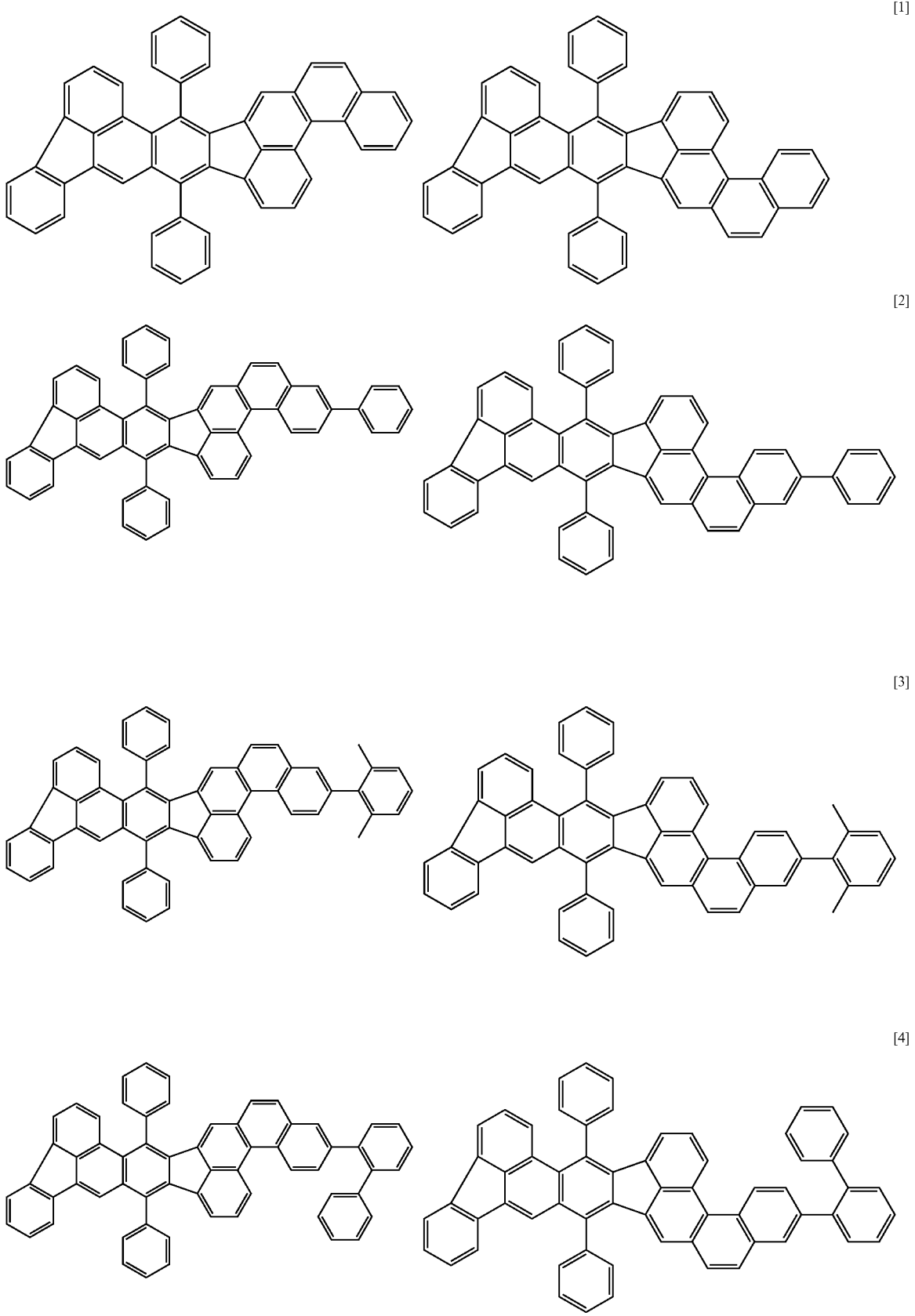

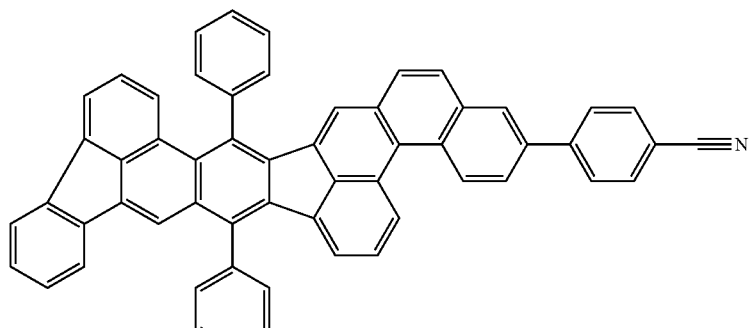
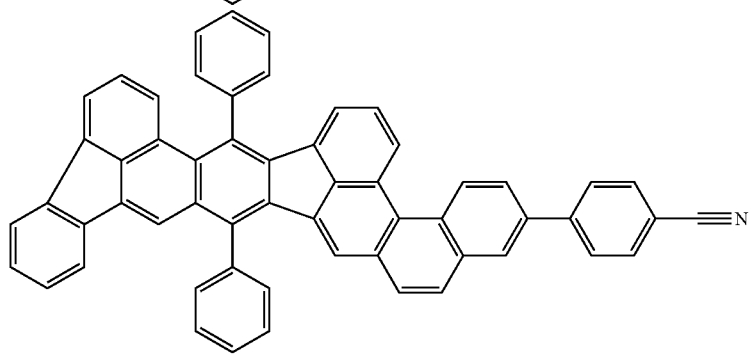
[5]
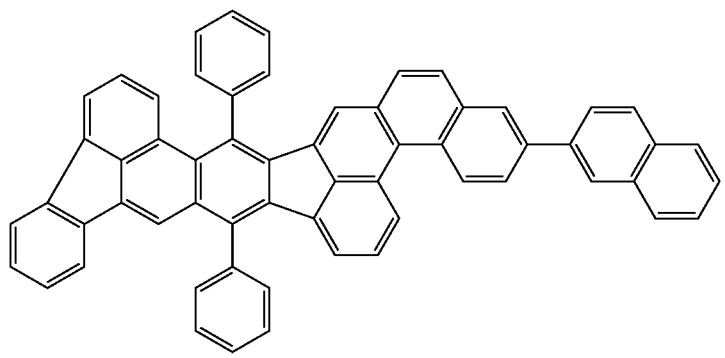
[6]
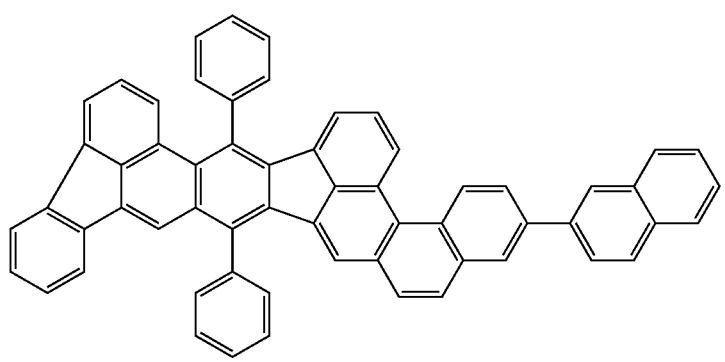

[Formula 50]
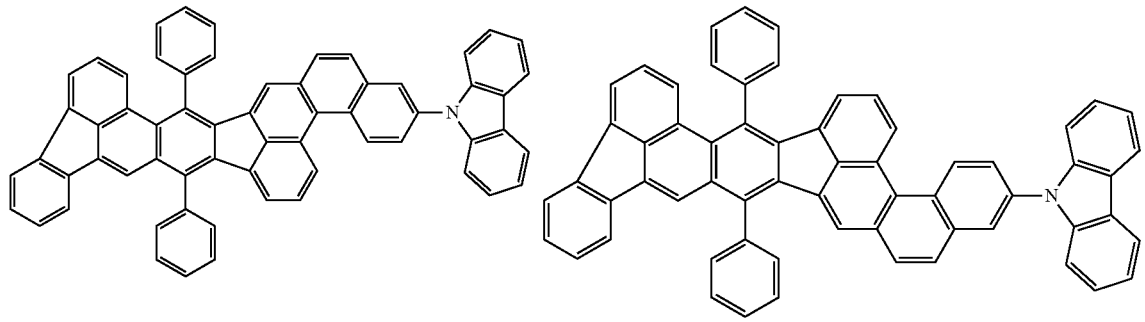
[7]
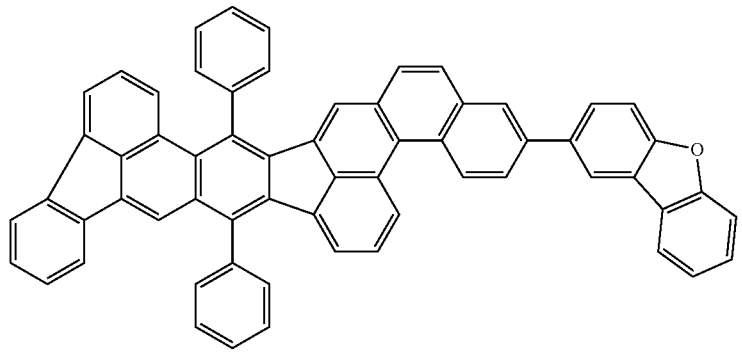
[8]
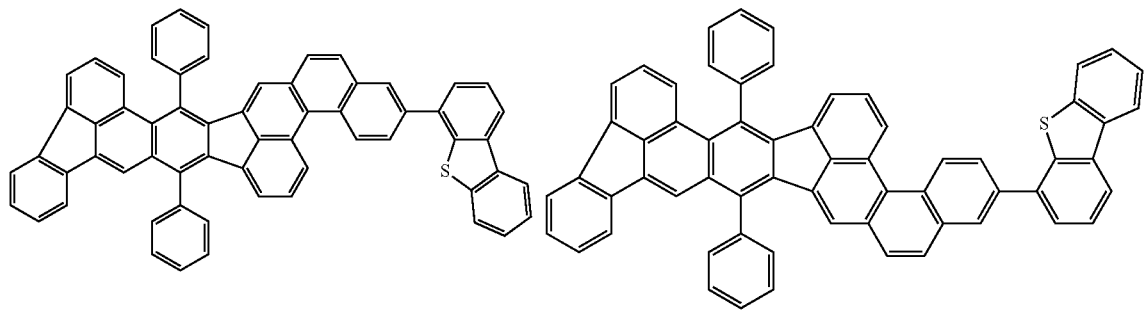
[9]

[10]
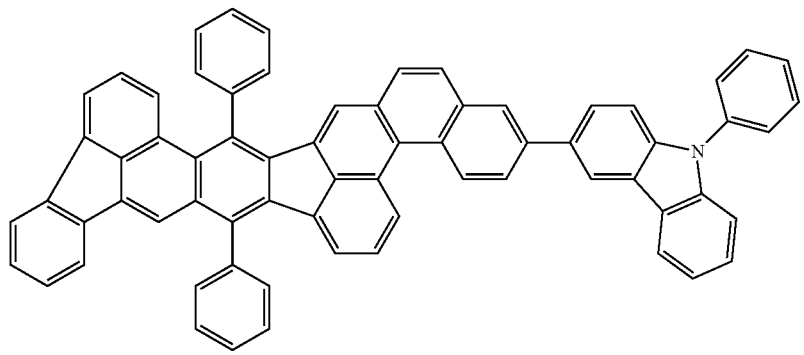
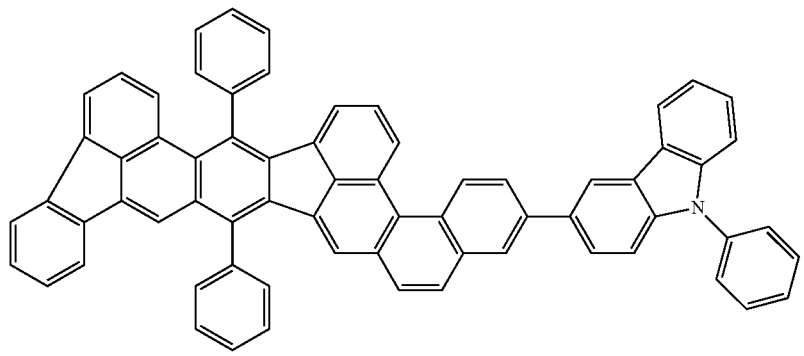
[11]
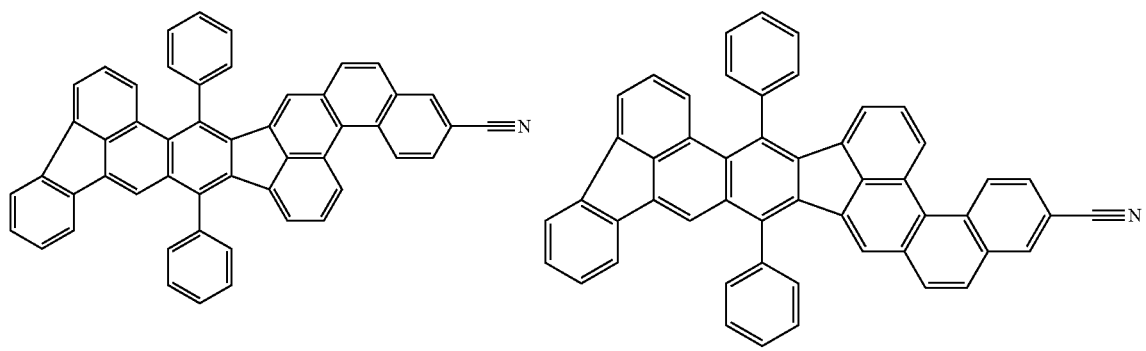
[12]
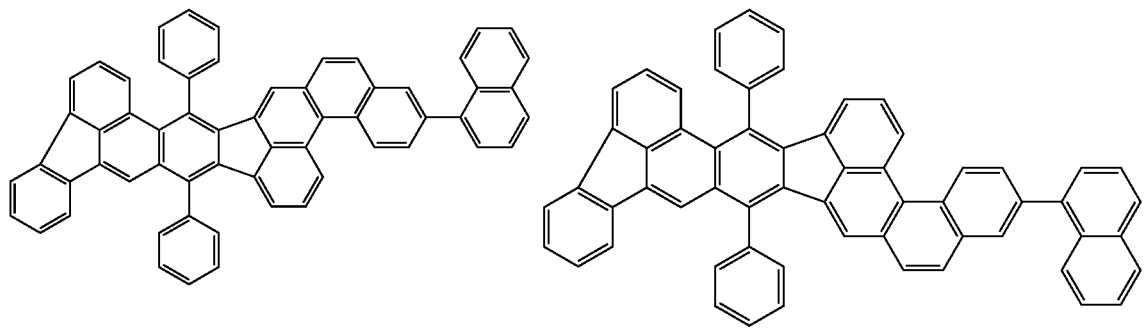

[Formula 51]
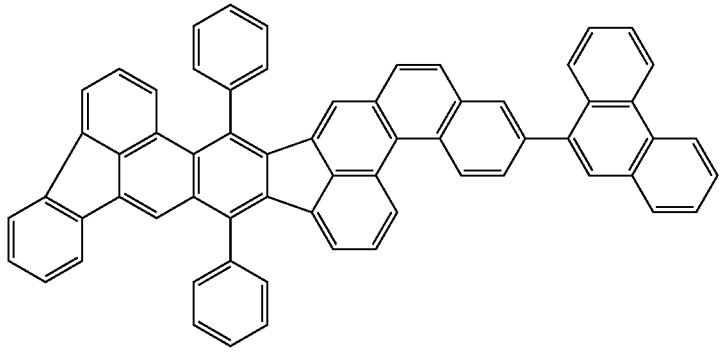
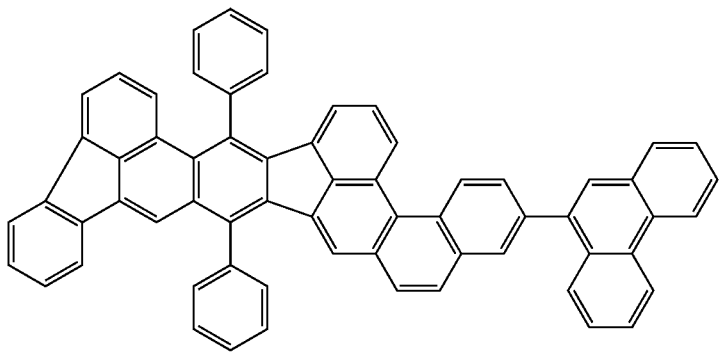
[13]
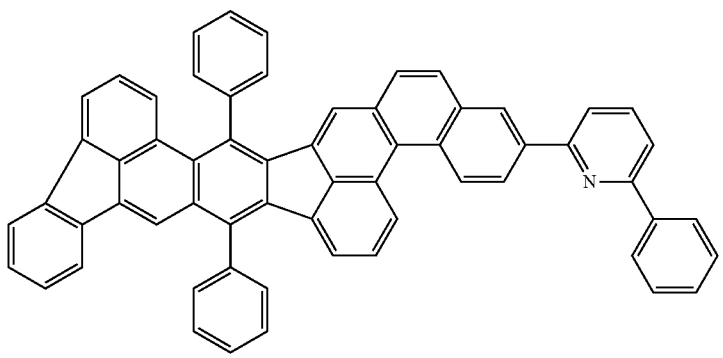
[14]
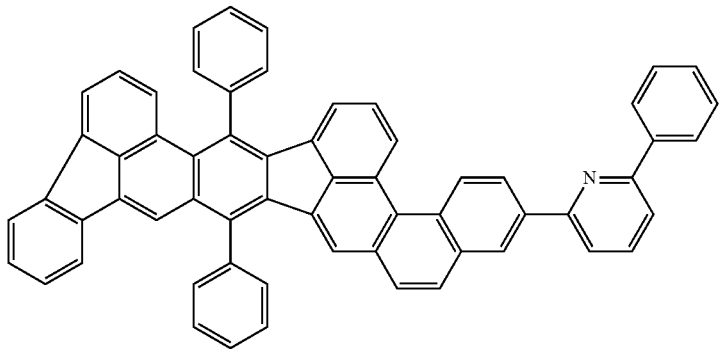

-continued
[15]
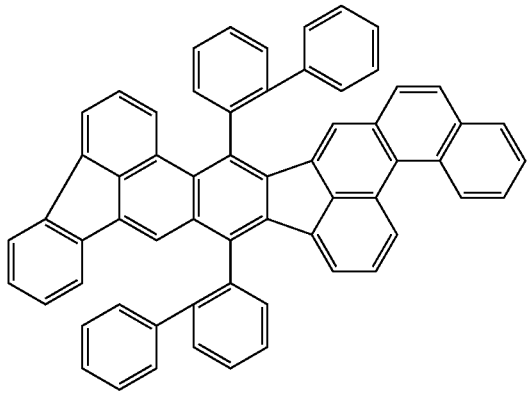
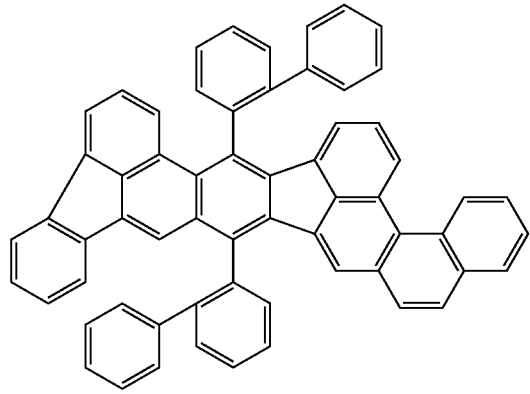
[16]
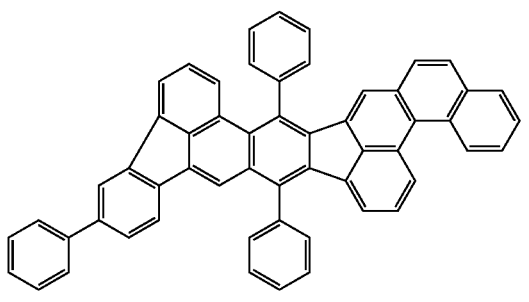
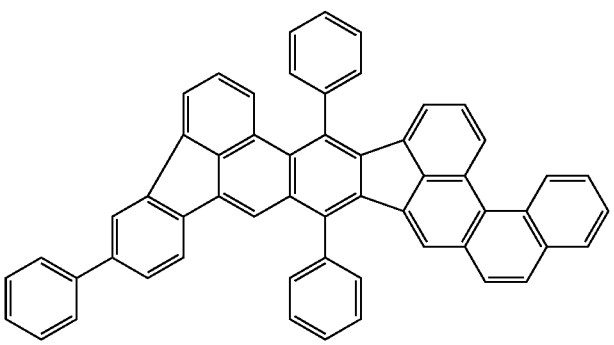
[17]
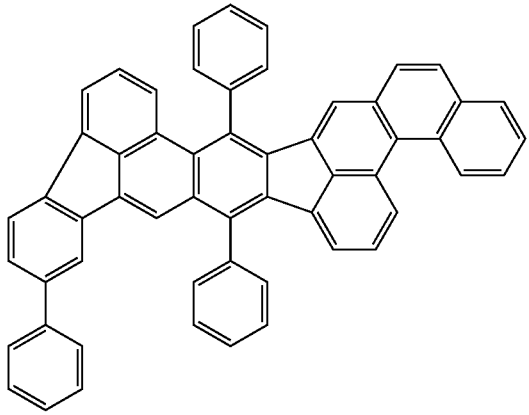
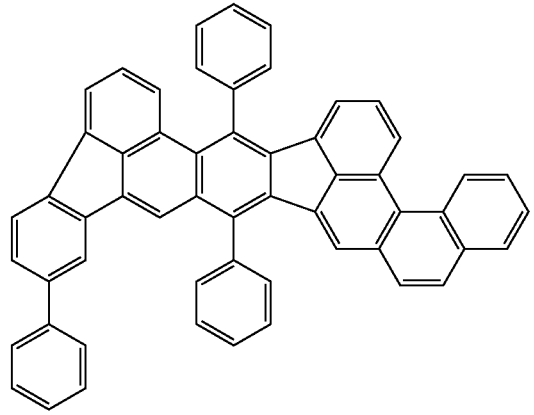
[18]
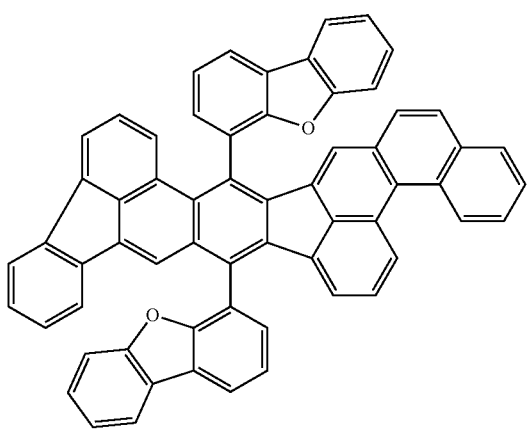
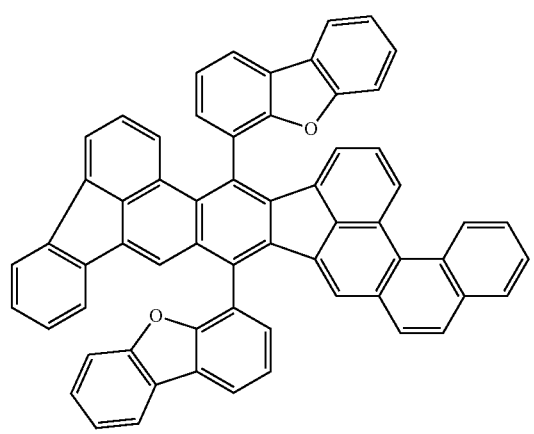

[Formula 52]
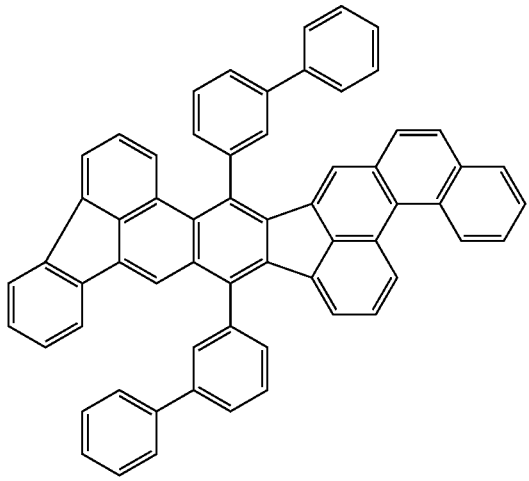
[19]
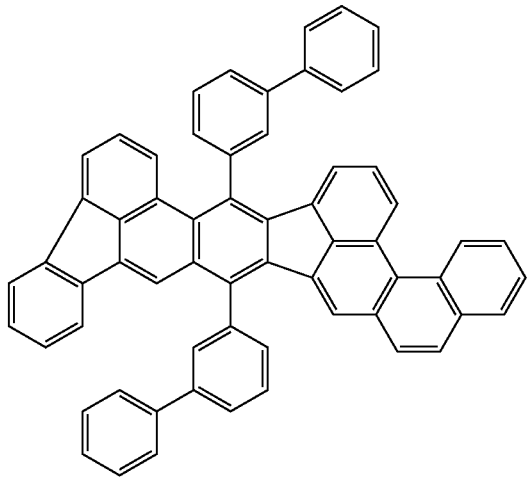
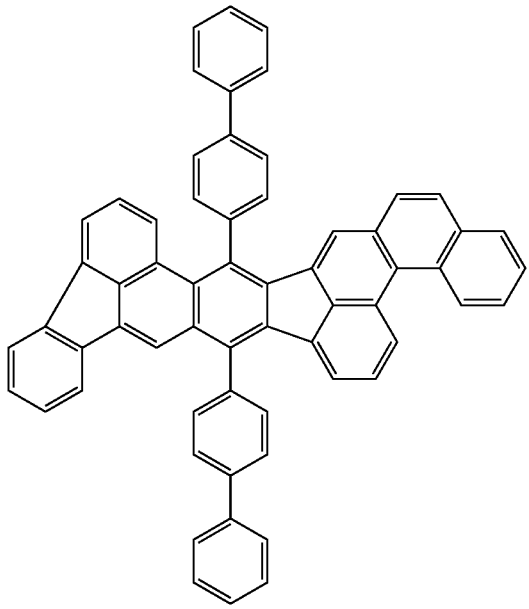
[20]
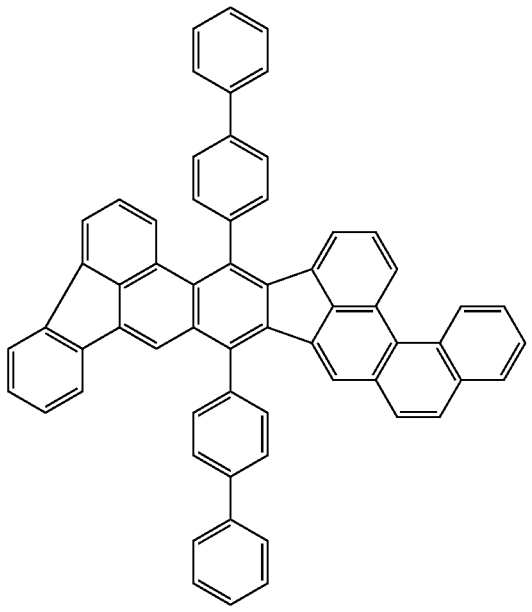
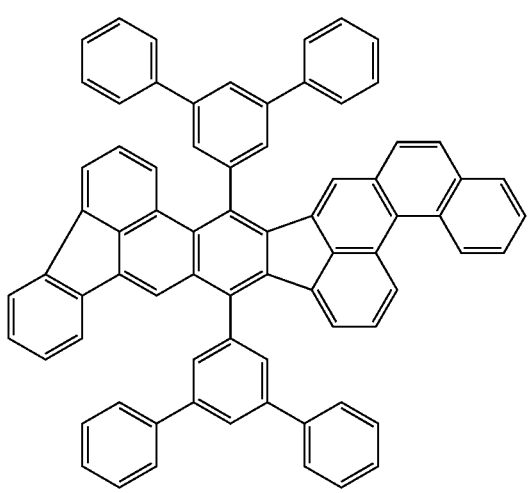
[21]
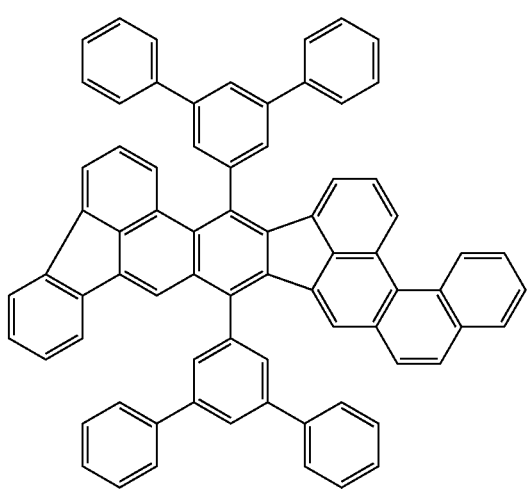

[22]
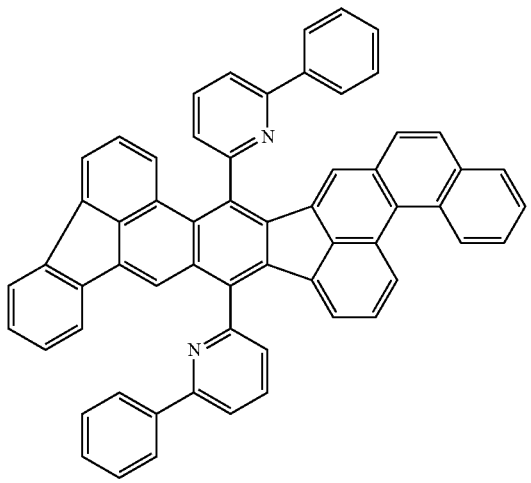
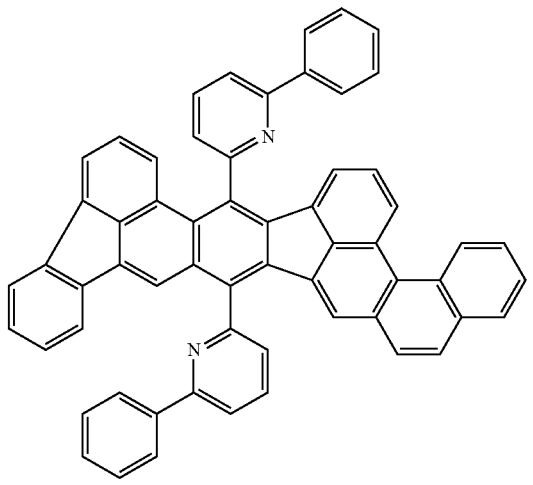
[23]
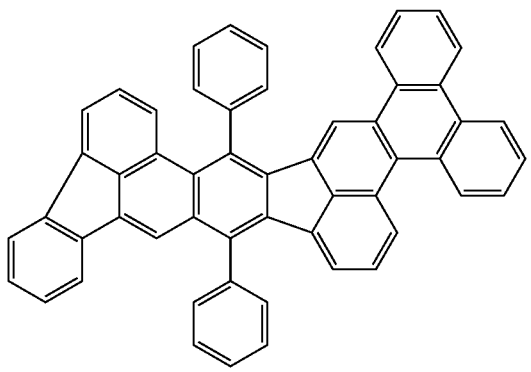
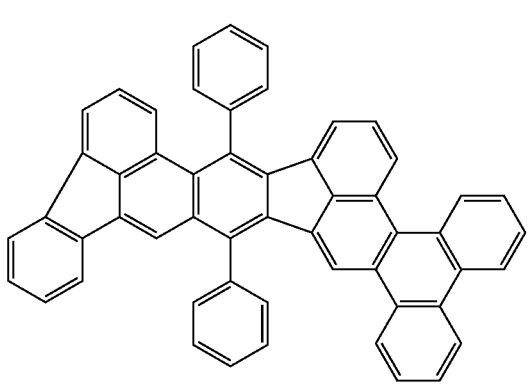
[24]
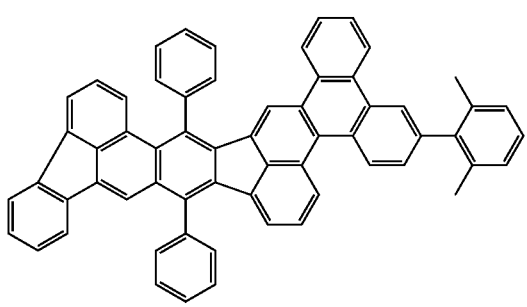
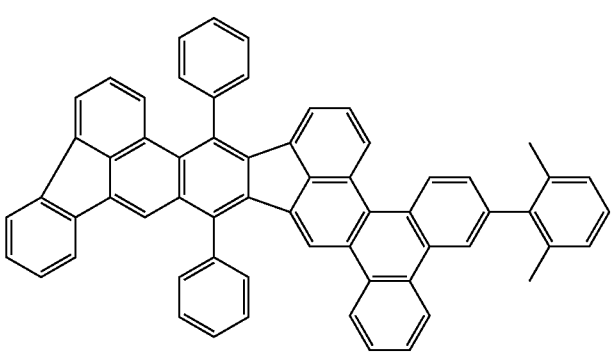
[Formula 53]
[25]
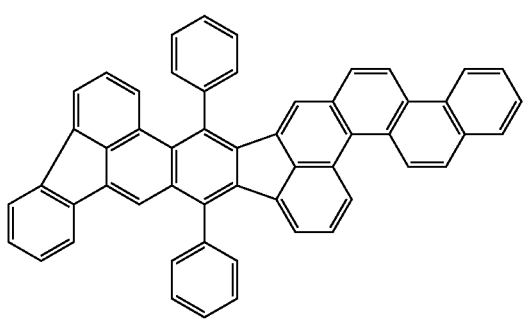
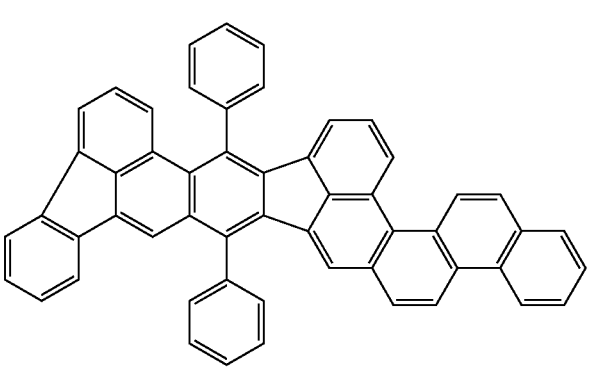

-continued
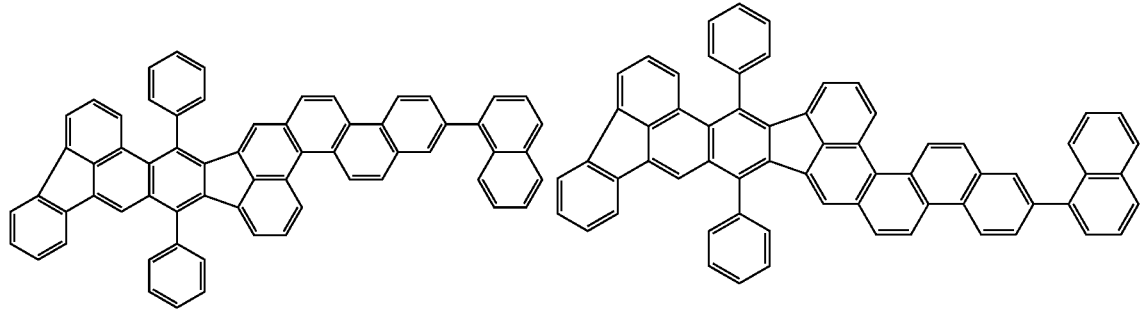
[26]
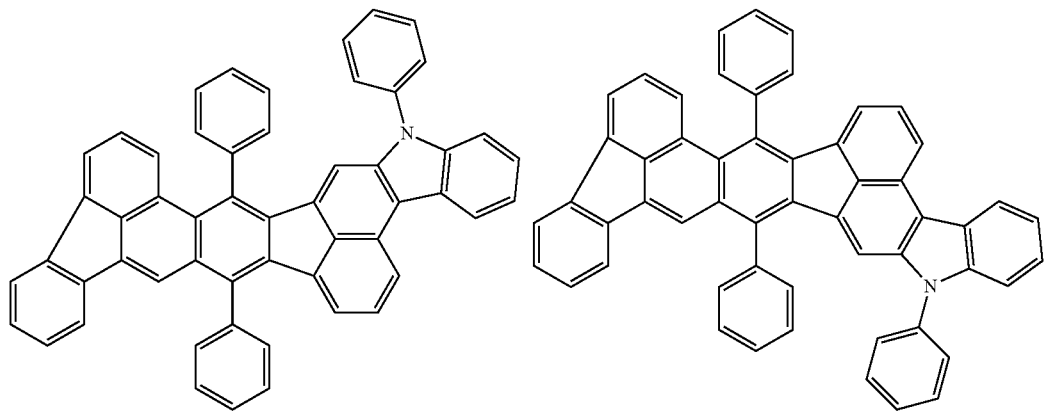
[27]
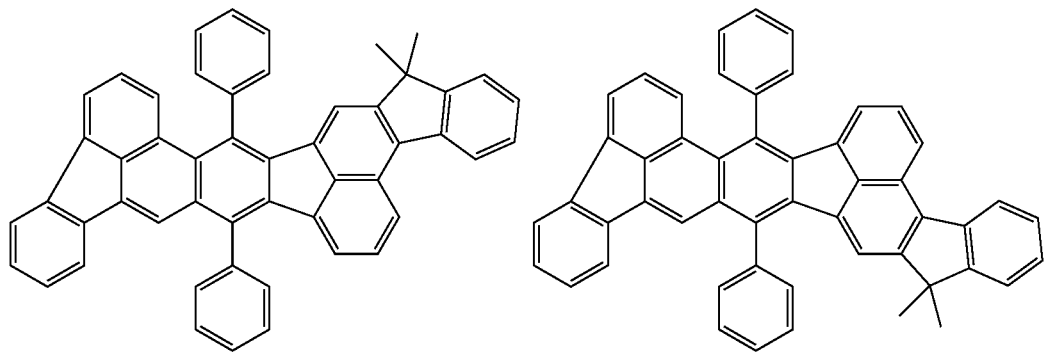
[28]
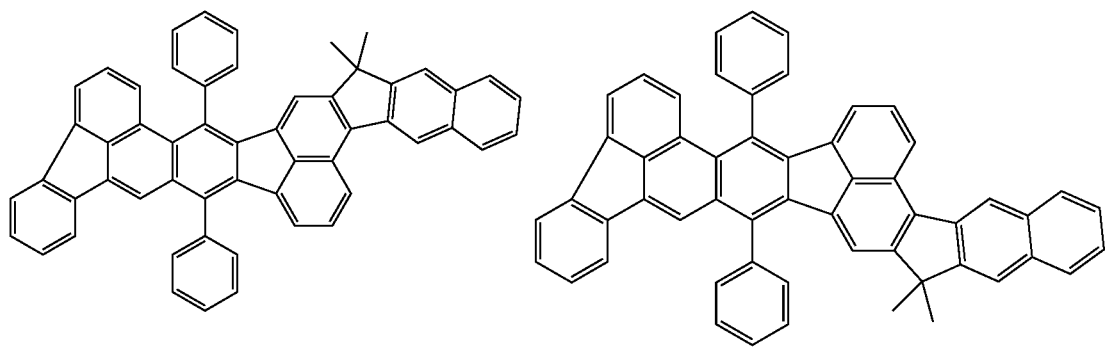
[29]

[30]
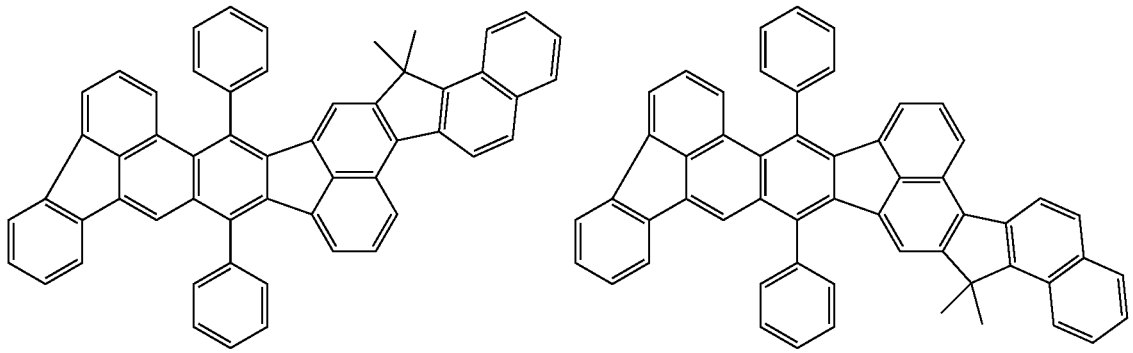
[Formula 54]
[31]
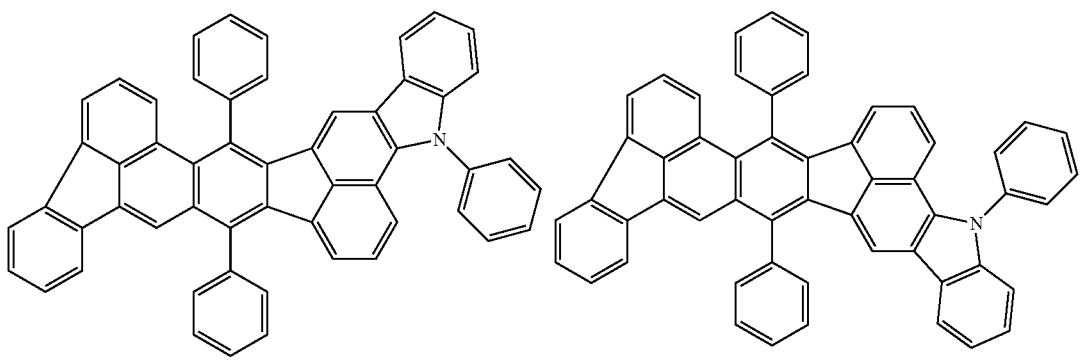
[32]
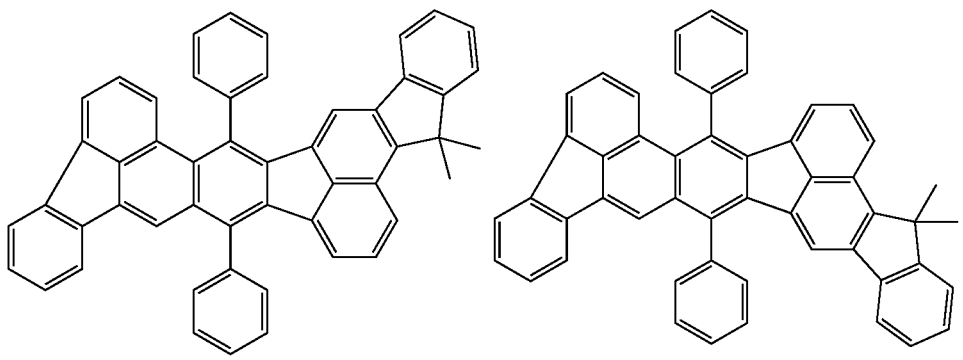
[33]
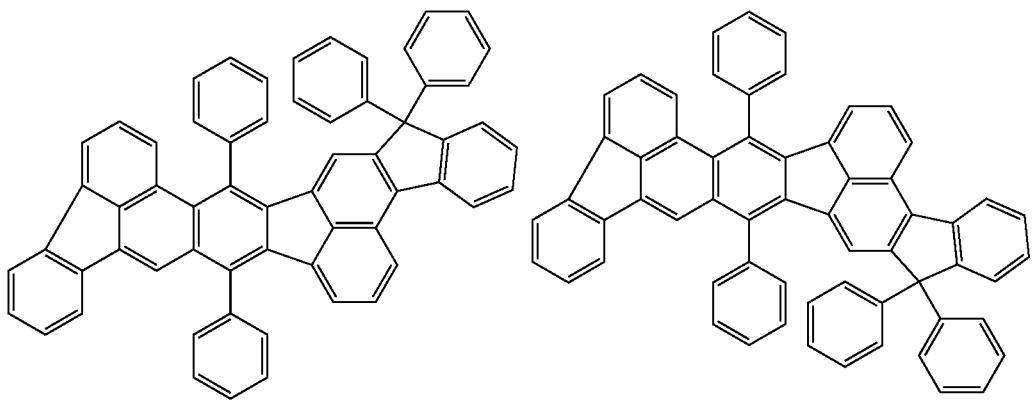

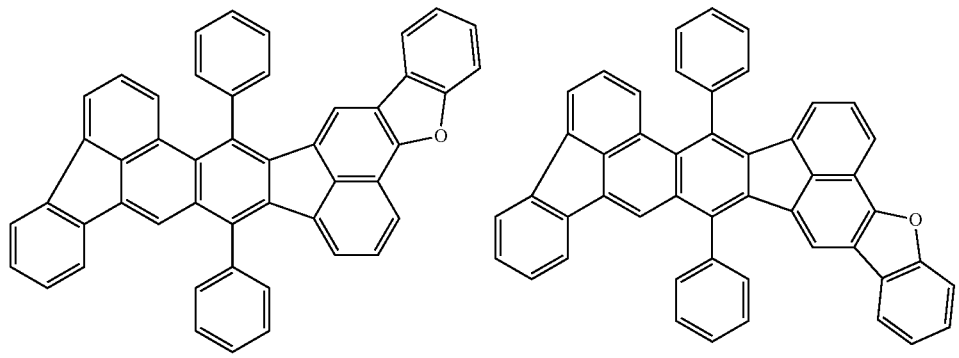
[34]
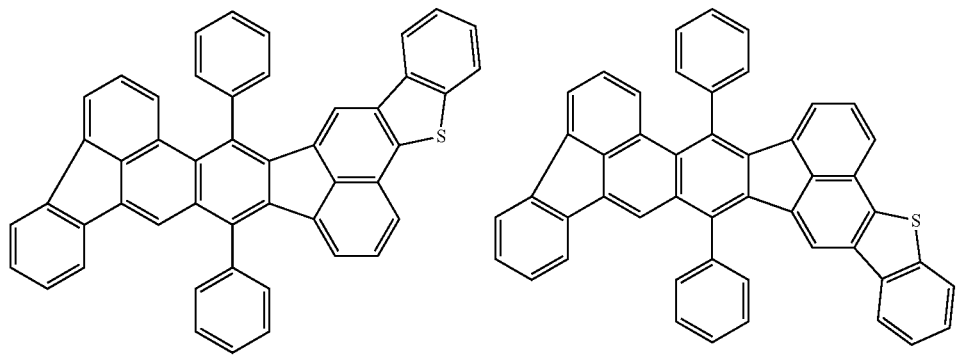
[35]
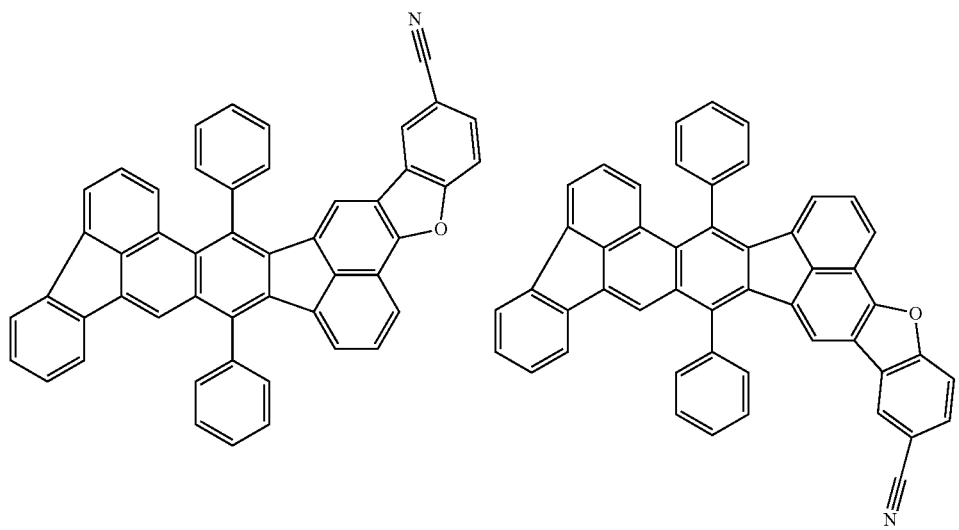
[36]

[Formula 55]
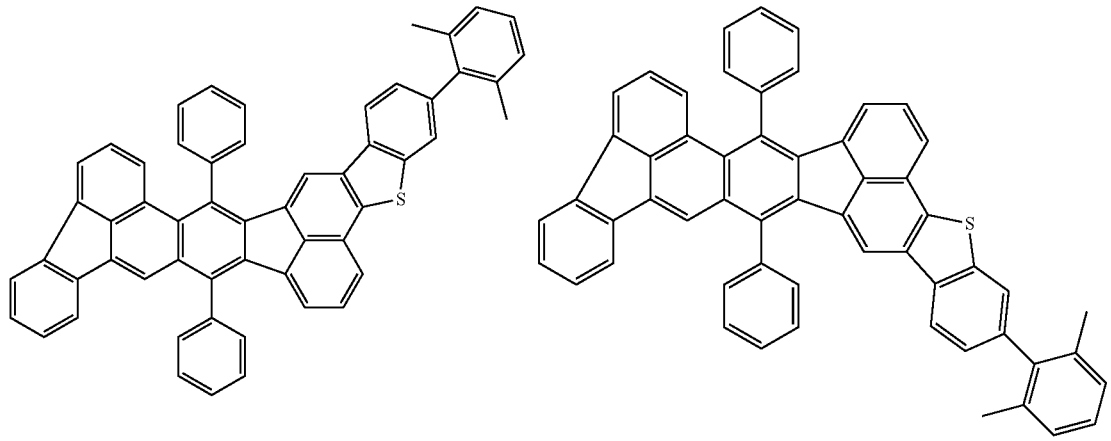
[37]
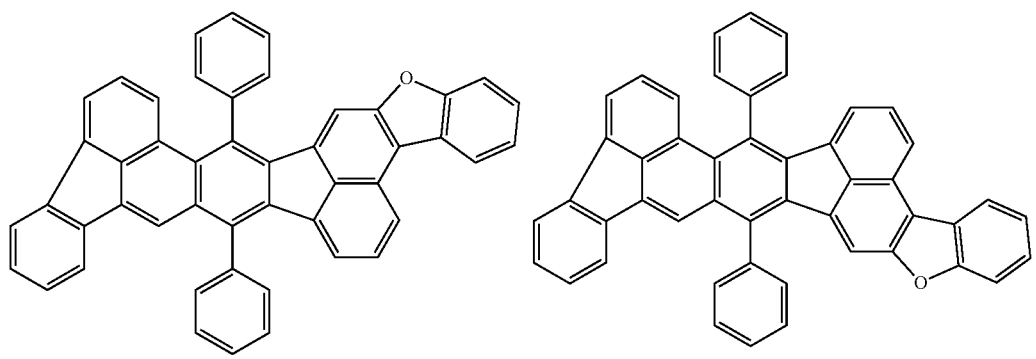
[38]
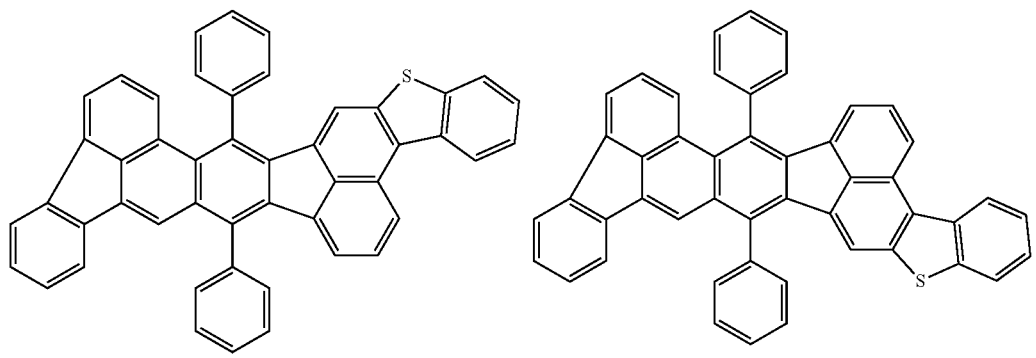
[39]
[Formula 56]
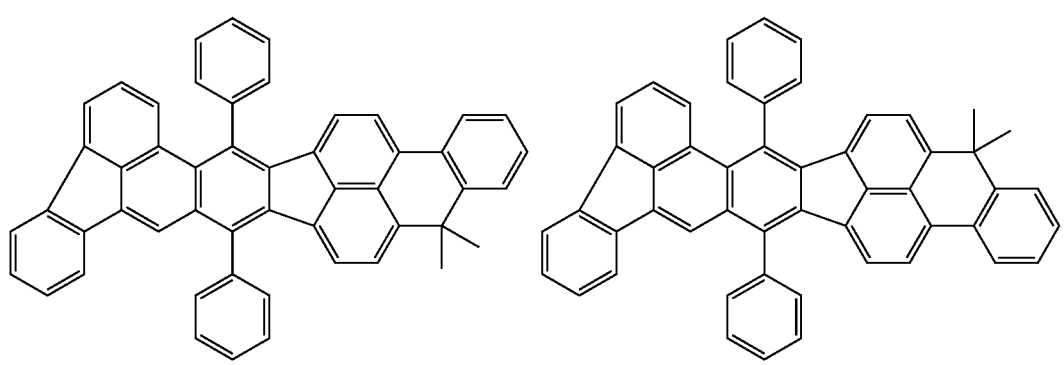
[40]

[41]
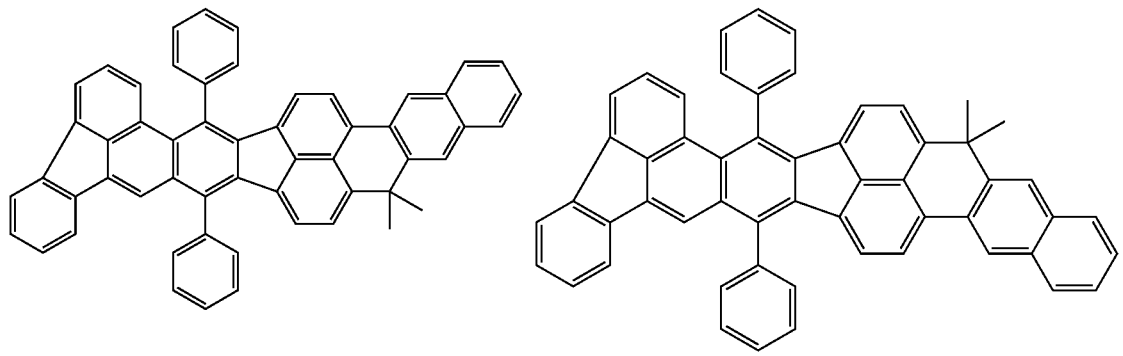
[42]
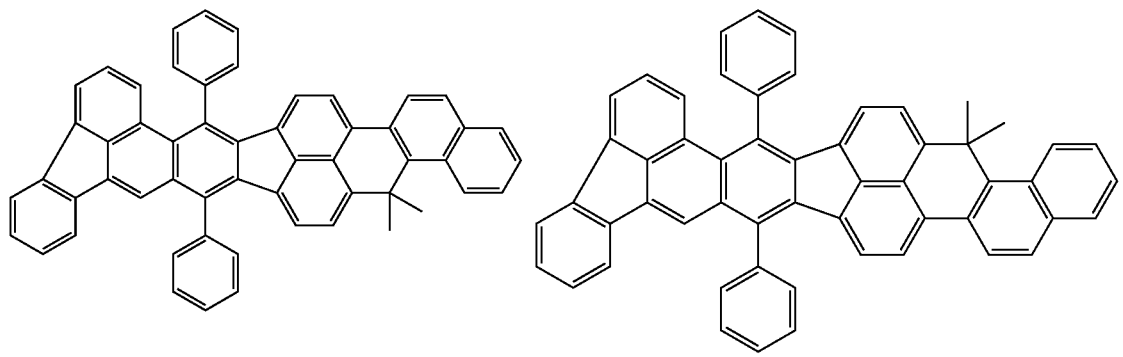
[43]
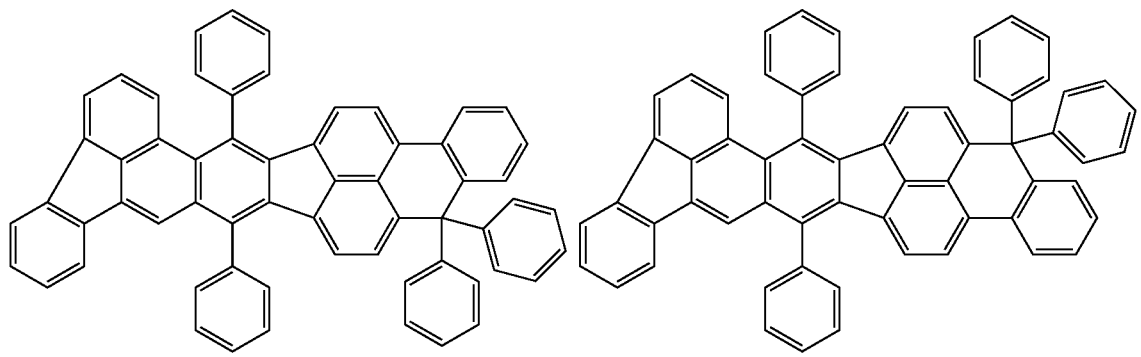
[44]
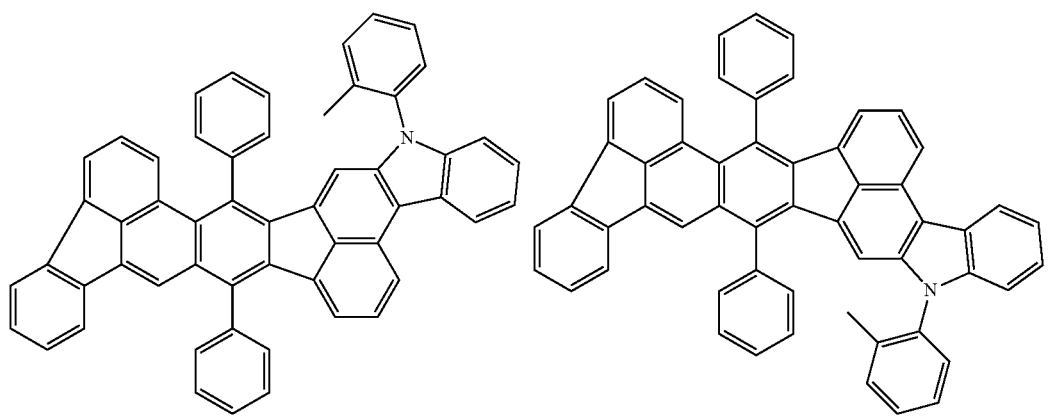

[45]
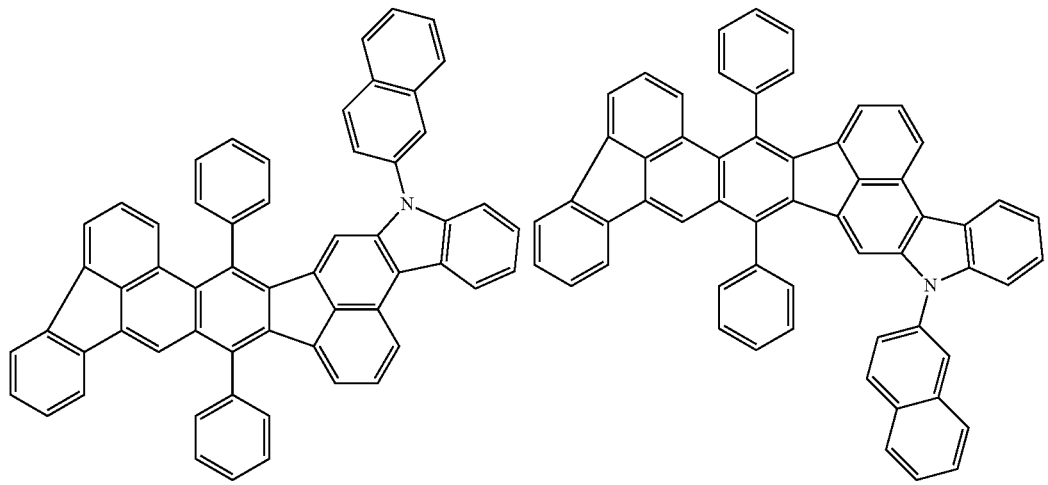
[Formula 57]
[46]
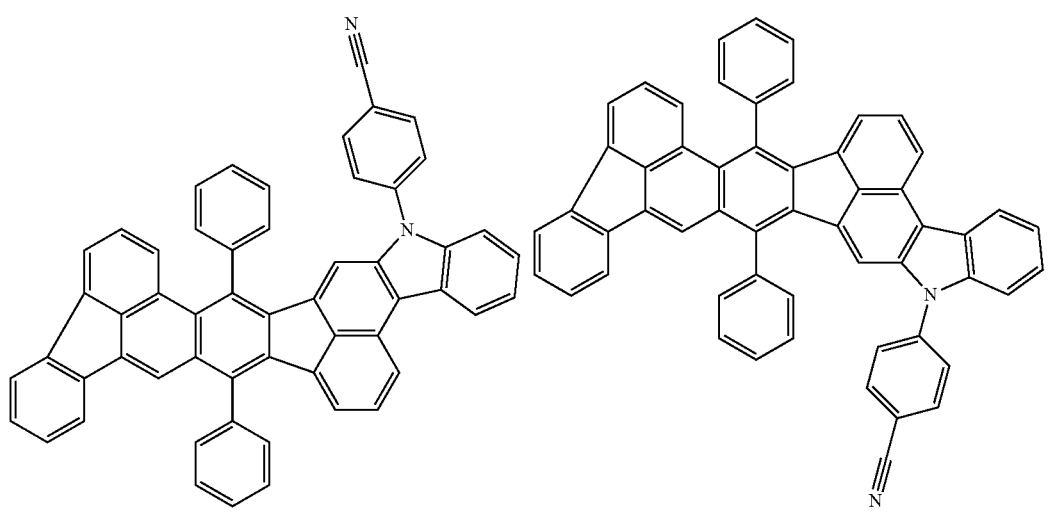
[47]
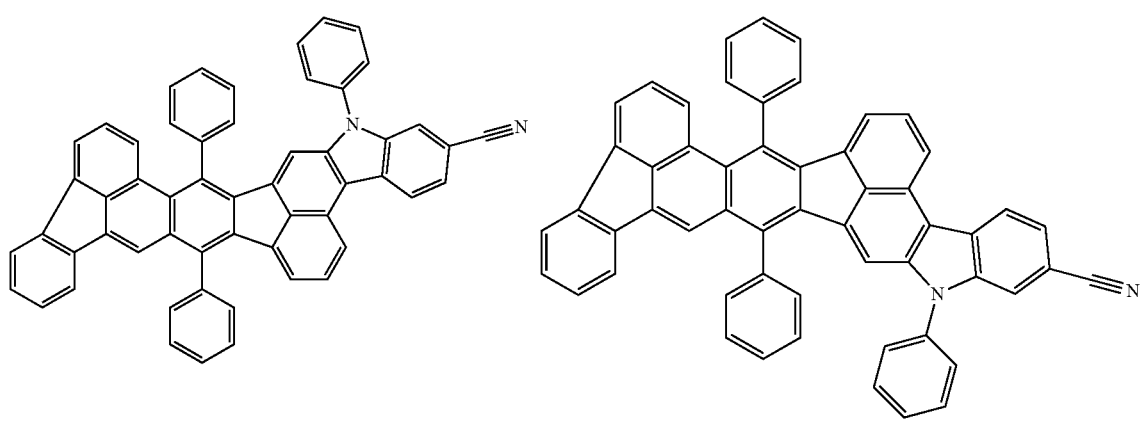

[48]
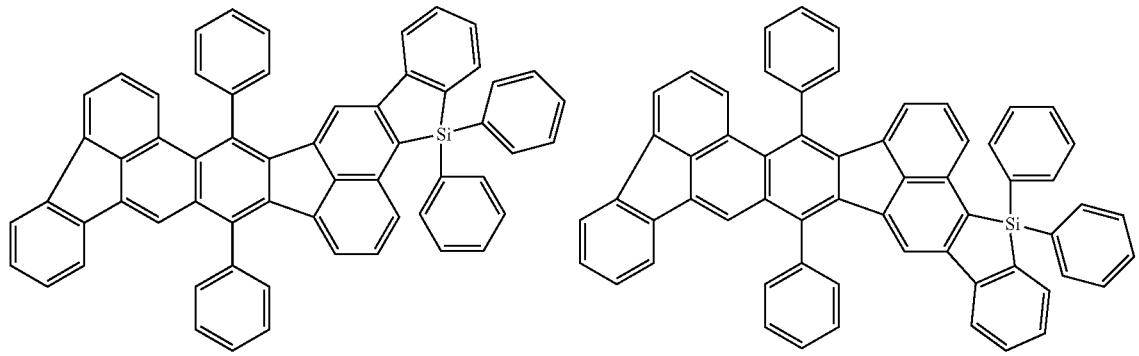
[49]
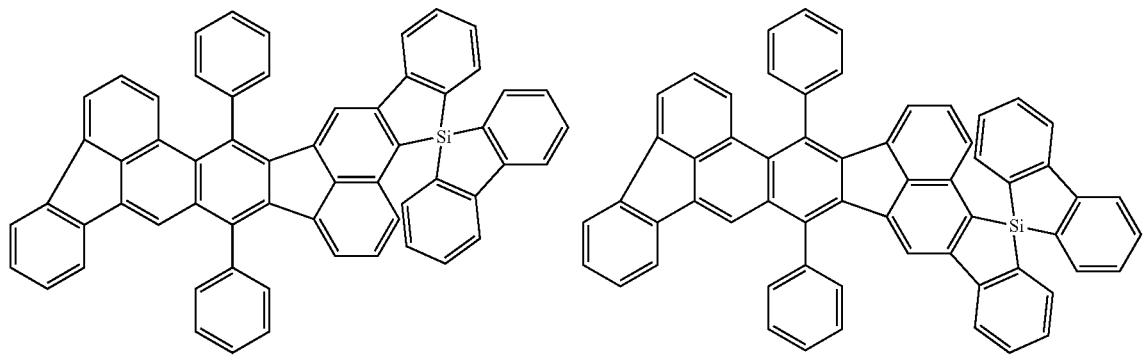
[50]
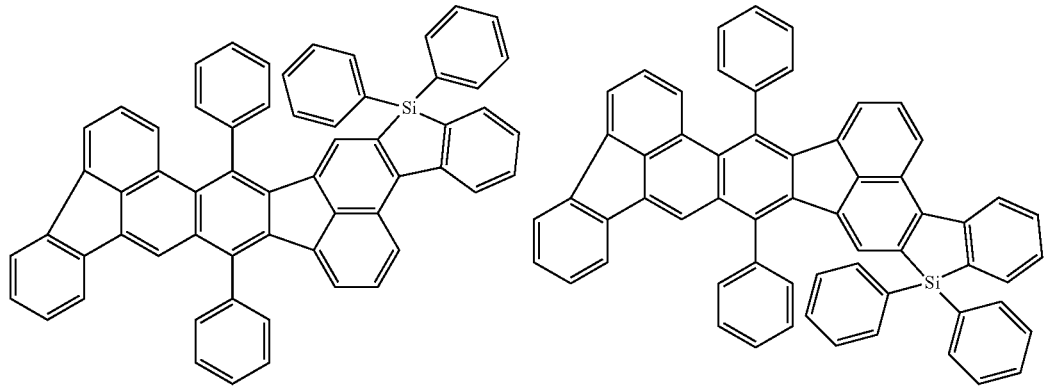
[51]
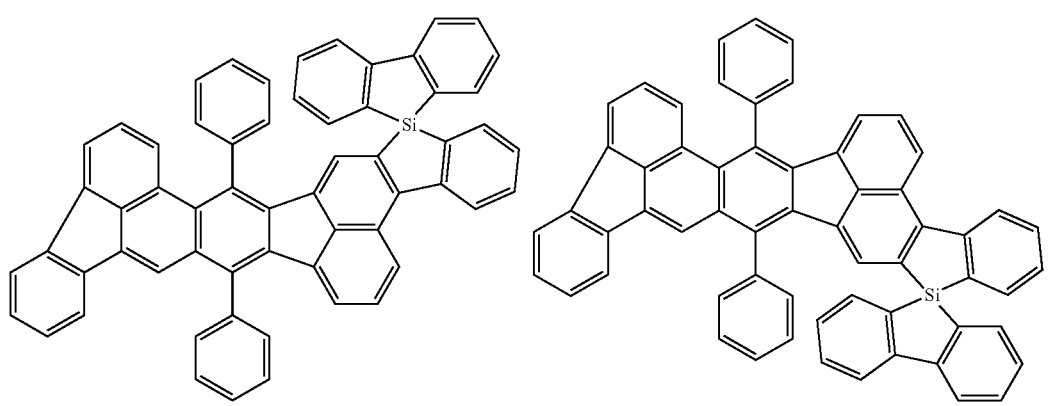

The composition of the exemplary embodiment can improve a luminous efficiency of the organic EL device.

Moreover, the composition of the exemplary embodiment can improve the luminous efficiency of the organic EL device particularly in the blue wavelength region.

Organic EL Device

Arrangement(s) of Organic EL Device

Arrangement(s) of an organic EL device according to an exemplary embodiment will be described below.

The organic EL device in the exemplary embodiment includes a pair of electrodes and an organic layer between the pair of electrodes. The organic layer includes at least one layer formed of an organic compound. Alternatively, the organic layer includes a plurality of layers each formed of an organic compound. The organic layer may further include an inorganic compound. In the organic EL device in the exemplary embodiment, at least one layer of the organic layer(s) is the emitting layer. Specifically, for instance, the organic layer may consist of a single emitting layer, or may include layers usable in a typical organic EL device. The layers usable in a typical organic EL device are not limited to particular ones, but, for instance, at least one layer selected from the group consisting of a hole injecting layer, a hole transporting layer, an electron injecting layer, an electron transporting layer and a blocking layer.

Typical device arrangements of the organic EL device include the following arrangements (a) to (f) and the like:

(a) anode/emitting layer/cathode;

(b) anode/hole injecting-transporting layer/emitting layer/cathode;

(c) anode/emitting layer/electron injecting-transporting layer/cathode;

(d) anode/hole injecting-transporting layer/emitting layer/electron injecting-transporting layer/cathode;

(e) anode/hole injecting-transporting layer/emitting layer/blocking layer/electron injecting-transporting layer/cathode; and (f) anode/hole injecting-transporting layer/blocking layer/emitting layer/blocking layer/electron injecting-transporting layer/cathode.

The arrangement (d) is preferably used among the above arrangements. However, the arrangement according to the invention is not limited to the above arrangements. The "emitting layer" refers to an organic layer having an emitting function. The term "hole injecting-transporting layer" means at least one of a hole injecting layer and a hole transporting layer. The term "electron injecting-transporting layer" means at least one of an electron injecting layer and an electron transporting layer. When the organic EL device includes the hole injecting layer and the hole transporting layer, the hole injecting layer is preferably provided between the hole transporting layer and the anode. When the organic EL device includes the electron injecting layer and the electron transporting layer, the electron injecting layer is preferably provided between the electron transporting layer and the cathode. The hole injecting layer, the hole transporting layer, the electron transporting layer and the electron injecting layer may each consist of a single layer or a plurality of layers.

FIG. 1 schematically shows an arrangement of an exemplary organic EL device according to the exemplary embodiment.

An organic EL device 1 includes a light-transmissive substrate 2, an anode 3, a cathode 4 and an organic layer 10 disposed between the anode 3 and the cathode 4. The organic layer 10 includes a hole injecting layer 6, a hole transporting layer 7, an emitting layer 5, an electron transporting layer 8, and an electron injecting layer 9. In the organic layer 10, the hole injecting layer 6, the hole transporting layer 7, the emitting layer 5, the electron transporting layer 8, and the electron injecting layer 9 are laminated on the anode 3 in this sequence.

Emitting Layer

The emitting layer 5 of the organic EL device 1 contains a first compound and a second compound. The emitting layer 5 may include a metal complex. The emitting layer 5 preferably includes no phosphorescent metal complex.

The first compound is also preferably a host material (occasionally referred to as a matrix material). The second compound is also preferably a dopant material (occasionally referred to as a guest material, emitter or luminescent material).

In the exemplary embodiment, the emitting layer 5 may include a plurality of the second compounds.

In the exemplary embodiment, an arrangement in which the emitting layer 5 includes a plurality of the second compounds also encompasses, for instance, an arrangement in which the emitting layer 5 includes the composition of the above exemplary embodiment.

First Compound

The first compound may be a delayed fluorescent compound or a compound exhibiting no delayed fluorescence. The first compound is preferably a delayed fluorescent compound.

The first compound in a form of a delayed fluorescent compound is preferably a compound represented by a formula (1) below.

[Formula 58]

(1)

In the formula (1): A is a group having a partial structure selected from the group consisting of partial structures represented by formulae (a-1) to (a-7) below.

A plurality of A are mutually the same or different.

The plurality of A are mutually bonded to form a saturated or unsaturated ring, or not bonded.

B is a group having a partial structure selected from the group consisting of partial structures represented by formulae (b-1) to (b-6) below.

A plurality of B are mutually the same or different.

The plurality of B are mutually bonded to form a saturated or unsaturated ring, or not bonded.

a, b and d are each independently an integer of 1 to 5.

c is an integer of 0 to 5.

When c is 0, A is bonded to B by a single bond or a spiro bond.

When c is an integer of 1 to 5, L is a linking group selected from the group consisting of a substituted or unsubstituted aryl group having 6 to 30 ring carbon atoms, and a substituted or unsubstituted heteroaryl group having 5 to 30 ring atoms, When c is an integer of 2 to 5, a plurality of L are mutually the same or different.

The plurality of L are mutually bonded to form a saturated or unsaturated ring, or not bonded.

[Formula 59]

(a-1) 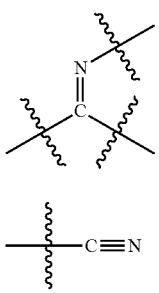

(a-2) 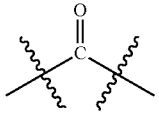

(a-3) 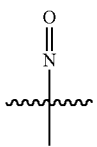

(a-4) 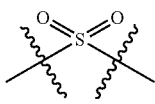

(a-5) 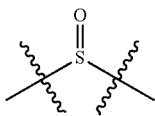

(a-6) 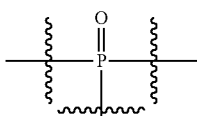

(a-7) 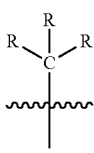

[Formula 60]

(b-1) 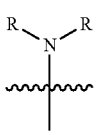

(b-2)

(b-3) 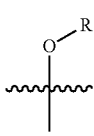

(b-4) 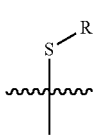

(b-5) 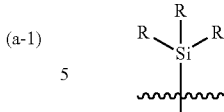

(b-6) 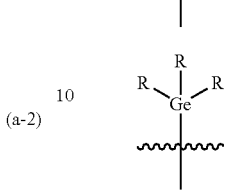

In the formulae (b-1) to (b-6): R each independently represents a hydrogen atom or a substituent.

R as the substituent is each independently selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms.

A plurality of R are mutually the same or different.

The plurality of R are mutually bonded to form a saturated or unsaturated ring, or not bonded.

In the formula (1), A is an acceptor (electron accepting) moiety and B is a donor (electron donating) moiety.

Examples of the group having the partial structure selected from the group consisting of the partial structures represented by the respective formulae (a-1) to (a-7) are shown below.

For instance, a group having the partial structure of the formula (a-3) is exemplified by a group represented by a formula (a-3-1).

[Formula 61]

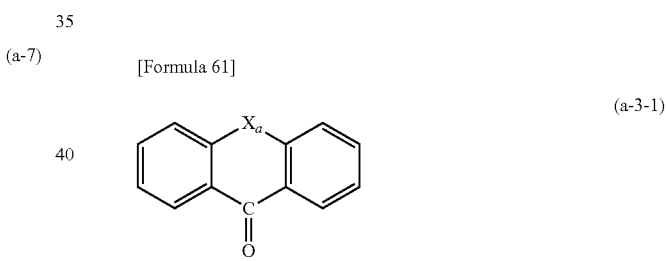

(a-3-1)

In the formula (a-3-1), $X_a$ is a single bond, an oxygen atom, a sulfur atom, or a carbon atom to be bonded to L or B in the formula (1).

For instance, a group having the partial structure of the formula (a-5) is exemplified by a group represented by a formula (a-5-1).

[Formula 62]

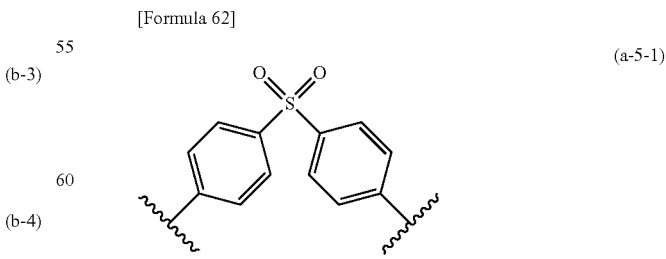

(a-5-1)

Examples of the group having the partial structure selected from the group consisting of the partial structures represented by the formulae (b-1) to (b-6) are shown below.

For instance, a group having the partial structure of the formula (b-2) is exemplified by a group represented by a formula (b-2-1).

[Formula 63]

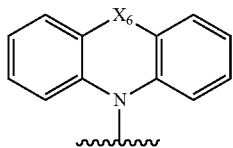

(b-2-1)

In the formula (b-2-1), $X_b$ is a single bond, an oxygen atom, a sulfur atom, $CR_{b1}R_{b2}$ or a carbon atom to be bonded to L or A in the formula (1).

The group represented by the formula (b-2-1) in which $X_b$ is a single bond is a group represented by a formula (b-2-2). The group represented by the formula (b-2-1) in which $X_b$ is an oxygen atom is a group represented by a formula formula (b-2-3). The group represented by the formula (b-2-1) in which $X_b$ is a sulfur atom is a group represented by a formula (b-2-4). The group represented by the formula (b-2-1) in which $X_b$ is $CR_{b1}R_{b2}$ is a group represented by a formula (b-2-5).

[Formula 64]

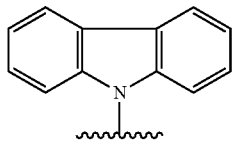

(b-2-2)

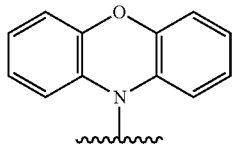

(b-2-3)

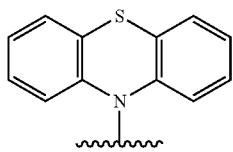

(b-2-4)

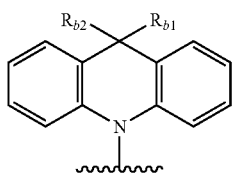

(b-2-5)

$R_{b1}$ and $R_{b2}$ are each independently a hydrogen atom or a substituent. $R_{b1}$ and $R_{b2}$ as the substituents are each independently selected from the group consisting of a substituted or unsubstituted alkyl group having 1 to 30 carbon atoms and a substituted or unsubstituted aryl group having 6 to 30 ring carbon atoms. $R_{b1}$ and $R_{b2}$ are each independently preferably a substituent selected from the group consisting of a substituted or unsubstituted alkyl group having 1 to 30 carbon atoms, and a substituted or unsubstituted aryl group having 6 to 30 ring carbon atoms, more preferably a substituent selected from the group consisting of a substituted or unsubstituted alkyl group having 1 to 30 carbon atoms.

In the organic EL device of the exemplary embodiment, A is preferably a group having the partial structure selected from the group consisting of the partial structures represented by the respective formulae (a-1), (a-2), (a-3) and (a-5).

In the organic EL device of the exemplary embodiment, B is preferably a group having the partial structure selected from the group consisting of the partial structures represented by the respective formulae (b-2), (b-3) and (b-4).

Examples of a bonding pattern of the compound represented by the formula (1) include bonding patterns shown in Table 1.

TABLE 1

| No. | a | b | c | d | Bonding Pattern |
|---|---|---|---|---|---|
| (1A) | 1 | 1 | 0 | 1 | B—A |
| (1B) | 1 | 1 | 1 | 1 | B—L—A |
| (1C) | 2 | 1 | 0 | 1 | B—A—A, B<A/A |
| (1D) | 1 | 2 | 0 | 1 | B—B—A, B\A/B |
| (1E) | 2 | 1 | 1 | 1 | B—L—A—A, B—L<A/A |
| (1F) | 1 | 2 | 1 | 1 | B—B—L—A, B\L—A/B |
| (1G) | 1 | 1 | 2 | 1 | B—L—L—A |
| (1H) | 1 | 1 | 1 | 2 | B—L\A, B—L/ B—L—B—L—A |

B of the formula (1) is also preferably represented by a formula (100) below.

[Formula 65]

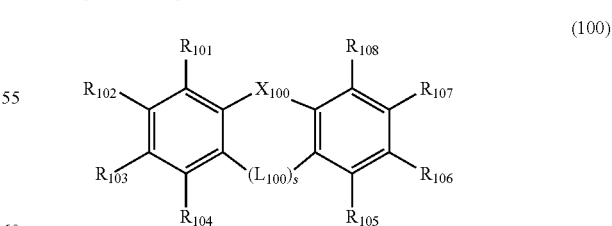

(100)

In the formula (100), $R_{101}$ to $R_{108}$ each independently represent a hydrogen atom or a substituent.

$R_{101}$ to $R_{108}$ as the substituents are each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted silyl group, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms.

In any pair selected from the group consisting of a pair of $R_{101}$ and $R_{102}$, a pair of $R_{102}$ and $R_{103}$, a pair of $R_{103}$ and $R_{104}$, a pair of $R_{105}$ and $R_{106}$, a pair of $R_{106}$ and $R_{107}$, and a pair of $R_{107}$ and $R_{108}$, the substituents form a saturated or unsaturated ring or do not form a ring.

$L_{100}$ is a linking group selected from linking groups represented by formulae (111) to (117) below.

s is an integer of 0 to 3. A plurality of $L_{100}$ are mutually the same or different.

$X_{100}$ is a linking group selected from linking groups represented by formulae (121) to (125) below.

[Formula 66]

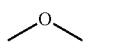
(111)

(112)

(113)

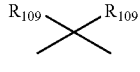
(114)

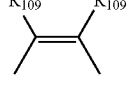
(115)

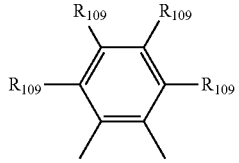
(116)

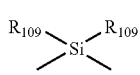
(117)

In the formulae (113) to (117), $R_{109}$ each independently represent the same as $R_{101}$ to $R_{108}$ of the formula (100).

In the formula (100), one of $R_{101}$ to $R_{108}$ or one of $R_{109}$ is a single bond to be bonded to L or A in the formula (1).

In a pair of $R_{109}$ and $R_{104}$ of the formula (100) or a pair of $R_{109}$ and $R_{105}$ of the formula (100), the substituents form a saturated or unsaturated ring or do not form a ring.

A plurality of $R_{109}$ are mutually the same or different.

[Formula 67]

(121)

(122)

(123)

(124)

(125)

In the formulae (123) to (125), $R_{110}$ each independently represents a hydrogen atom or a substituent.

$R_{110}$ as the substituent is selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms.

A plurality of $R_{110}$ are mutually the same or different.

In a pair of $R_{110}$ and $R_{101}$ of the formula (100) or a pair of $R_{110}$ and $R_{108}$ of the formula (100), the substituents form a saturated or unsaturated ring or do not form a ring.

s in the formula (100) is preferably 0 or 1.

When s is 0 in the formula (100), B in the formula (1) is represented by a formula (100A) below.

[Formula 68]

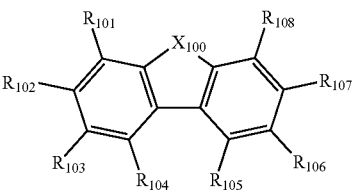
(100A)

$X_{100}$ and $R_{101}$ to $R_{108}$ in the formula (100A) respectively represent the same as $X_{100}$ and $R_{101}$ to $R_{108}$ in the formula (100).

$L_{100}$ is preferably represented by one of the formulae (111) to (114), more preferably represented by the formula (113) or (114).

$X_{100}$ is preferably represented by one of the formulae (121) to (124), more preferably represented by the formula (123) or (124).

In the organic electroluminescence device of the exemplary embodiment, the first compound is also preferably a compound represented by a formula (11) below.

[Formula 69]

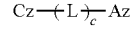
(11)

In the formula (11), Az is a cyclic structure selected from the group consisting of a substituted or unsubstituted pyridine ring, a substituted or unsubstituted pyrimidine ring, a substituted or unsubstituted triazine ring, and a substituted or unsubstituted pyrazine ring.

c is an integer of 0 to 5.

When c is 0, Cz and Az are bonded to each other by a single bond.

When c is an integer of 1 to 5, L is a linking group selected from the group consisting of a substituted or unsubstituted aryl group having 6 to 30 ring carbon atoms, and a substituted or unsubstituted heteroaryl group having 5 to 30 ring atoms.

When c is an integer of 2 to 5, a plurality of L are mutually the same or different.

The plurality of L are mutually bonded to form a ring, or not bonded.

Cz is represented by a formula (12) below.

[Formula 70]

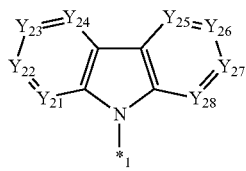

(12)

In the formula (12), $Y_{21}$ to $Y_{28}$ are each independently a nitrogen atom or $CR_y$.

$R_y$ each independently represents a hydrogen atom or a substituent.

$R_y$ as the substituent is each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of $R_y$ are mutually the same or different.

When a plurality of ones of $Y_{21}$ to $Y_{28}$ are $CR_y$ and $R_y$ is a substituent, a plurality of $R_y$ as the substituents are bonded to each other to form a ring, or are not bonded.

*1 represents a bonding position with a carbon atom in a structure of the linking group represented by L or a bonding position with a carbon atom of the cyclic structure represented by Az.

$Y_{21}$ to $Y_{28}$ are also preferably $CR_y$.

c in the formula (11) is also preferably 0 or 1.

The compound represented by the formula (11) is also preferably a compound represented by a formula (11A) below.

[Formula 71]

Cz-L-Az   (11A)

Az, Cz and L in the formula (11A) represent the same as Az, Cz and L in the formula (11).

L in the formula (11A) is preferably a linking group selected from the group consisting of a substituted or unsubstituted aryl group having 6 to 30 ring carbon atoms.

The compound represented by the formula (11A) is also preferably a compound represented by a formula (11B) below.

[Formula 72]

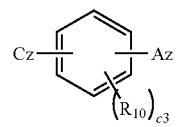

(11B)

Az and Cz in the formula (11B) represent the same as Az and Cz in the formula (11). c3 is 4. $R_{10}$ is a hydrogen atom or a substituent. $R_{10}$ as the substituent is a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to carbon atoms, a substituted phosphoryl group, a substituted silyl group, a cyano group, a nitro group, and a carboxy group. A plurality of $R_{10}$ are the same or different.

The compound represented by the formula (11A) is also preferably a compound represented by a formula (11C) below.

[Formula 73]

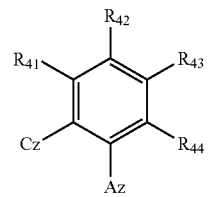

(11c)

In the formula (11C), Az and Cz represent the same as Az and Cz in the formula (11).

$R_{41}$ to $R_{44}$ each independently represent a hydrogen atom or a substituent.

$R_{41}$ to $R_{44}$ as the substituents are each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

Cz is also preferably represented by a formula (12a), (12b) or (12c) below.

[Formula 74]

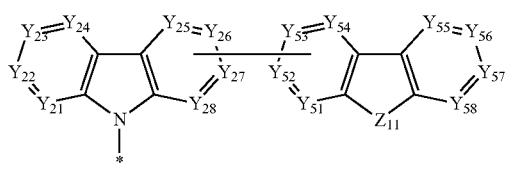
(12a)

[Formula 75]

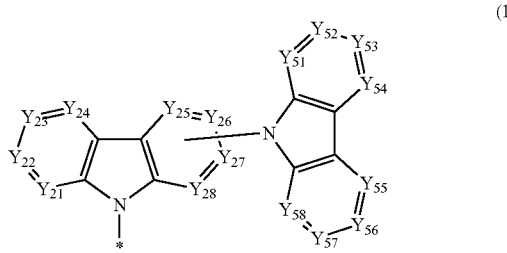
(12b)

[Formula 76]

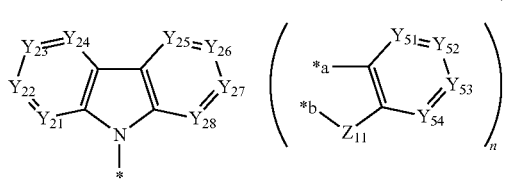
(12c)

In the formulae (12a), (12b) and (12c), $Y_{21}$ to $Y_{28}$ and $Y_{51}$ to $Y_{58}$ each independently represent a nitrogen atom or $CR_y$.

In the formula (12a), at least one of $Y_{25}$ to $Y_{28}$ is a carbon atom bonded to one of $Y_{51}$ to $Y_{54}$ while at least one of $Y_{51}$ to $Y_{54}$ is a carbon atom bonded to one of $Y_{25}$ to $Y_{28}$.

In the formula (12b), at least one of $Y_{25}$ to $Y_{28}$ is a carbon atom bonded to a nitrogen atom in a five-membered ring of a nitrogen-containing fused ring including $Y_{51}$ to $Y_{58}$.

In the formula (12c), *a and *b each represent a bonding position with one of $Y_{21}$ to $Y_{28}$. At least one of $Y_{25}$ to $Y_{28}$ is bonded to the bonding position represented by *a. At least one of $Y_{25}$ to $Y_{28}$ is bonded to the bonding position represented by *b.

n is an integer of 1 to 4.

$R_y$ each independently represents a hydrogen atom or a substituent.

$R_y$ as the substituent is each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of $R_y$ are mutually the same or different.

When a plurality of ones of $Y_{21}$ to $Y_{28}$ are $CR_y$ and $R_y$ is a substituent, a plurality of $R_y$ are bonded to each other to form a ring, or are not bonded.

When a plurality of ones of $Y_{51}$ to $Y_{58}$ are $CR_y$ and $R_y$ is a substituent, a plurality of $R_y$ are bonded to each other to form a ring, or are not bonded.

$Z_{11}$ is one selected from the group consisting of an oxygen atom, a sulfur atom, $NR_{45}$, and $CR_{46}R_{47}$.

$R_{45}$ to $R_{47}$ each independently represent a hydrogen atom or a substituent.

$R_{45}$ to $R_{47}$ as the substituents are each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of $R_{45}$ are mutually the same or different.
A plurality of $R_{46}$ are mutually the same or different.
A plurality of $R_{47}$ are mutually the same or different.

When $R_{46}$ and $R_{47}$ are mutually substituents, the substituents are bonded to each other to form a ring, or are not bonded to each other.

* represents a bonding position with a carbon atom in the cyclic structure represented by Az.

$Z_{11}$ is preferably $NR_{45}$.

When $Z_{11}$ is $NR_{45}$, $R_{45}$ is preferably a substituted or unsubstituted aryl group having 6 to 30 ring carbon atoms.

$Y_{51}$ to $Y_{58}$ are preferably $CR_y$. At this time, at least one of $Y_{51}$ to $Y_{58}$ is a carbon atom bonded to the cyclic structure represented by the formula (12).

Cz is preferably represented by the formula (12c) in which n is 1.

Cz is also preferably represented by a formula (12c-1) below. A group represented by the formula (12c-1) is an exemplary group obtained by bonding $Y_{26}$ to the bonding position represented by *a and bonding $Y_{27}$ to the bonding position represented by *b in the formula (12c).

[Formula 77]

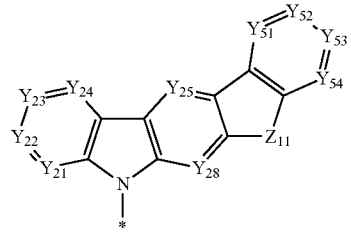
(12c-1)

In the formula (12c-1), $Y_{21}$ to $Y_{25}$, $Y_{28}$, and $Y_{51}$ to $Y_{54}$ are each independently a nitrogen atom or $CR_y$.

$R_y$ each independently represents a hydrogen atom or a substituent.

$R_y$ as the substituent is each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of $R_y$ are mutually the same or different.

When a plurality of ones of $Y_{21}$ to $Y_{25}$ and $Y_{28}$ are $CR_y$ and $R_y$ is a substituent, a plurality of $R_y$ are bonded to each other to form a ring, or are not bonded.

When a plurality of ones of $Y_{51}$ to $Y_{54}$ are $CR_y$ and $R_y$ is a substituent, a plurality of $R_y$ are bonded to each other to form a ring, or are not bonded.

$Z_{11}$ is one selected from the group consisting of an oxygen atom, a sulfur atom, $NR_{45}$, and $CR_{46}R_{47}$.

$R_{45}$ to $R_{47}$ each independently represent a hydrogen atom or a substituent.

$R_{45}$ to $R_{47}$ as the substituents are each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of $R_{45}$ are mutually the same or different.
A plurality of $R_{46}$ are mutually the same or different.
A plurality of $R_{47}$ are mutually the same or different.

When $R_{46}$ and $R_{47}$ are mutually substituents, the substituents are bonded to each other to form a ring, or are not bonded to each other.

* represents a bonding position with a carbon atom in the cyclic structure represented by Az.

When n is 2 in the formula (12c), Cz is exemplarily represented by a formula (12c-2). When n is 2, two of structures each shown in brackets added with an index n are fused to the cyclic structure represented by the formula (12). Cz represented by the formula (12c-2) is obtained by bonding $Y_{22}$ to the bonding position represented by *b and bonding $Y_{23}$ to the bonding position represented by *a while bonding $Y_{26}$ to the bonding position represented by *a and bonding $Y_{27}$ to the bonding position represented by *b, in the formula (12c).

[Formula 78]

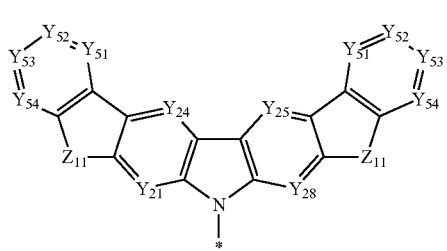

(12c-2)

In the formula (12c-2), $Y_{21}$, $Y_{24}$, $Y_{25}$, $Y_{28}$, $Y_{51}$ to $Y_{54}$, $Z_{11}$, and * represent the same as $Y_{21}$, $Y_{24}$, $Y_{25}$, $Y_{28}$, $Y_{51}$ to $Y_{54}$, $Z_{11}$, and * in the formula (12c-1). A plurality of $Y_{51}$ are mutually the same or different. A plurality of $Y_{52}$ are mutually the same or different. A plurality of $Y_{53}$ are mutually the same or different. A plurality of $Y_{54}$ are mutually the same or different. A plurality of $Z_{11}$ are mutually the same or different.

Az is preferably a cyclic structure selected from the group consisting of a substituted or unsubstituted pyrimidine ring and a substituted or unsubstituted triazine ring.

It is more preferable that Az is a cyclic structure selected from the group consisting of a substituted pyrimidine ring and a substituted triazine ring, and a substituent for each of the pyrimidine ring and the triazine ring is selected from the group consisting of a substituted or unsubstituted aryl group having 6 to 30 ring carbon atoms and a substituted or unsubstituted heteroaryl group having 5 to 30 ring atoms, further preferably a substituted or unsubstituted aryl group having 6 to ring carbon atoms.

When the pyrimidine ring and the triazine ring as Az have a substituted or unsubstituted aryl group as the substituent, the aryl group preferably has 6 to 20 ring carbon atoms, more preferably 6 to 14 ring carbon atoms, further preferably 6 to 12 ring carbon atoms.

When Az has a substituted or unsubstituted aryl group as the substituent, the substituent is preferably selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably selected from the group consisting of a substituted or unsubstituted phenyl group, a substituted or unsubstituted biphenyl group, and a substituted or unsubstituted naphthyl group.

When Az has a substituted or unsubstituted heteroaryl group as the substituent, the substituent is preferably selected from the group consisting of a substituted or unsubstituted carbazolyl group, a substituted or unsubstituted dibenzofuranyl group, and a substituted or unsubstituted dibenzothiophenyl group.

$R_y$ is each independently a hydrogen atom or a substituent. $R_y$ as the substituent is preferably selected from the group consisting of a substituted or unsubstituted aryl group having 6 to 30 ring carbon atoms and a substituted or unsubstituted heteroaryl group having 5 to 30 ring atoms.

When $R_y$ as the substituent is a substituted or unsubstituted aryl group having 6 to 30 ring carbon atoms, $R_y$ as the substituent is preferably selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably selected from the group consisting of a substituted or unsubstituted phenyl group, a substituted or unsubstituted biphenyl group, and a substituted or unsubstituted naphthyl group.

When $R_y$ as the substituent has a substituted or unsubstituted heteroaryl group having 5 to 30 ring atoms, $R_y$ as the substituent is preferably selected from the group consisting of a substituted or unsubstituted carbazolyl group, a substituted or unsubstituted dibenzofuranyl group, and a substituted or unsubstituted dibenzothiophenyl group.

$R_{45}$ to $R_{47}$ as the substituents are each independently preferably selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms.

The first compound is also preferably a compound represented by a formula (13) below.

[Formula 79]

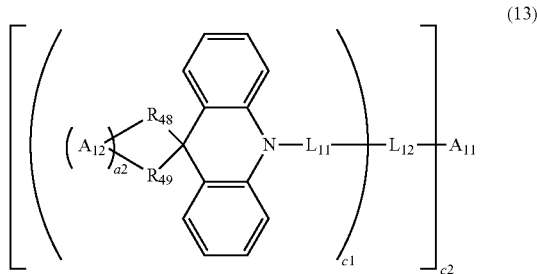

(13)

In the formula (13), c is 2. a2 is 0 or 1. A plurality of a2 are mutually the same or different. c1 is an integer of 1 to 5. A plurality of c1 are mutually the same or different. When a2 is 0, $R_{48}$ and $R_{49}$ each independently represent a hydrogen atom or a monovalent substituent.

$R_{48}$ and $R_{49}$ as the substituents are each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group.

When a2 is 1, $R_{48}$ and $R_{49}$ are each independently a linking group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 carbon atoms, and a substituted silyl group.

A plurality of $R_{48}$ are mutually the same or different.

A plurality of $R_{49}$ are mutually the same or different.

$A_{11}$ and $A_{12}$ are each independently a group having the partial structure selected from the partial structures represented by the formulae (a-1) to (a-7).

A plurality of $A_{12}$ are mutually the same or different.

$L_{12}$ represents a single bond or a linking group.

$L_{12}$ as the linking group is selected from the group consisting of a substituted or unsubstituted aryl group having 6 to 30 ring carbon atoms, and a substituted or unsubstituted heteroaryl group having 5 to 30 ring atoms.

A plurality of $L_{12}$ are mutually the same or different.

$L_{11}$ represents a single bond or a linking group.

$L_{11}$ as the linking group is selected from the group consisting of a substituted or unsubstituted aryl group having 6 to 30 ring carbon atoms, and a substituted or unsubstituted heteroaryl group having 5 to 30 ring atoms.

A plurality of $L_{11}$ are mutually the same or different.

When a2 is 0 in the formula (13), the first compound is represented by a formula (131) below. c1, c2, $A_{11}$, $L_{11}$, $L_{12}$, $R_{48}$ and $R_{49}$ in the formula (131) respectively represent the same as c1, c2, $A_{11}$, $L_{11}$, $L_{12}$, $R_{48}$ and $R_{49}$ described above.

[Formula 80]

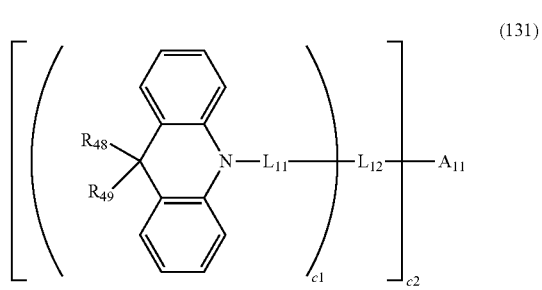

(131)

In the formula (131), $R_{48}$ and $R_{49}$ are preferably a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, and a substituted silyl group, more preferably a substituent selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group 1 to 30 carbon atoms.

When a2 is 1 in the formula (13), the first compound is represented by a formula (132) below. c1, c2, $A_{11}$, $A_{12}$, $L_{11}$, $L_{12}$, $R_{48}$ and $R_{49}$ in the formula (132) respectively represent the same as c1, c2, $A_{11}$, $A_{12}$, $L_{11}$, $L_{12}$, $R_{48}$ and $R_{49}$ described above.

[Formula 81]

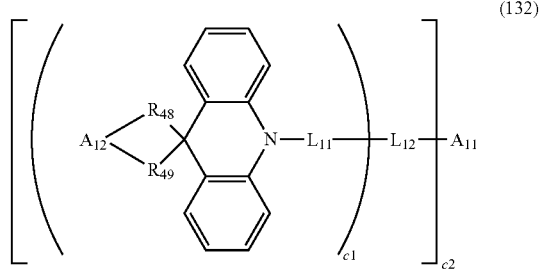

(132)

In the formula (132), $R_{48}$ and $R_{49}$ are preferably a linking group selected from the group consisting of a substituted or unsubstituted aryl group having 6 to 30 ring carbon atoms, a substituted or unsubstituted heteroaryl group having 5 to 30 ring atoms, and a substituted silyl group, more preferably a linking group selected from the group consisting of a substituted or unsubstituted aryl group having 6 to 30 ring carbon atoms and a substituted or unsubstituted heteroaryl group having 5 to ring atoms.

The first compound is also preferably an exemplary compound represented by a formula (14).

[Formula 82]

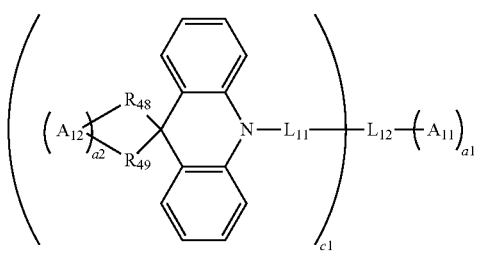

(14)

In the formula (14), a1 is 0 or 1. a2 is 0 or 1. a1+a2≥1. c1 is an integer of 1 to 5.

When a2 is 0, $R_{48}$ and $R_{49}$ each independently represent a hydrogen atom or a monovalent substituent.

$R_{48}$ and $R_{49}$ as the substituents are each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group.

When a2 is 1, $R_{48}$ and $R_{49}$ are each independently a linking group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group.

A plurality of $R_{48}$ are mutually the same or different.

A plurality of $R_{49}$ are mutually the same or different.

$A_{11}$ and $A_{12}$ are each independently a group having the partial structure selected from the partial structures represented by the formulae (a-1) to (a-7).

A plurality of $A_{12}$ are mutually the same or different.

When a1 is 0, $L_{12}$ is a hydrogen atom or a monovalent substituent.

$L_{12}$ as the monovalent substituent is selected from the group consisting of a substituted or unsubstituted aryl group having 6 to 30 ring carbon atoms, and a substituted or unsubstituted heteroaryl group having 5 to 30 ring atoms.

When a1 is 1, $L_{12}$ is a single bond or a linking group.

$L_{12}$ as the linking group is selected from the group consisting of a substituted or unsubstituted aryl group having 6 to 30 ring carbon atoms, and a substituted or unsubstituted heteroaryl group having 5 to 30 ring atoms.

$L_{11}$ represents a single bond or a linking group.

$L_{11}$ as the linking group is selected from the group consisting of a substituted or unsubstituted aryl group having 6 to 30 ring carbon atoms, and a substituted or unsubstituted heteroaryl group having 5 to 30 ring atoms.

A plurality of $L_{11}$ are mutually the same or different.

The compound represented by the formula (14) is exemplified by a compound represented by a formula (14A).

[Formula 83]

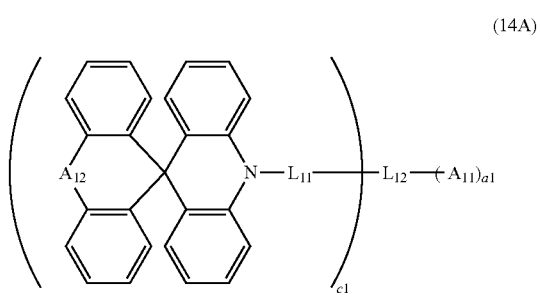

(14A)

In the formula (14A), a1, c1, $A_{11}$, $A_{12}$, $L_{11}$ and $L_{12}$ respectively represent the same as a1, c1, $A_{11}$, $A_{12}$, $L_{11}$ and $L_{12}$ in the formula (14).

The compound represented by the formula (13) or (14) is exemplified by compounds represented by formulae (10B) to (10E).

[Formula 84]

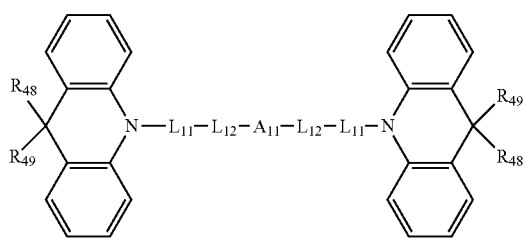

(10B)

[Formula 85]

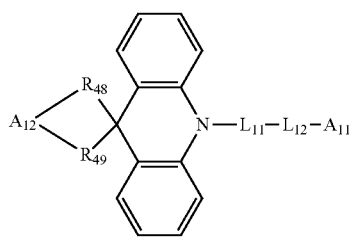

(10C)

[Formula 86]

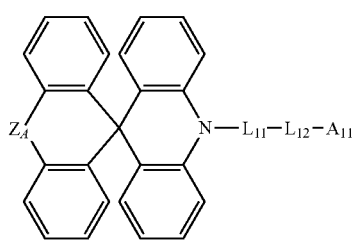

(10D)

[Formula 87]

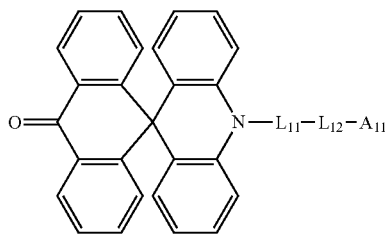

(10E)

In the formula (10D), $Z_A$ is selected from the group consisting of =N-$L_{11}$-$L_{12}$-$A_{11}$, an oxygen atom, a sulfur atom, and a selenium atom.

In the formulae (10B), (10C), (10D), and (10E), $R_{48}$, $R_{49}$, $A_{11}$, $A_{12}$, $L_{11}$, and $L_{12}$ respectively represent the same as $R_4$, $R_{49}$, $A_{11}$, $A_{12}$, $L_{11}$, and $L_{12}$ in the formula (14).

The compound represented by the formula (131) is also preferably a compound represented by a formula (10F) below.

[Formula 88]

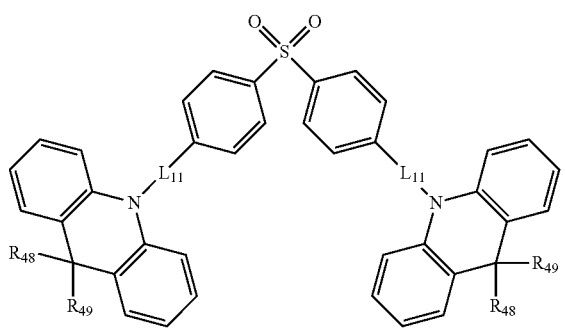

(10F)

In the formula (10F), $R_{48}$, $R_{49}$, and $L_{11}$ respectively represent the same as $R_{48}$, $R_{49}$, and $L_{11}$ in the formula (13). A plurality of $R_{48}$ are mutually the same or different. A plurality of $R_{49}$ are mutually the same or different. A plurality of $L_{11}$ are mutually the same or different.

Delayed Fluorescence

Delayed fluorescence (thermally activated delayed fluorescence) is described, for instance, on pages 261 to 268 of "Yuki Hando-tai no Debaisu Bussei (Device Physics of Organic Semiconductors)", edited by ADACHI, Chihaya and published by Kodansha Ltd. This literature describes that, when an energy gap $\Delta E_{13}$ between a singlet state and a triplet state can be decreased, an inverse energy transfer from the triplet state to the singlet state, which usually occurs at a low transition probability, occurs at a high efficiency to express thermally activated delayed fluorescence (TADF). Further, an occurrence mechanism of the delayed fluorescence is described in FIG. 10.38 of this literature. The first compound of the exemplary embodiment is a compound exhibiting thermally activated delayed fluorescence occurring in this mechanism.

Emission of the delayed fluorescence can be checked by measuring the transient PL (Photo Luminescence).

Behavior of the delayed fluorescence can be analyzed based on the decay curve obtained by the transient PL measurement. The transient PL measurement is a method of measuring decay behavior (transient characteristics) of the PL emission after radiating a pulse laser on a sample and stopping radiating. The PL emission in the TADF material is classified into a luminescence component from singlet excitons generated in first PL excitation and a luminescence component from singlet excitons generated through triplet excitons. A lifetime of the singlet excitons generated in the first PL excitation is very short in a nanosecond order. Accordingly, the emission from the singlet excitons rapidly decays after radiation of the pulse laser.

Figure 2:
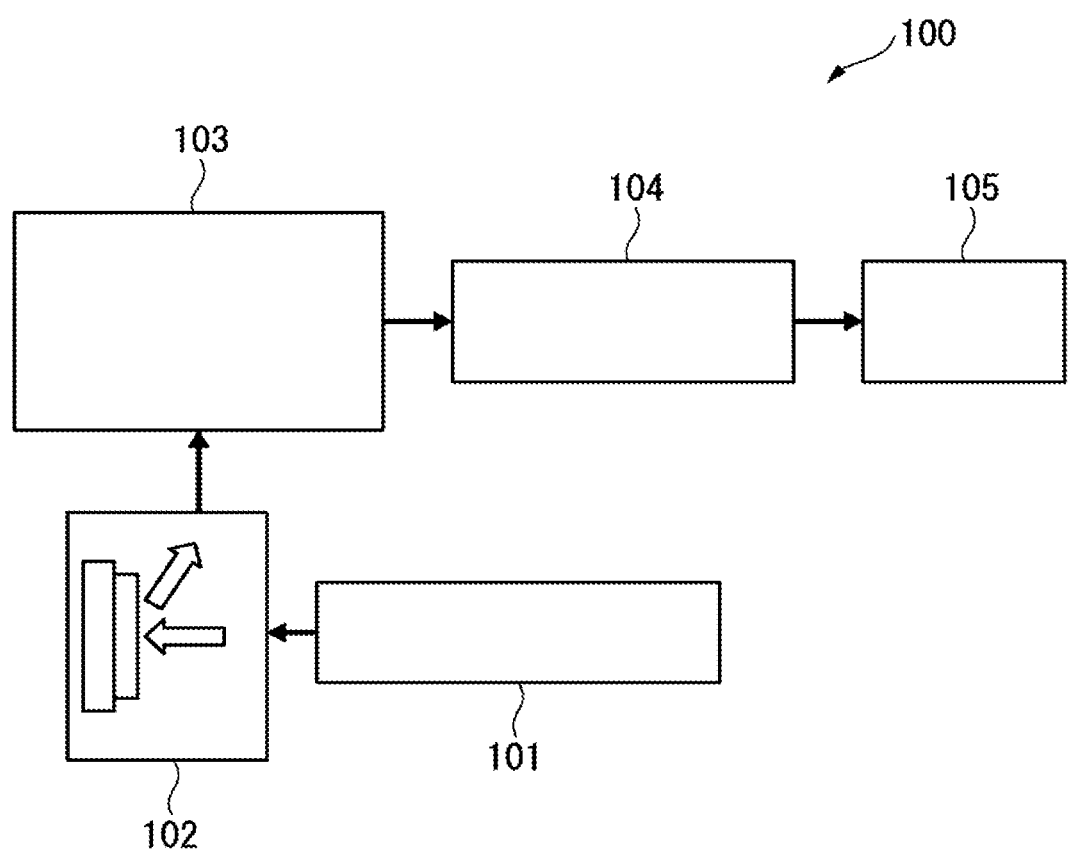
FIG. 2 is a schematic illustration of a measuring device of transient PL.

On the other hand, since delayed fluorescence provides an emission from singlet excitons generated through long-life triplet excitons, the delayed fluorescence gradually decays. Thus, there is a large difference in time between the emission from the singlet excitons generated in the first PL excitation and the emission from the singlet excitons through the triplet excitons. Accordingly, a luminous intensity derived from the delayed fluorescence is obtainable FIG. 2 schematically shows an exemplary device for measuring the transient PL.

A transient PL measuring device 100 in the exemplary embodiment includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a matrix material with a doping material at a concentration of 12 mass % and forming a thin film on a quartz substrate.

The thin film sample housed in the sample chamber 102 is radiated with a pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound H1 as the matrix material and a reference compound D1 as the doping material and was measured in terms of the transient PL.

[Formula 89]

Reference Compound H1

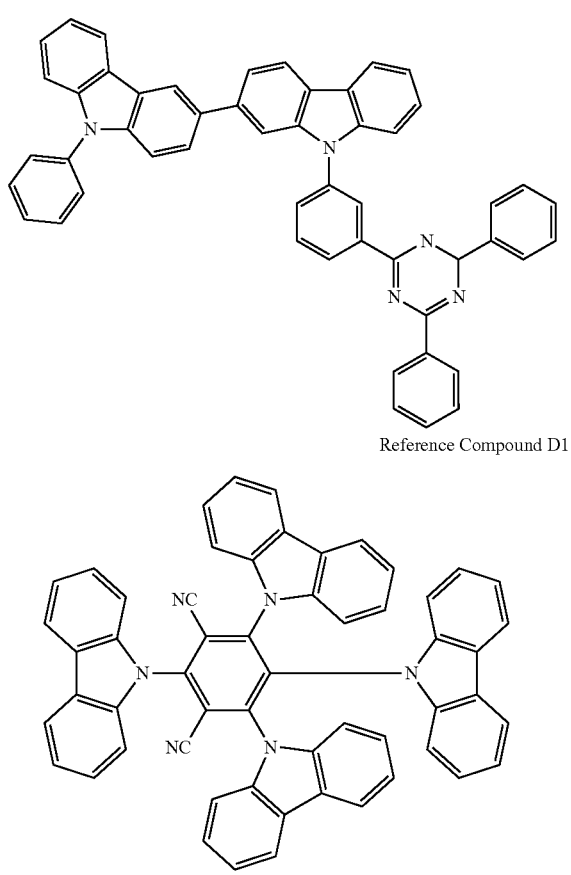

Reference Compound D1

The decay curve was analyzed with respect to the above thin film sample A and a film sample B. The thin film sample B was manufactured in the same manner as described above from a reference compound H2 as the matrix material and the reference compound D1 as the doping material.

Figure 3:
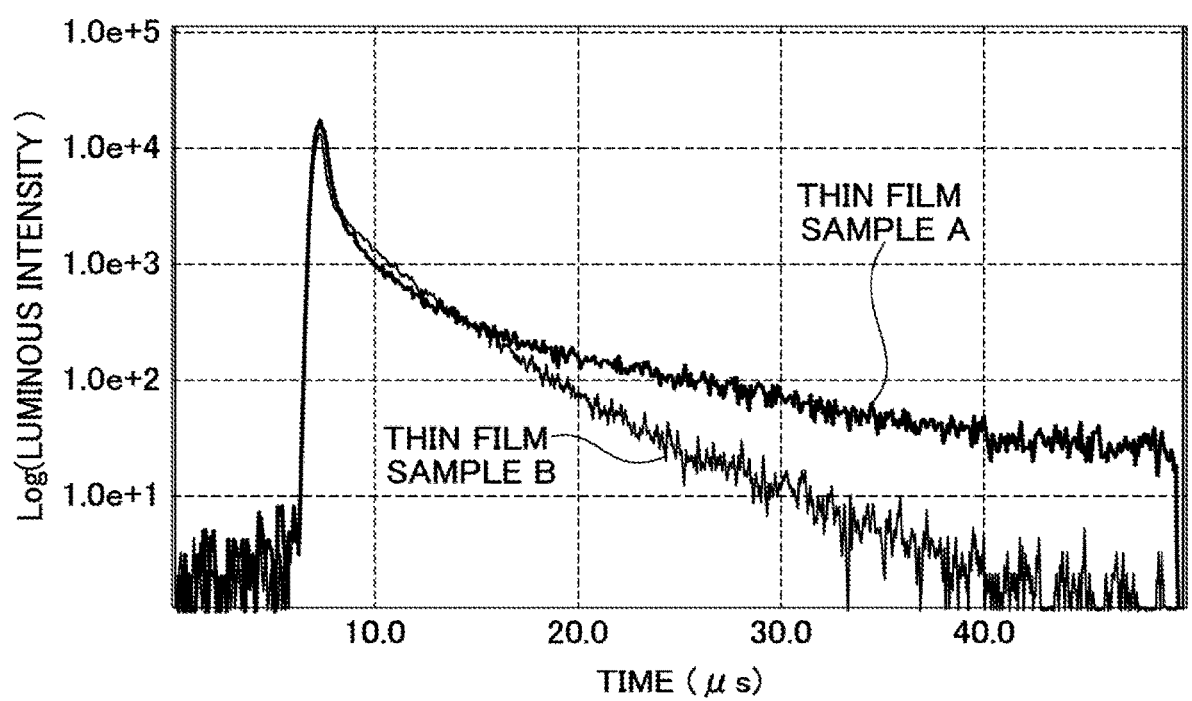
FIG. 3 shows an example of a decay curve of the transient PL.

FIG. 3 shows decay curves obtained from transient PL obtained by measuring the thin film samples A and B.

[Formula 90]

Reference Compound H2

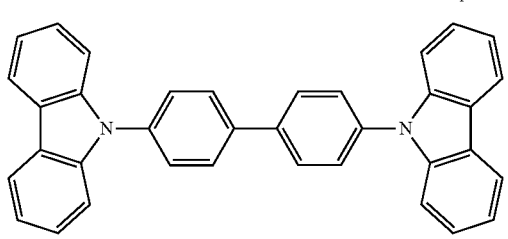

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

In the exemplary embodiment, an emission amount of the delayed fluorescence can be obtained using the device shown in FIG. 2. Prompt emission and Delay emission are observed in the first compound. Prompt emission is observed promptly when the excited state is achieved by exciting the first compound with a pulse beam (i.e., a beam emitted from a pulse laser) having a wavelength absorbable by the first compound. Delay emission is observed not promptly when the excited state is achieved but after the excited state is achieved. In the exemplary embodiment, the amount of Delay emission is preferably 5% or more relative to the amount of Prompt emission. Specifically, provided that the amount of Prompt emission is denoted by $X_P$ and the amount of Delay emission is denoted by $X_D$, a value of $X_D/X_P$ is preferably 0.05 or more.

The amount of Prompt emission and the amount of Delay emission can be obtained according to the same method as described in "Nature 492, 234-238, 2012." The amount of Prompt emission and the amount of Delay emission may be calculated using a device different from one described in the above literature.

Moreover, a sample usable for measuring delayed fluorescence is obtained, for instance, by co-depositing the first compound and a compound TH-2 on a quartz substrate at a ratio of the first compound of 12 mass % to form a 100-nm-thick thin film.

[Formula 91]

TH-2

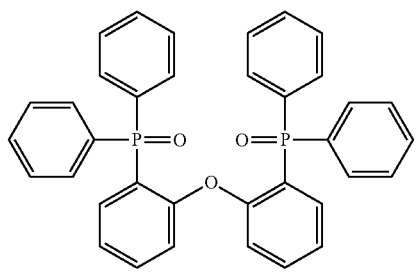

Manufacturing Method of First Compound

The first compound can be manufactured, for instance, by methods described in Chemical Communications, p. 10385-10387 (2013) and NATURE Photonics, p. 326-332 (2014). Moreover, the first compound also can be manufactured, for instance, by methods disclosed in International Publication No. WO2013/180241, International Publication No. WO2014/092083, International Publication No. WO2014/104346, and the like. Furthermore, the first compound can be manufactured, for instance, by application of known substitution reactions and/or materials depending on a target compound according to reactions described later in Examples.

Specific examples of the first compound of the exemplary embodiment are shown below. The first compound according to the invention is not limited to these specific examples.

[Formula 92]
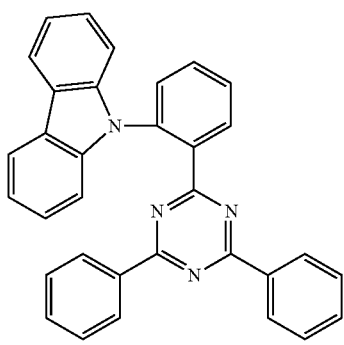
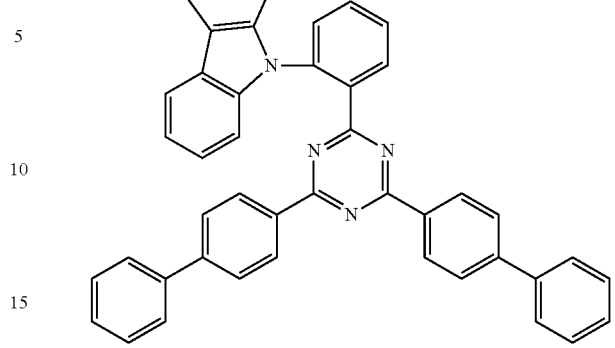
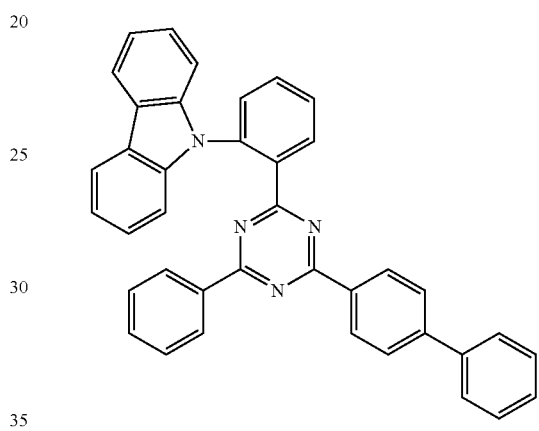
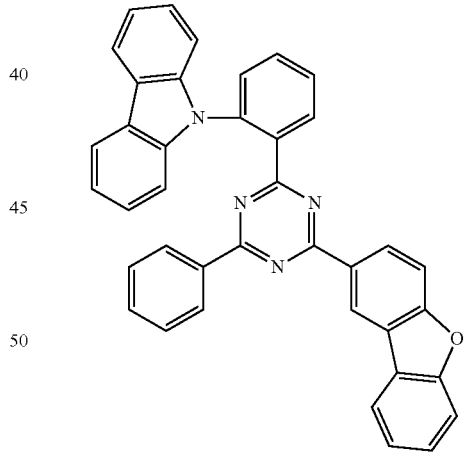
[Formula 93]
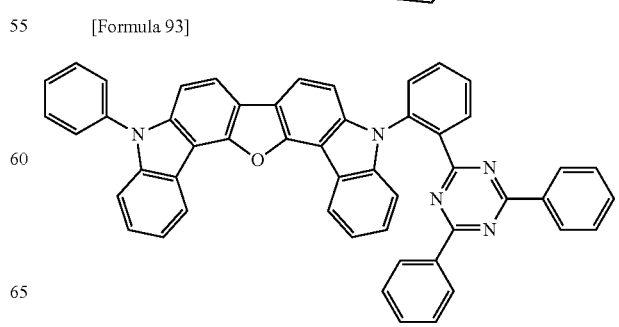

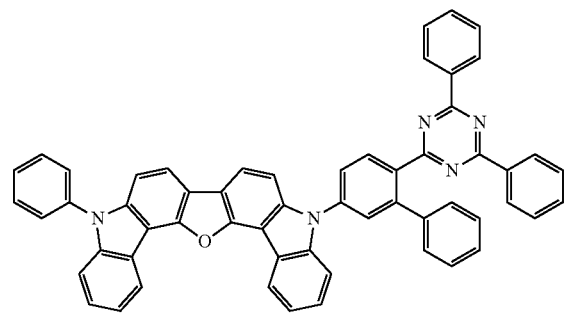
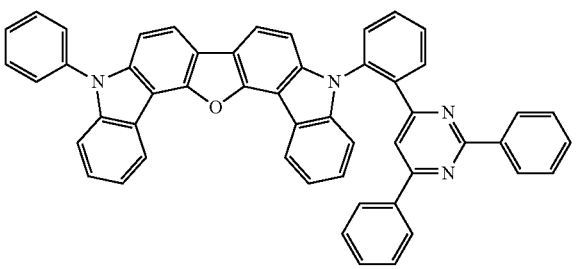
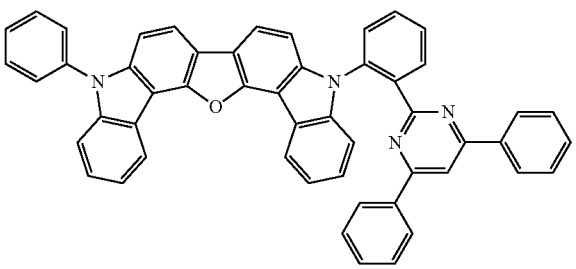
[Formula 94]
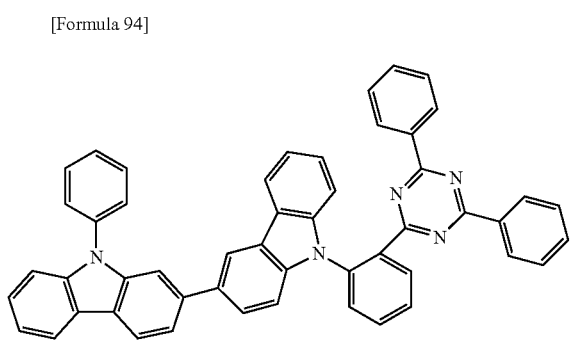
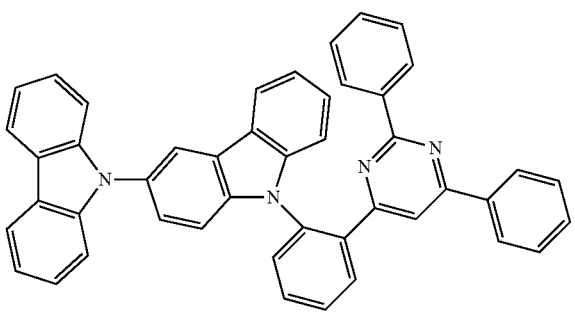
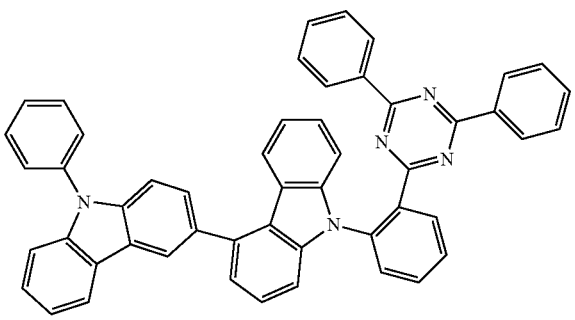
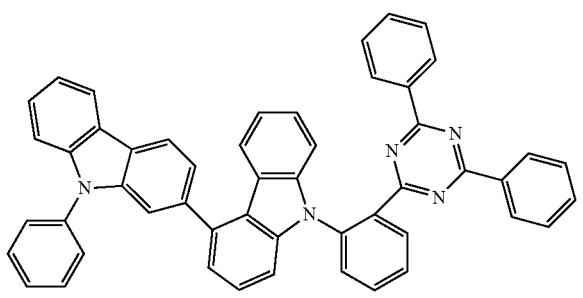
[Formula 95]
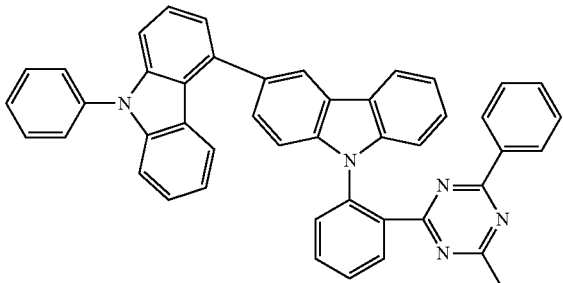
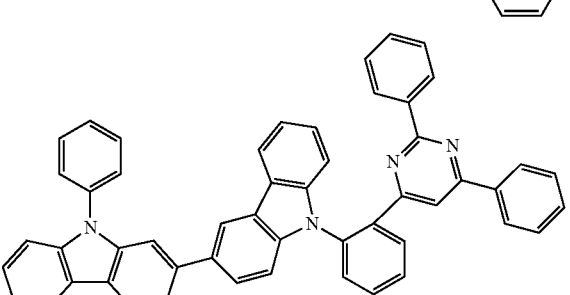
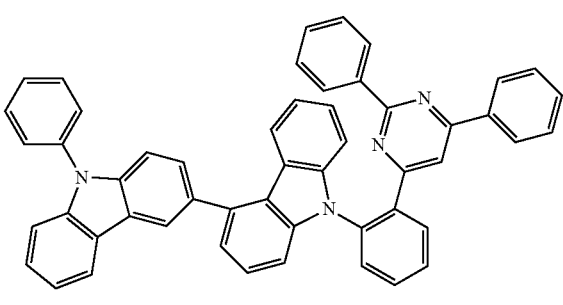

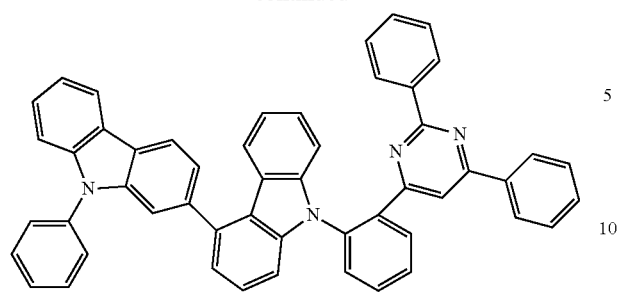
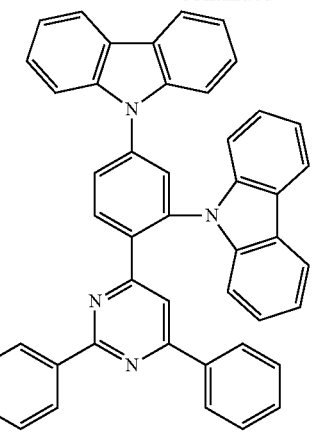
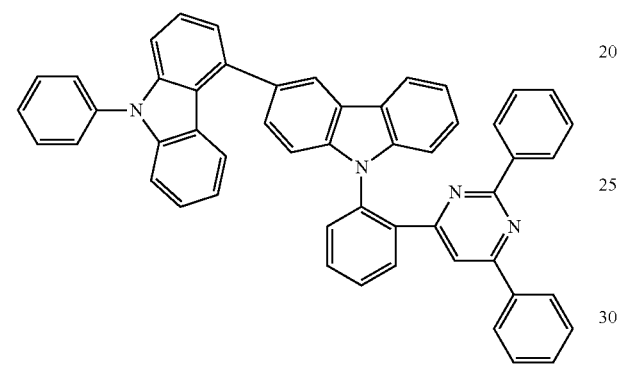
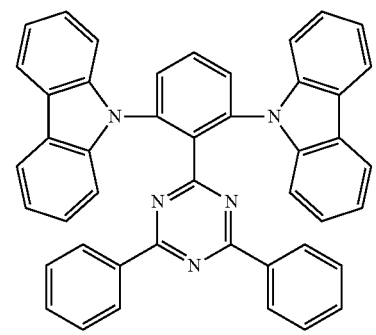
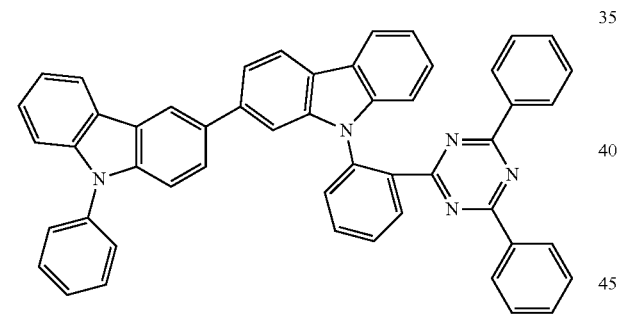
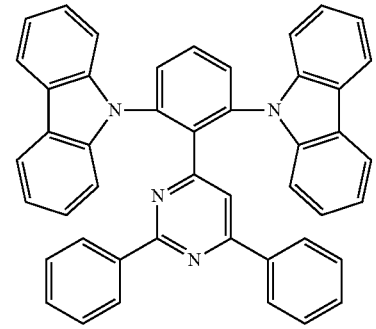
[Formula 96]
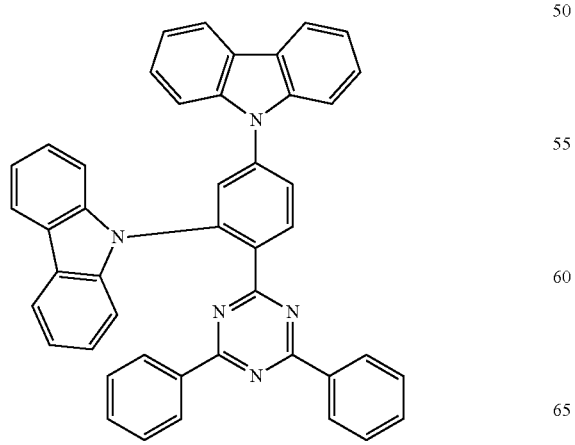
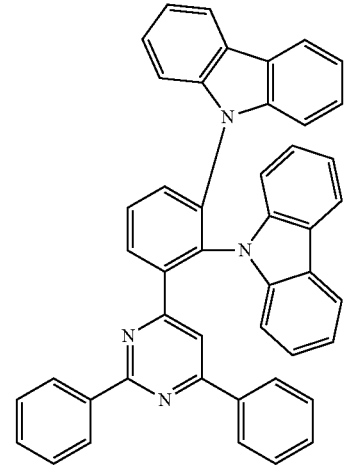

129
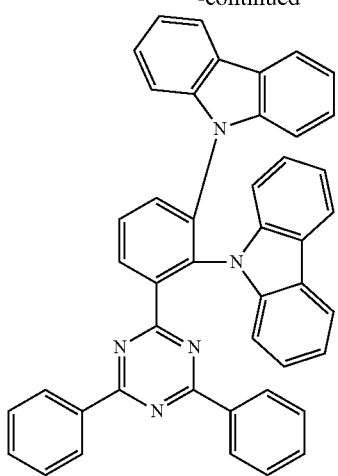
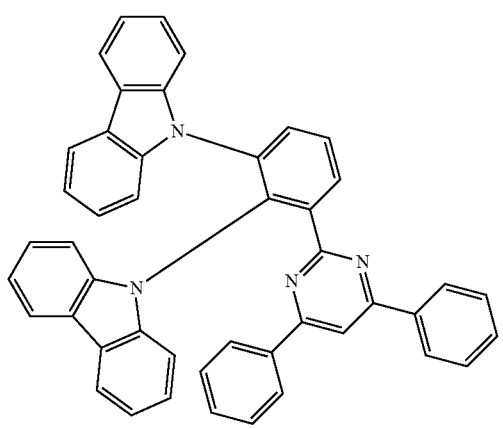
130
[Formula 97]
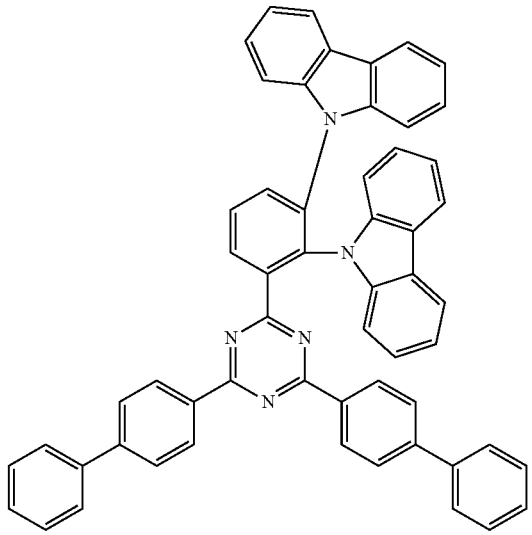
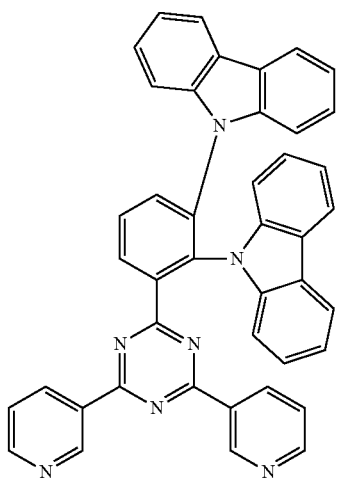
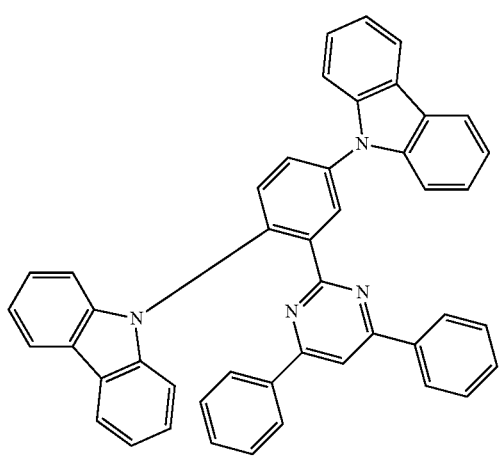
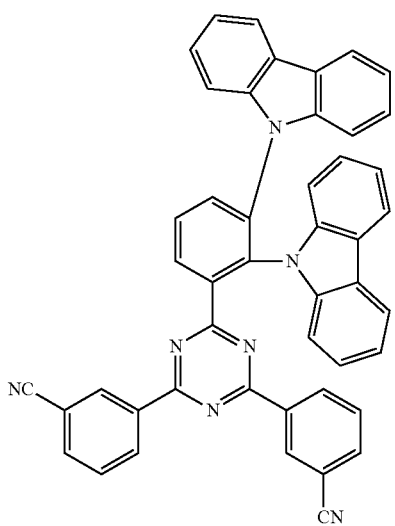

131
-continued
[Formula 98]
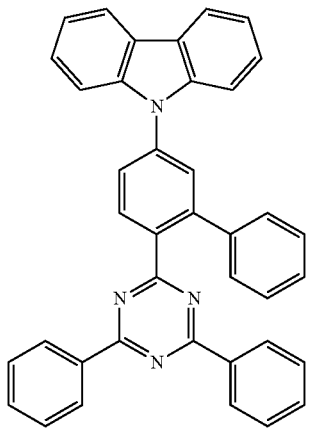
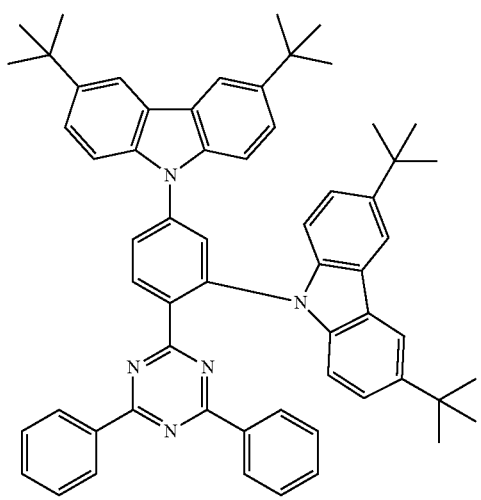
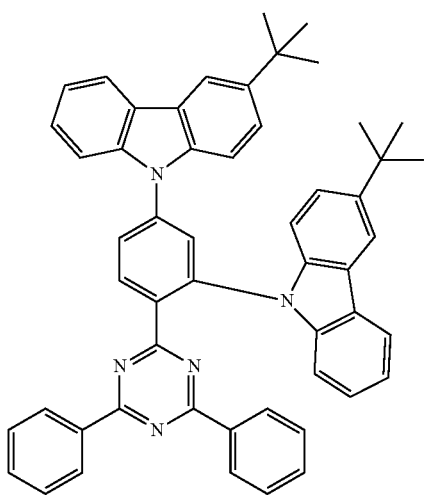
132
-continued
[Formula 99]
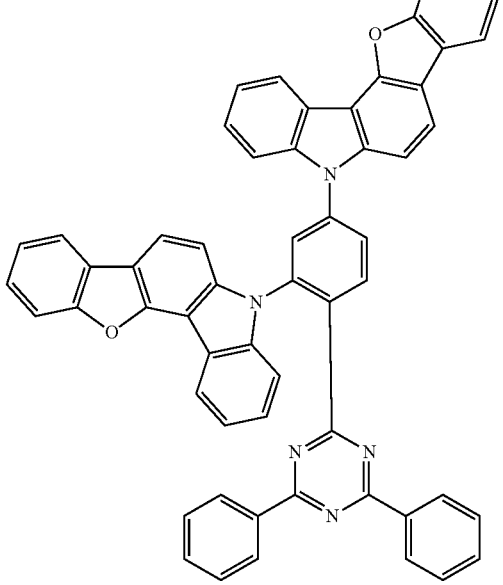
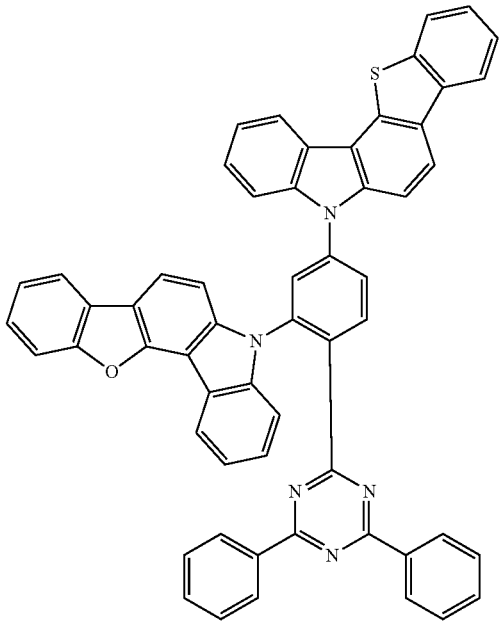

[Formula 100]
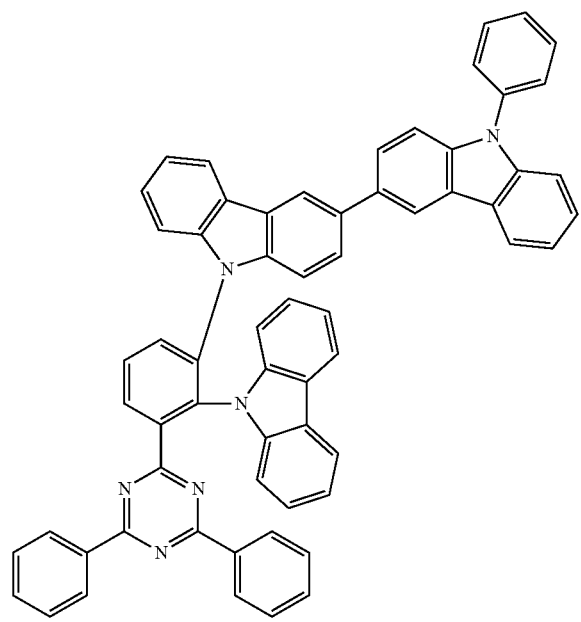
[Formula 101]
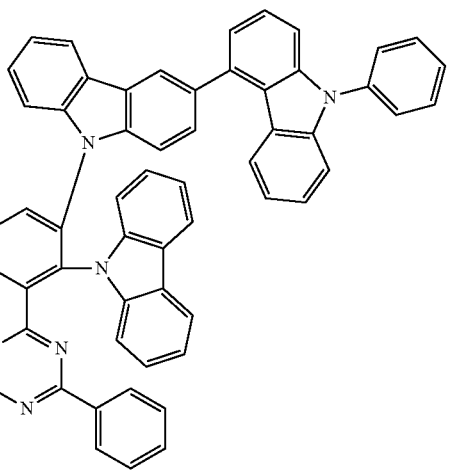
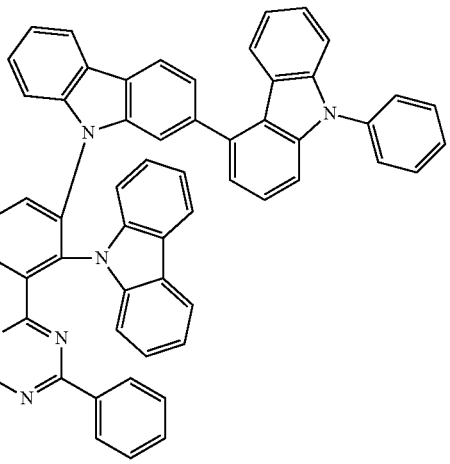
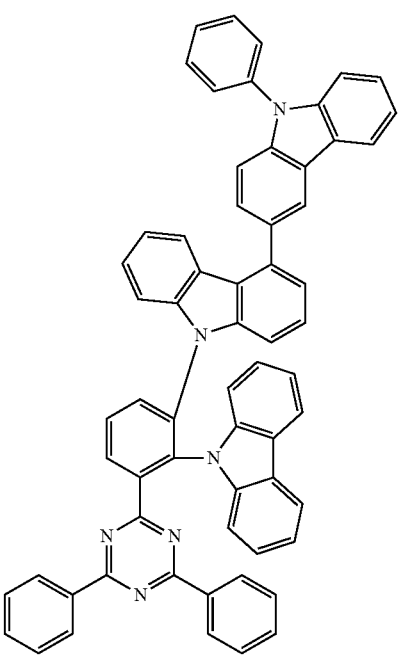

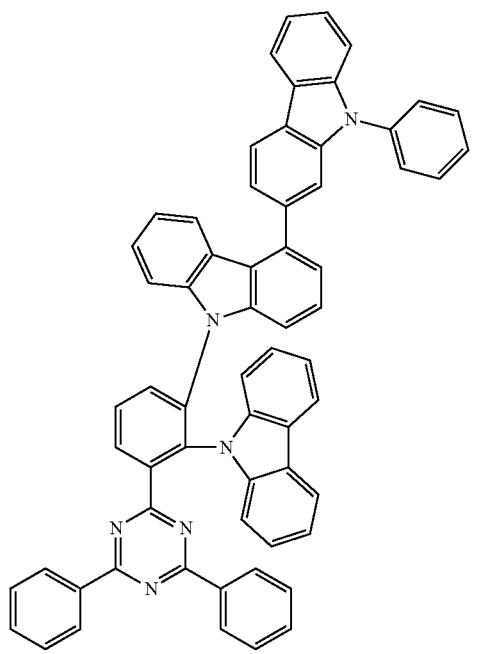
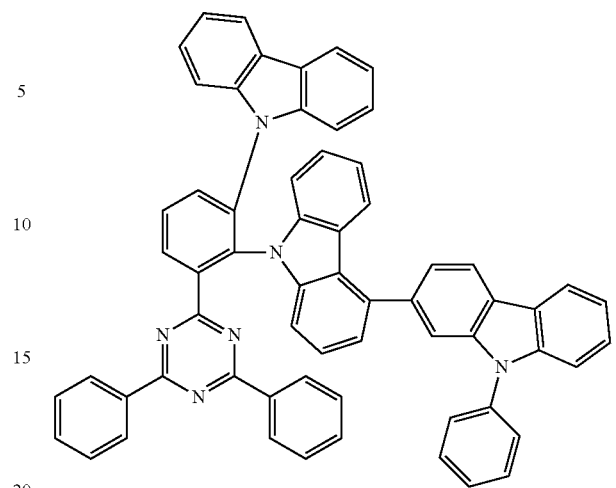
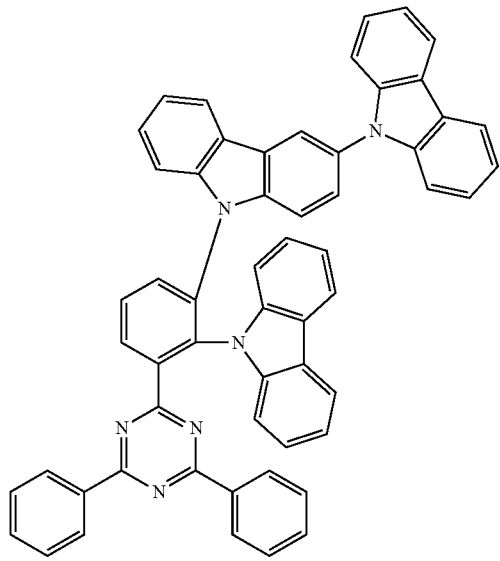
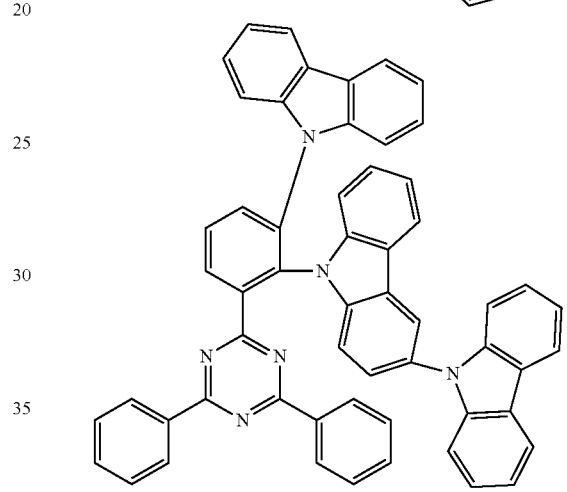
[Formula 102]
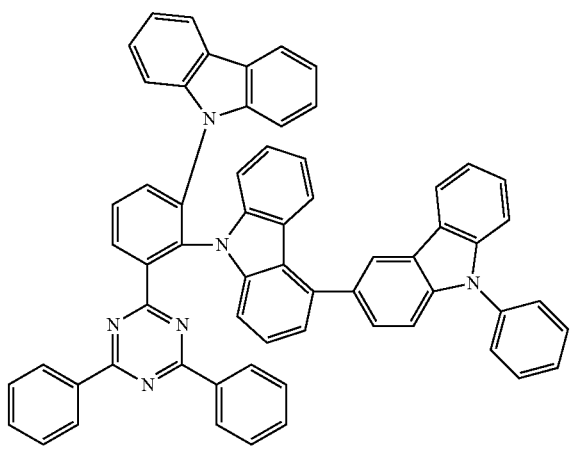
[Formula 103]
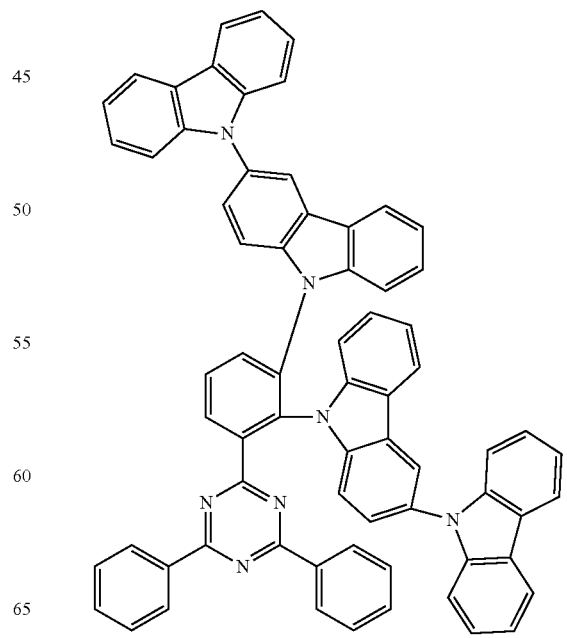

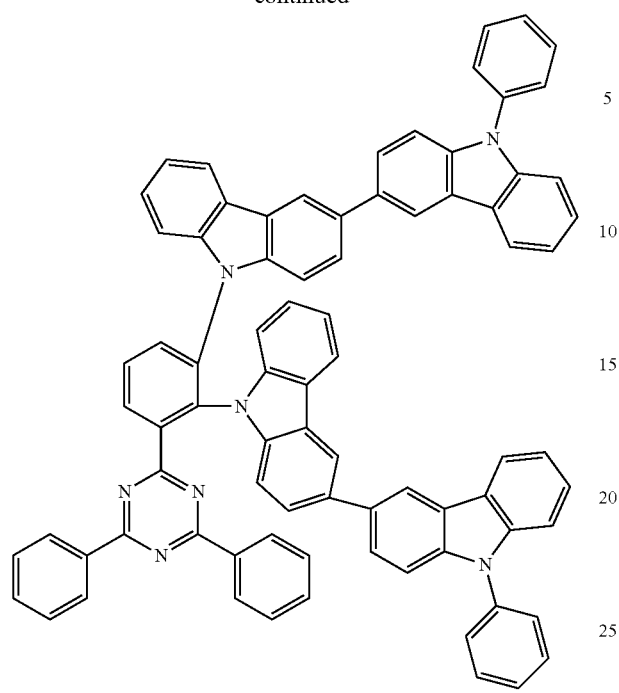
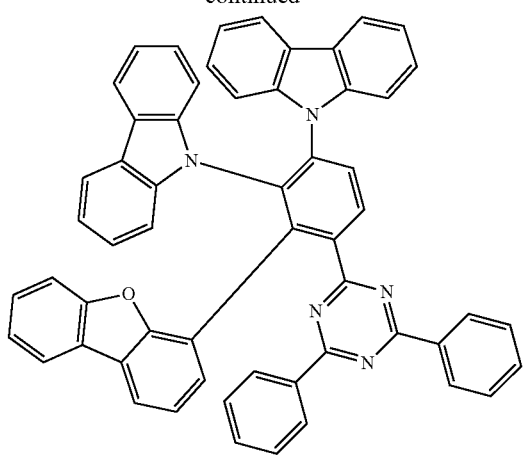
[Formula 105]
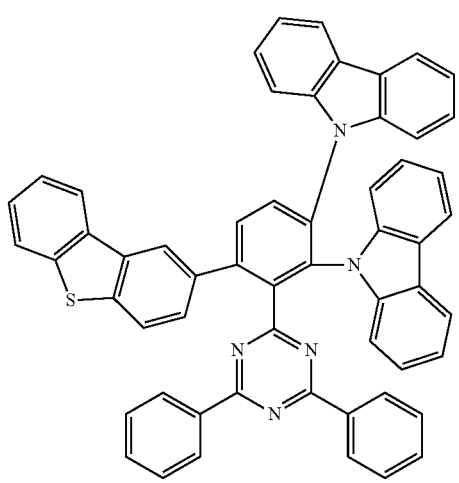
[Formula 104]
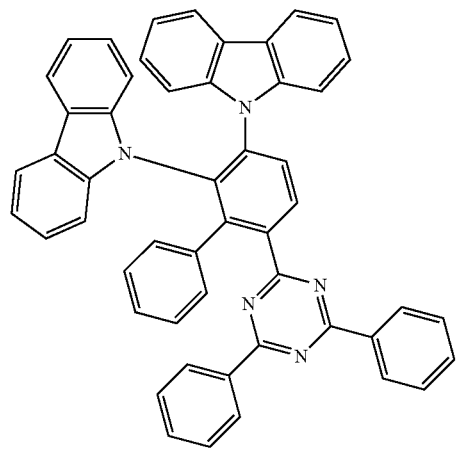
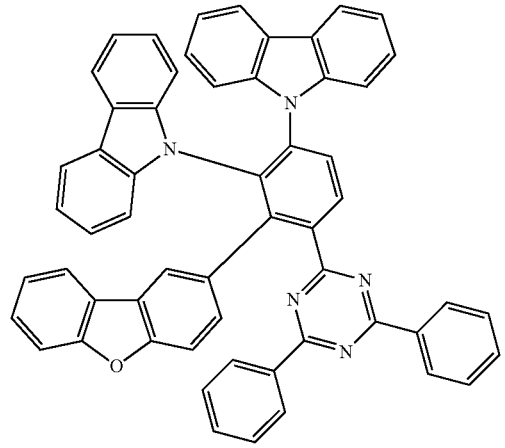
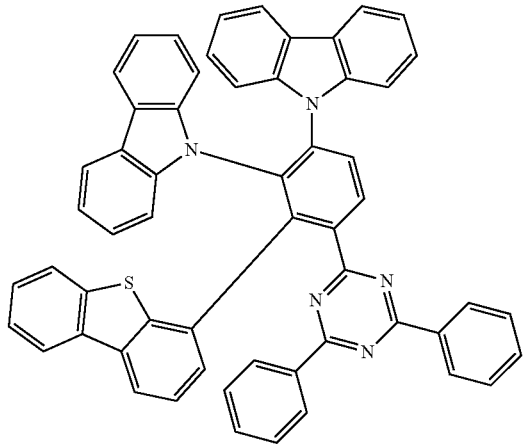

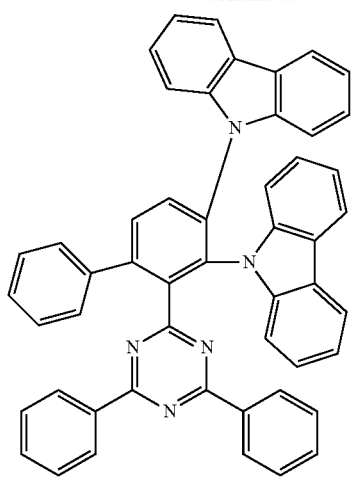
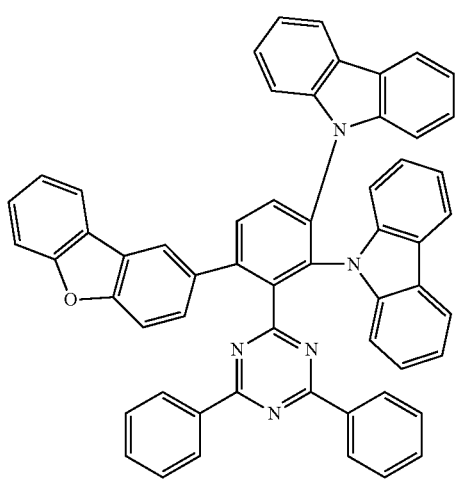
[Formula 106]
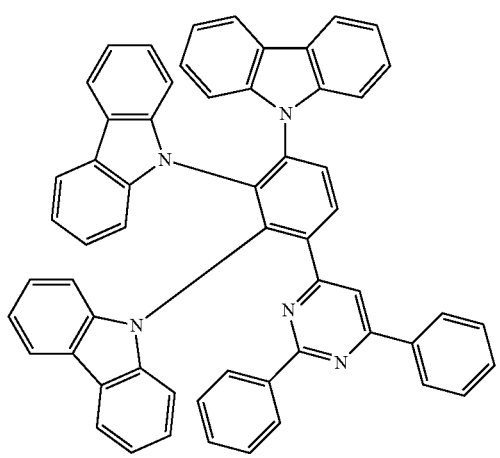
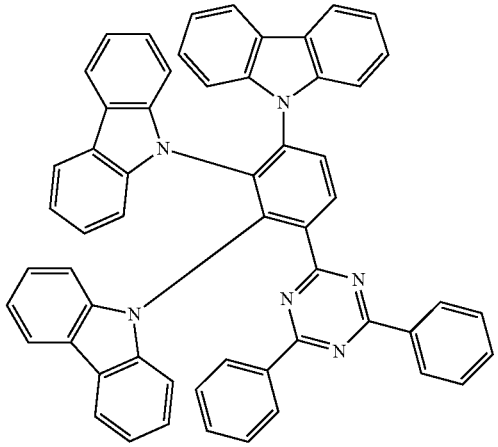
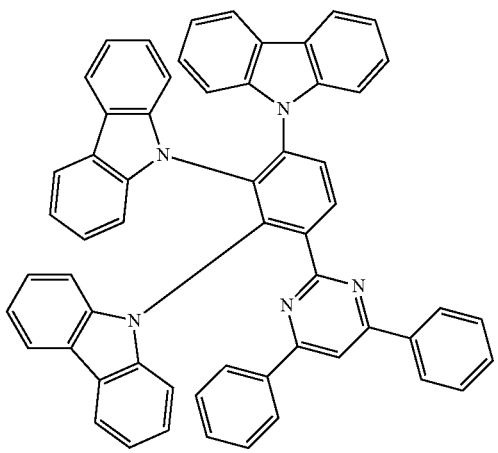
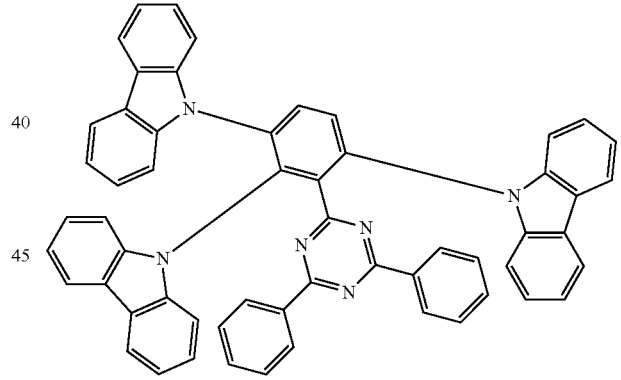
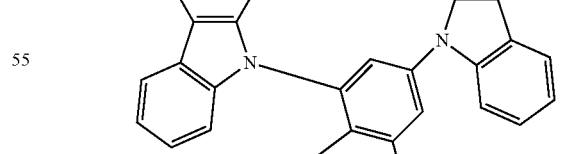
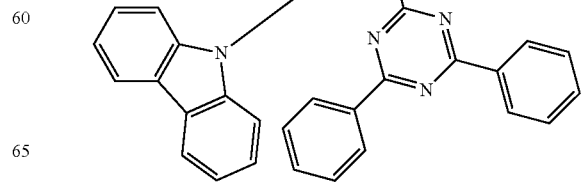

141
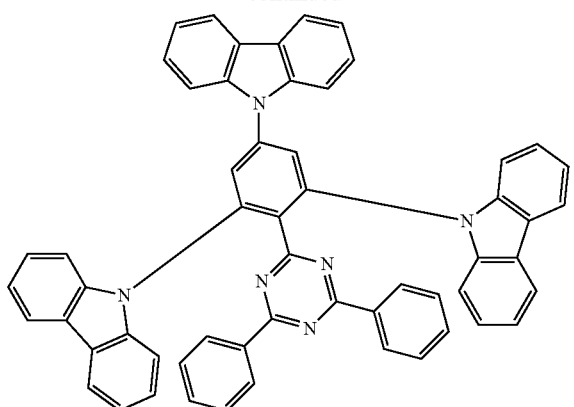
142
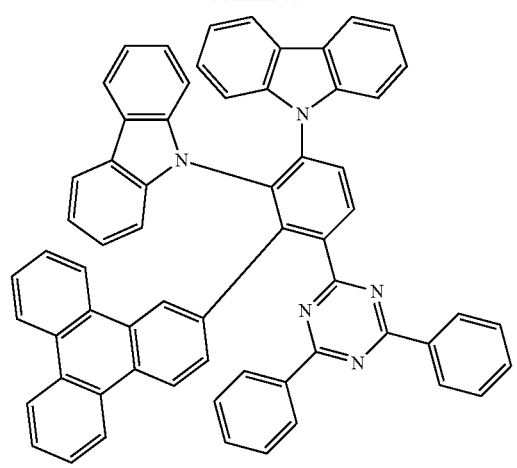
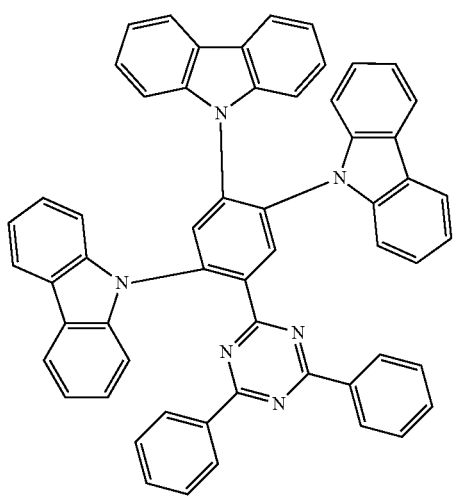
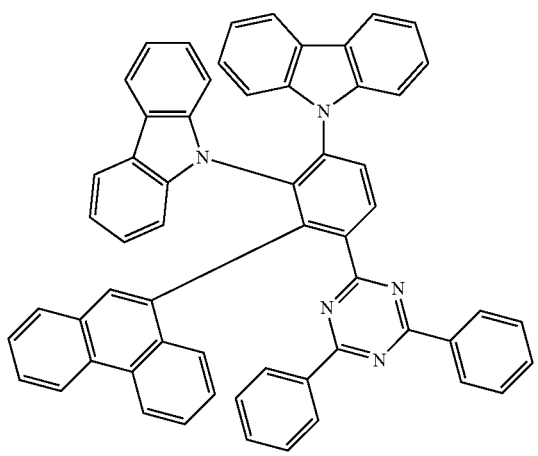
[Formula 107]
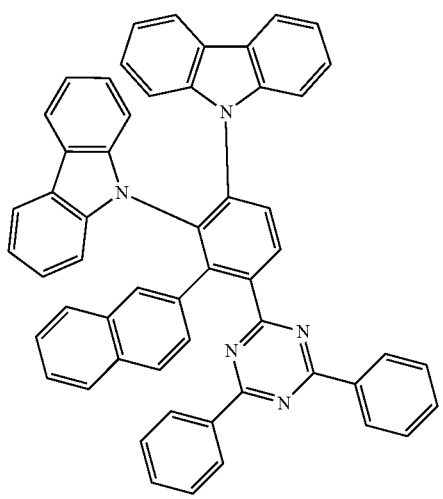
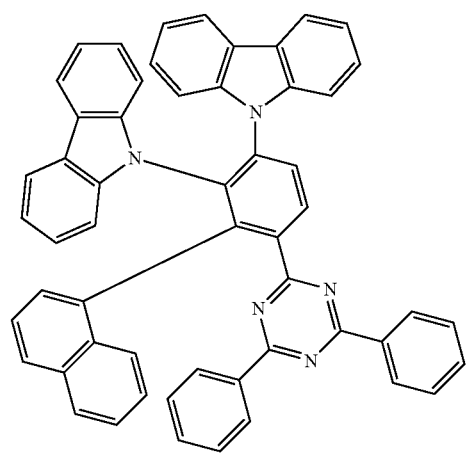

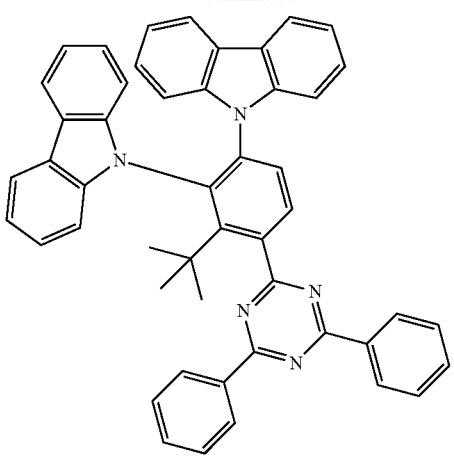
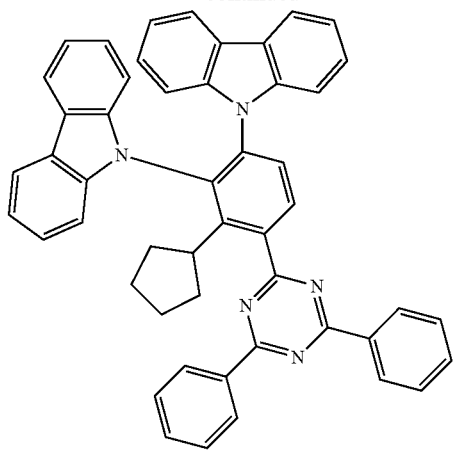
[Formula 108]
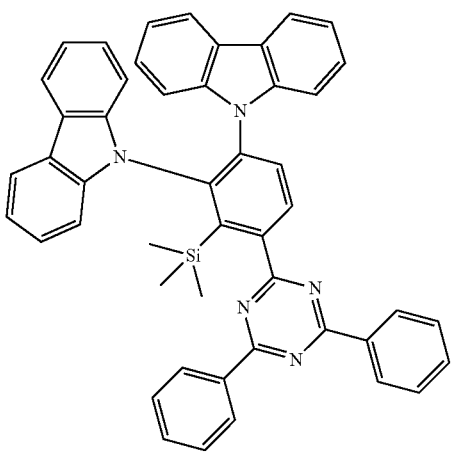
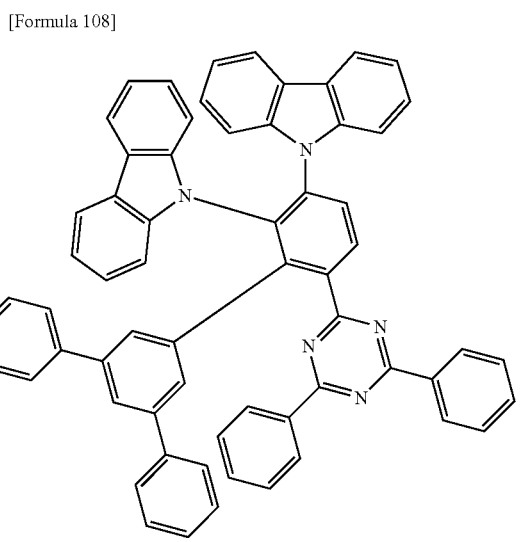
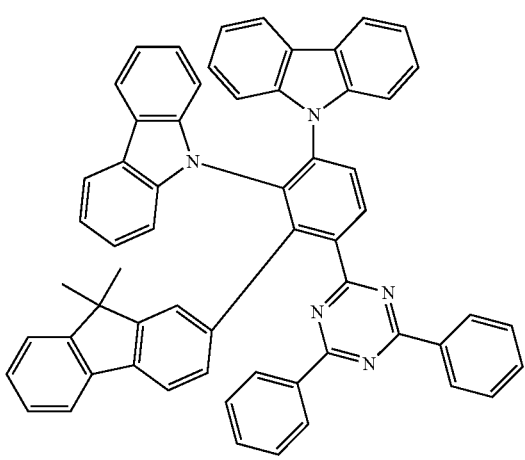
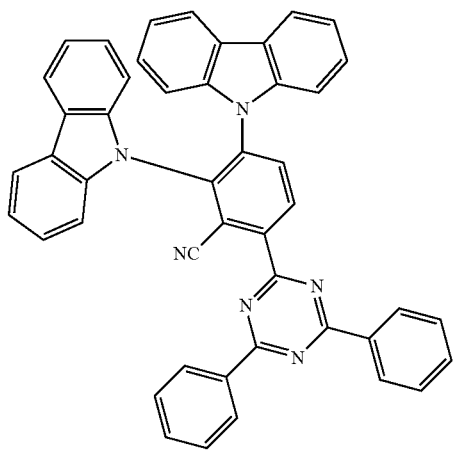

[Formula 109]
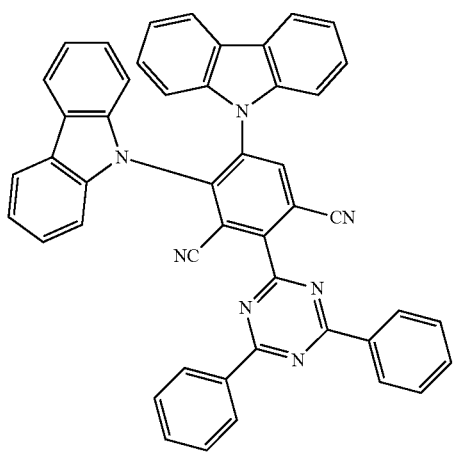
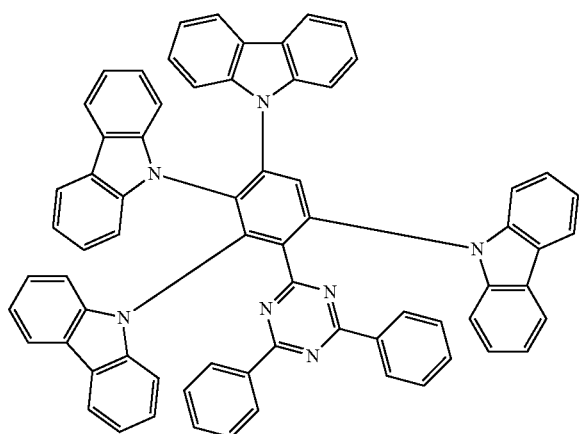
[Formula 110]
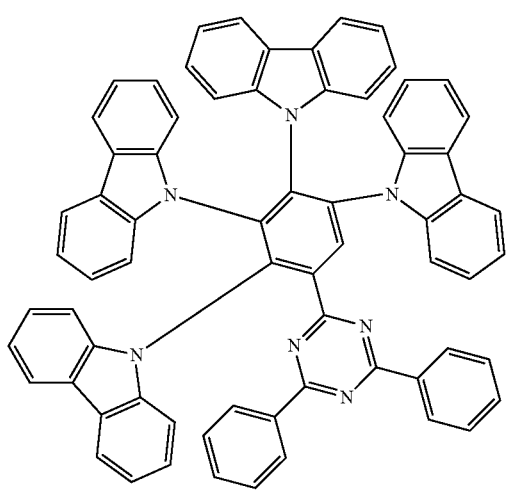

-continued
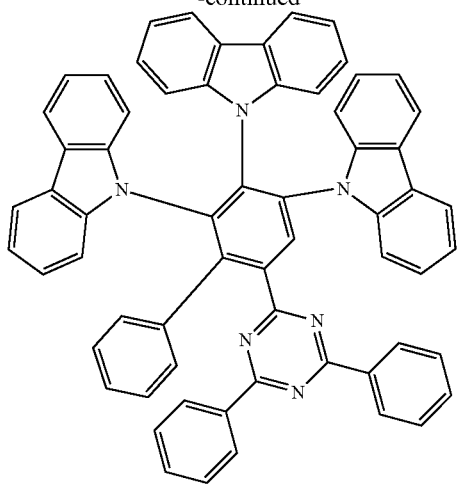
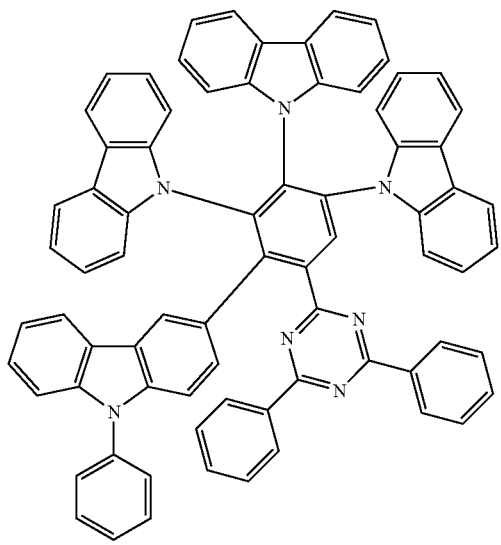
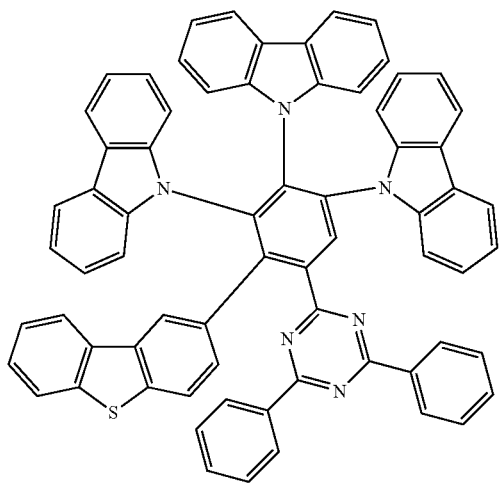
-continued
[Formula 111]
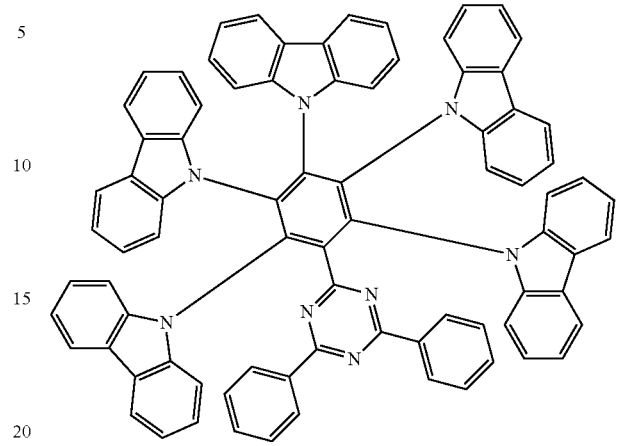
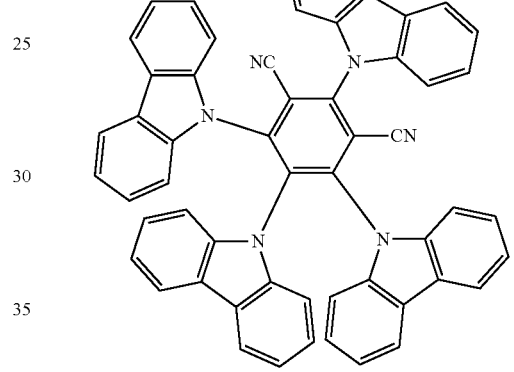
[Formula 112]
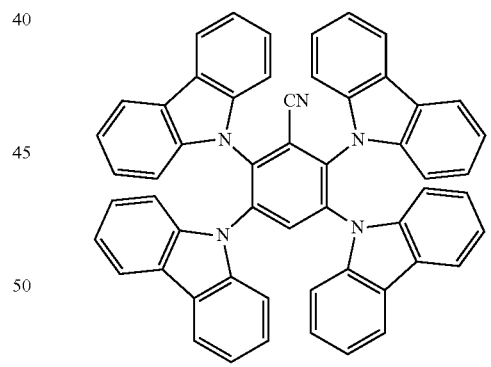
[Formula 113]
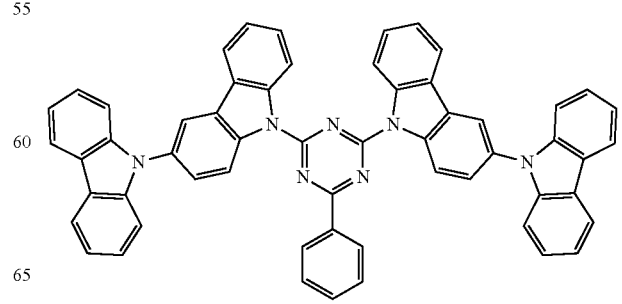

149
-continued
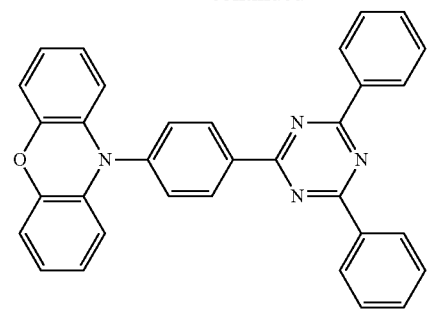
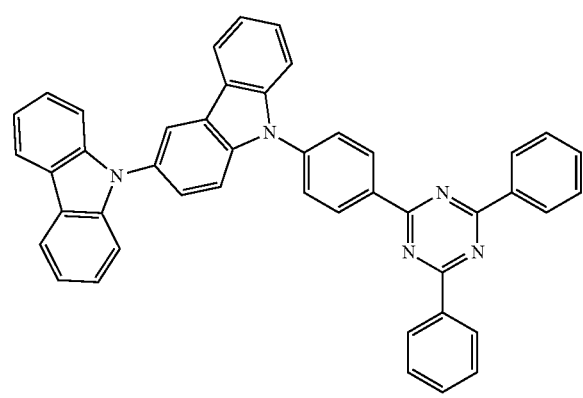
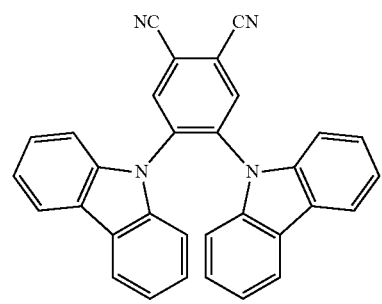
[Formula 114]
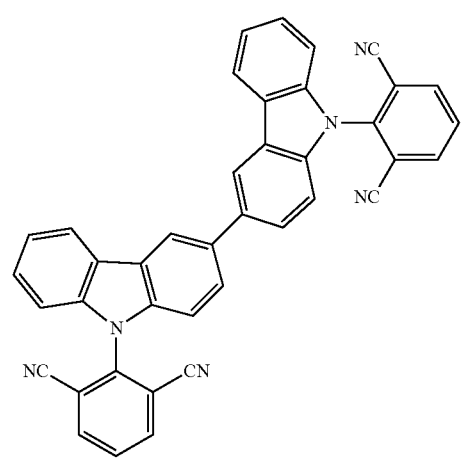
150
-continued
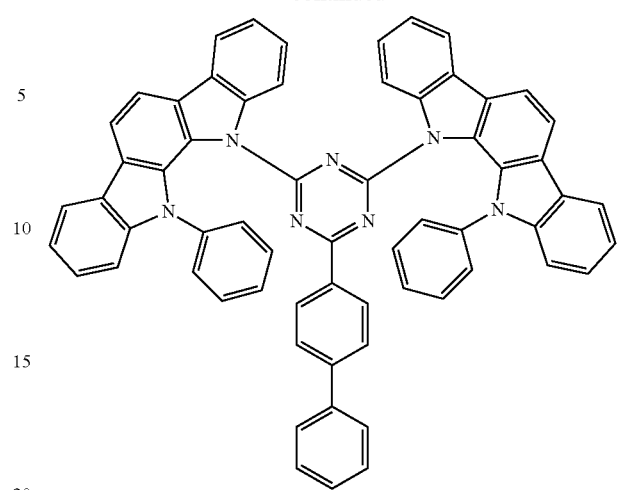
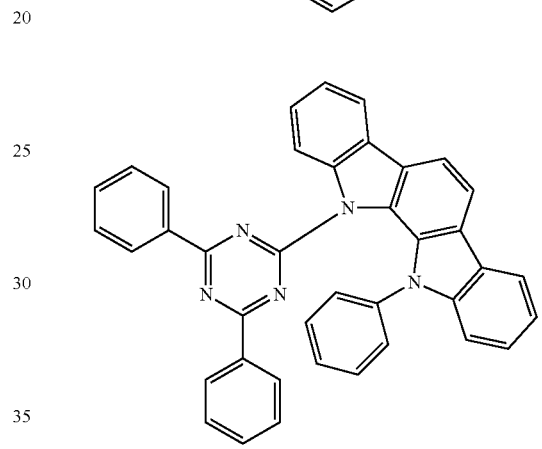
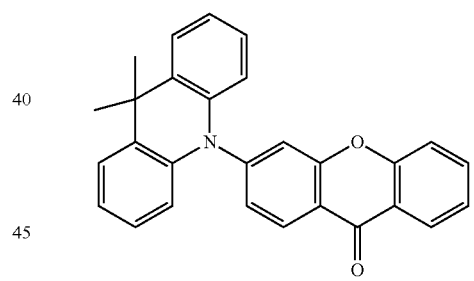
[Formula 115]
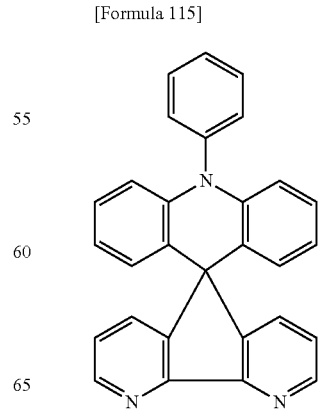

151
-continued
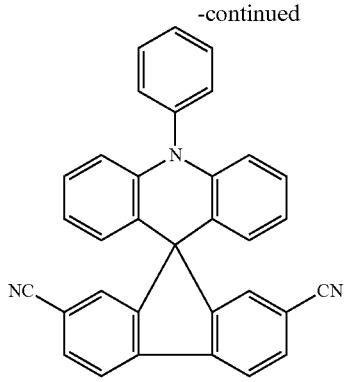
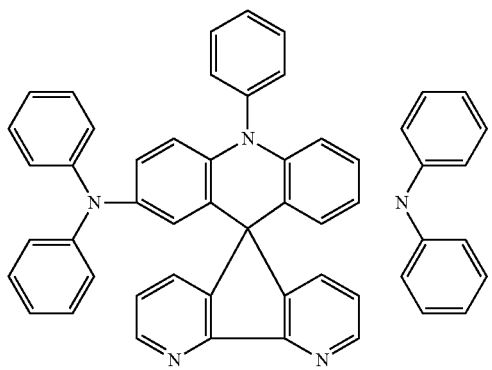
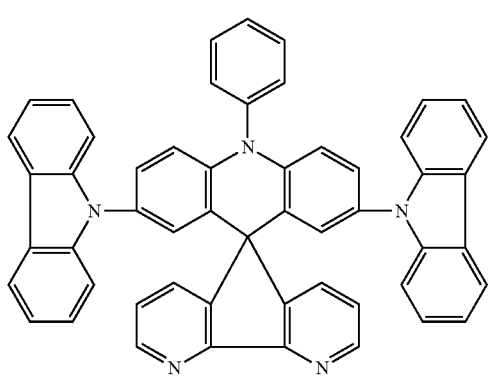
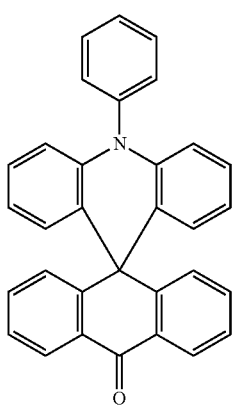
152
-continued
[Formula 116]
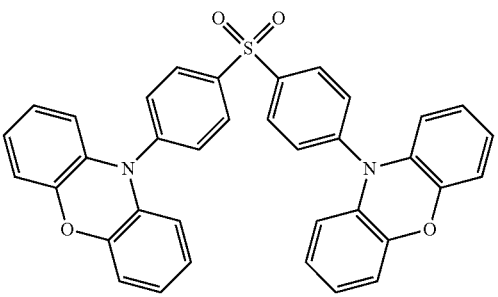
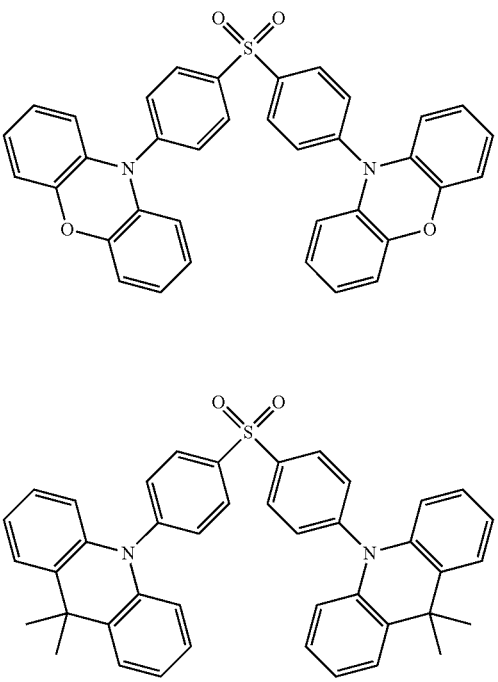
[Formula 117]
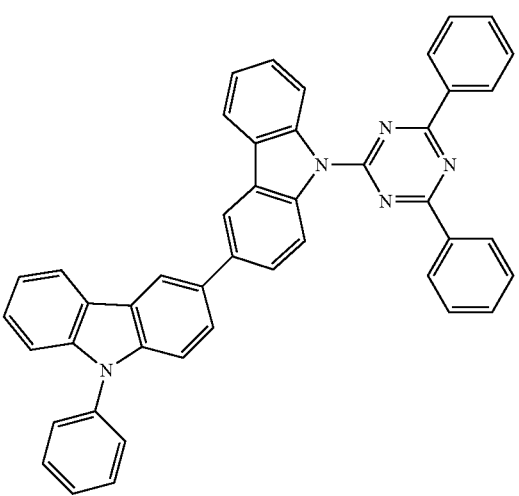

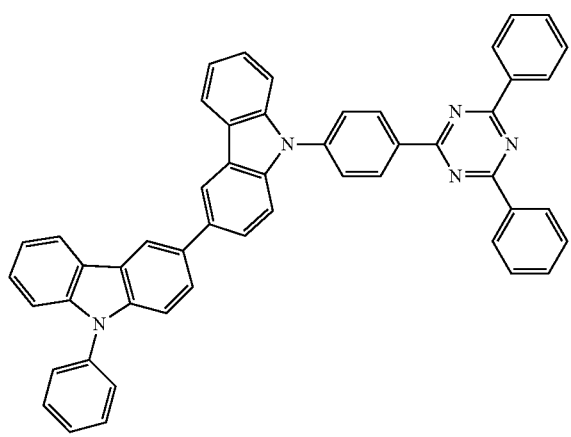
[Formula 118]
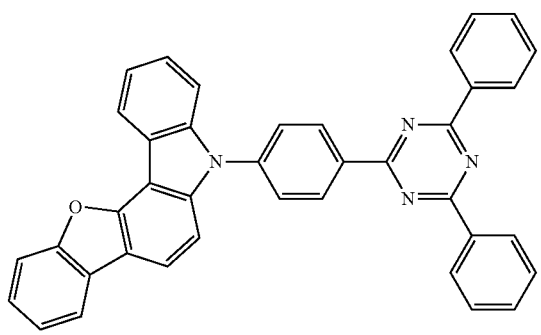
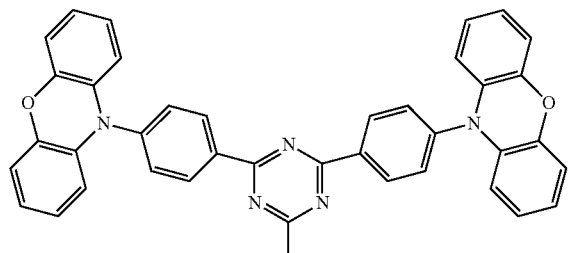
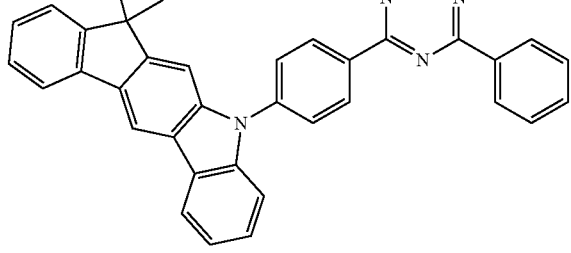
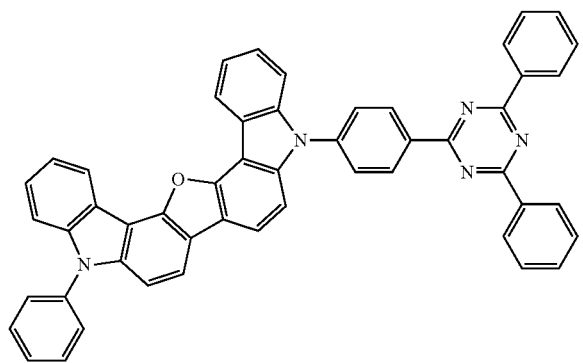
[Formula 119]
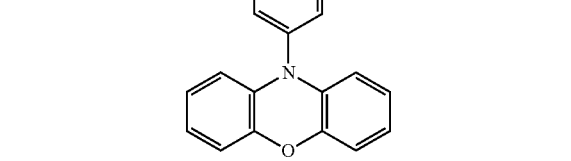

[Formula 120]
[Formula 121]
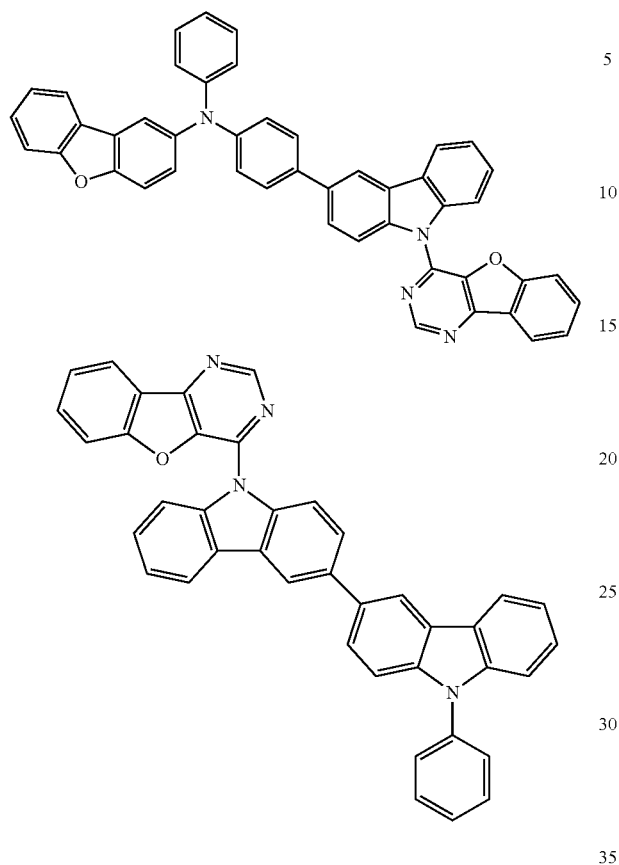
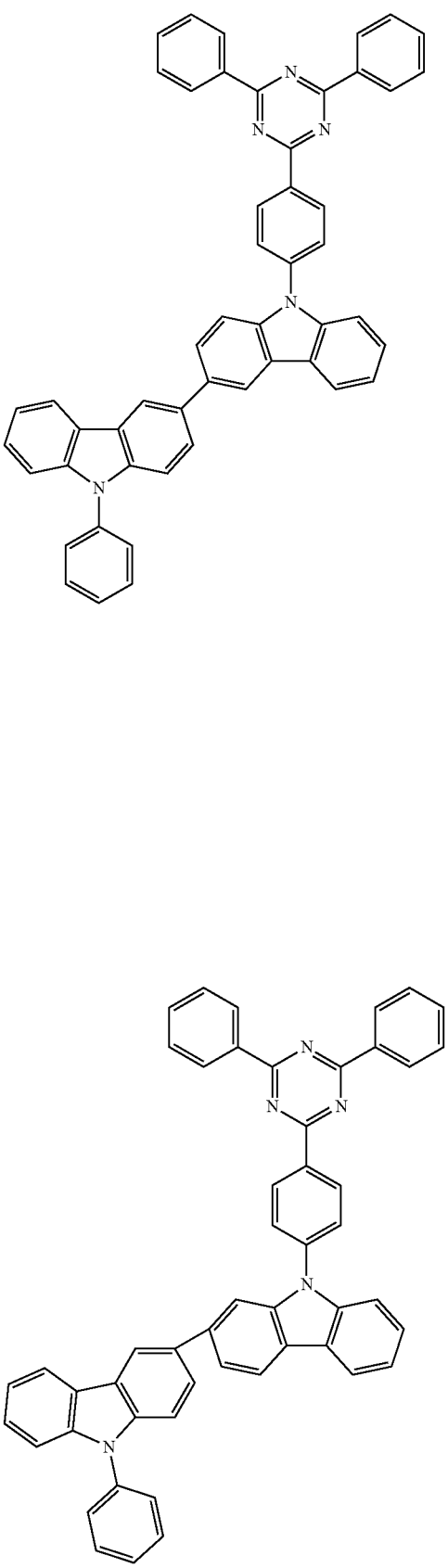

157
-continued
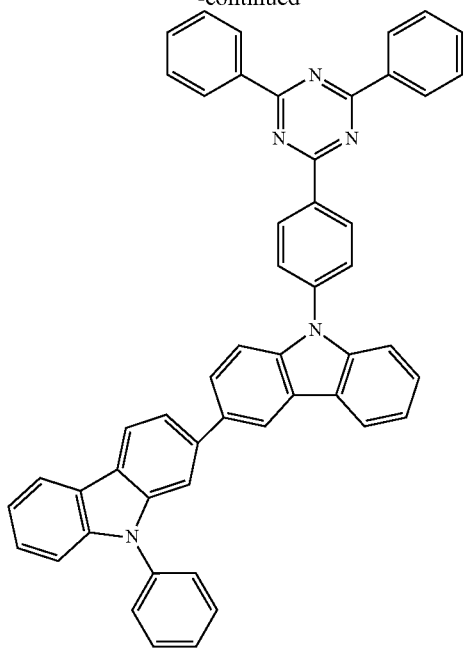
158
-continued
[Formula 122]
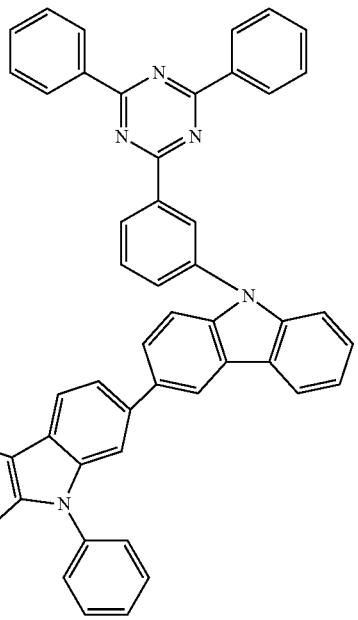
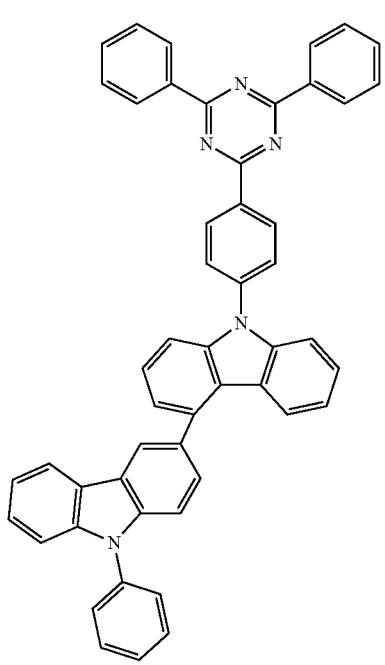

159
-continued
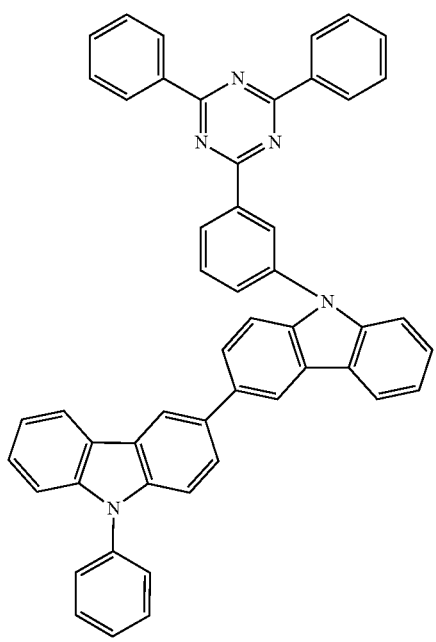
160
-continued
[Formula 123]
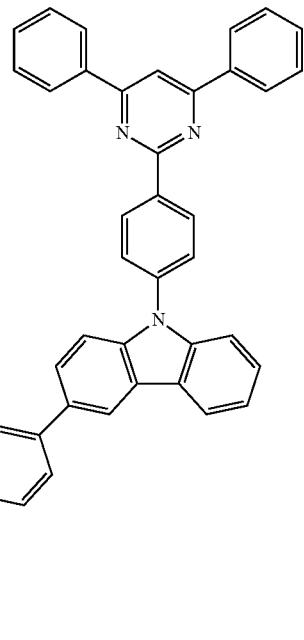
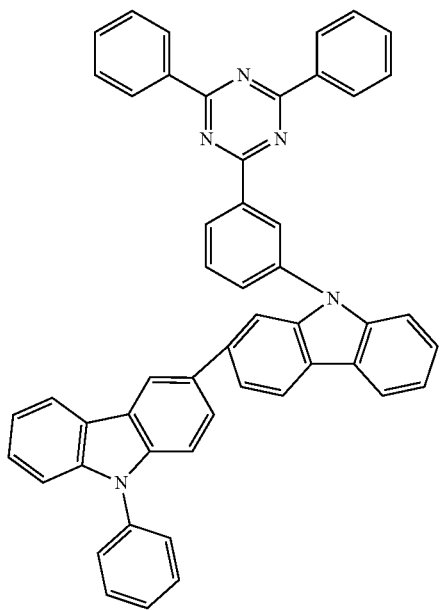
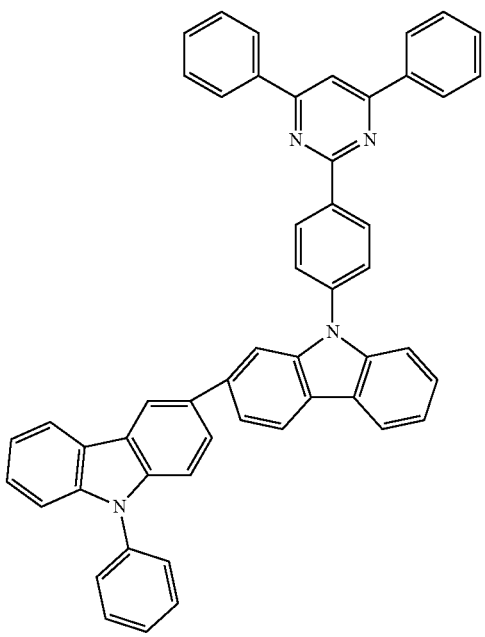

161
-continued
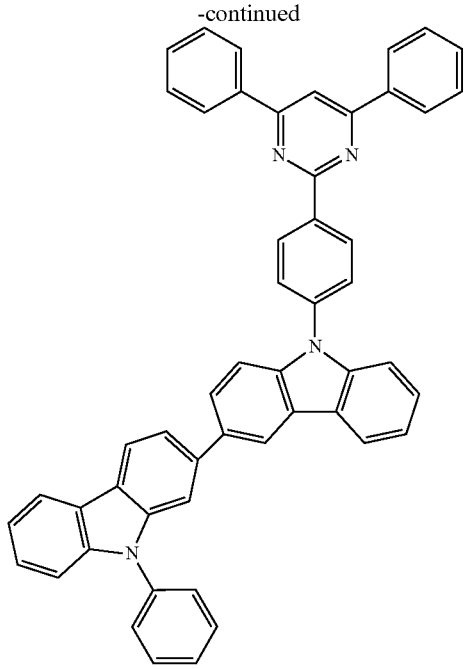
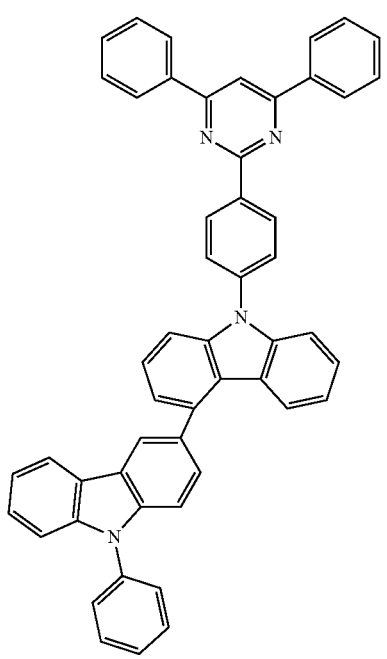
162
-continued
[Formula 124]
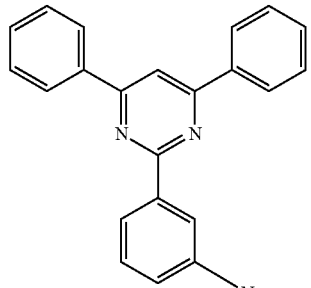
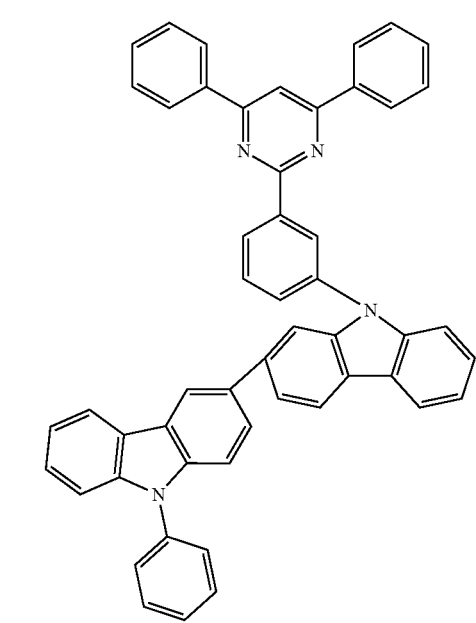

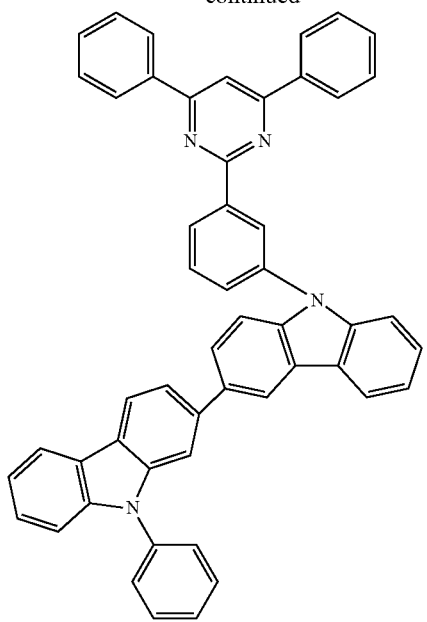
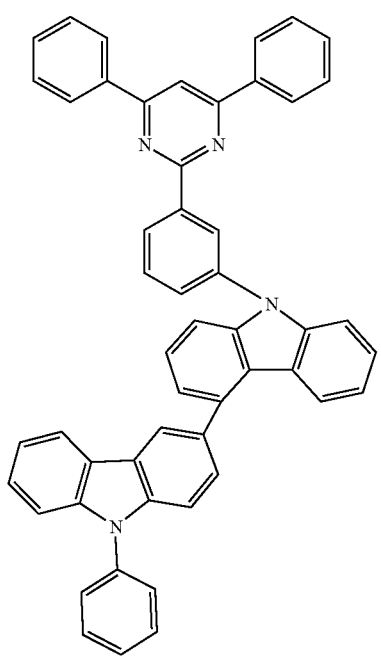
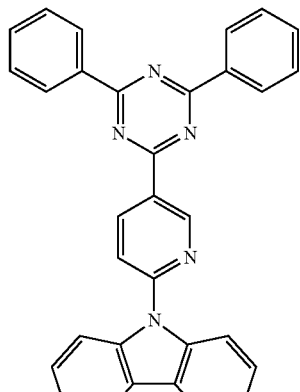
[Formula 125]
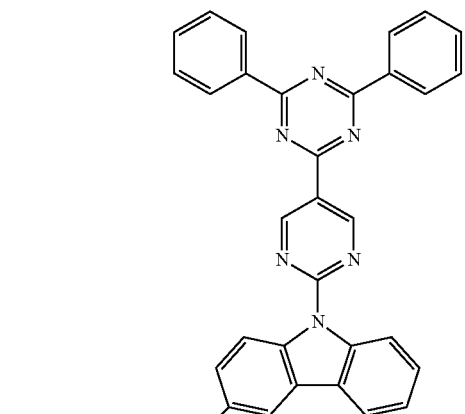
[Formula 126]
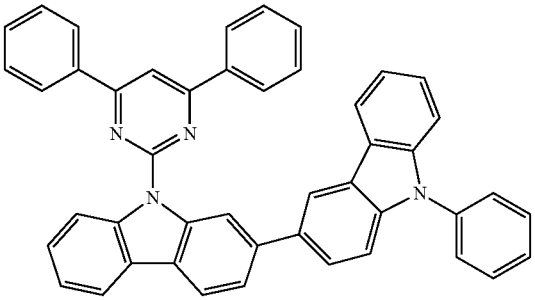

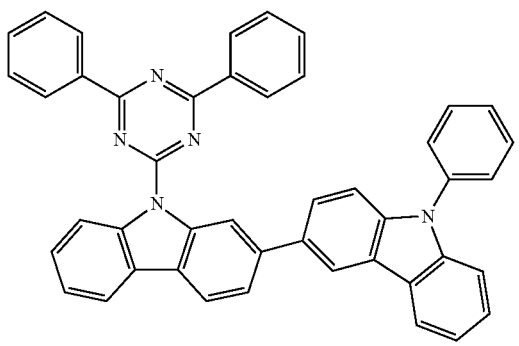
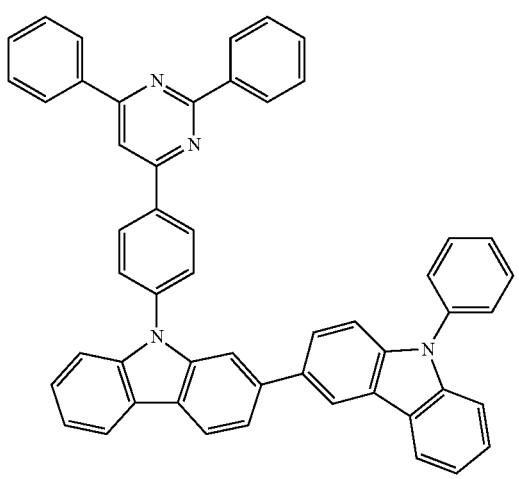
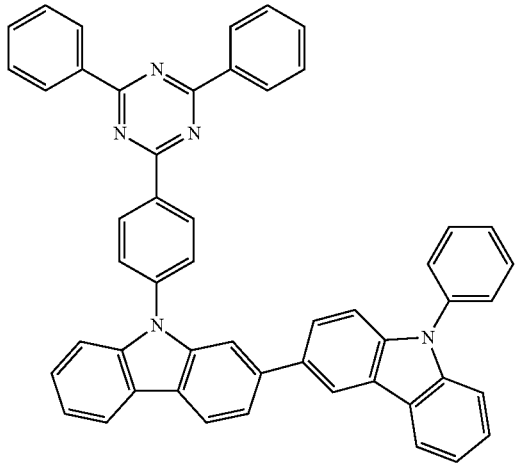
[Formula 127]
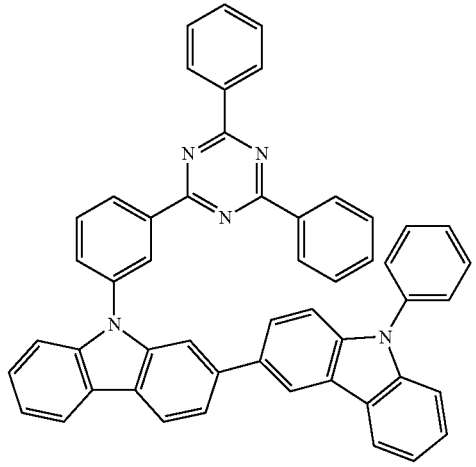
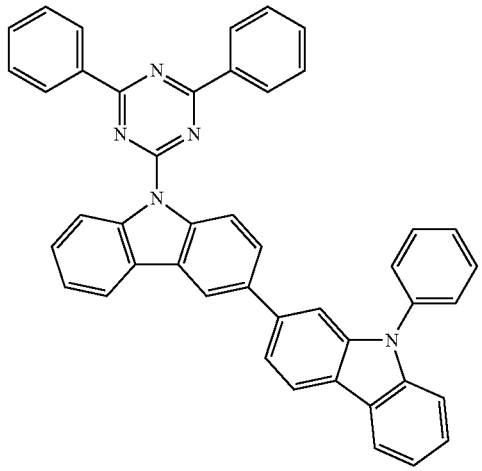
[Formula 128]
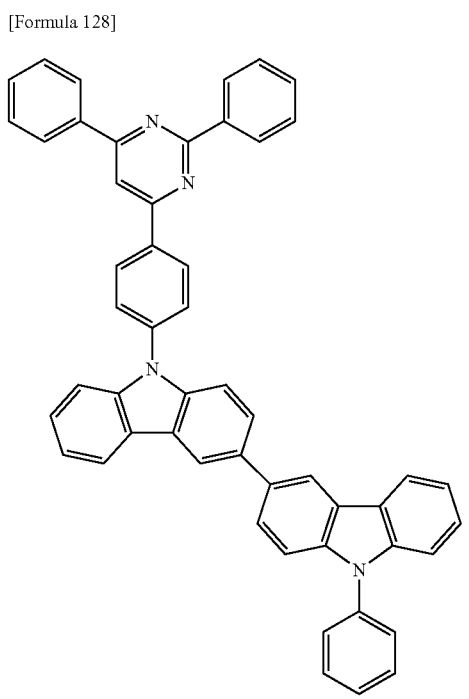

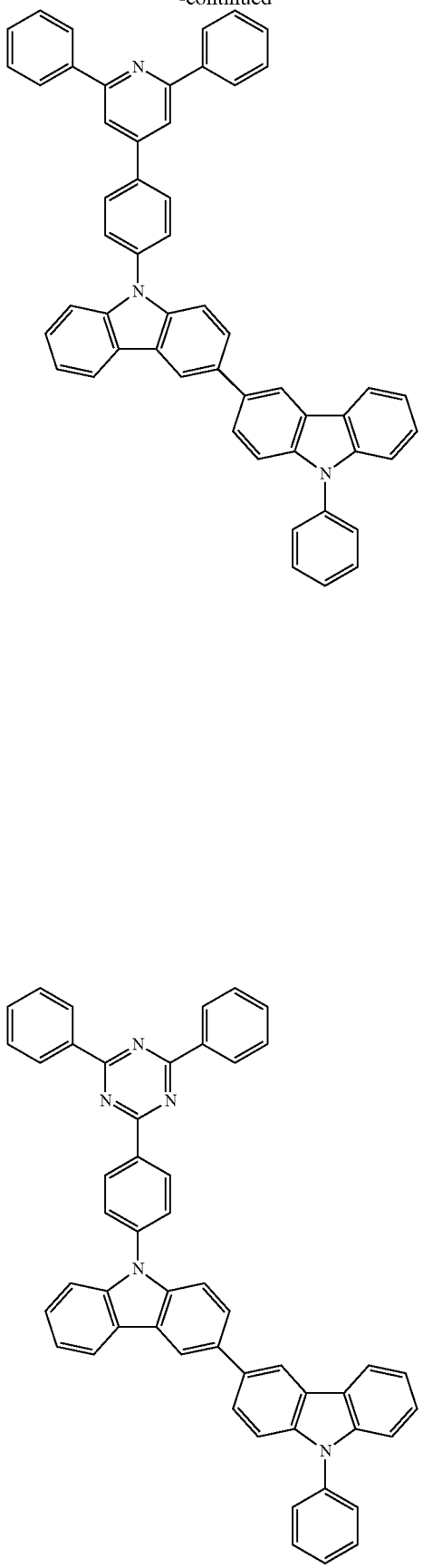
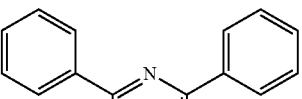
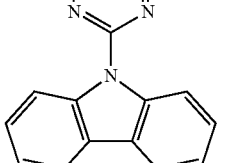
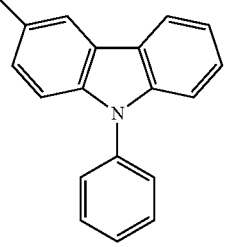
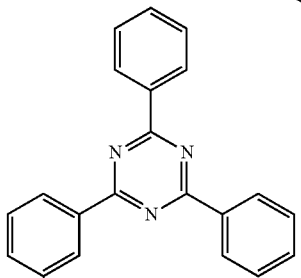
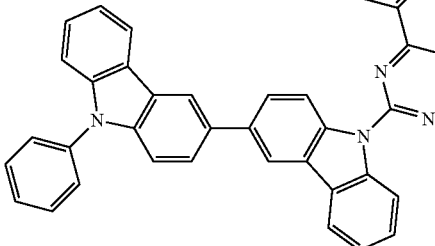
In the organic electroluminescence device of the exemplary embodiment, it is also preferable that the emitting layer contains the first compound in a form of a compound represented by a formula (15) below, and the second compound.
This arrangement also can improve a luminous efficiency of an organic EL device.

[Formula 130]

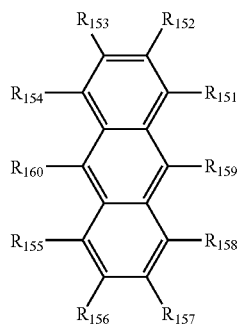

(15)

In the formula (15), $R_{151}$ to $R_{160}$ each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, —Si($R_{121}$)($R_{122}$)($R_{123}$), —C(=O)$R_{124}$, —COOR$_{125}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by -$L_{101}$-$Ar_{101}$.

In the formula (15), $R_{121}$ to $R_{125}$ each independently represent a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

At least one of $R_{151}$ to $R_{160}$ is a group represented by -$L_{101}$-$Ar_{101}$. $L_{101}$ represents a single bond, a substituted or unsubstituted arylene group having 6 to ring carbon atoms, or a substituted or unsubstituted heteroarylene group having to 30 ring atoms. $Ar_{101}$ represents a substituted or unsubstituted aryl group having 6 to 50 ring carbon atoms, or a substituted or unsubstituted heterocyclic group having 5 to 50 ring atoms.

When at least two of $L_{101}$ are present, the at least two of $L_{101}$ may be the same or different. When at least two of $Ar_{101}$ are present, the at least two of $Ar_{101}$ may be the same or different.

Among $R_{151}$ to $R_{160}$ in the formula (15), $R_{159}$ and $R_{160}$ are preferably each independently a group represented by -$L_{101}$-$Ar_{101}$, and at least one of $R_{159}$ and $R_{160}$ is preferably a group represented by -$L_{101}$-$Ar_{101}$.

Examples of the compound represented by the formula (15) include compounds shown below.

[Formula 131]

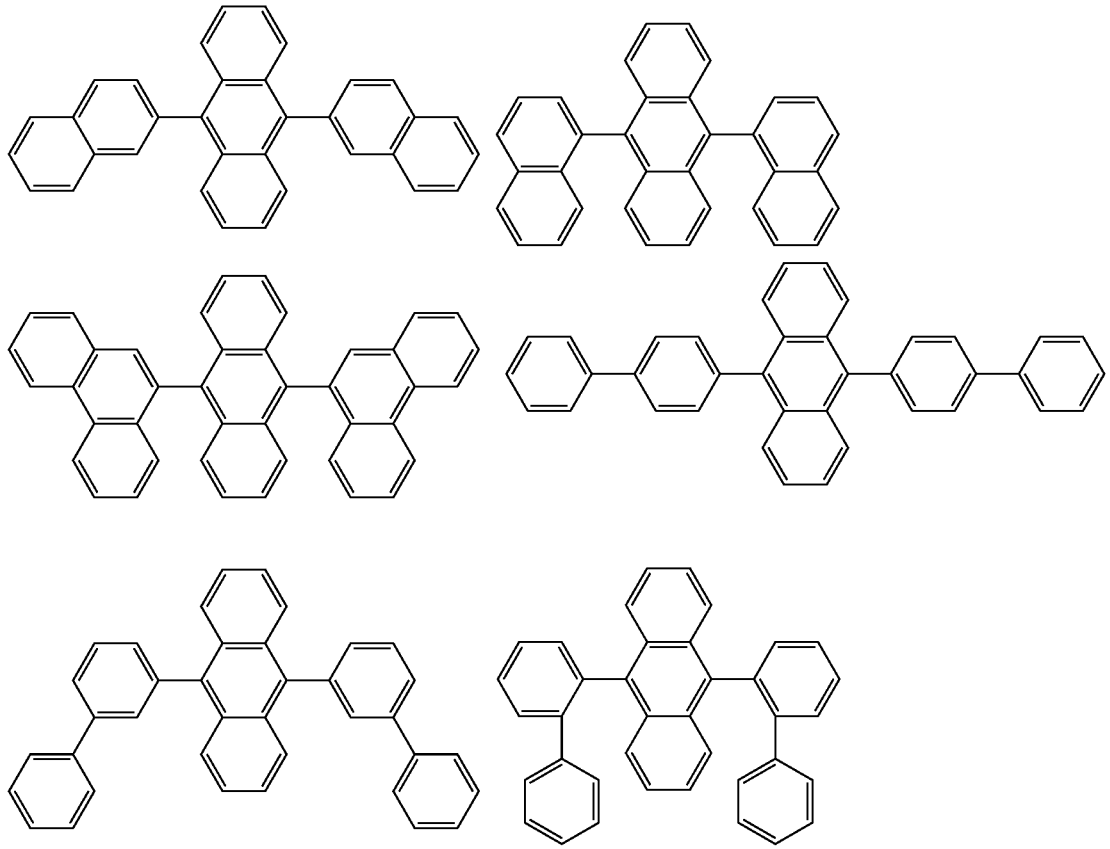

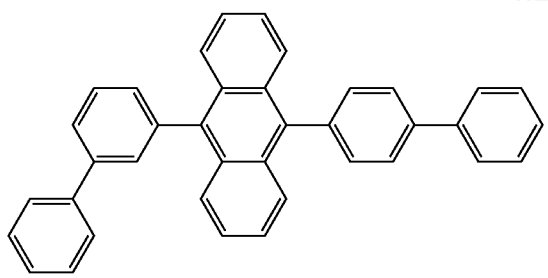
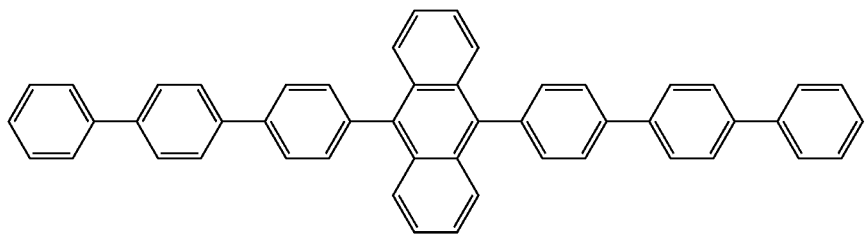
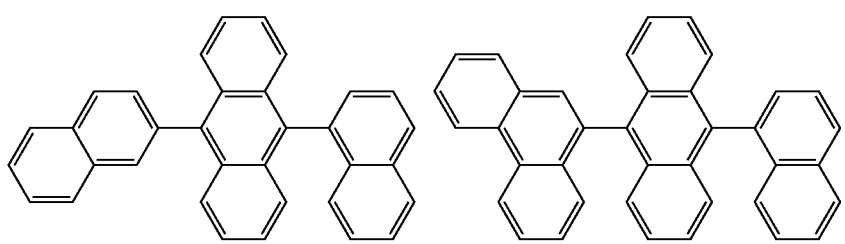
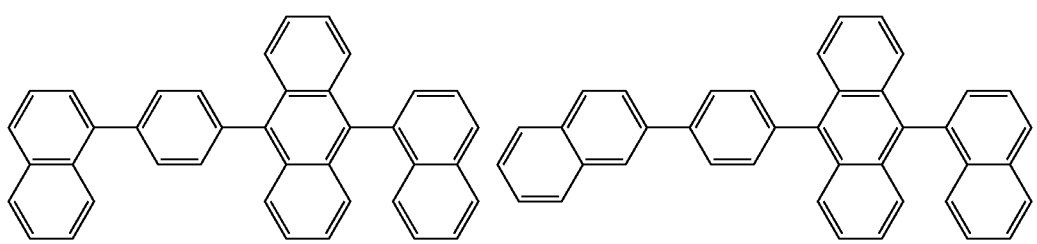
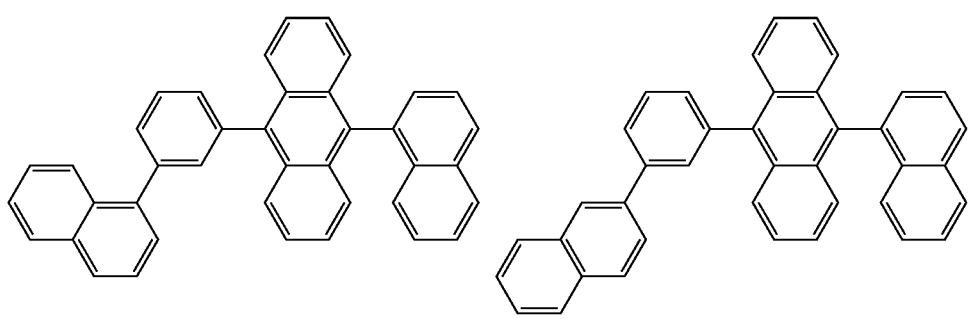
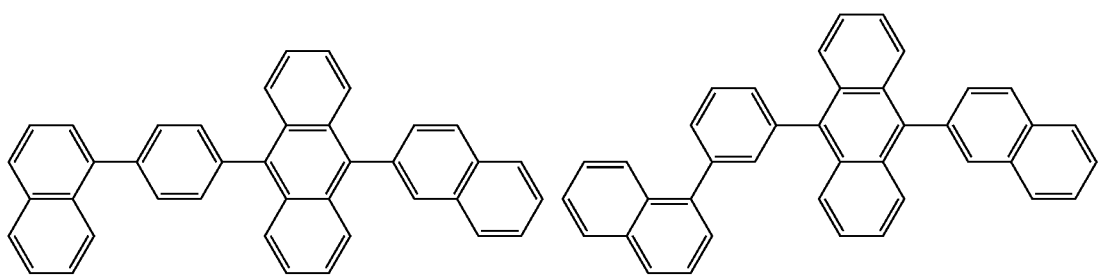

-continued
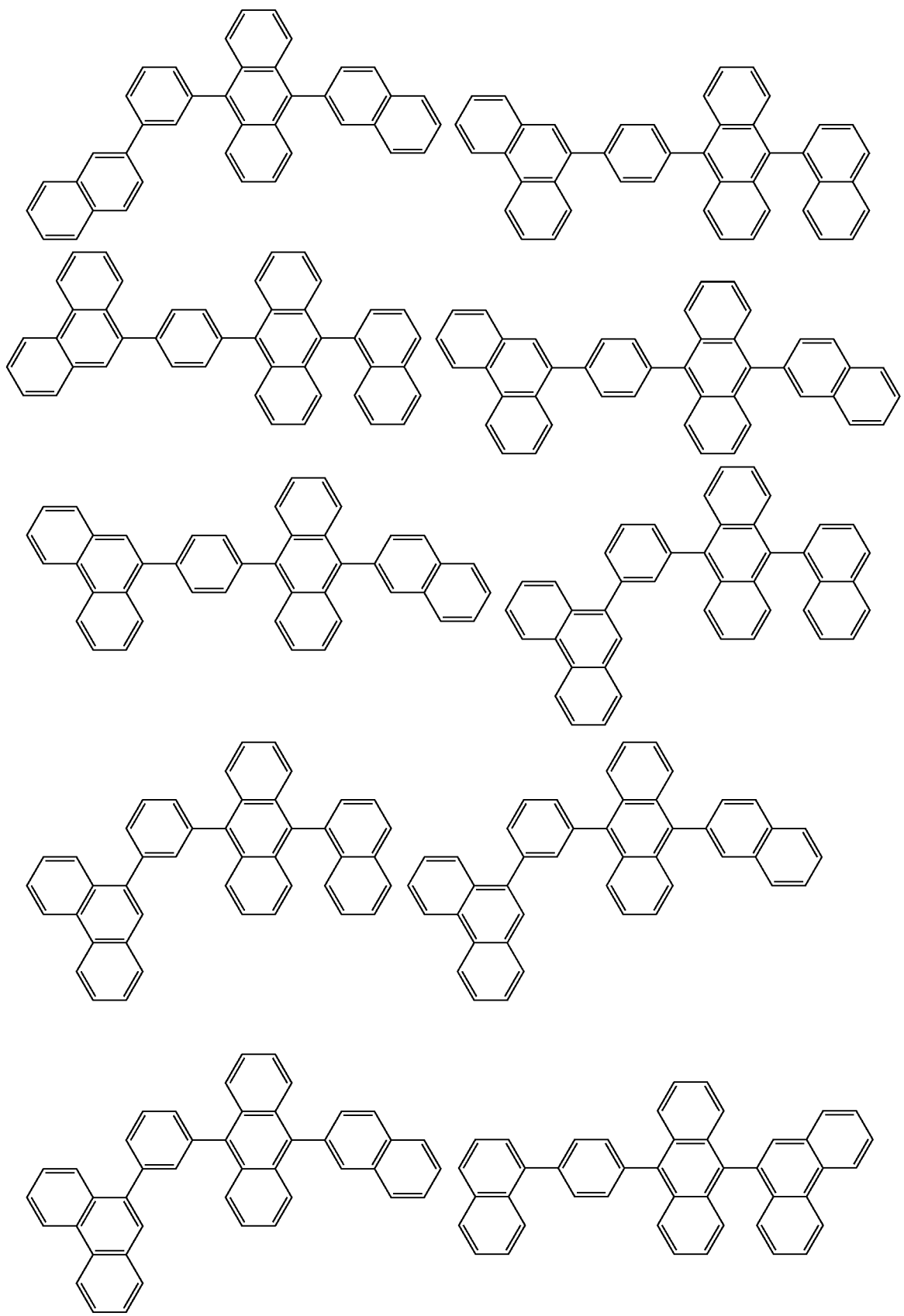

-continued
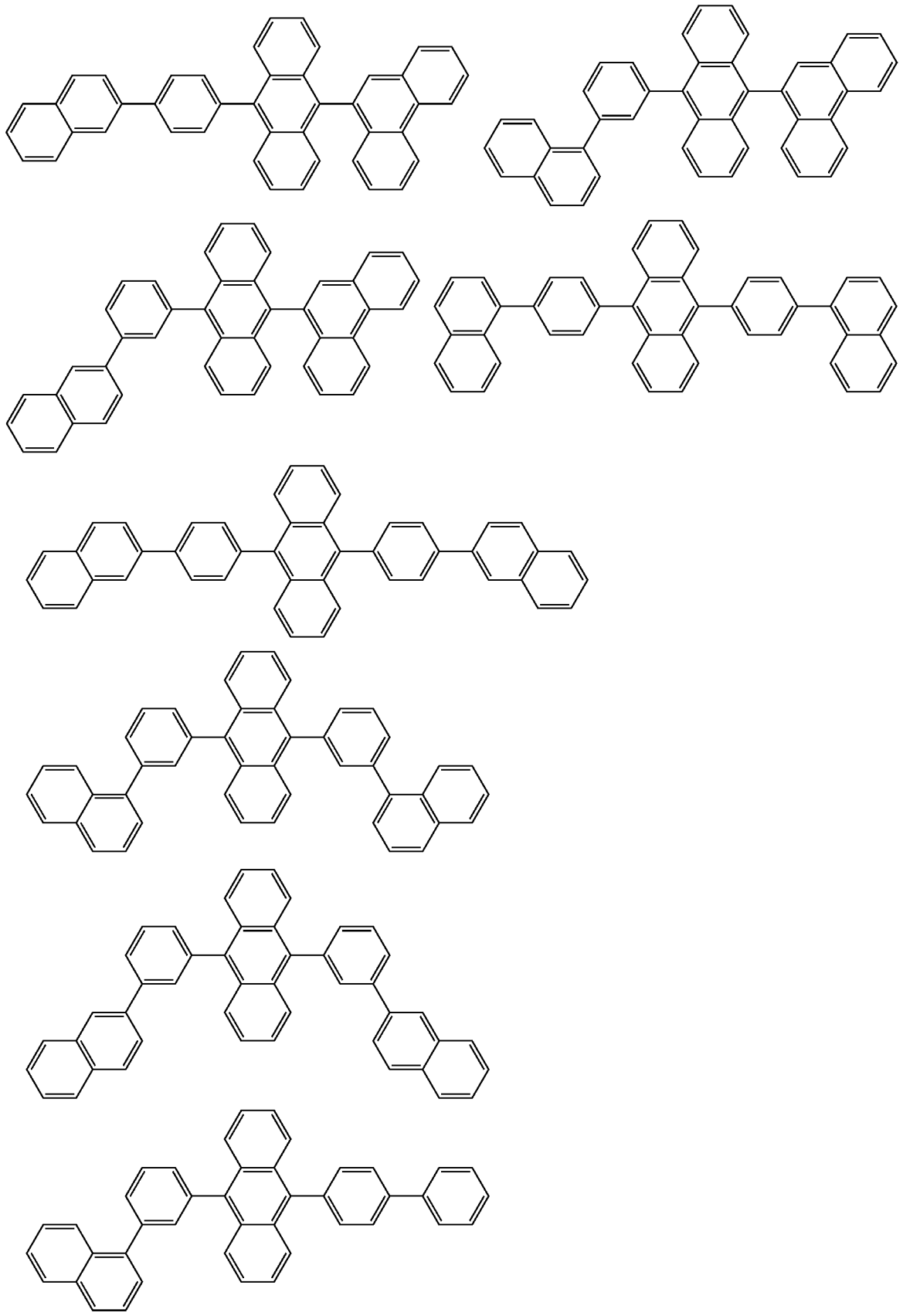

-continued
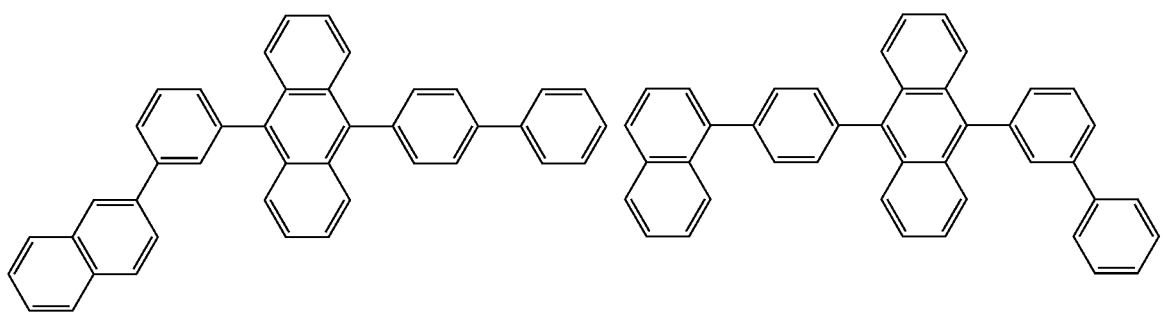
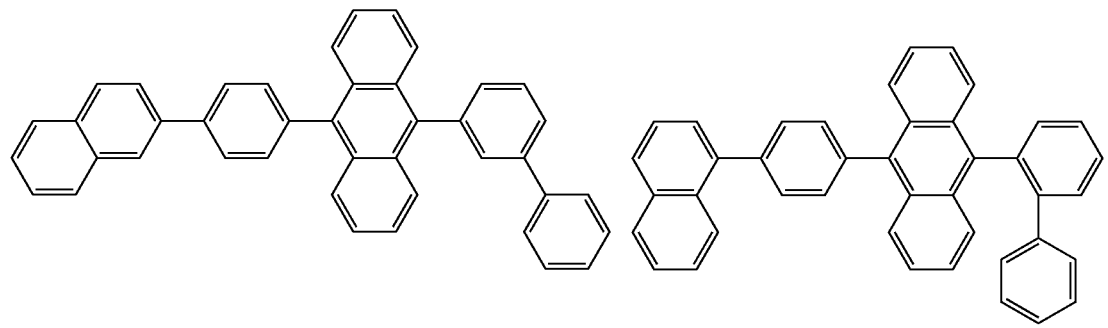
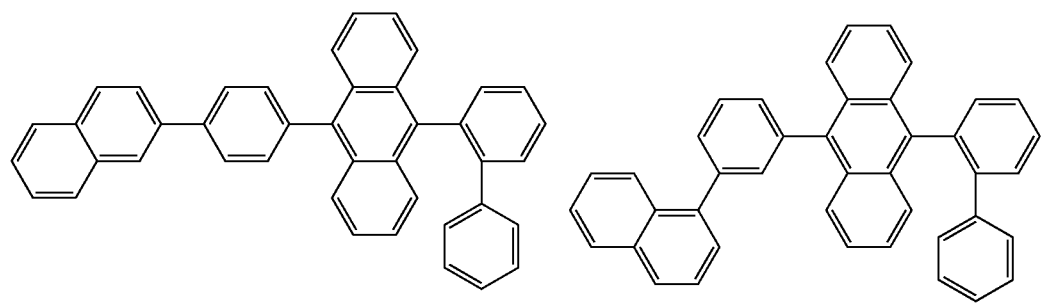
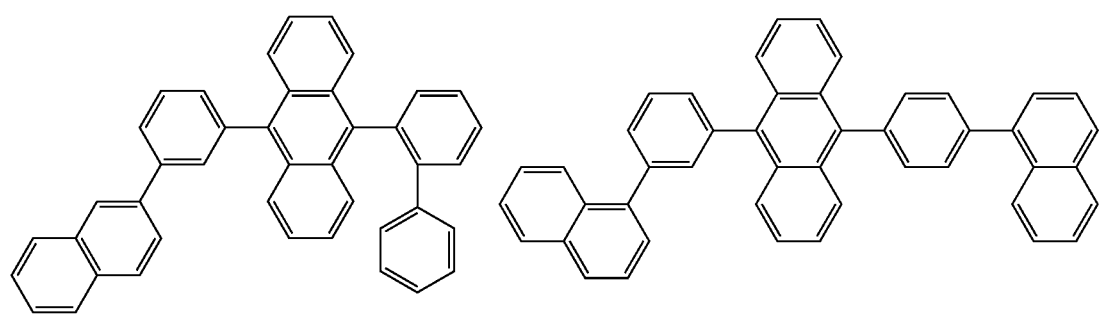
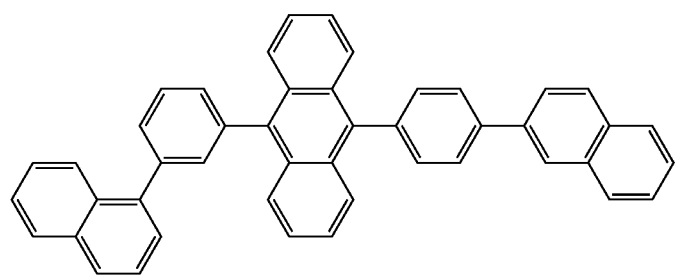

-continued
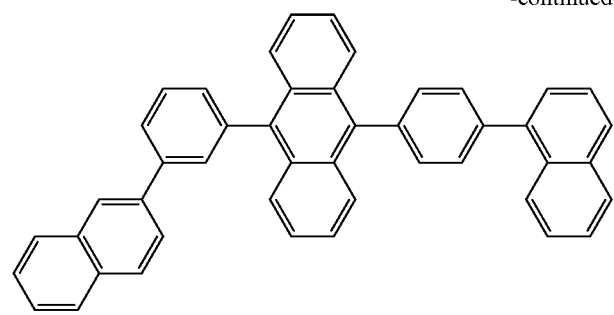
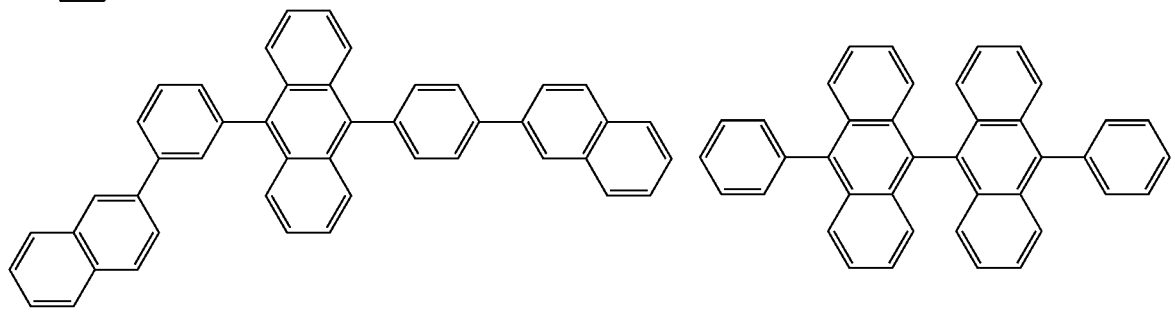
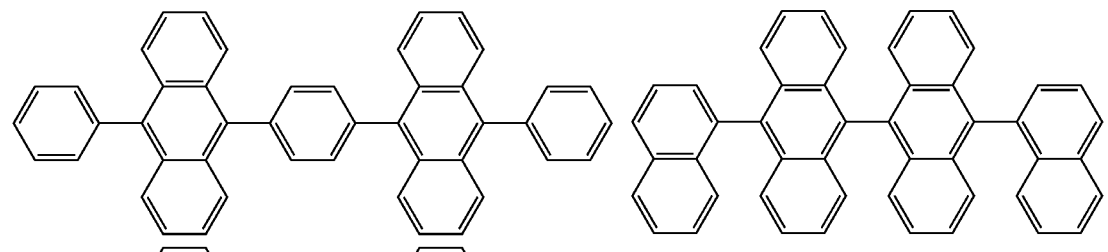
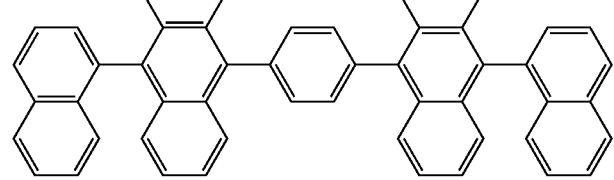
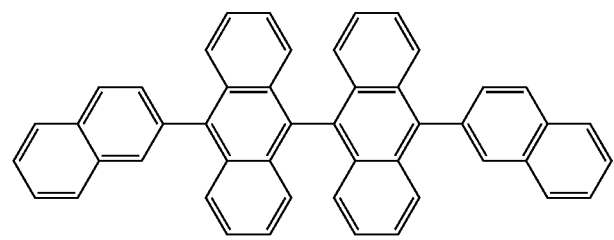
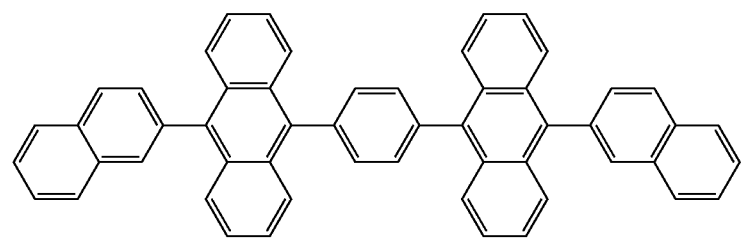

181
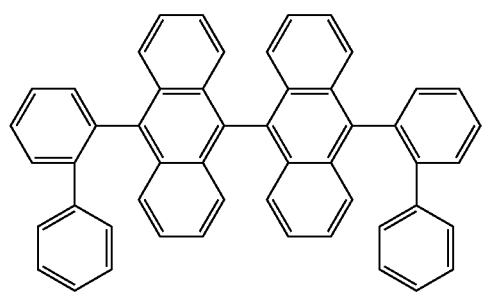
182
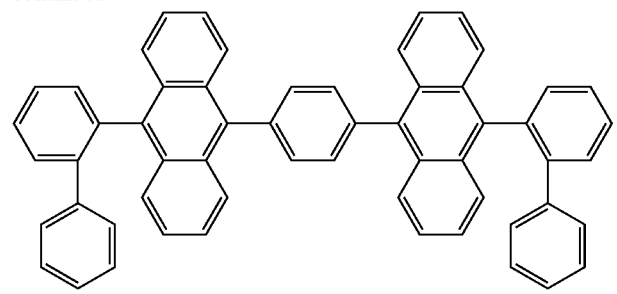
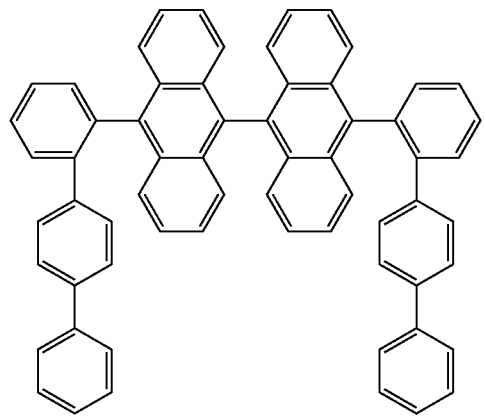
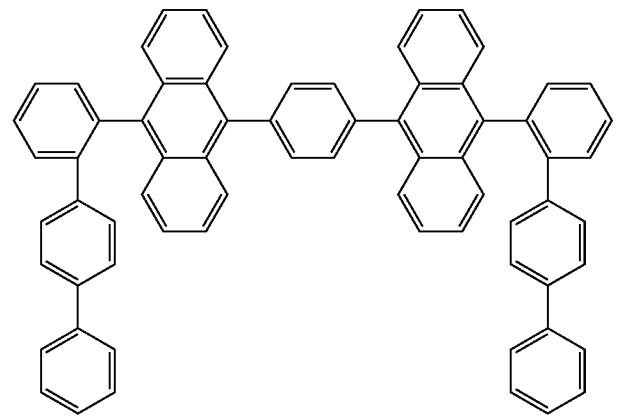
[Formula 132]
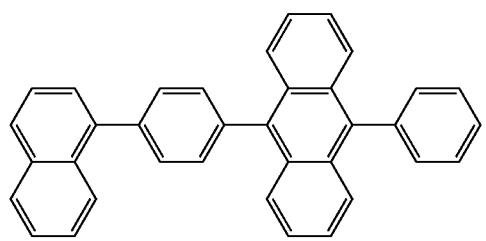
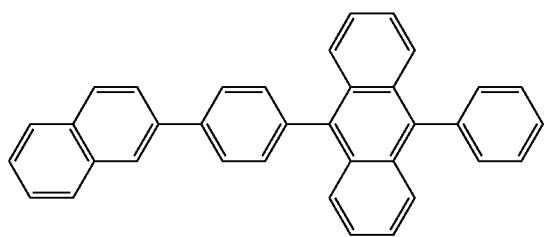
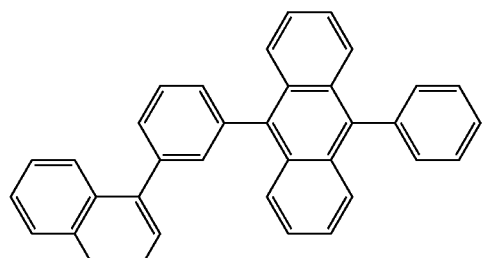
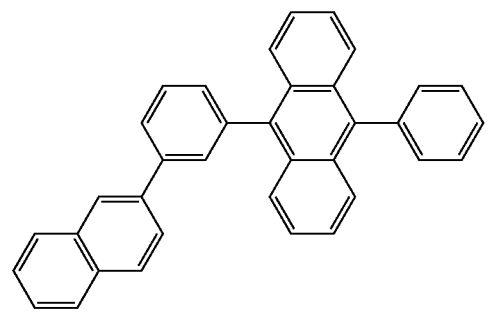
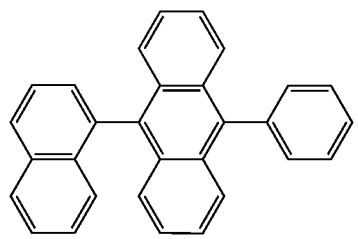
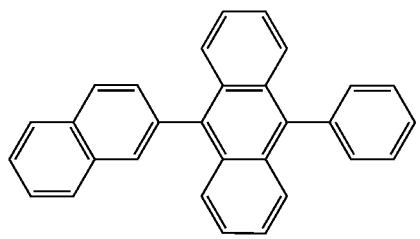

-continued
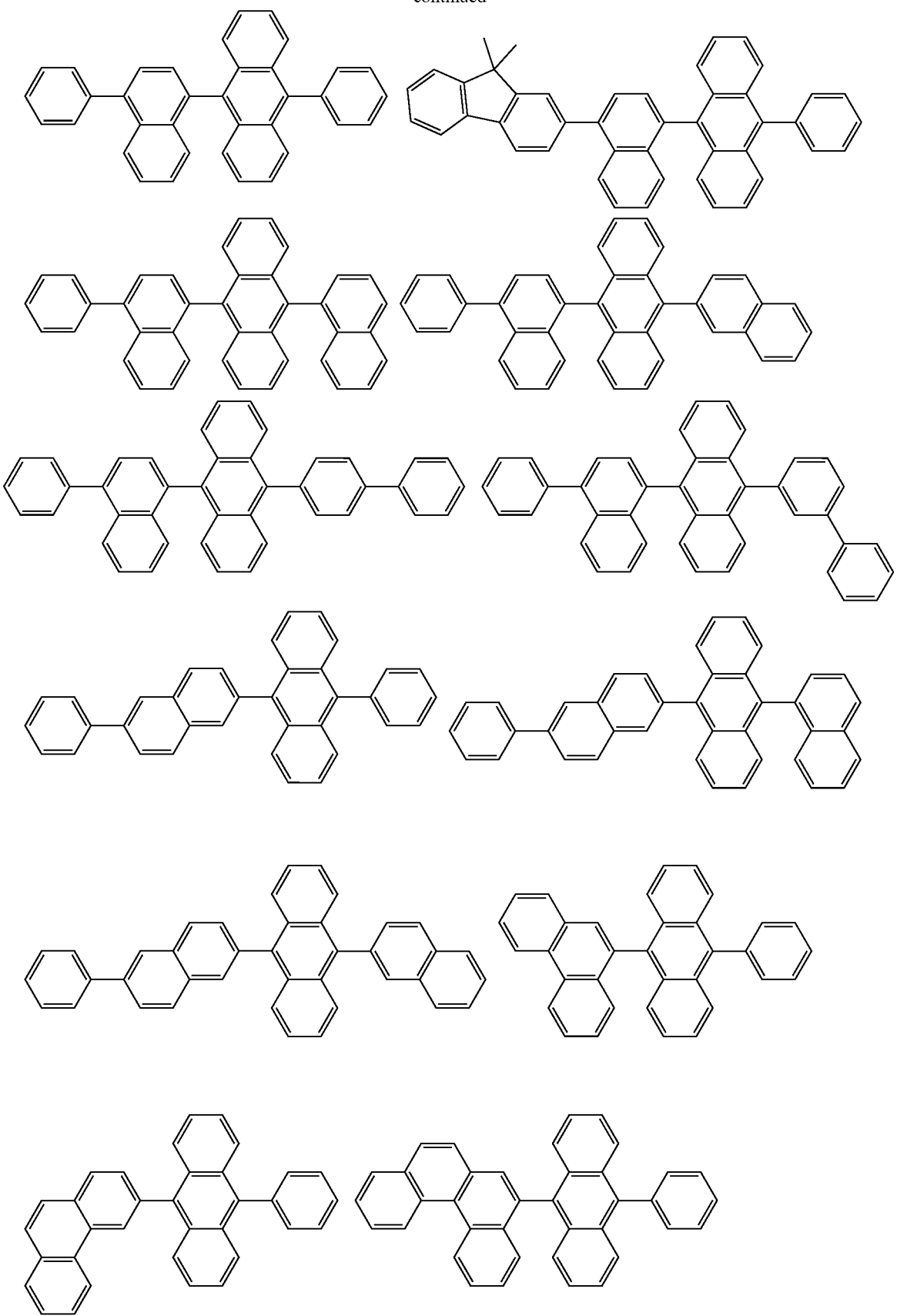

[Formula 133]
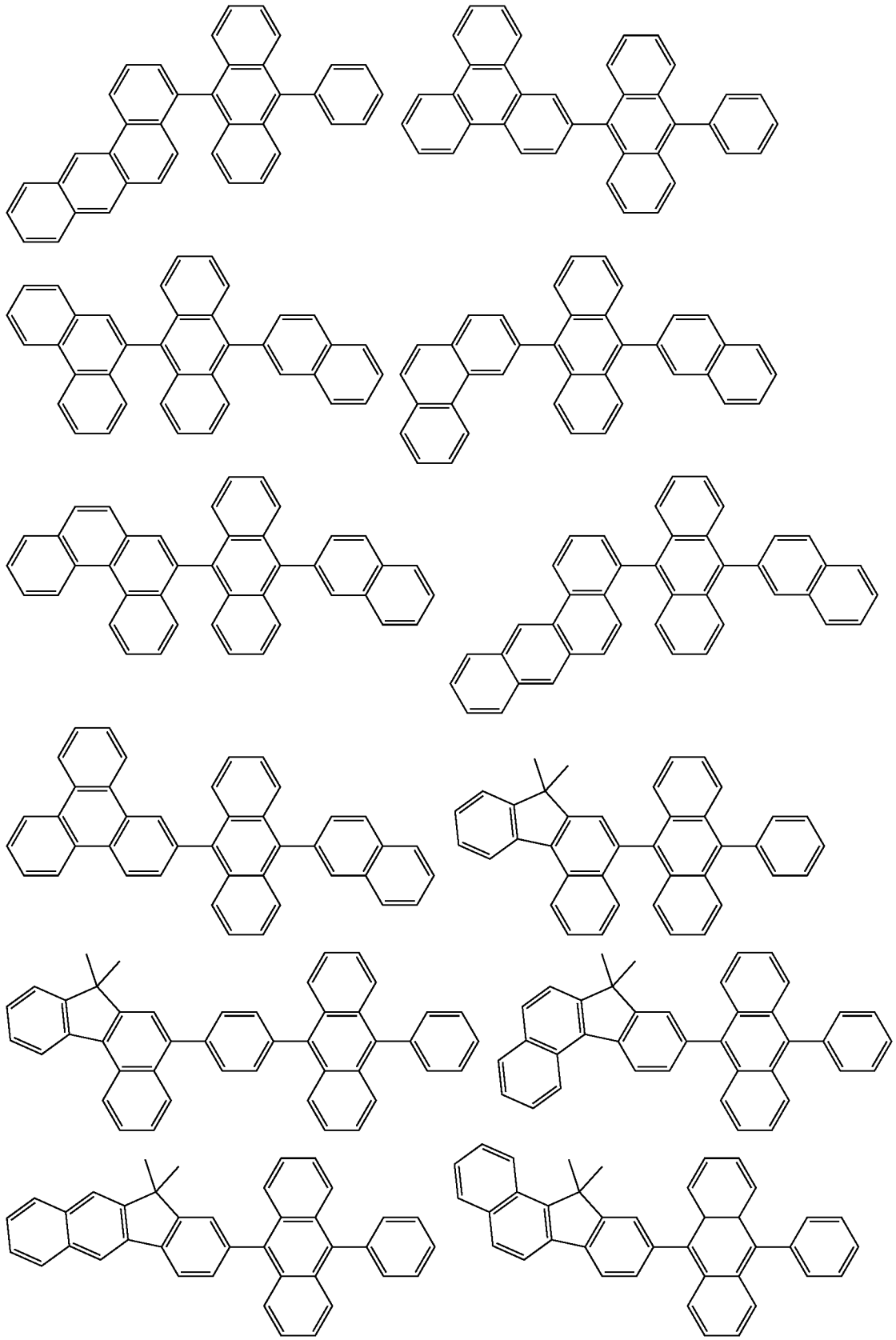

-continued
187
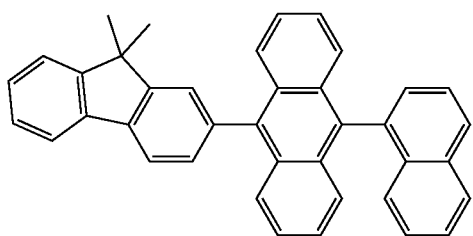
188
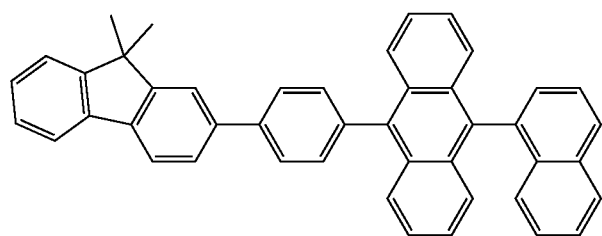
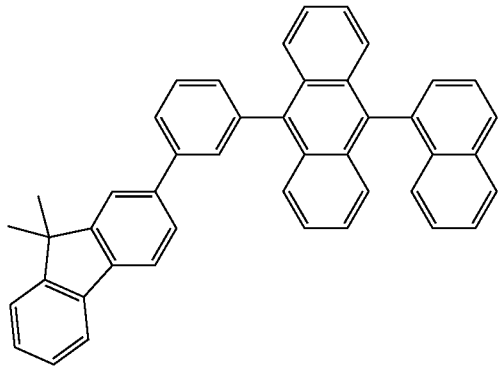
[Formula 134]
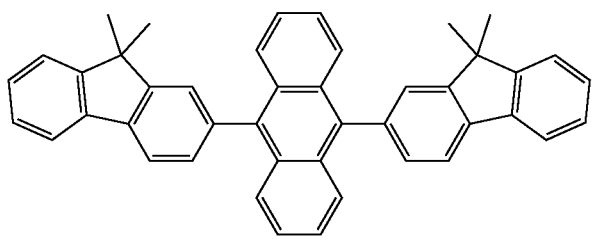
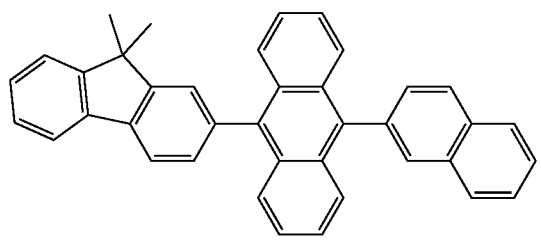
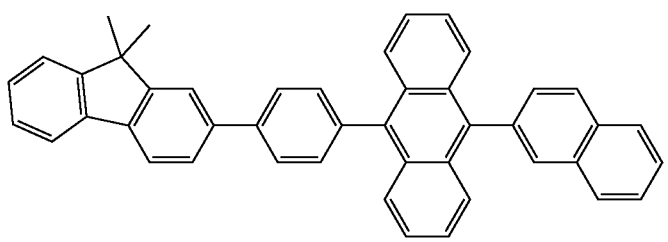
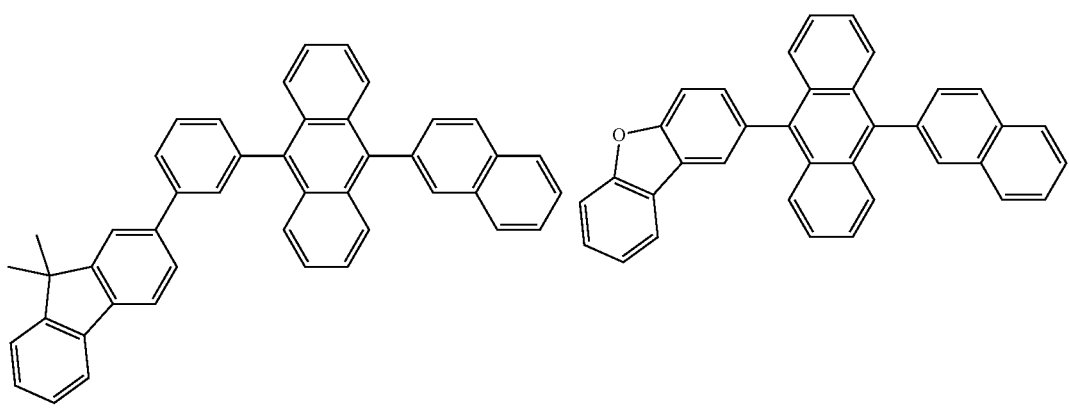

-continued
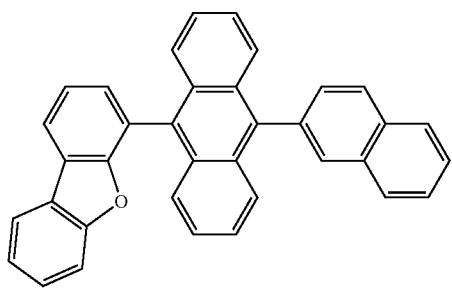
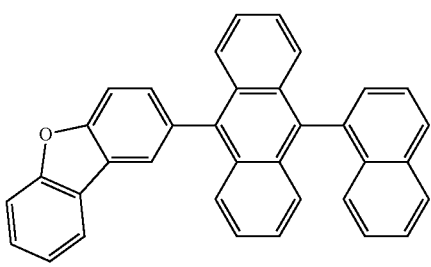
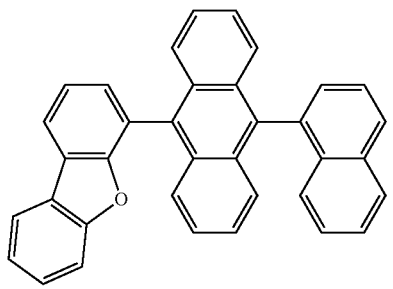
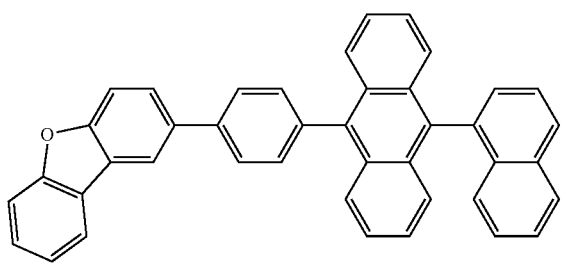
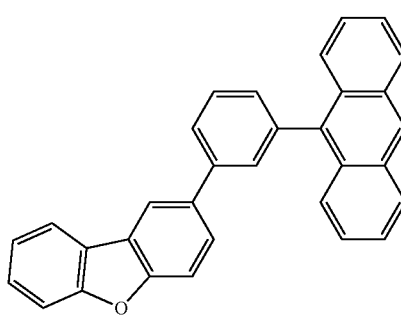
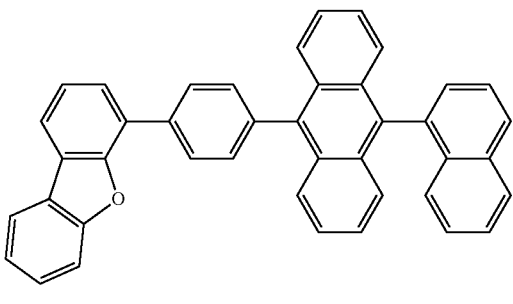
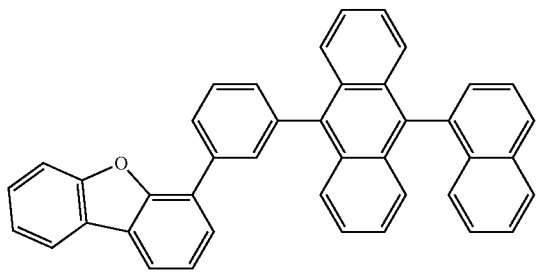
[Formula 135]
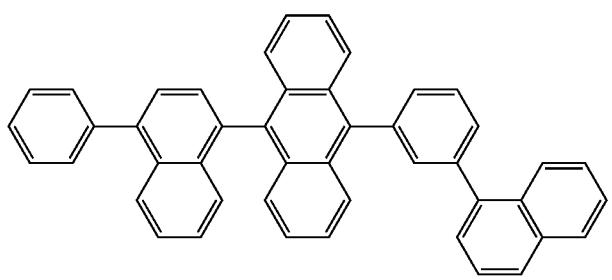

-continued
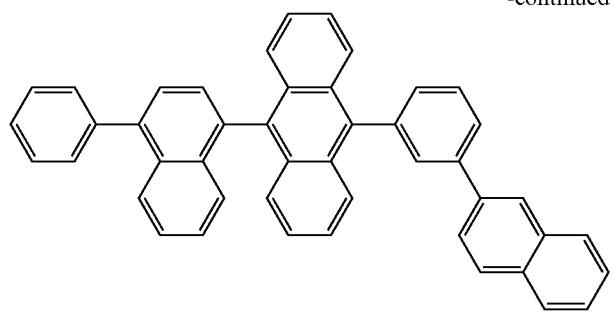
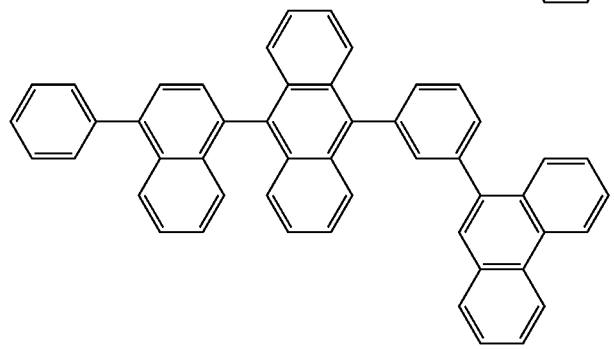
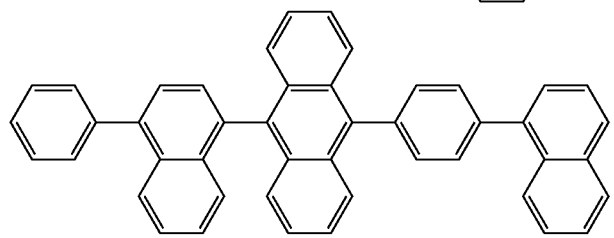
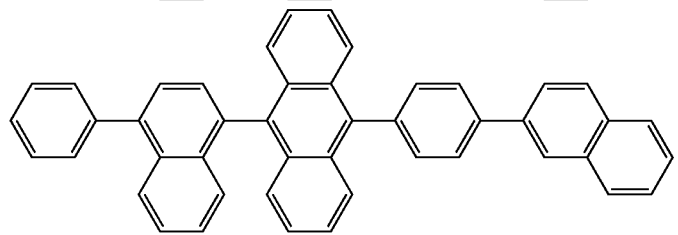
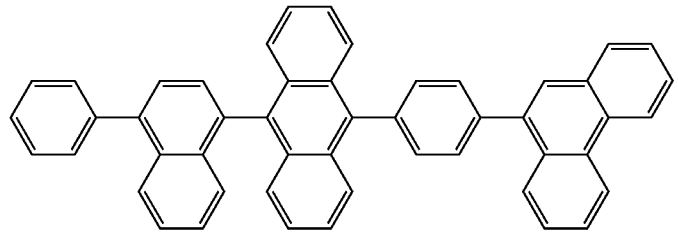
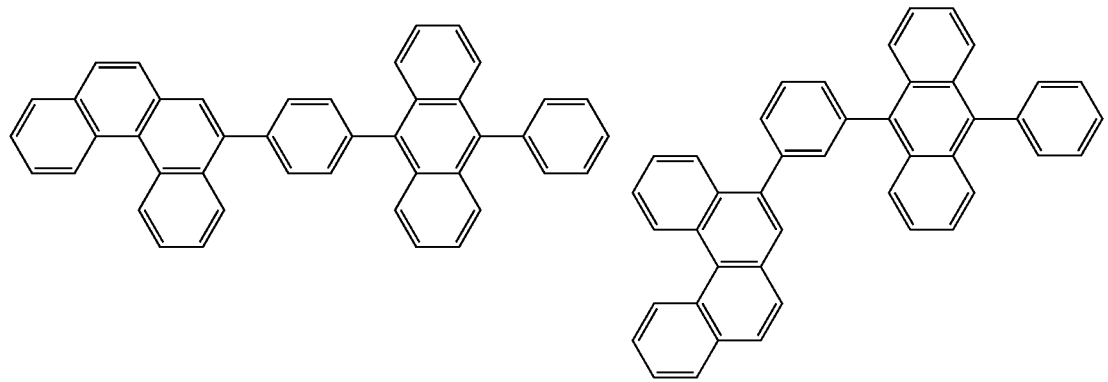

193 194
-continued
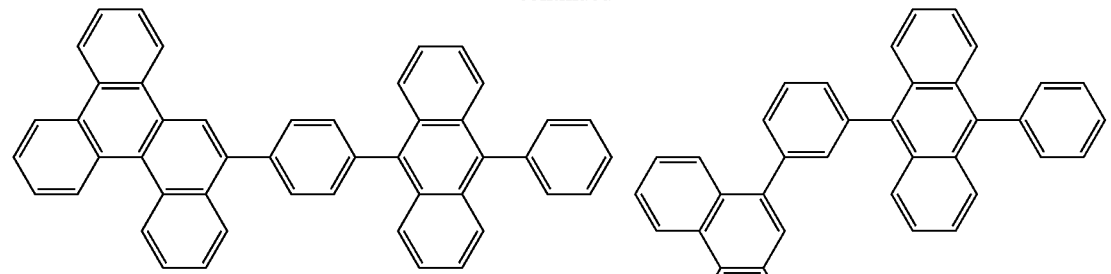

-continued
[Formula 136]
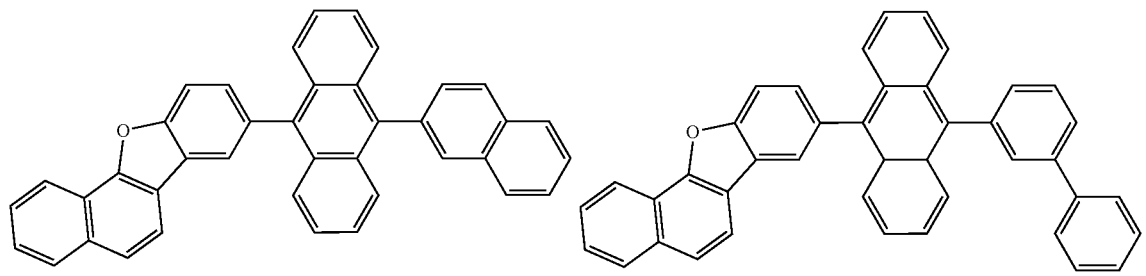
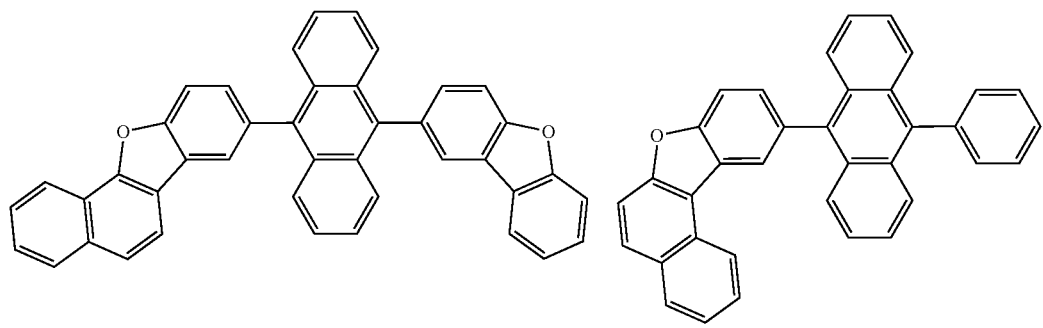
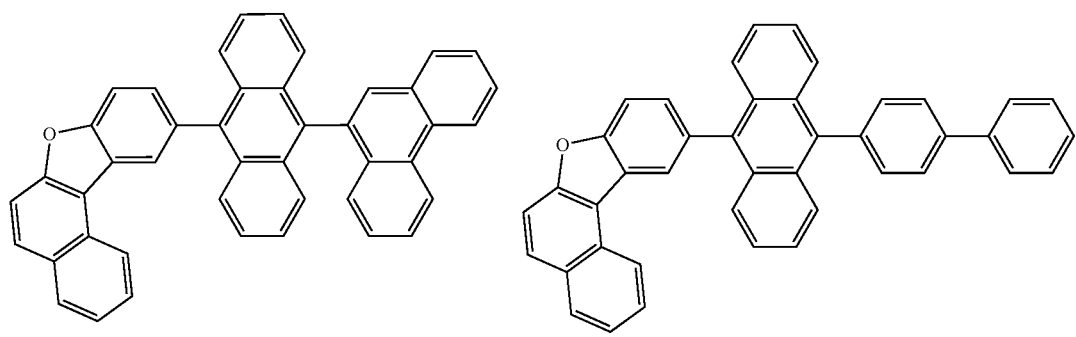
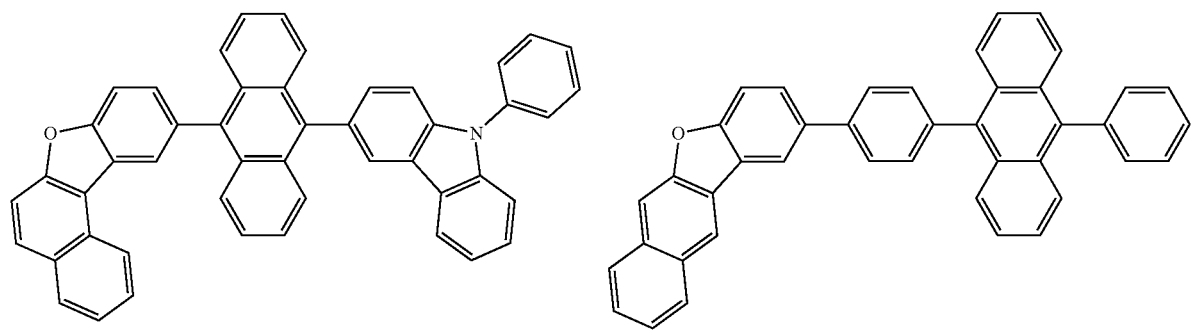
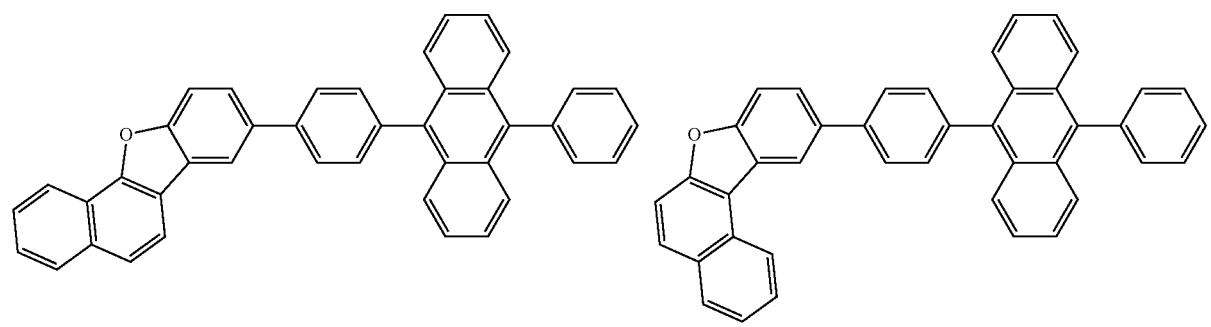

-continued
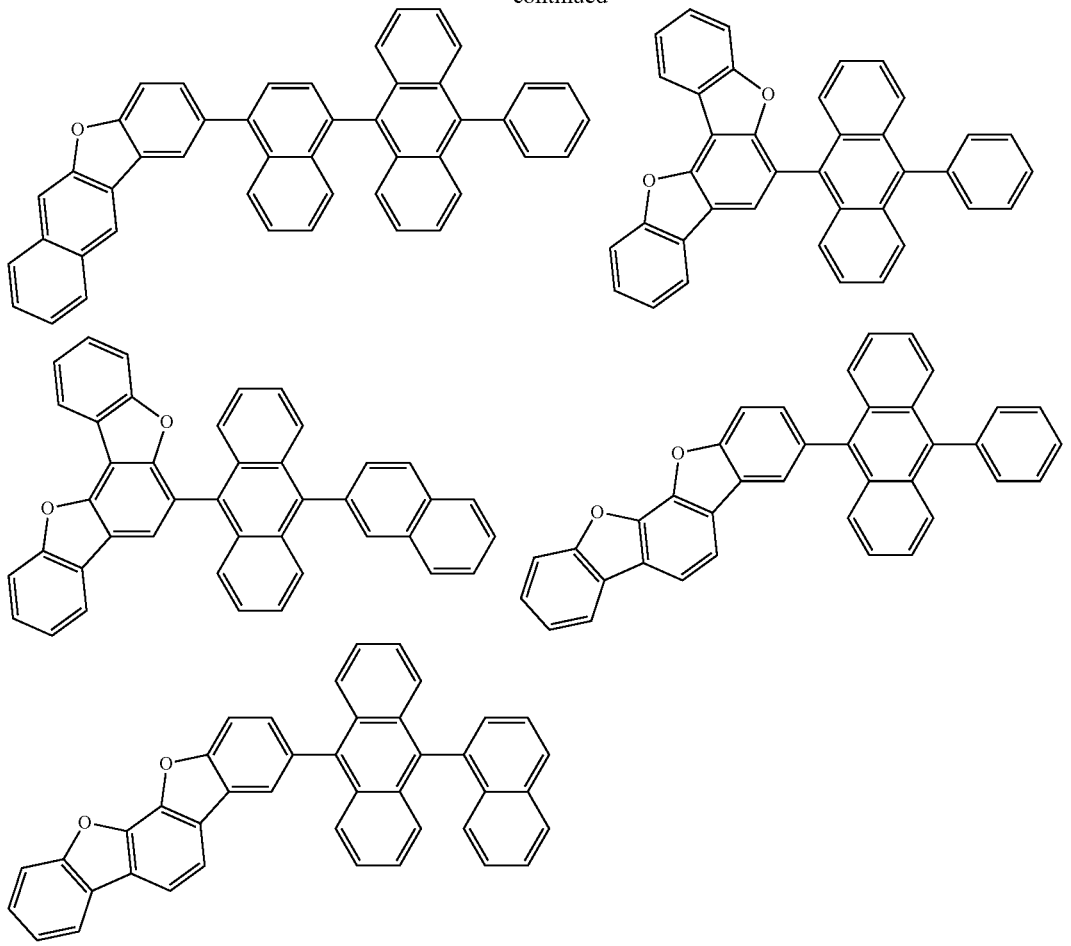
[Formula 137]
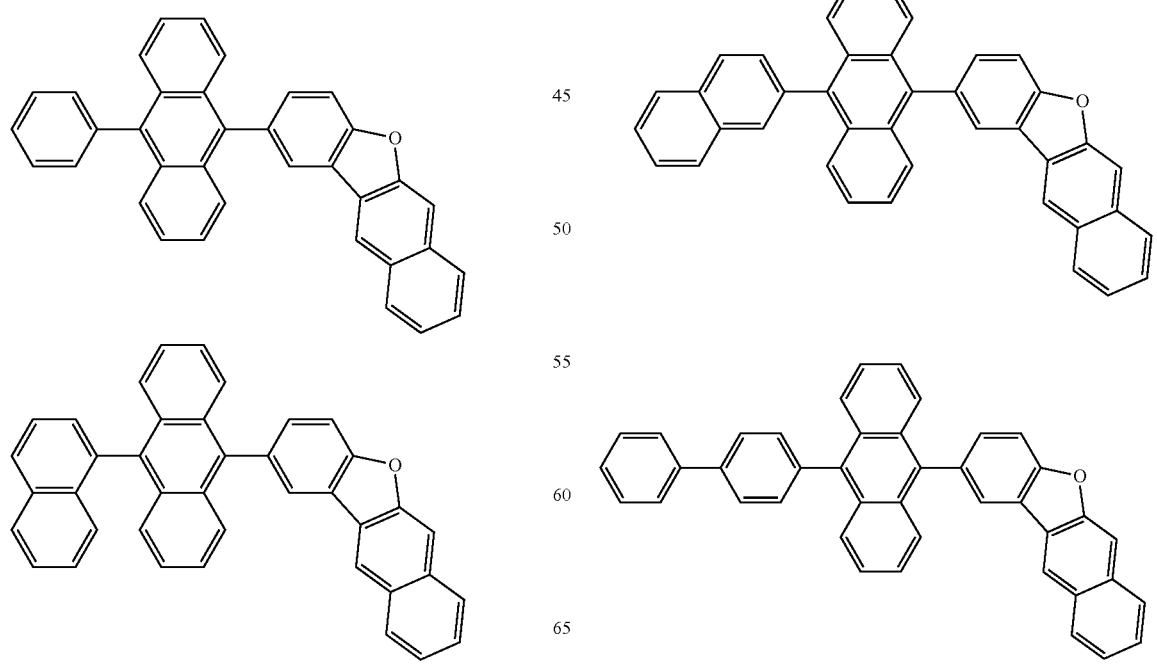

199
-continued
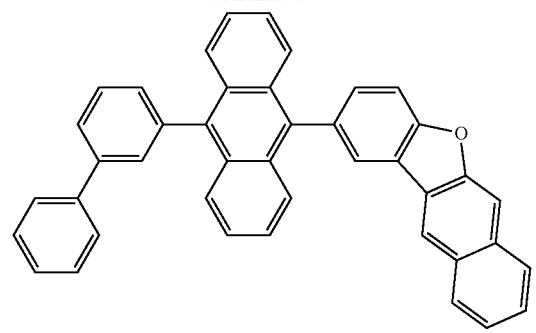
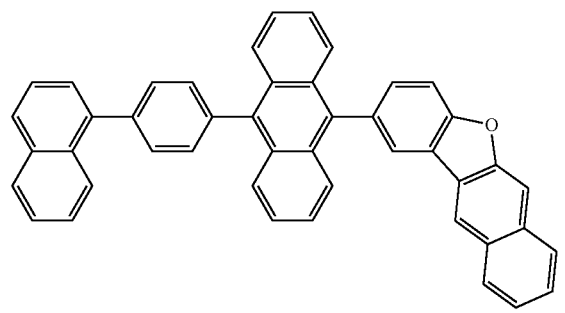
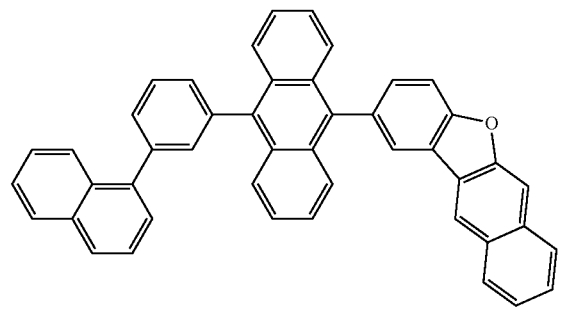
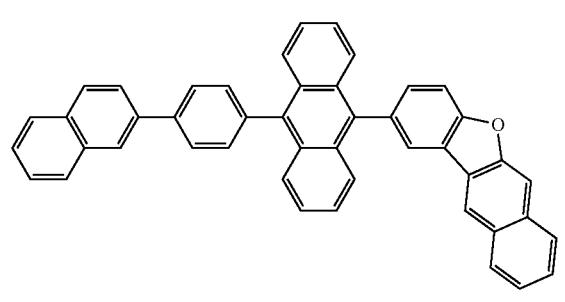
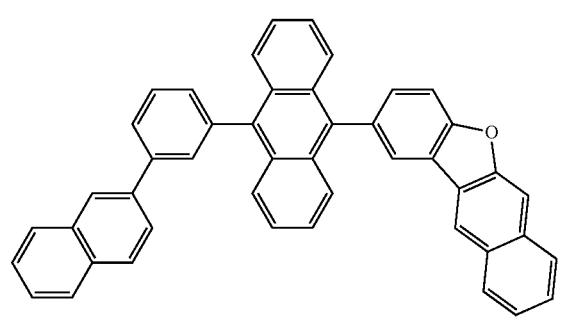
200
-continued
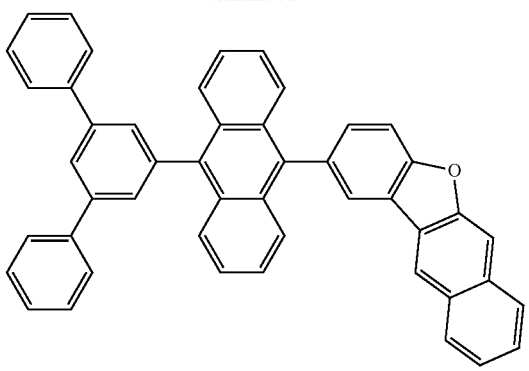
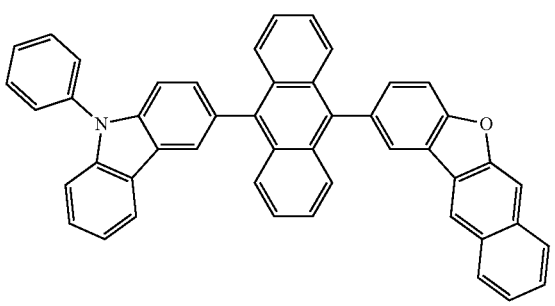
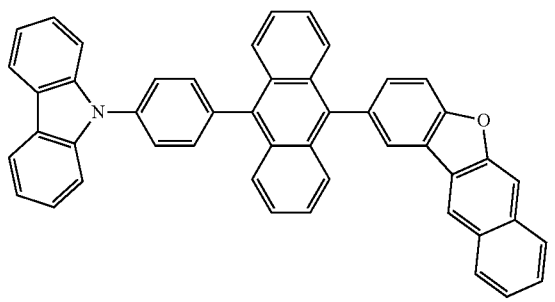
[Formula 138]
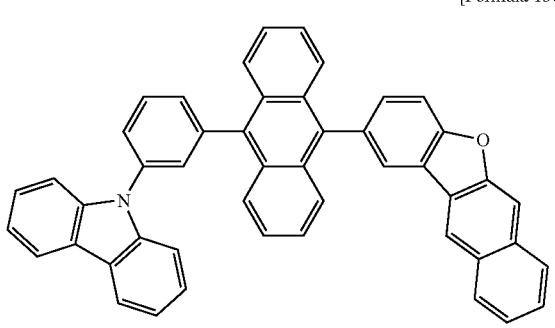
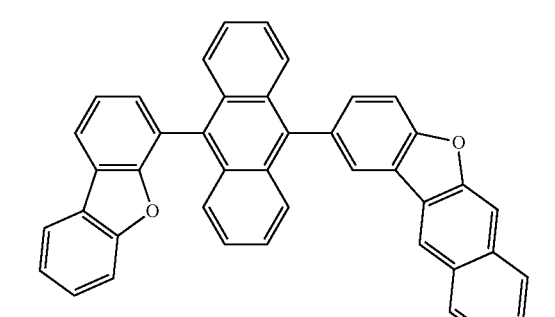

201
-continued
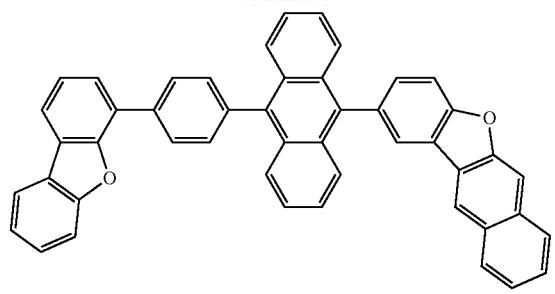
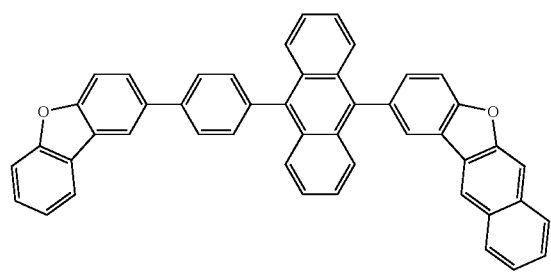
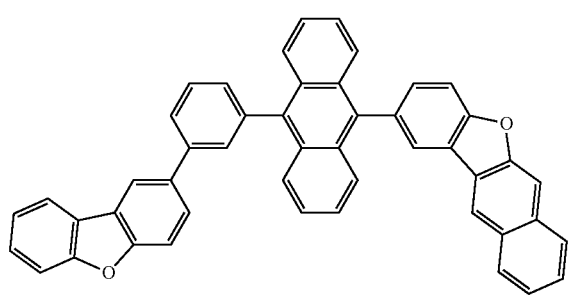
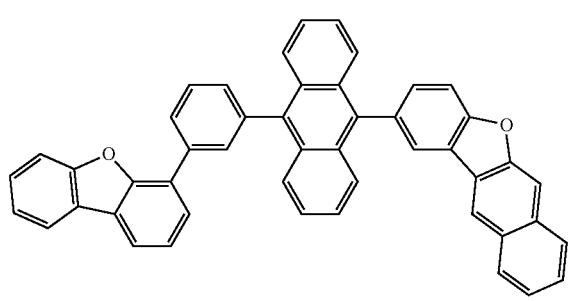
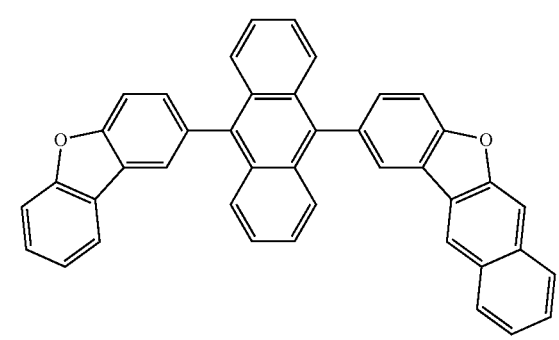
202
-continued
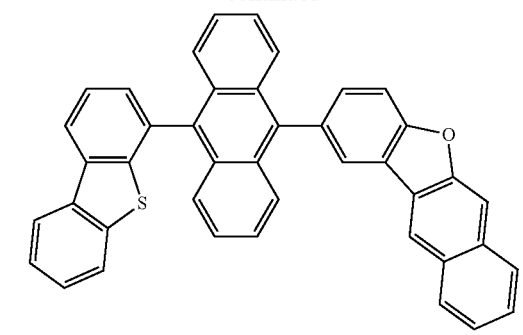
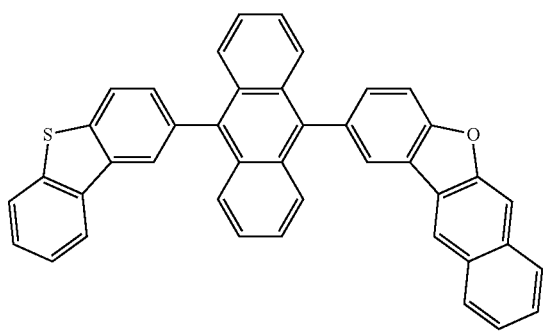
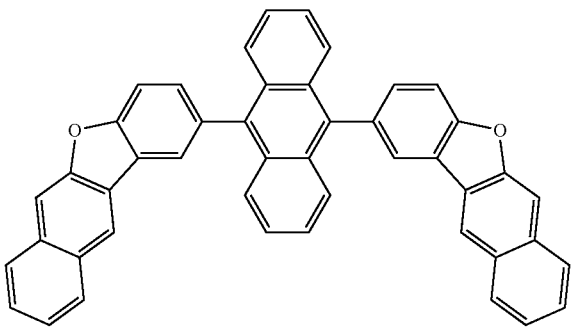
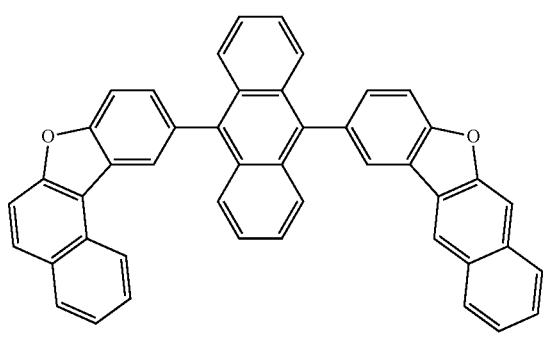
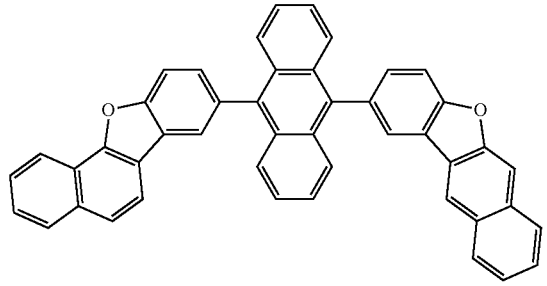

[Formula 139]
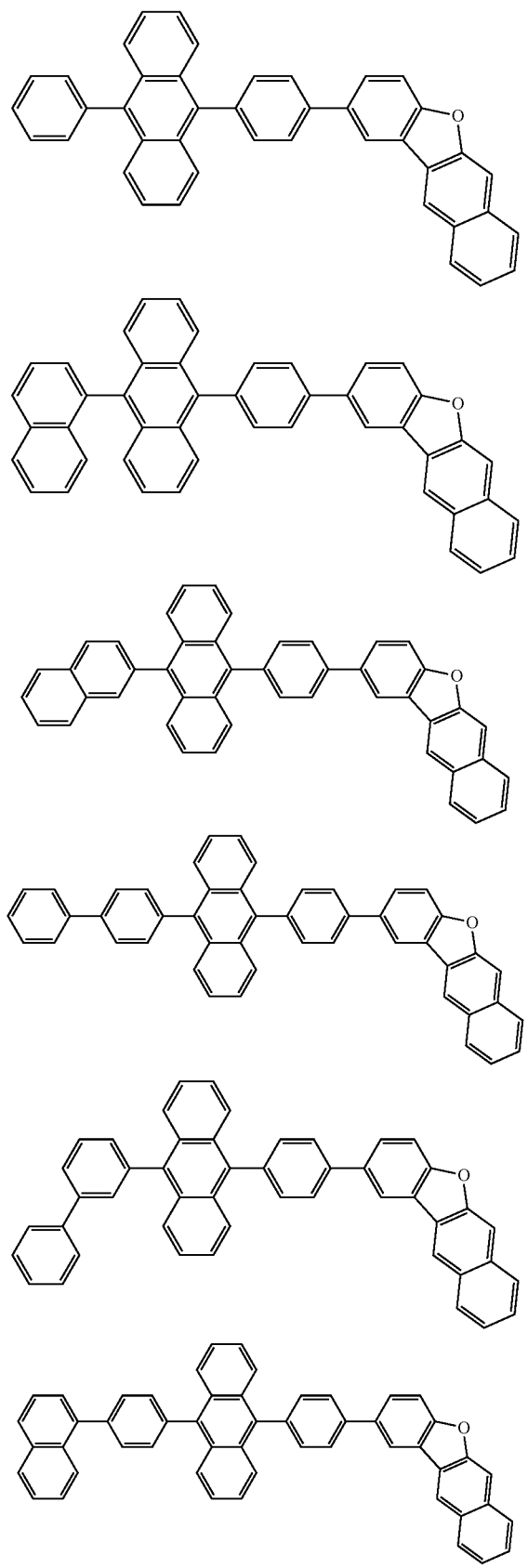
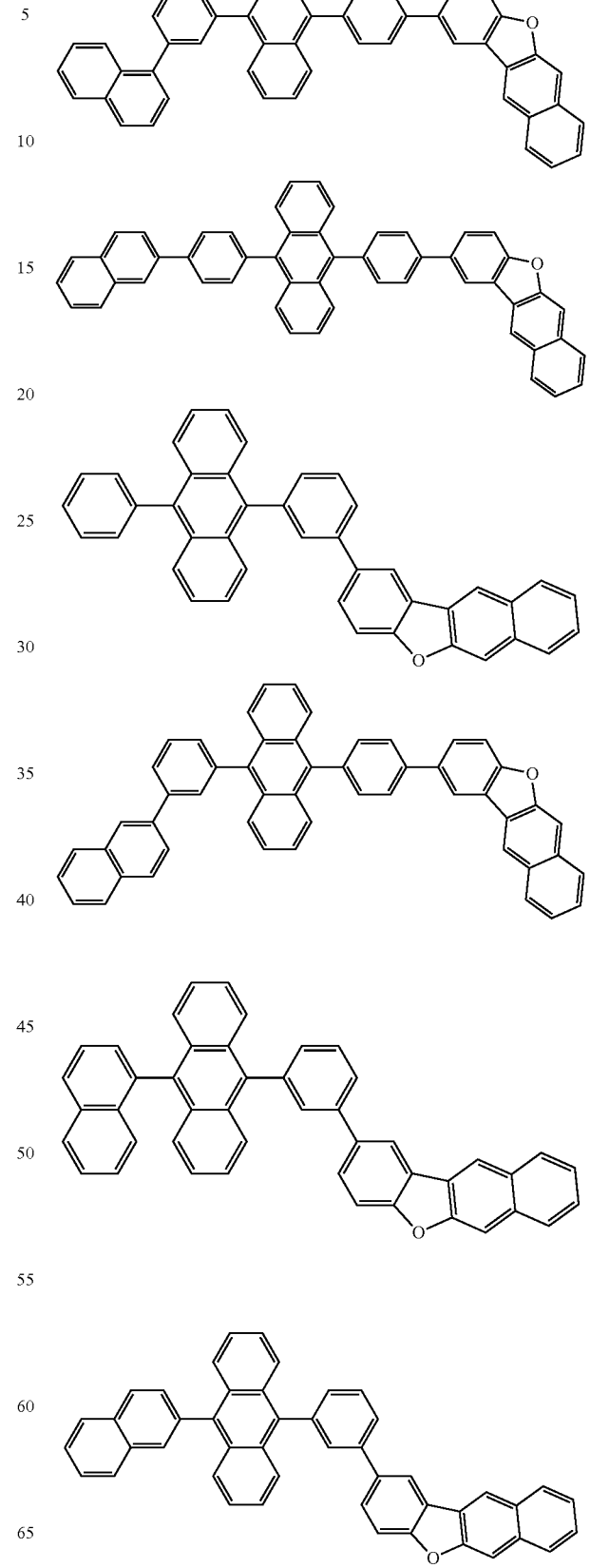

-continued
[Formula 140]
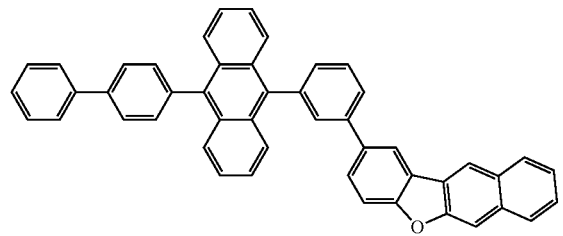
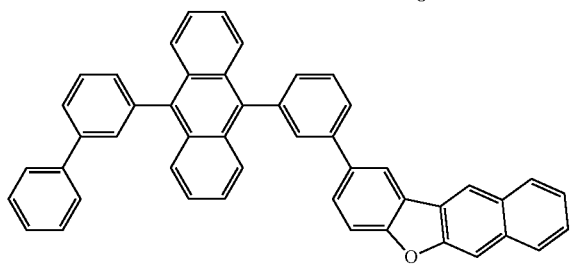
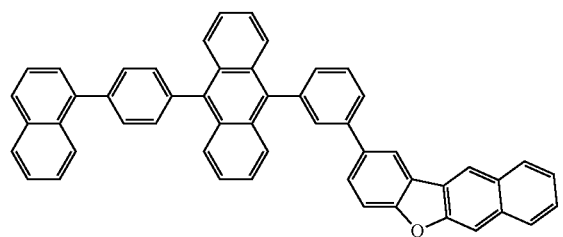
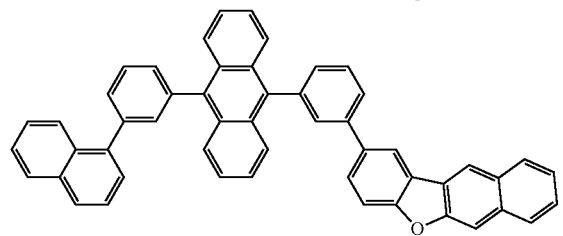
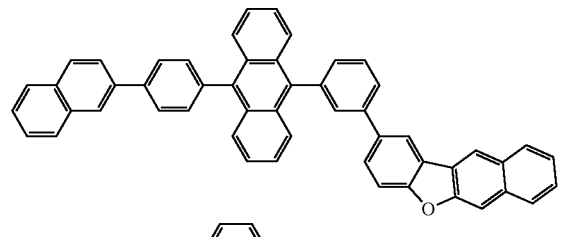
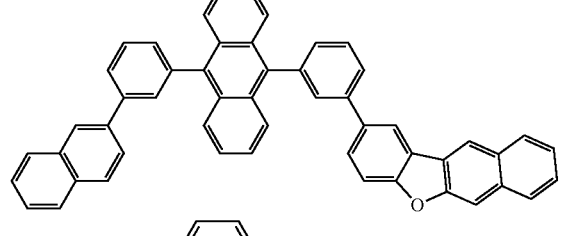
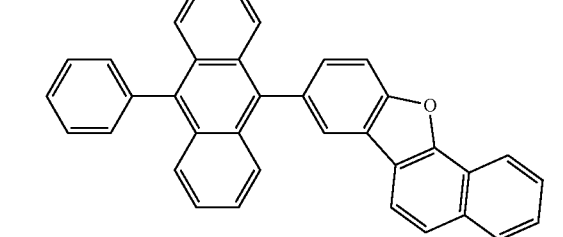
-continued
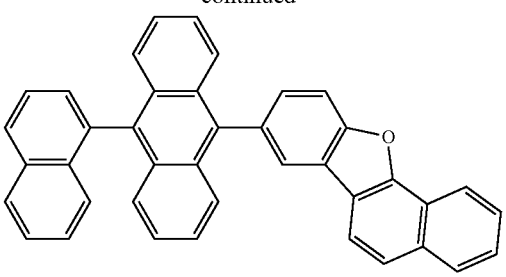
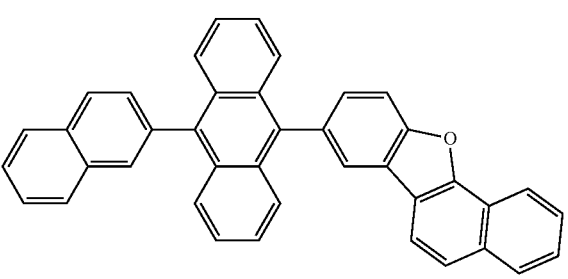
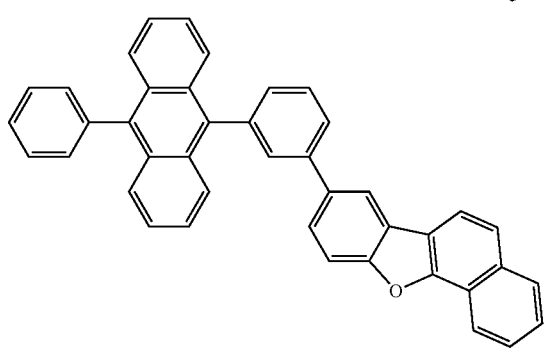
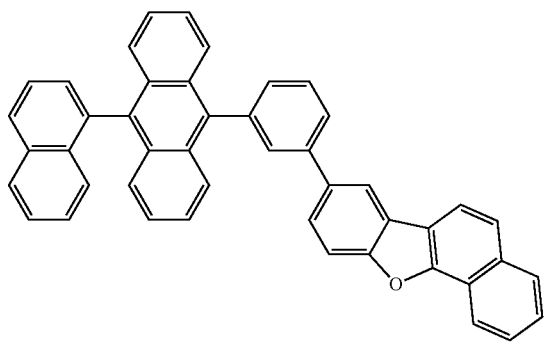
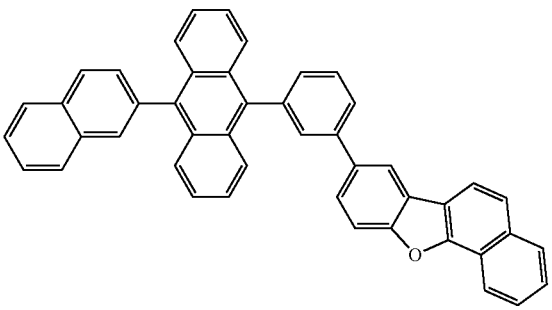

[Formula 141]
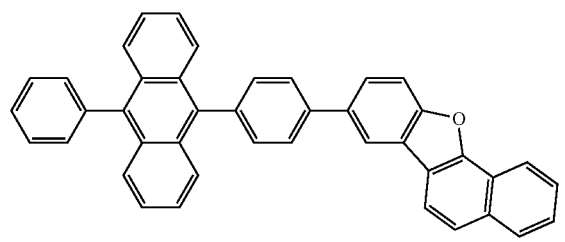
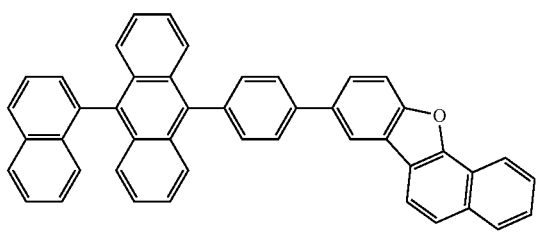
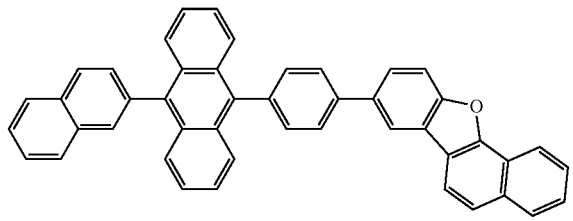
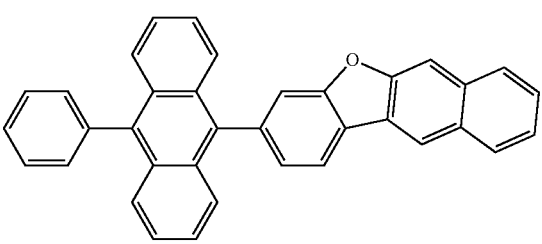
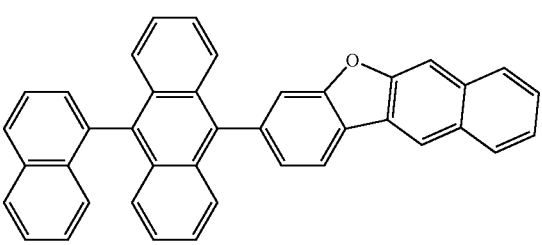
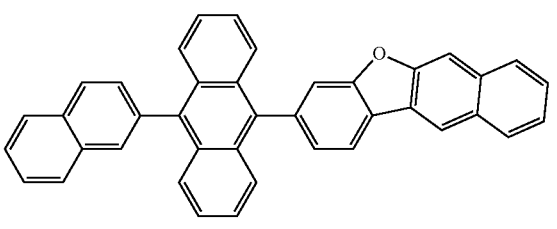
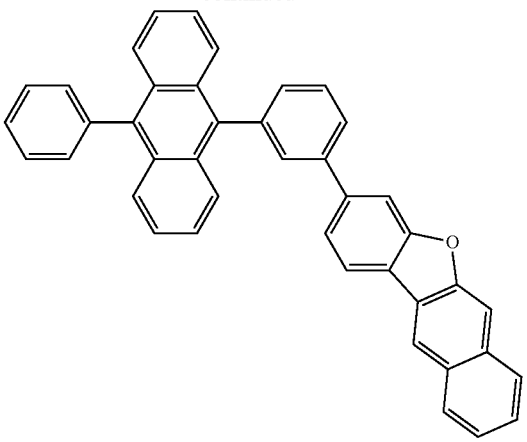
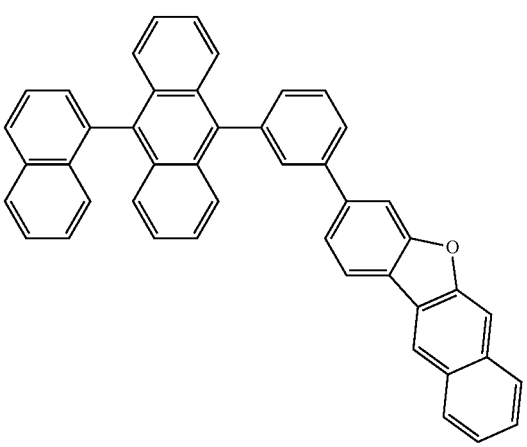
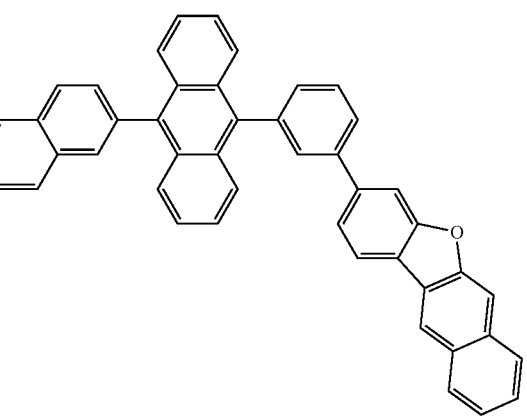
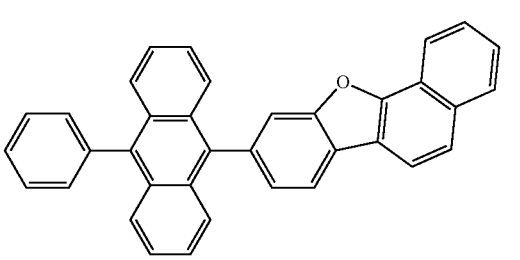

-continued
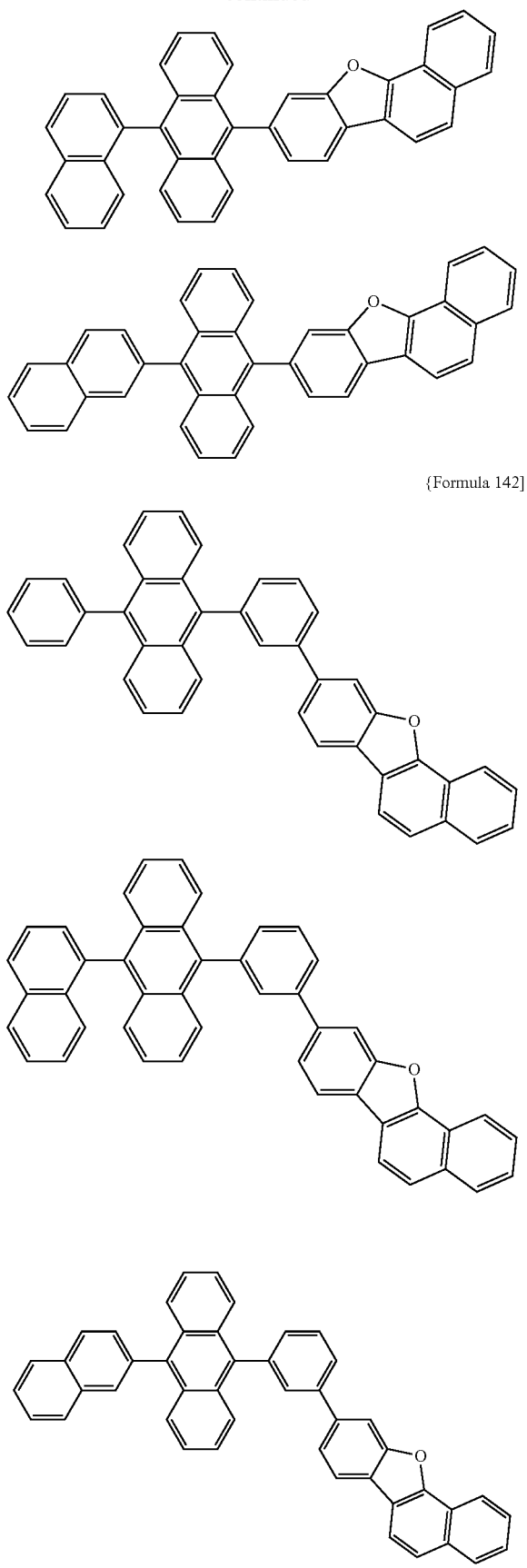
[Formula 142]
-continued
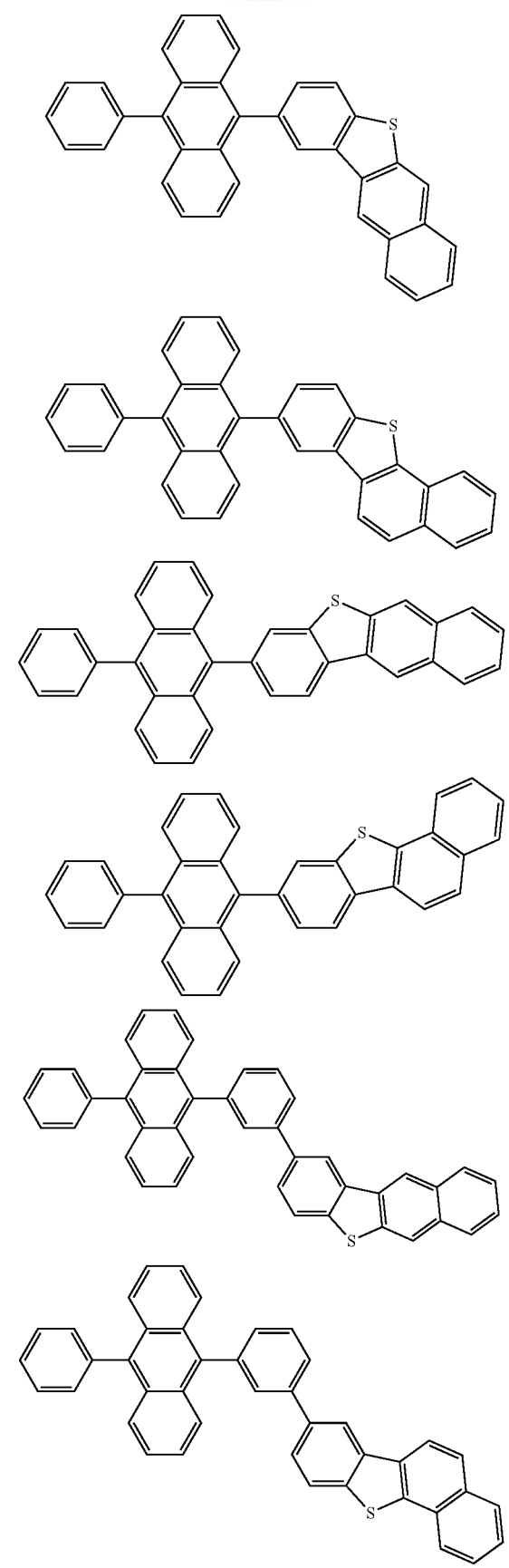

-continued
[Formula 143]
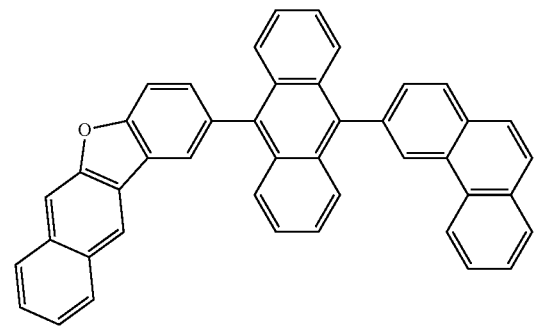
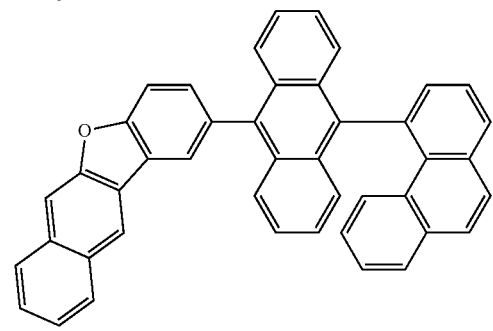
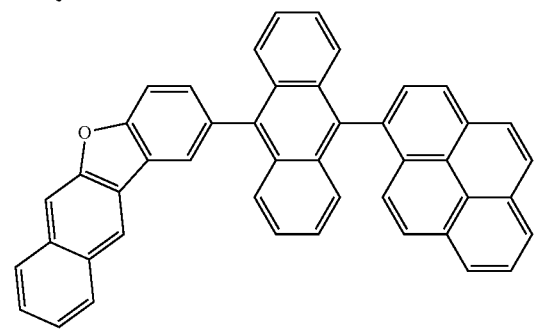
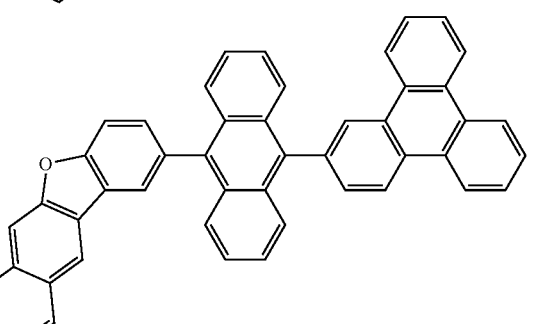
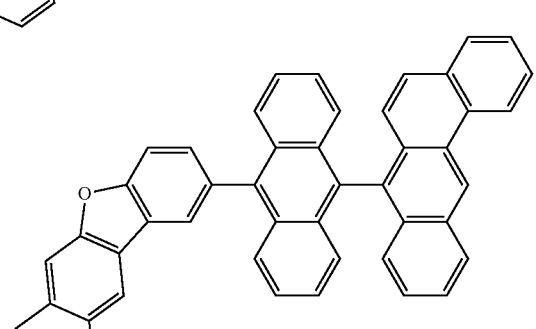
-continued
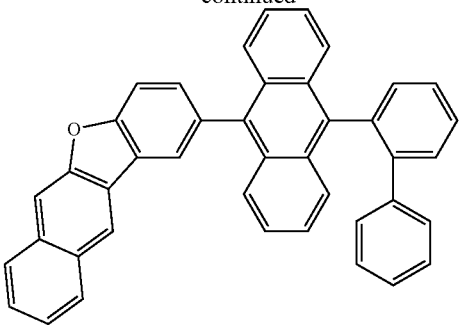
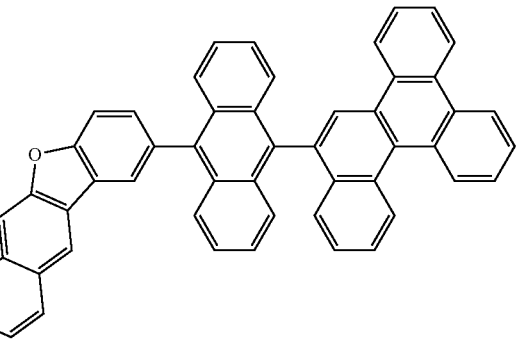
[Formula 144]
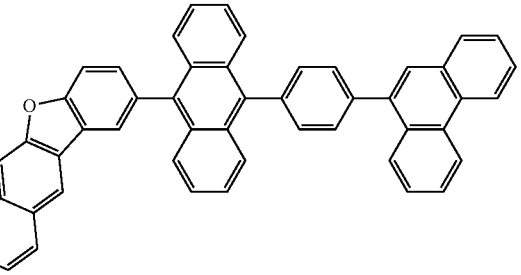
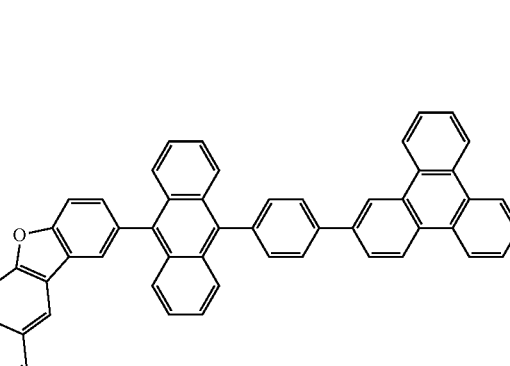
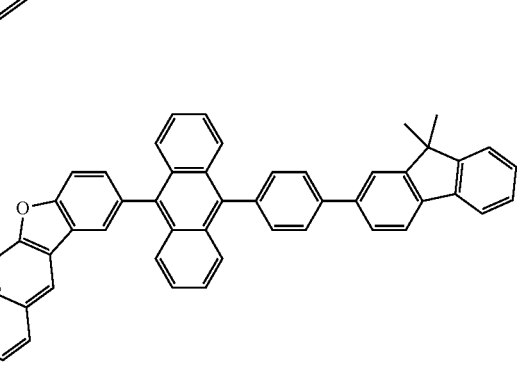

213
-continued
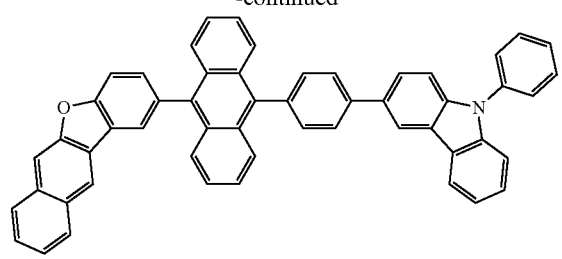
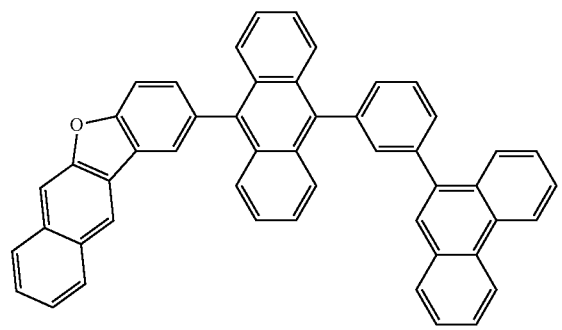
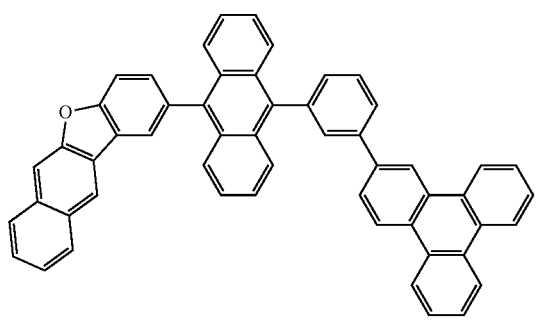
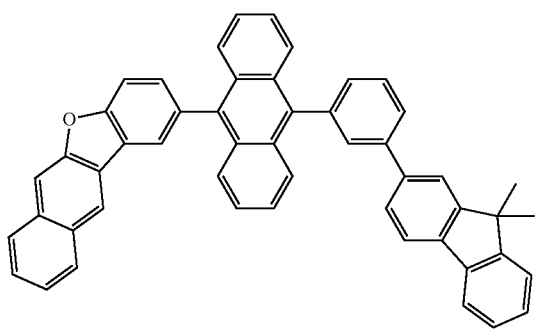
[Formula 145]
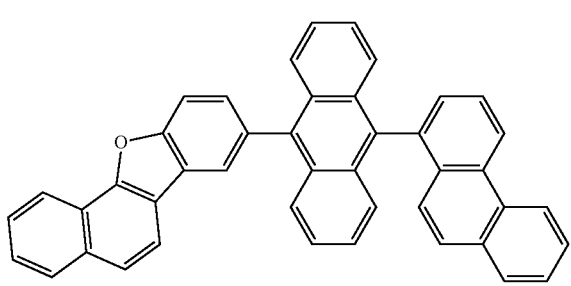
214
-continued
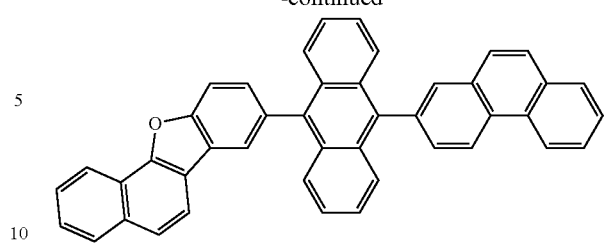
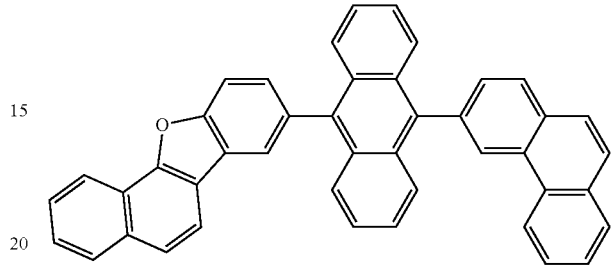
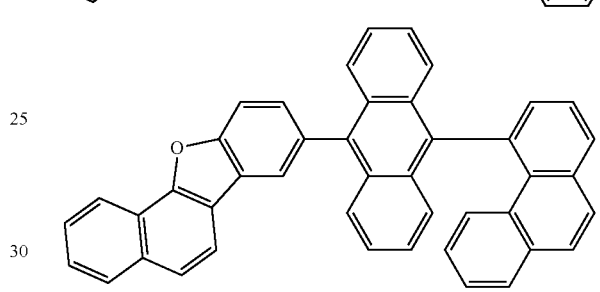
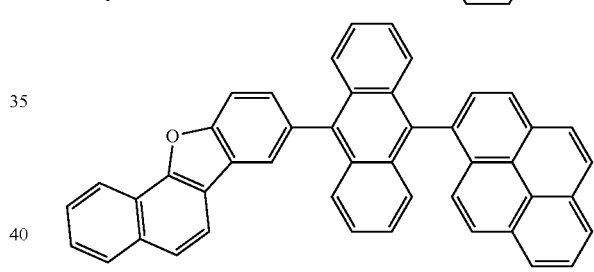
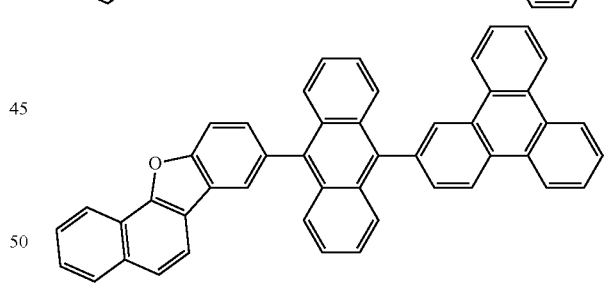
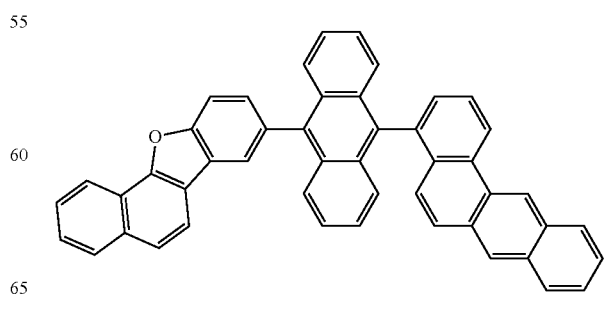

215
-continued
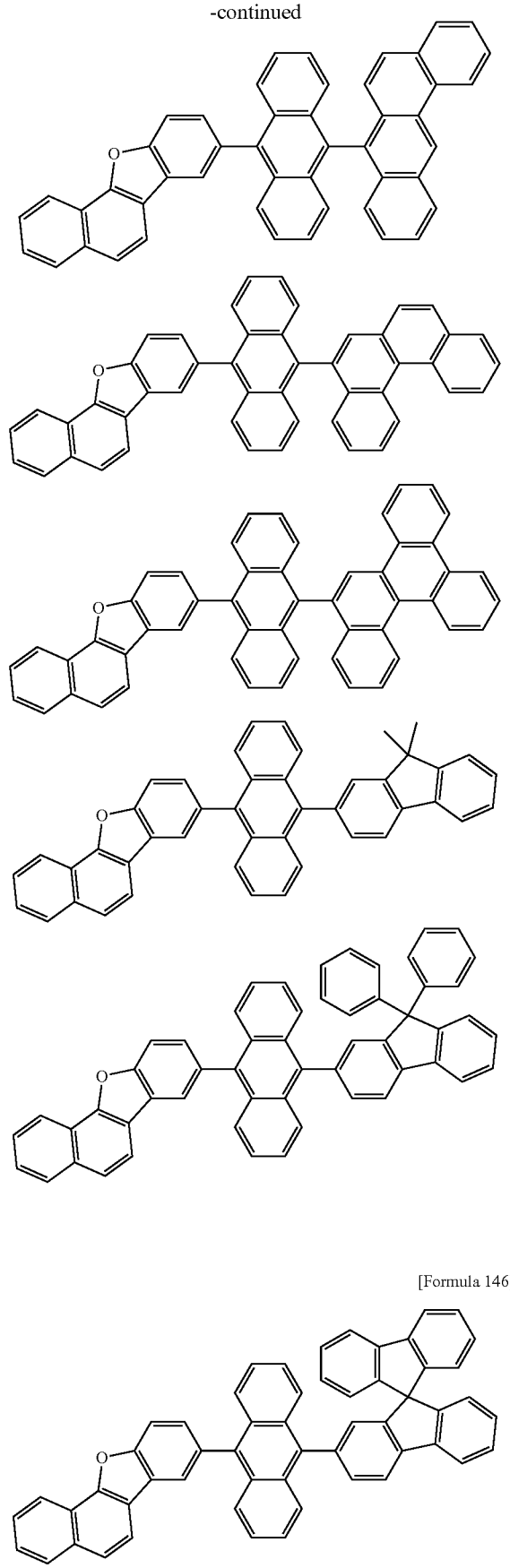
[Formula 146]
216
-continued
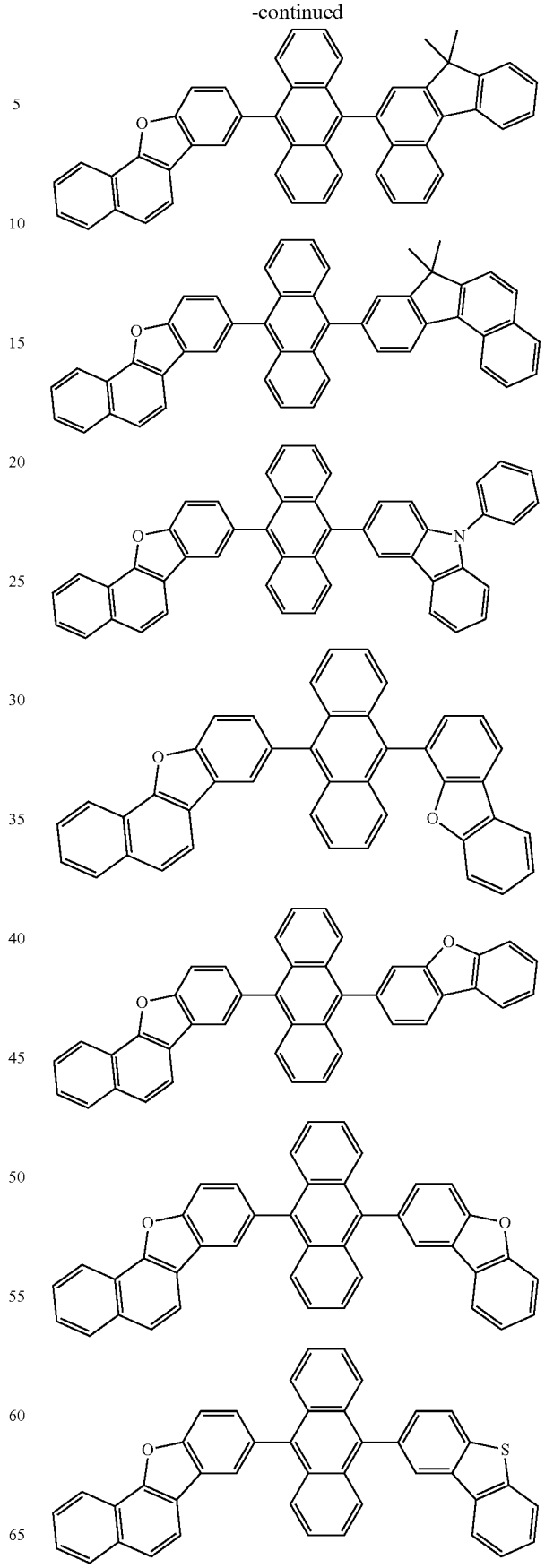
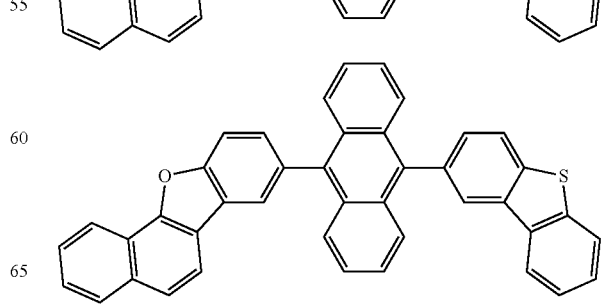

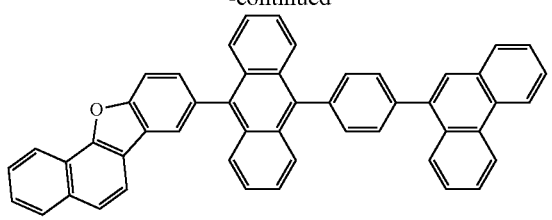
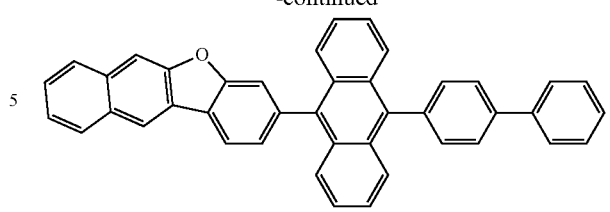
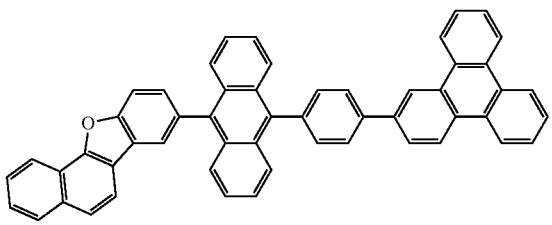
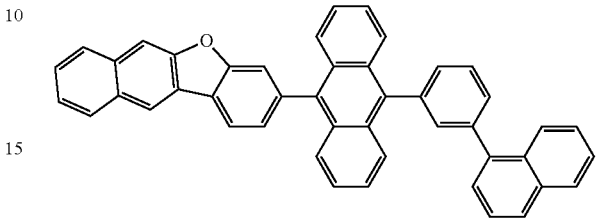
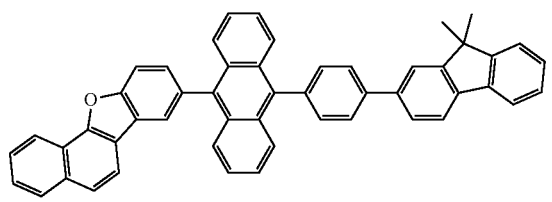
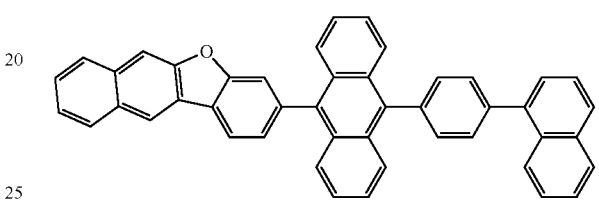
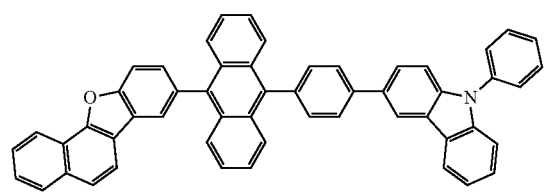
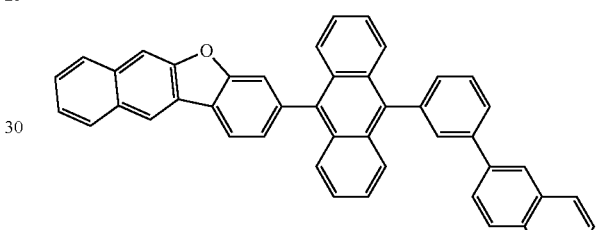
[Formula 147]
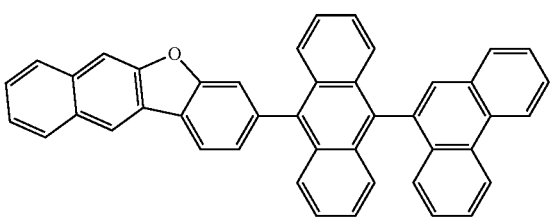
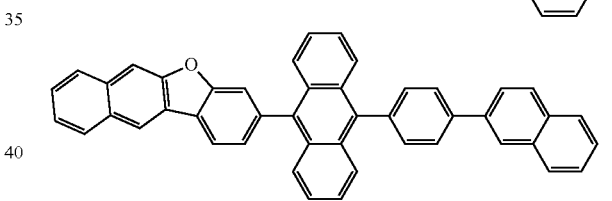
[Formula 148]
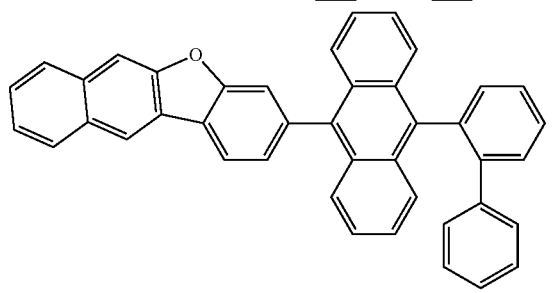
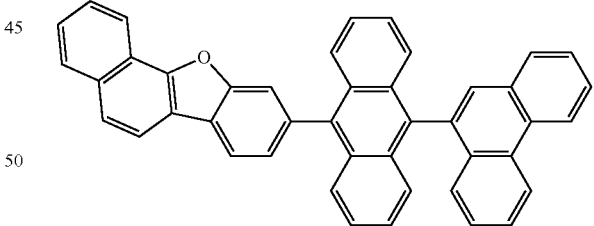
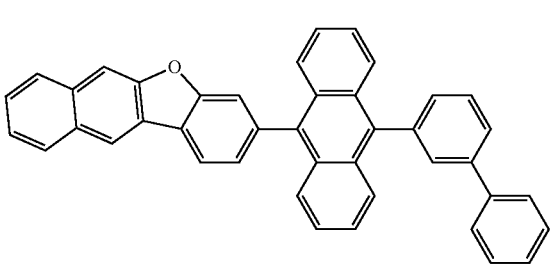
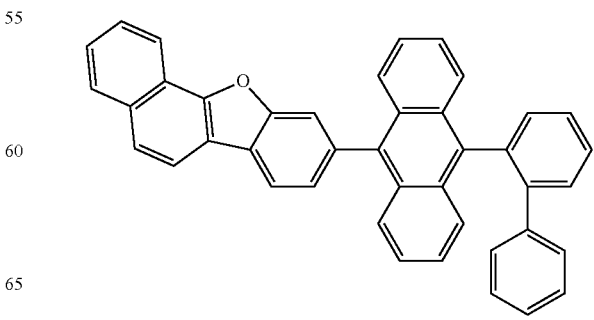

219
-continued
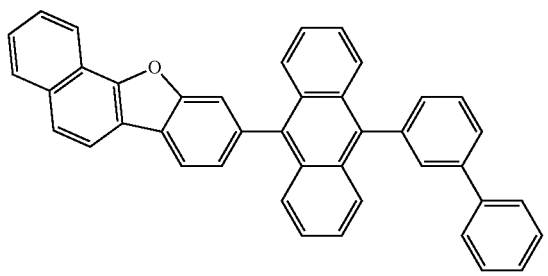
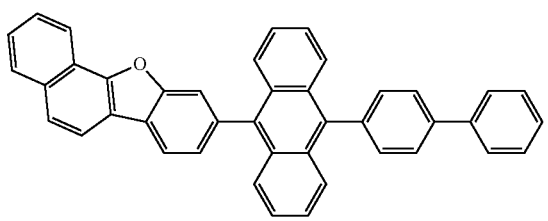
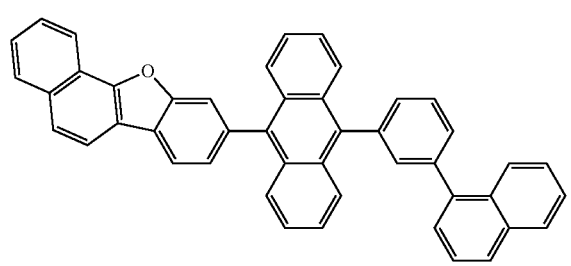
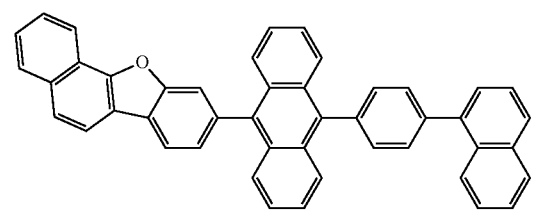
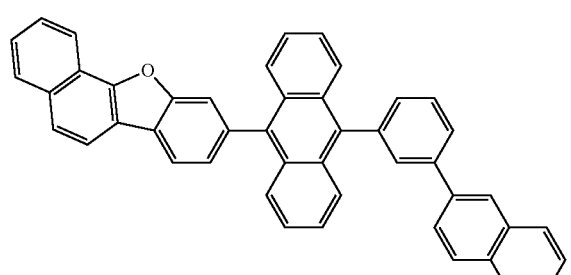
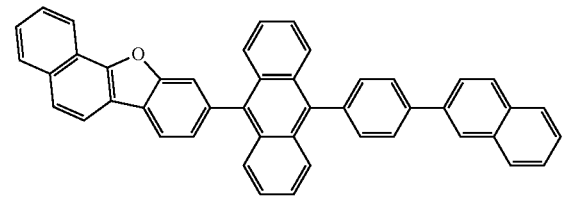
220
-continued
[Formula 149]
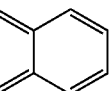
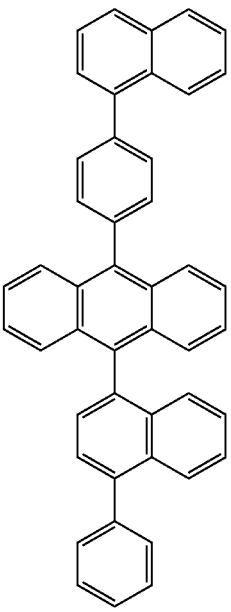
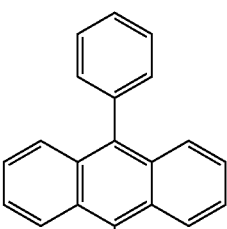
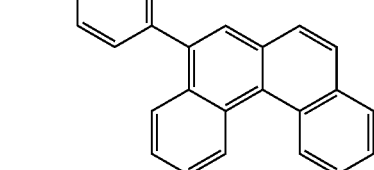
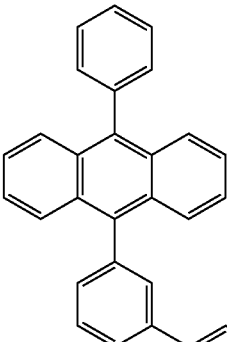
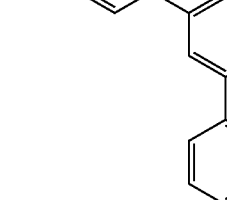

221
-continued
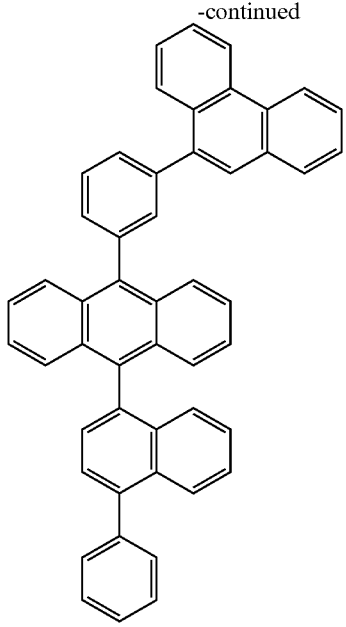
222
-continued
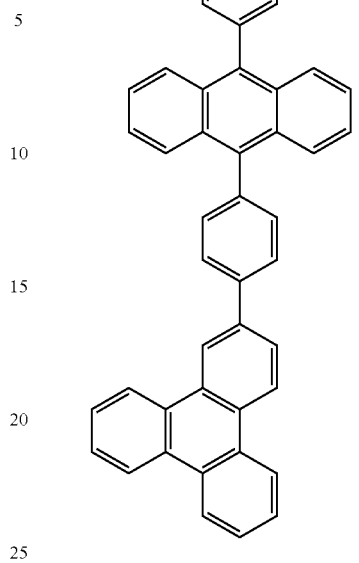
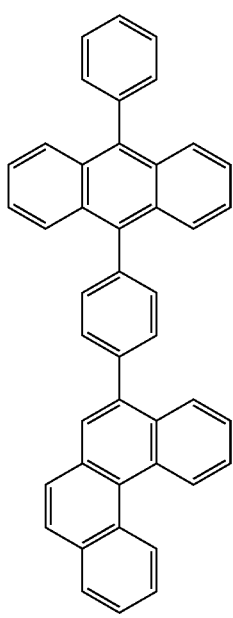
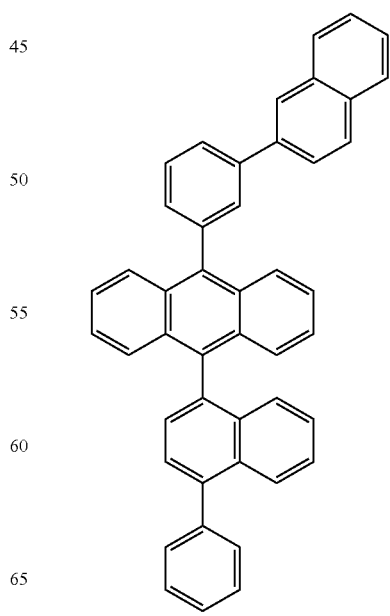

223
-continued
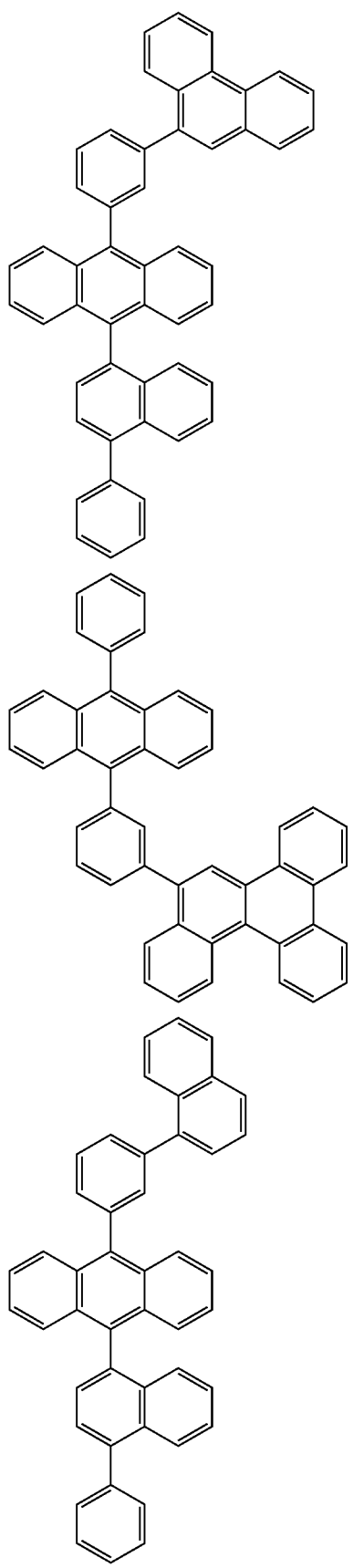
224
-continued
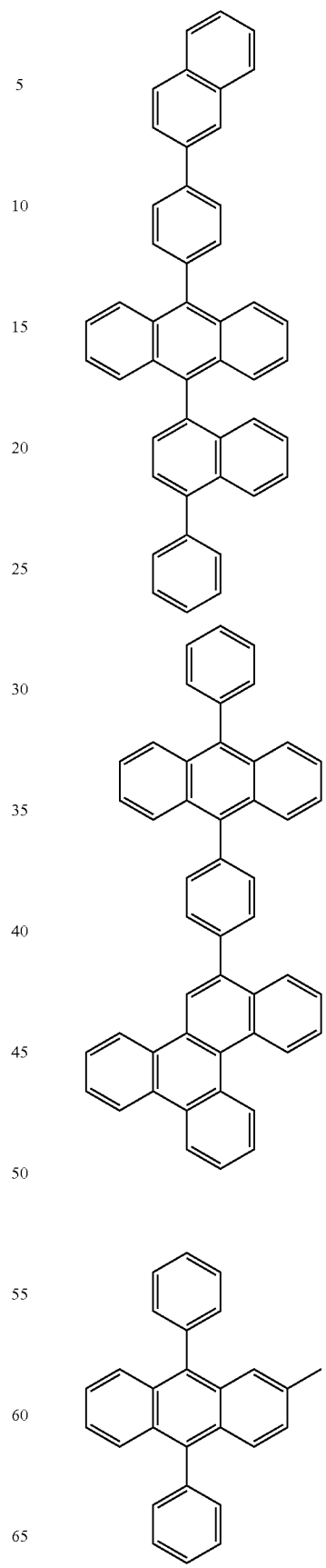
[Formula 150]

225
-continued
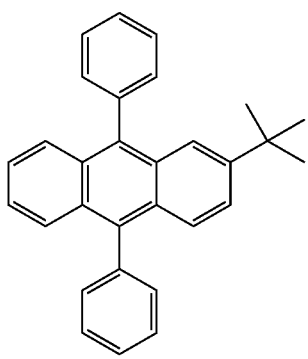
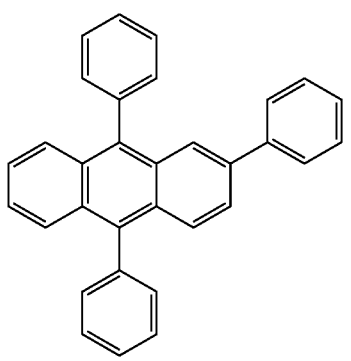
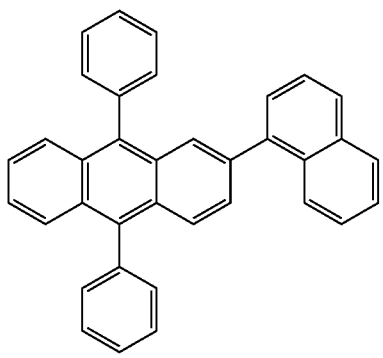
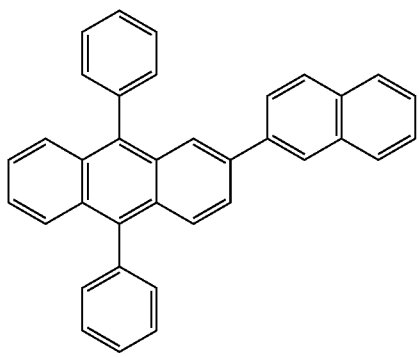
226
-continued
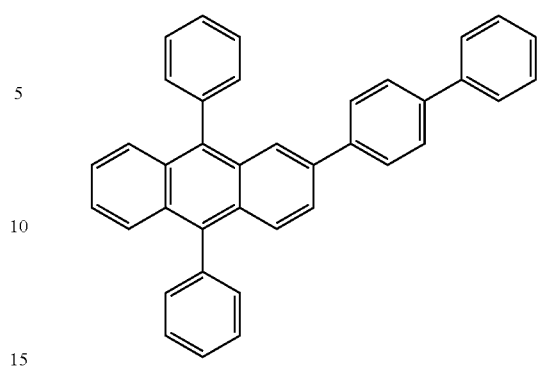
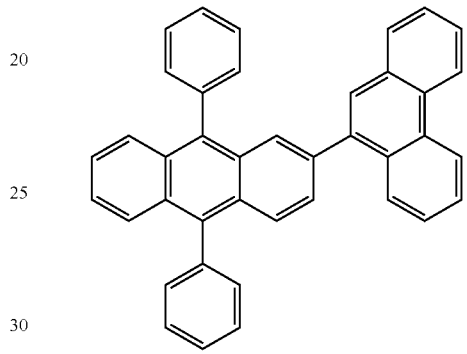
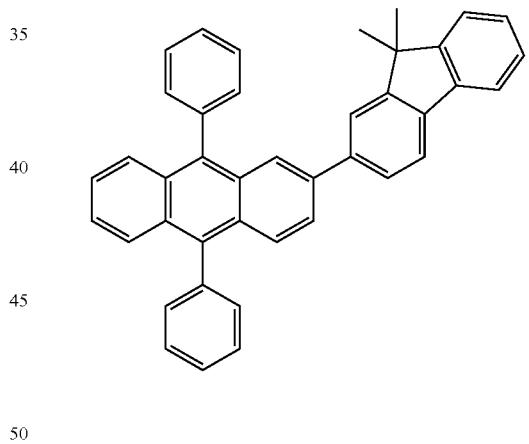
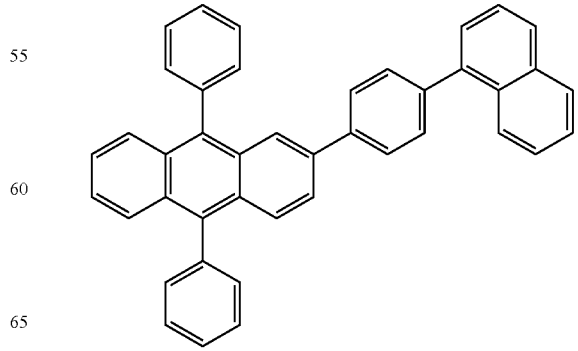

227
-continued
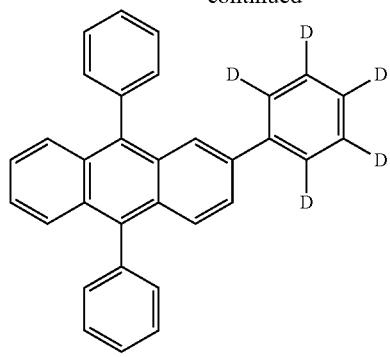
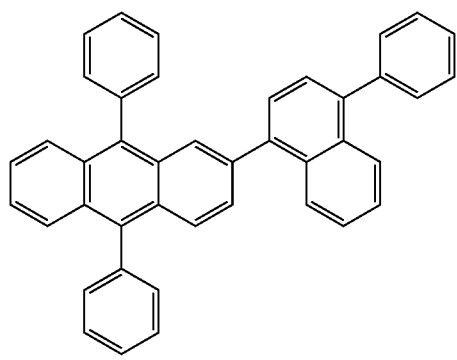
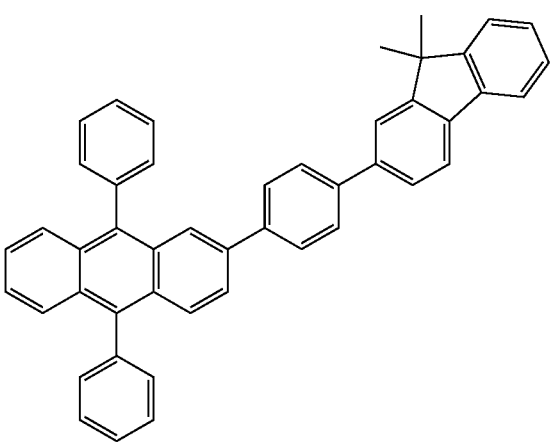
228
-continued
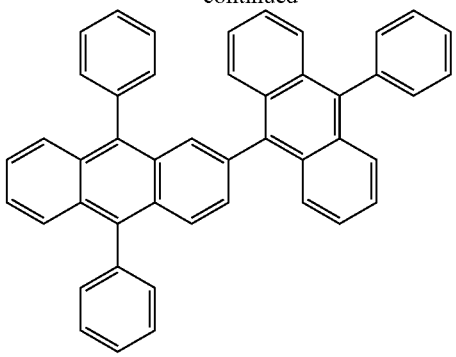
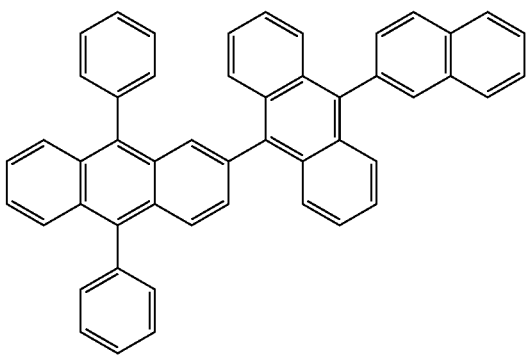
[Formula 151]
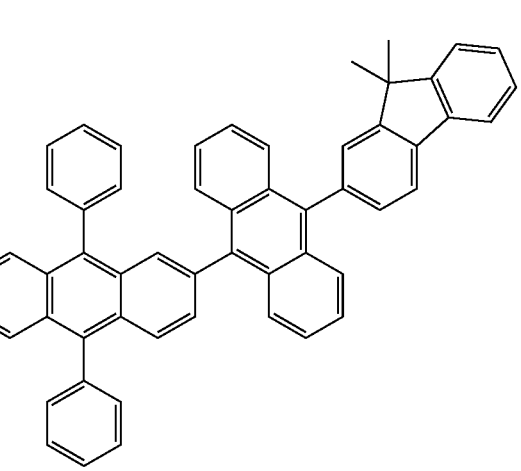

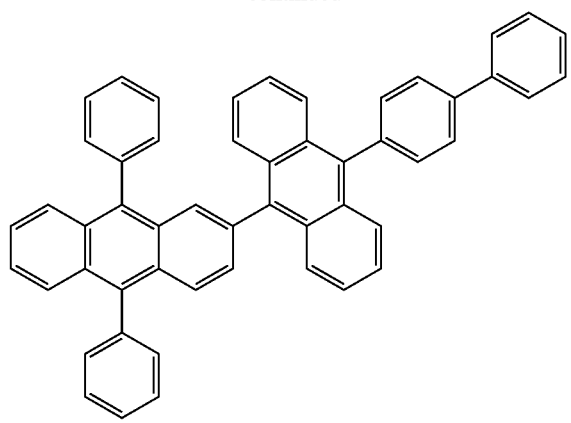
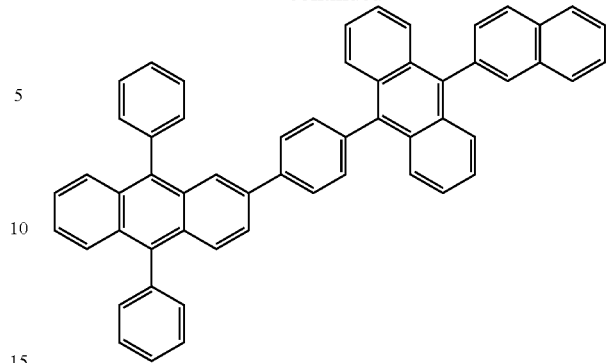
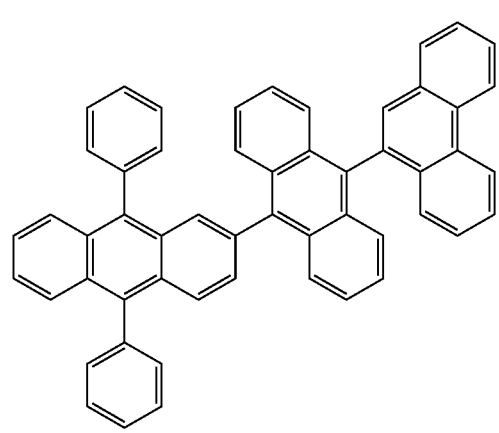
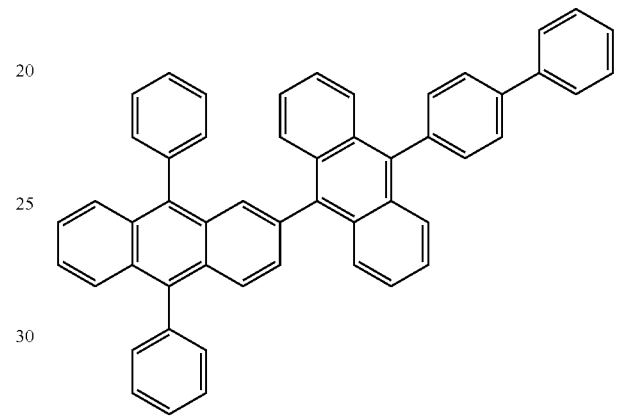
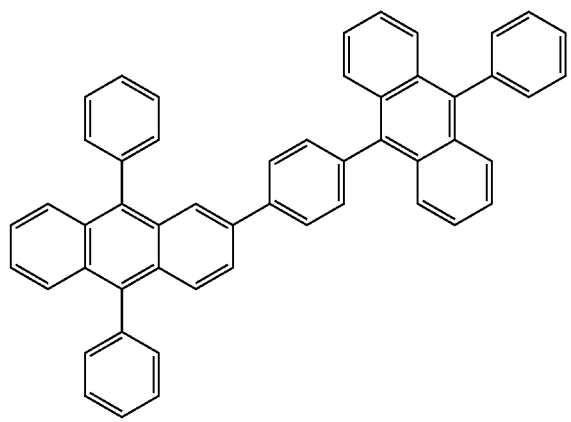
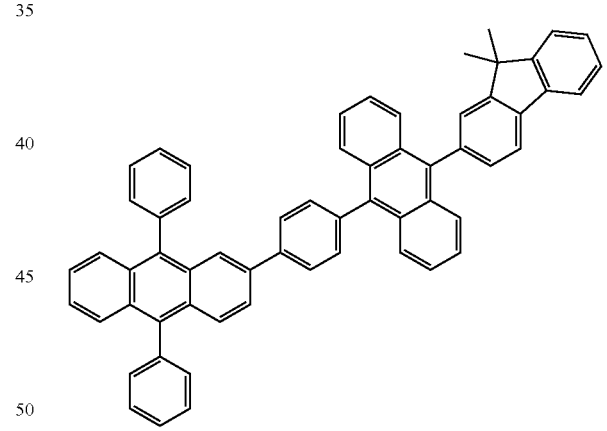
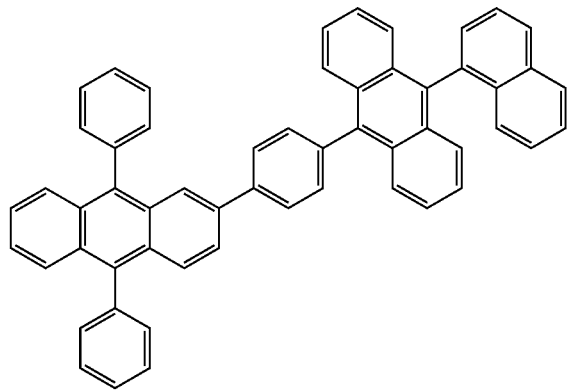
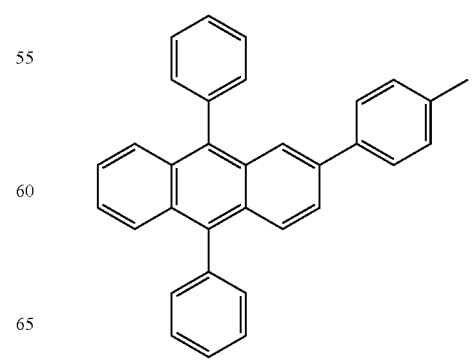

231
-continued
[Formula 152]
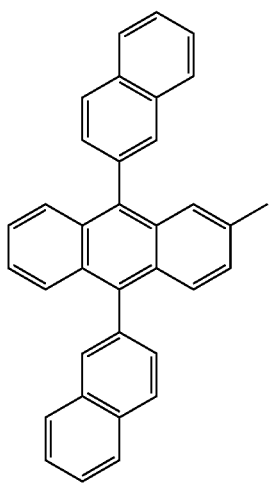
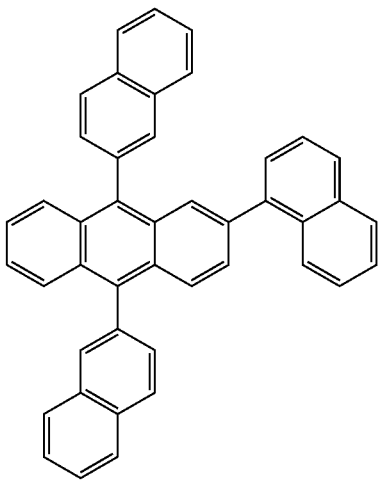
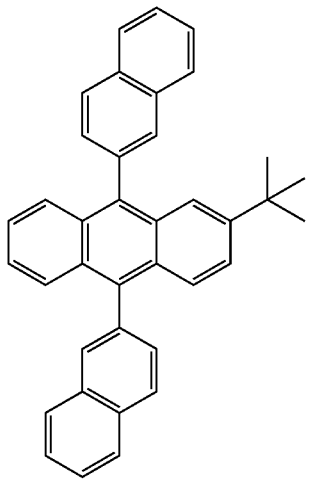
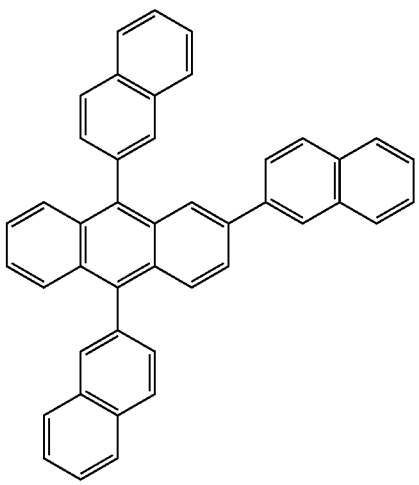
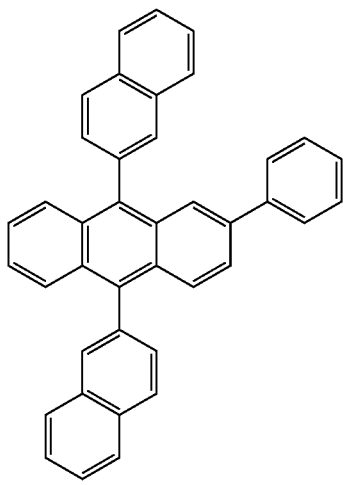
232
-continued 233
-continued
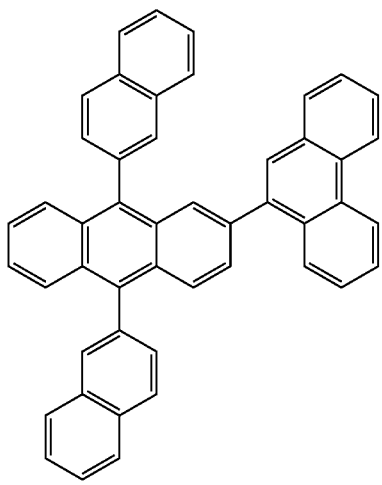
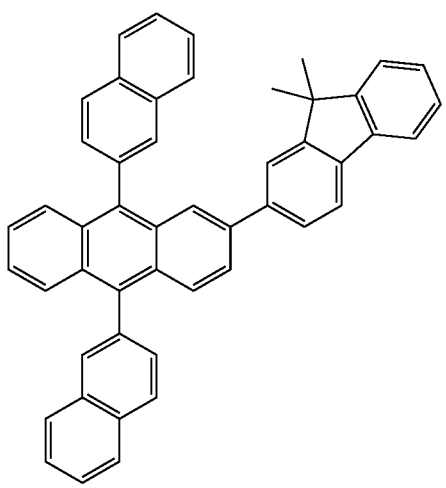
234
-continued
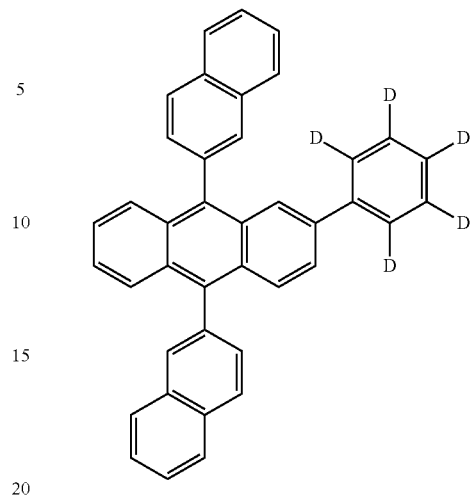
[Formula 153]
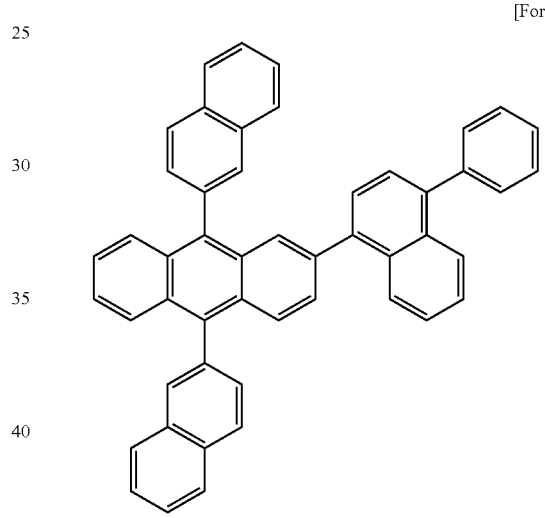
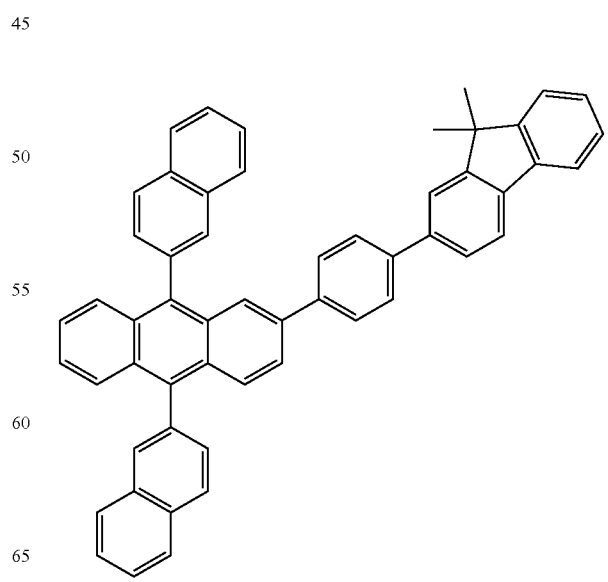

235
-continued
236
-continued
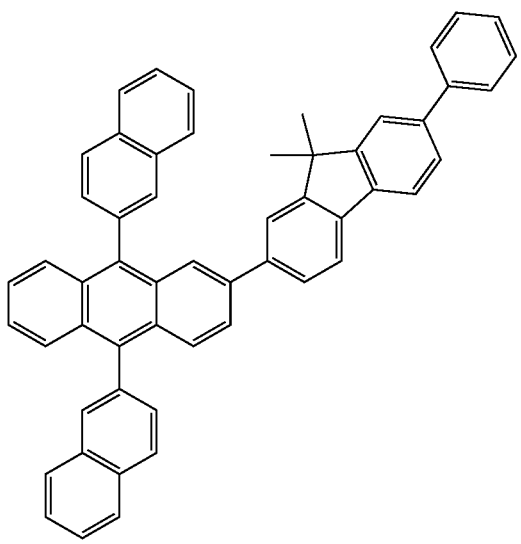
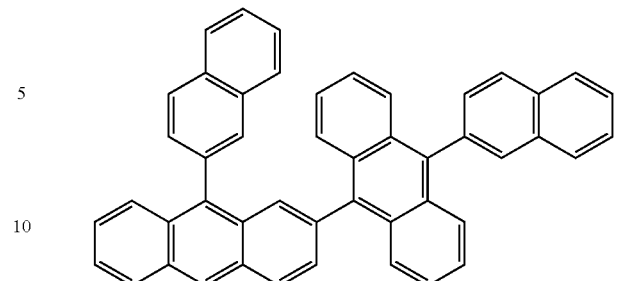
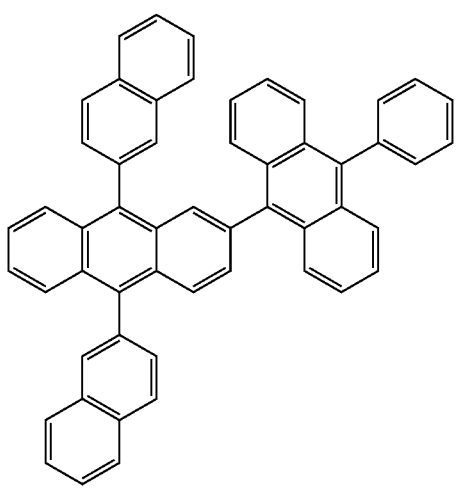
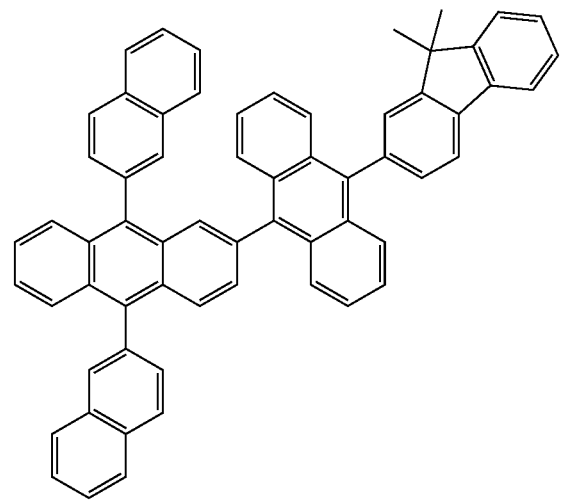
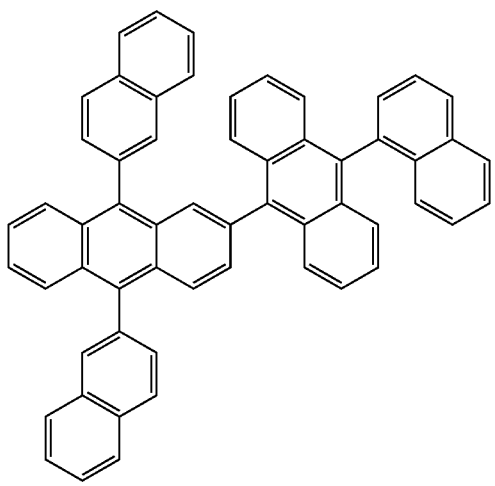

237
-continued
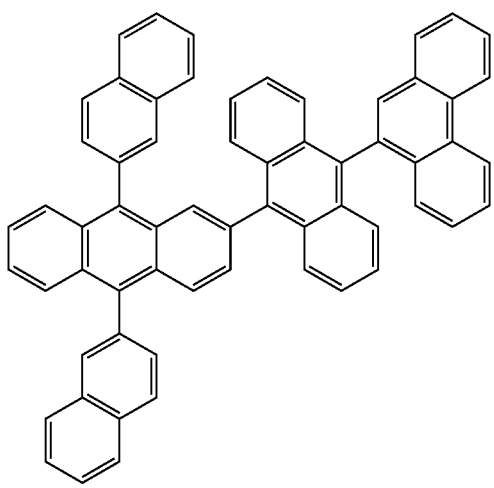
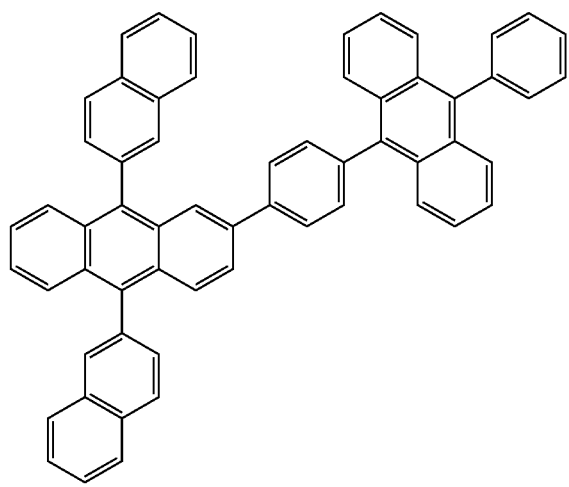
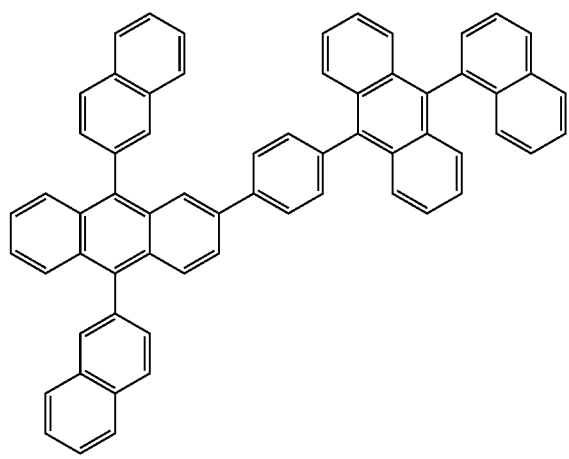
238
-continued
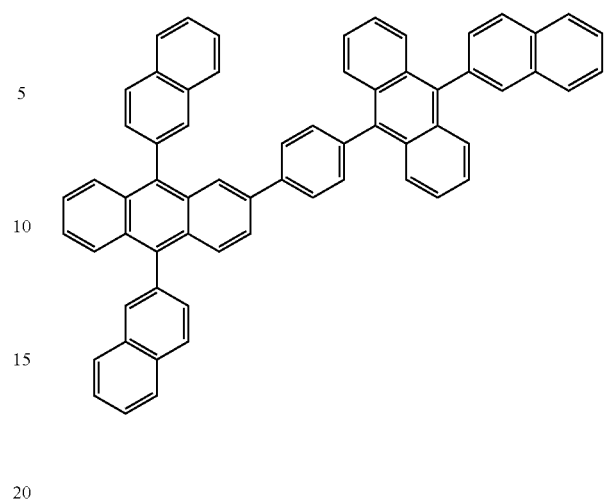
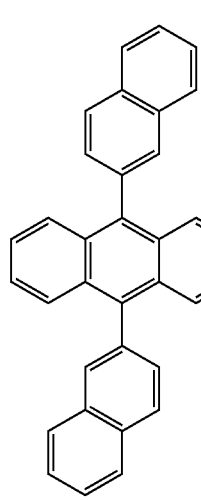
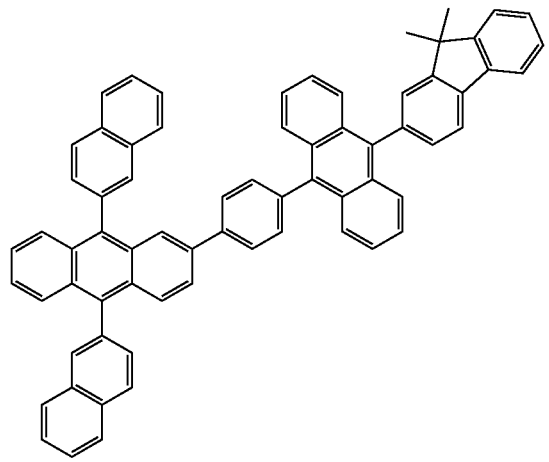

[Formula 154]
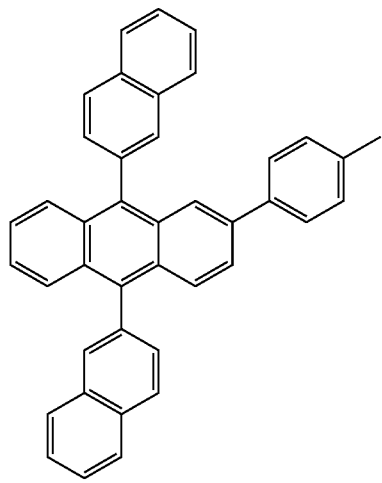
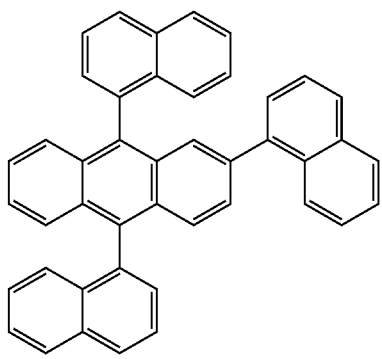
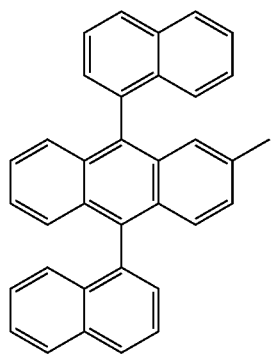
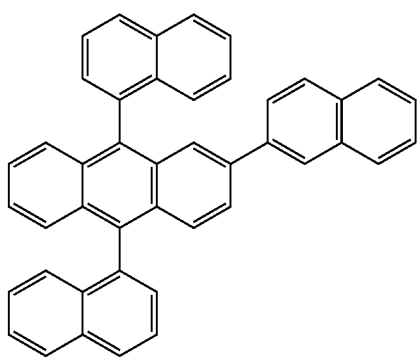
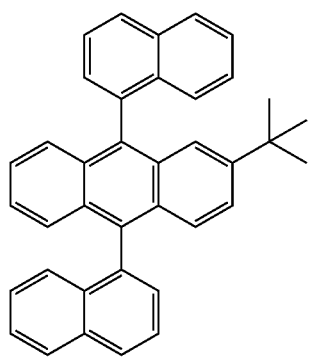
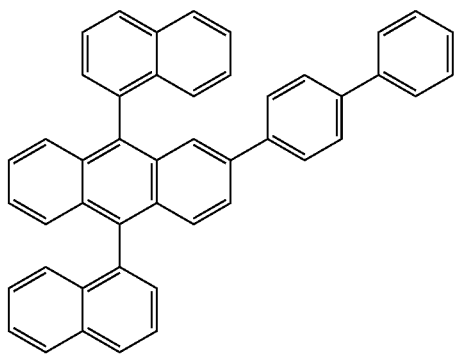
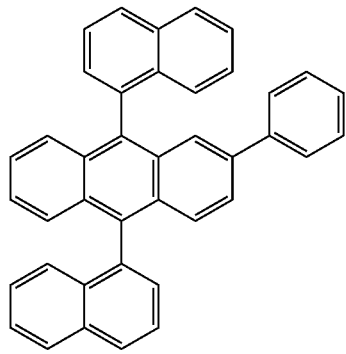
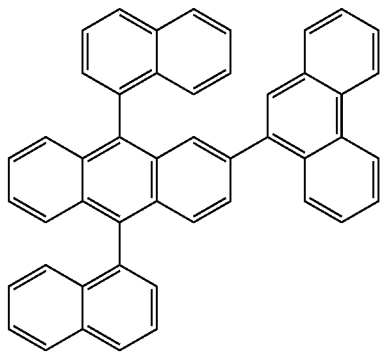

241
-continued
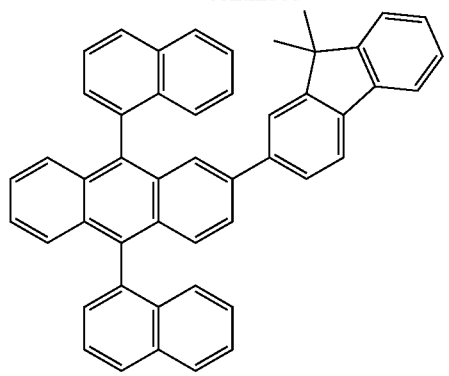
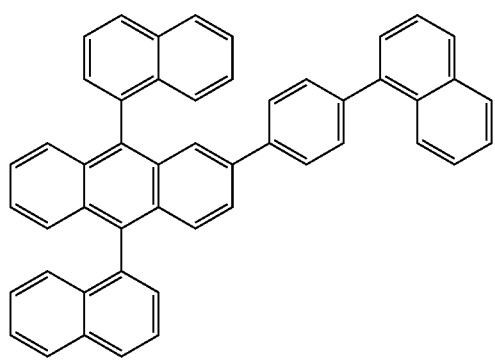
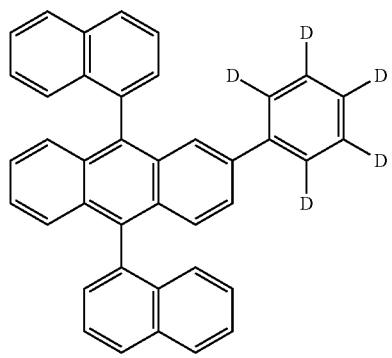
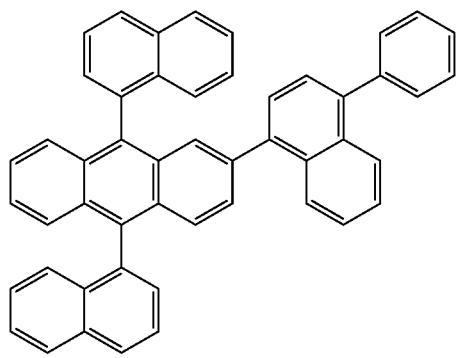
242
-continued
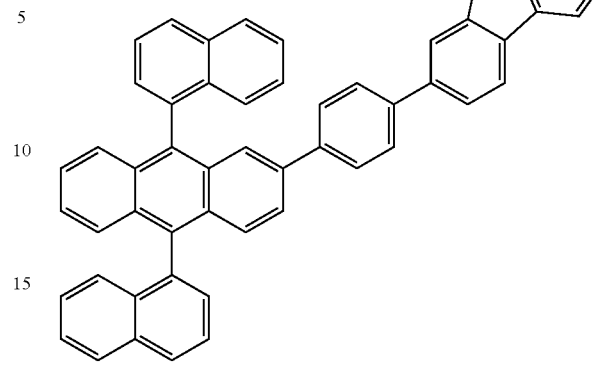
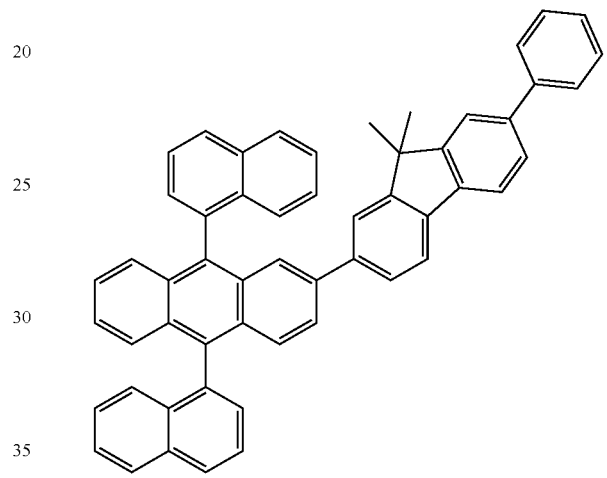
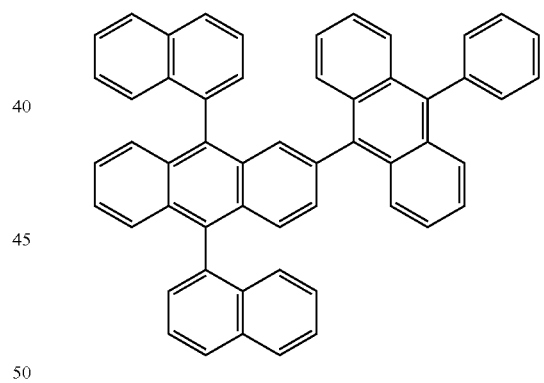
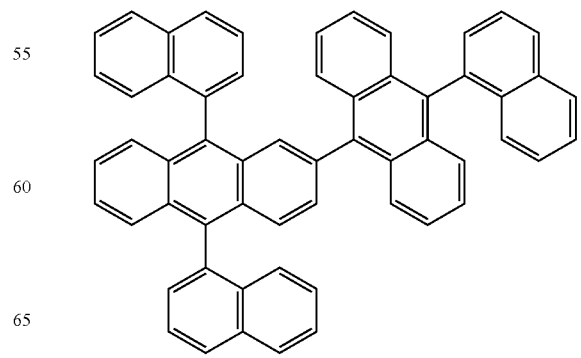

243
-continued
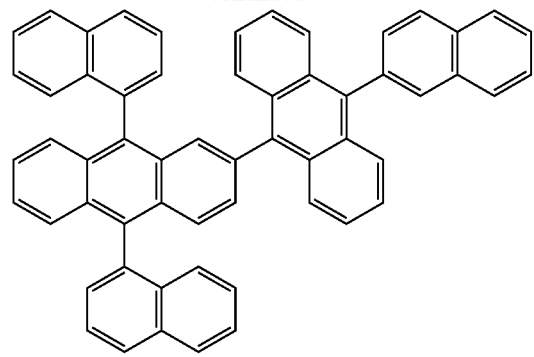
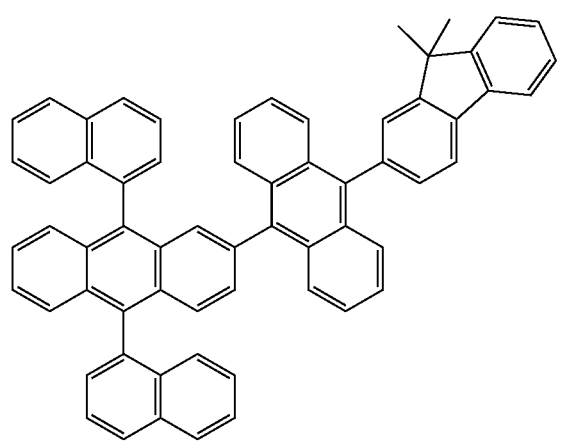
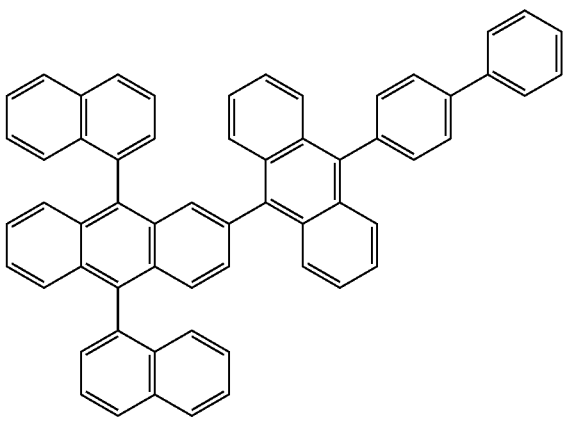
[Formula 155]
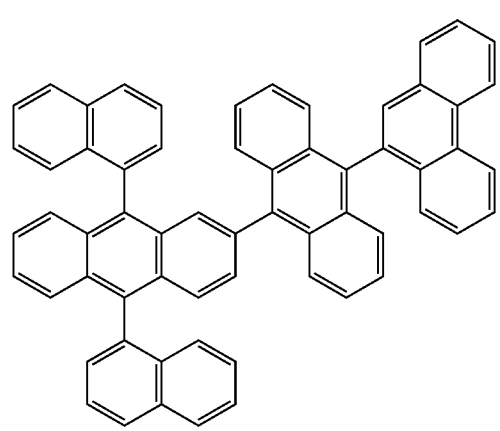
244
-continued
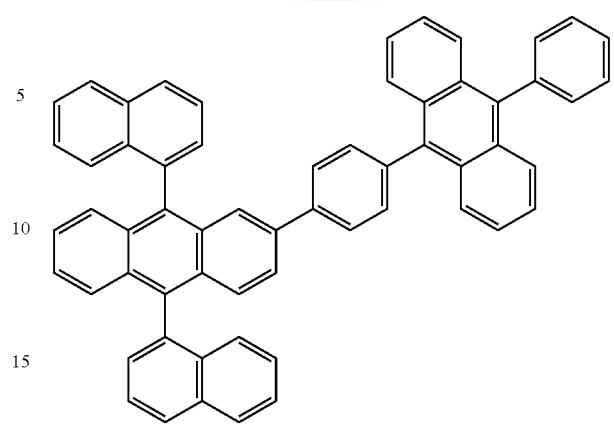
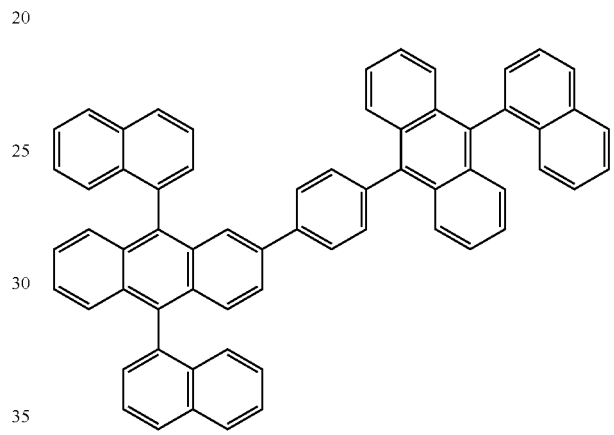
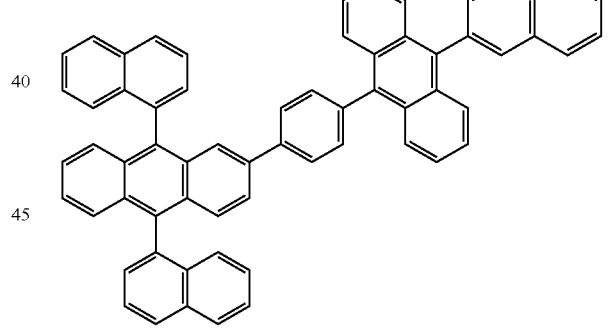
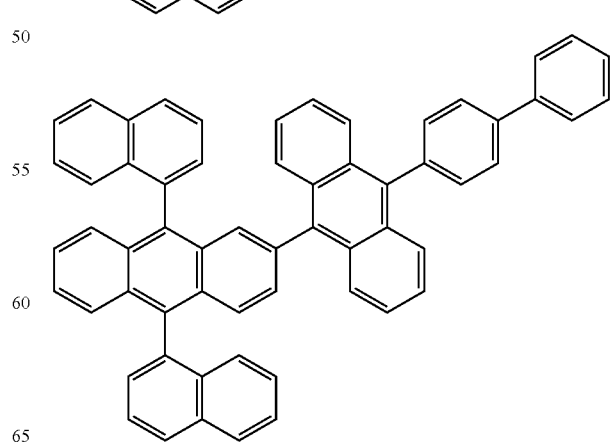

245
-continued
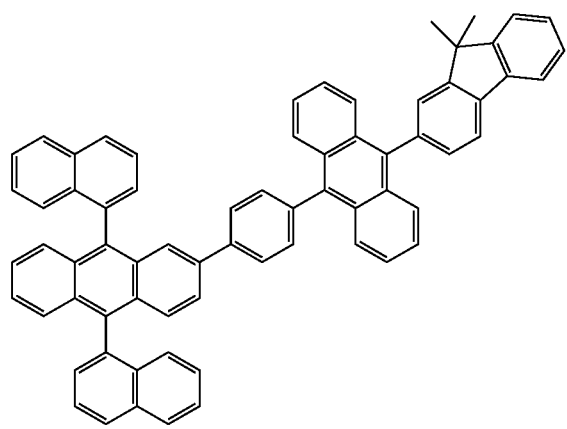
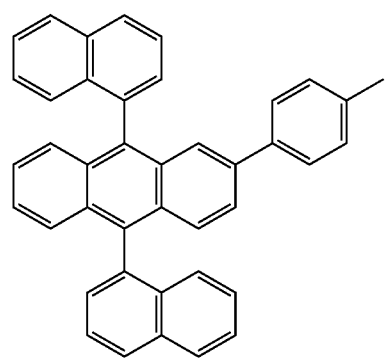
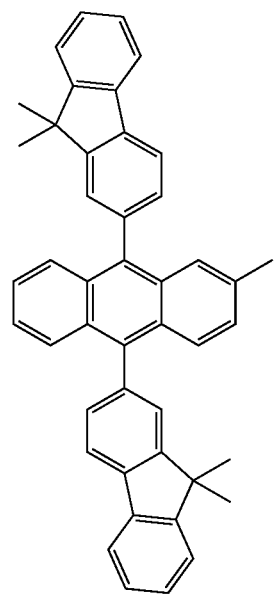
246
-continued
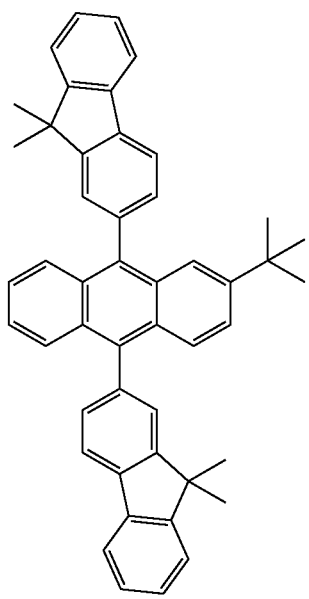
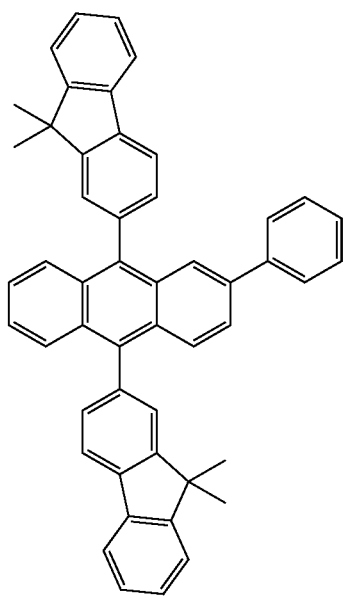

247
-continued
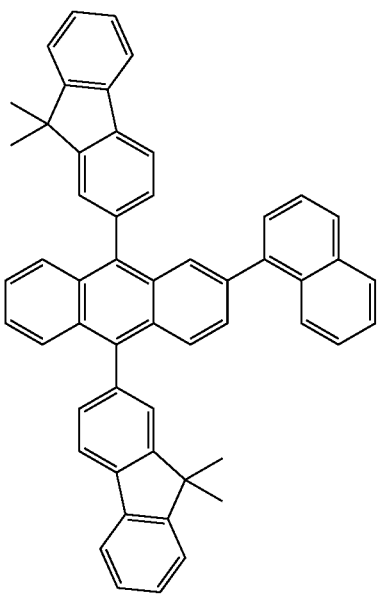
248
-continued
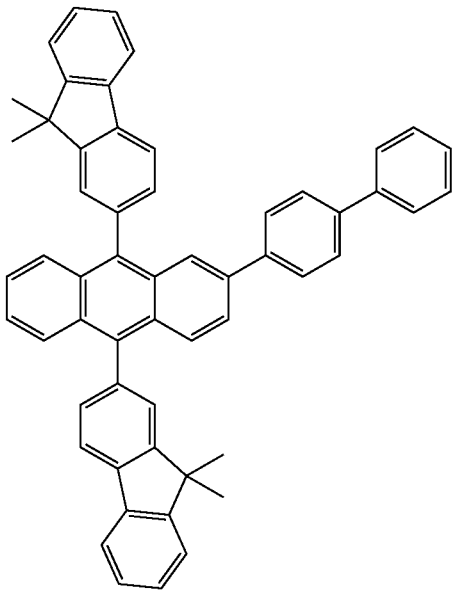
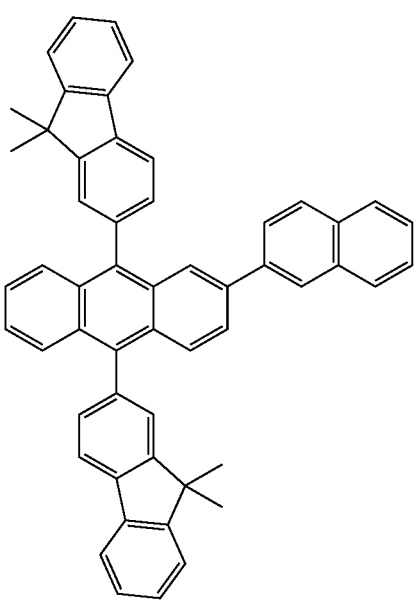
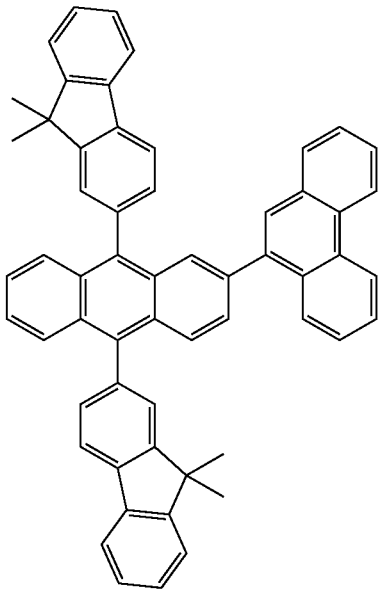

249
-continued
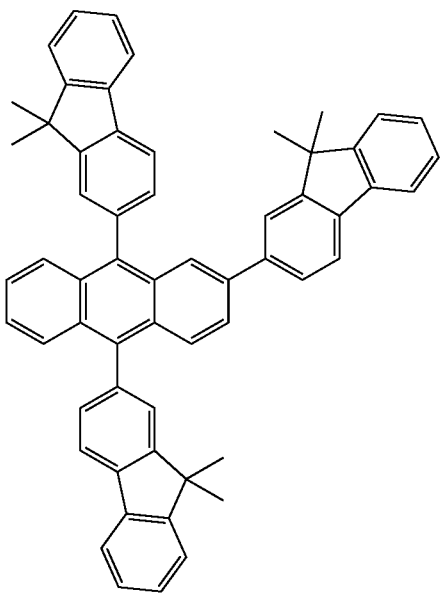
250
-continued
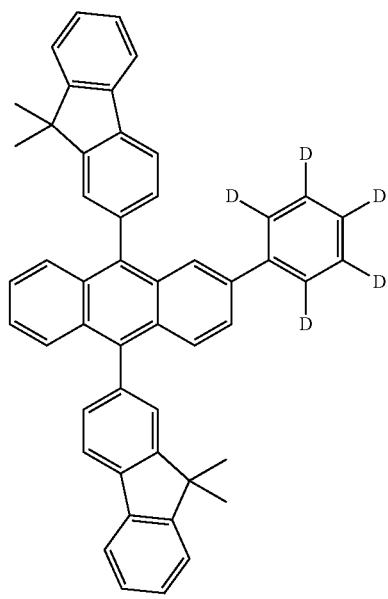
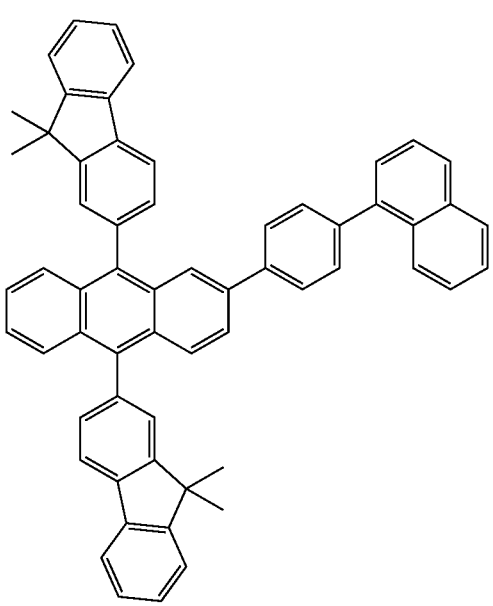
[Formula 156]
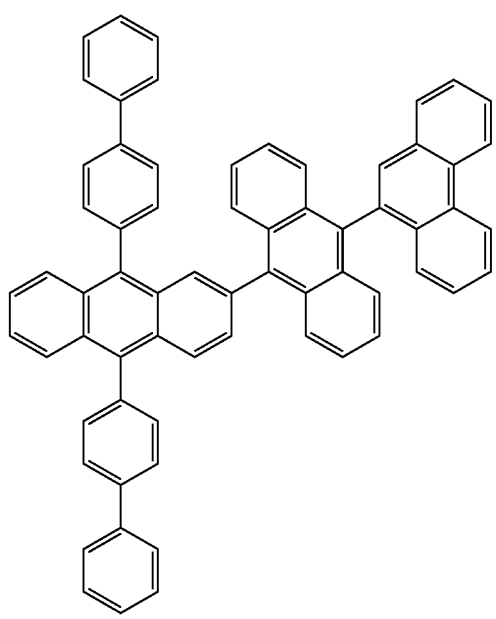

251
-continued
252
-continued
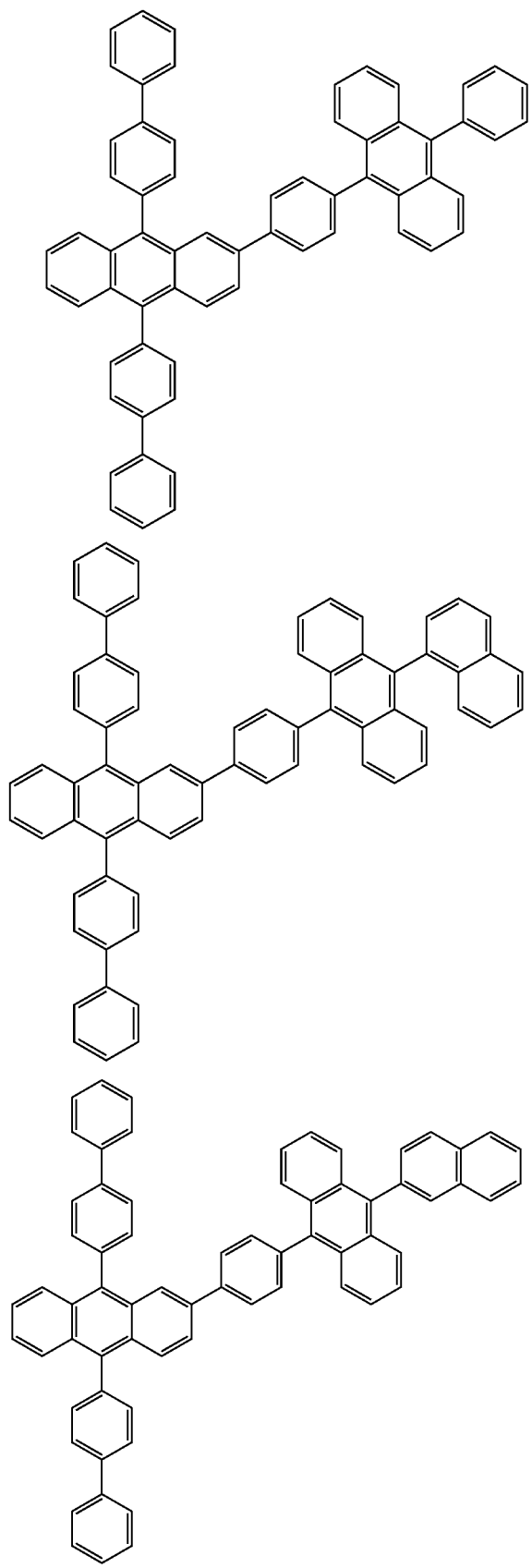
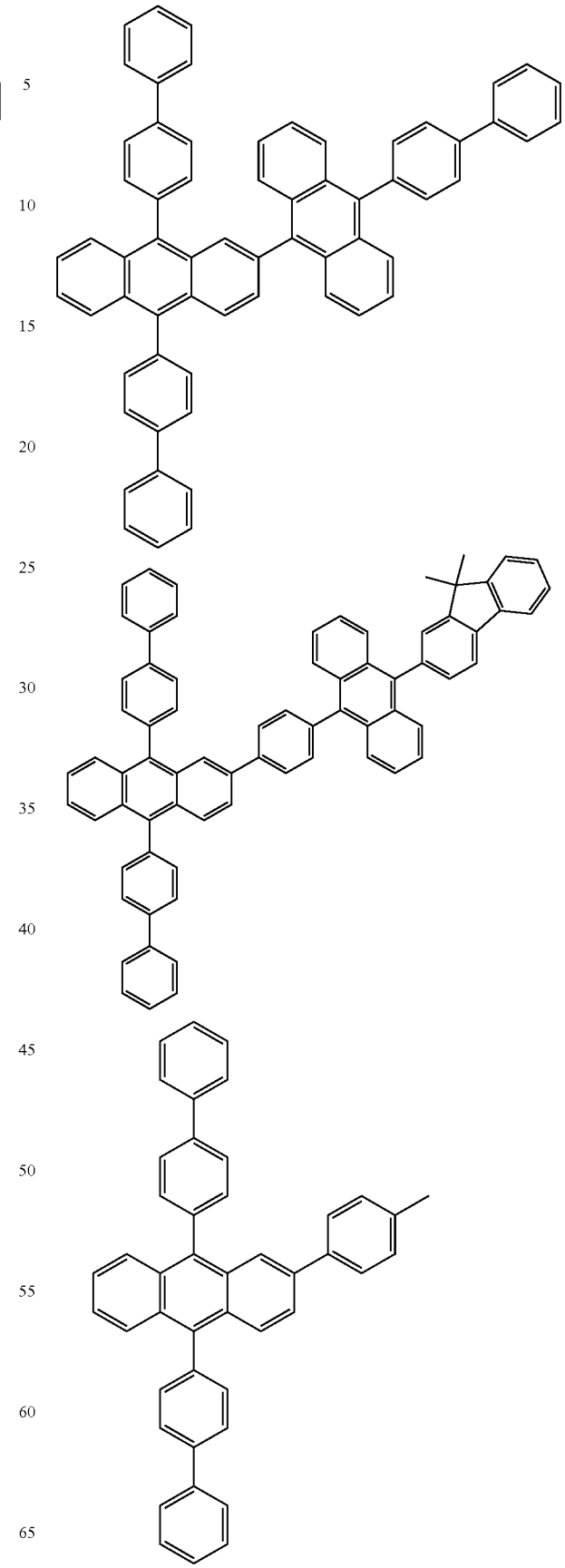

253
-continued
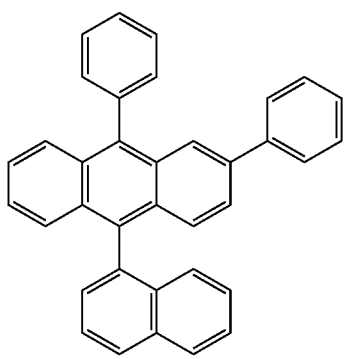
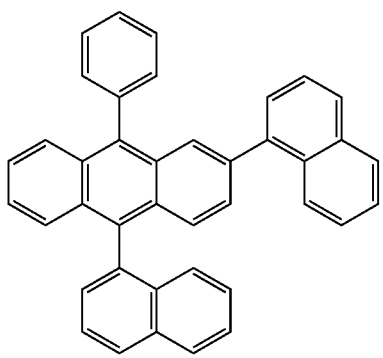
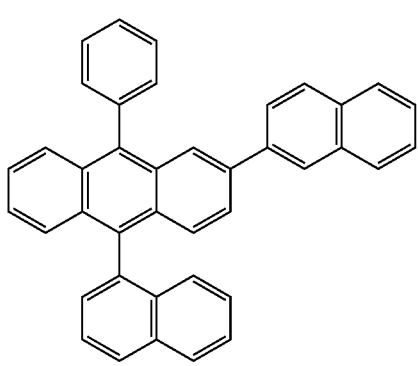
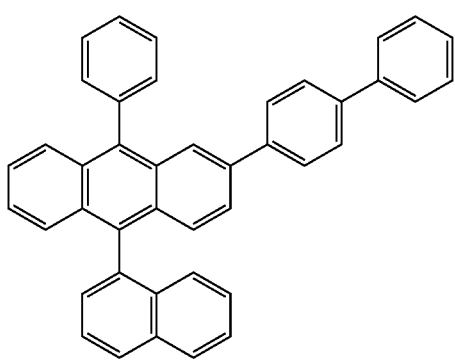
254
-continued
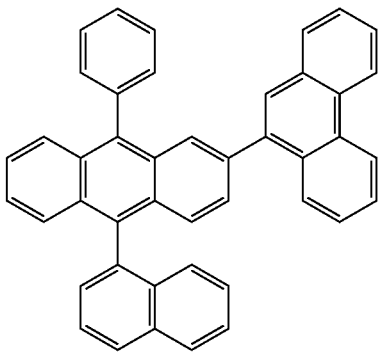
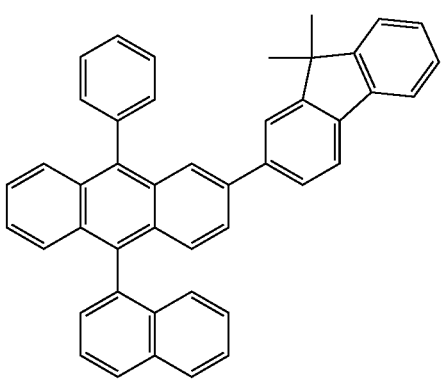
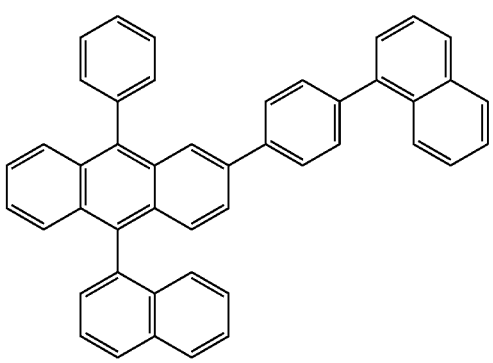
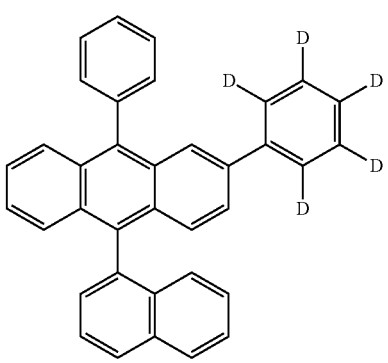

255
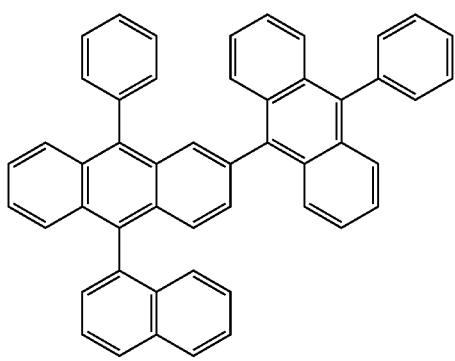
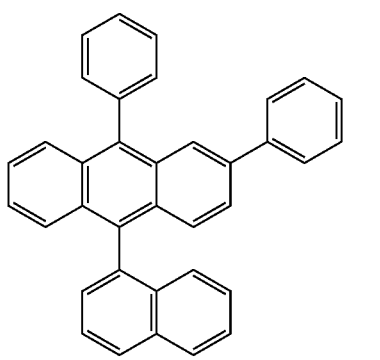
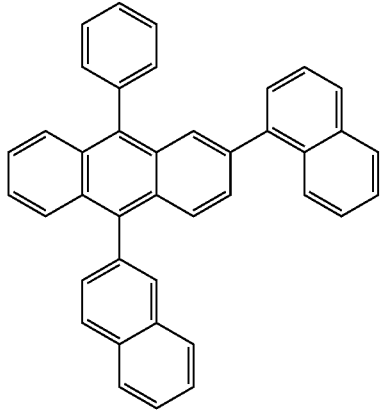
[Formula 157]
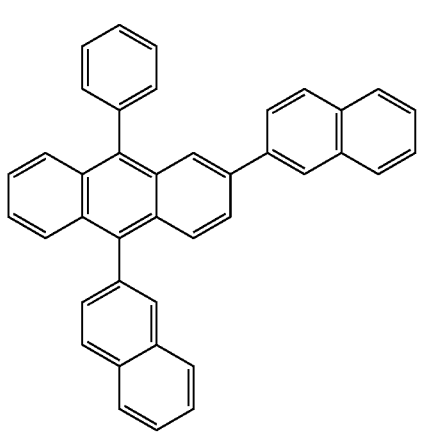
256
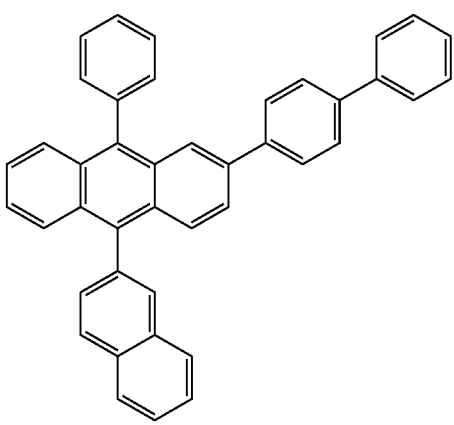
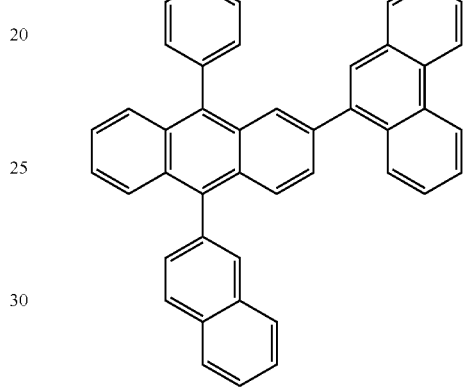
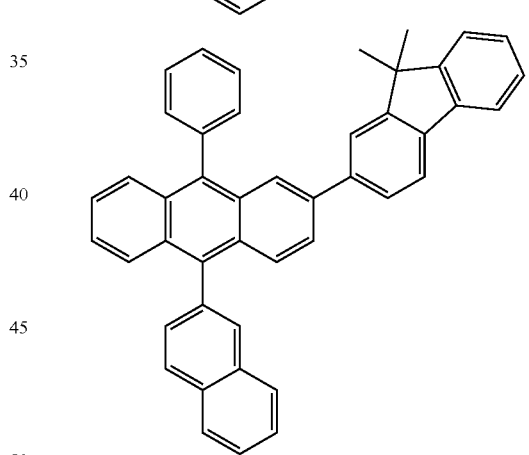
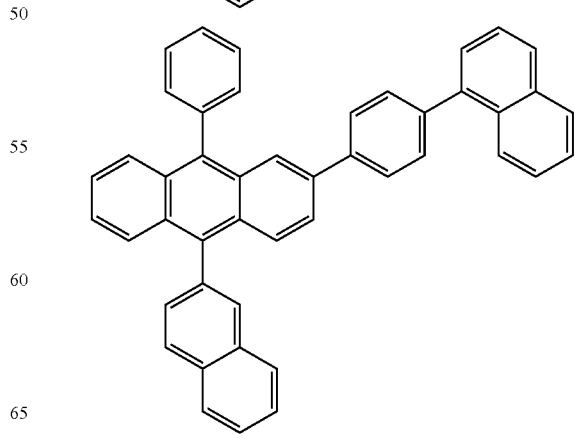

257
-continued
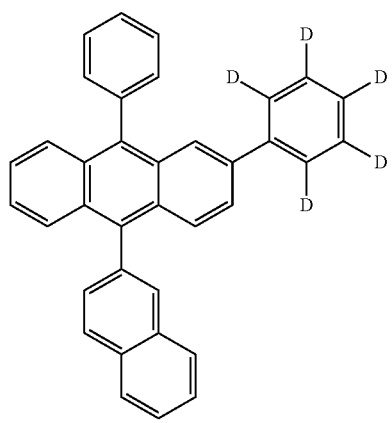
258
-continued
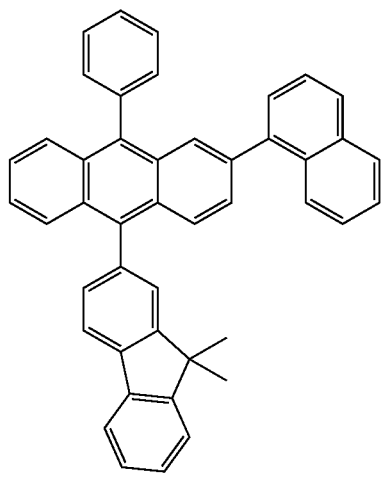
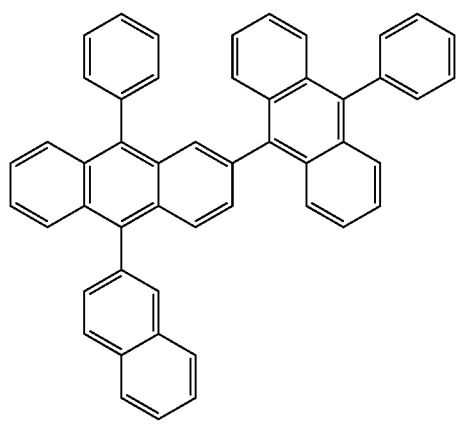
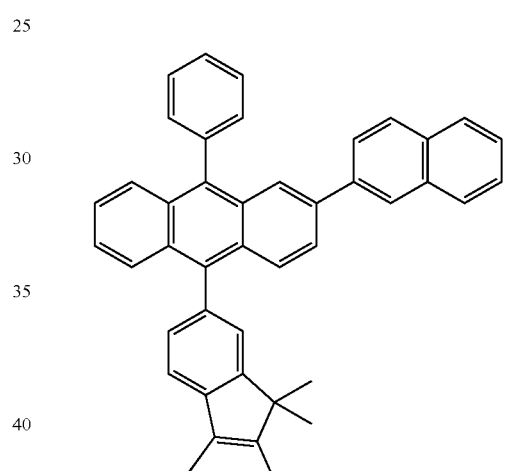
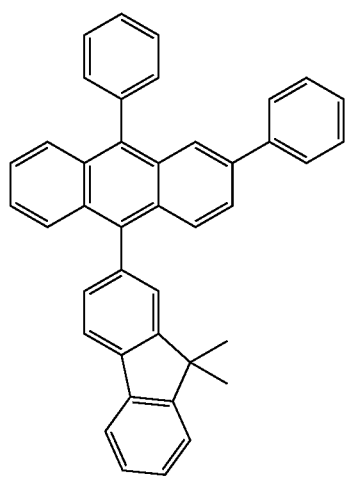

259
-continued
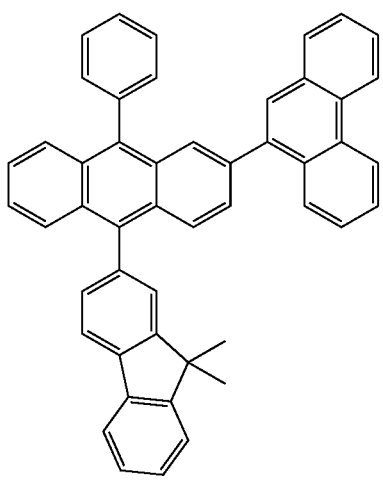
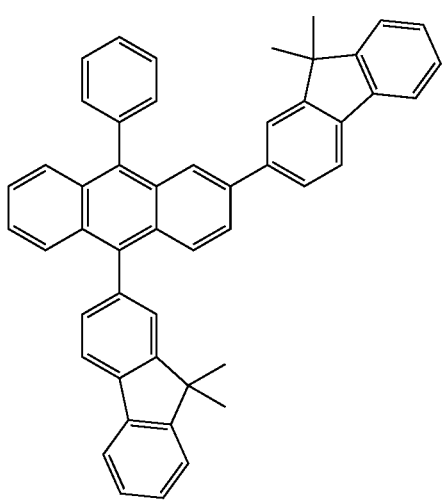
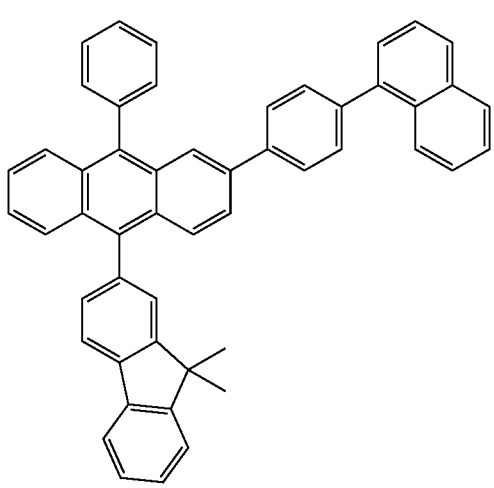
260
-continued
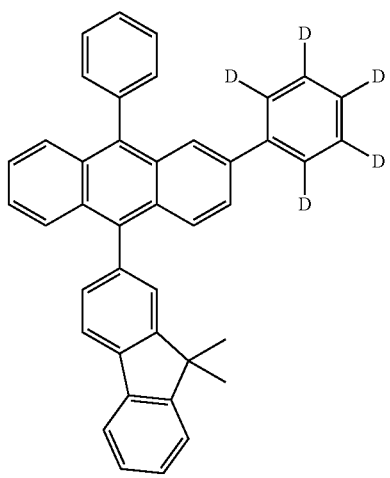
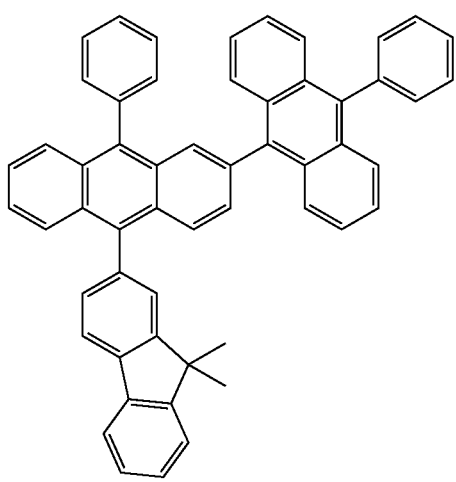
[Formula 158]
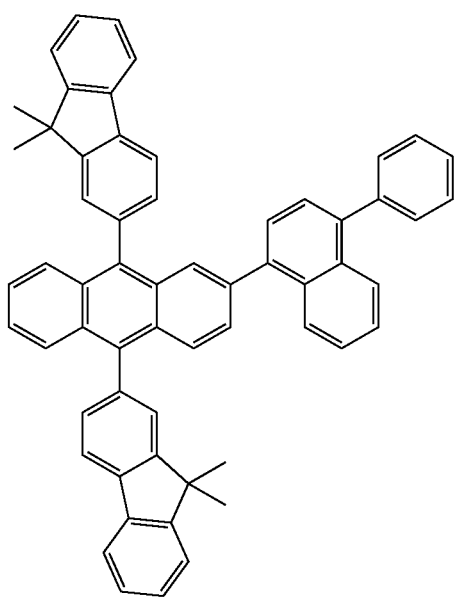

261
-continued
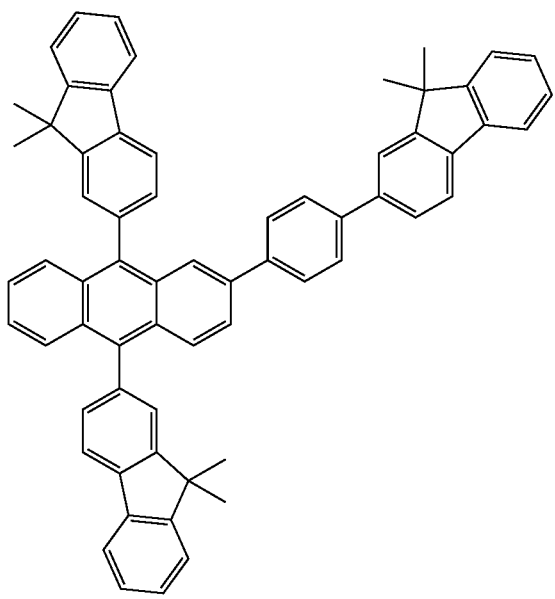
262
-continued
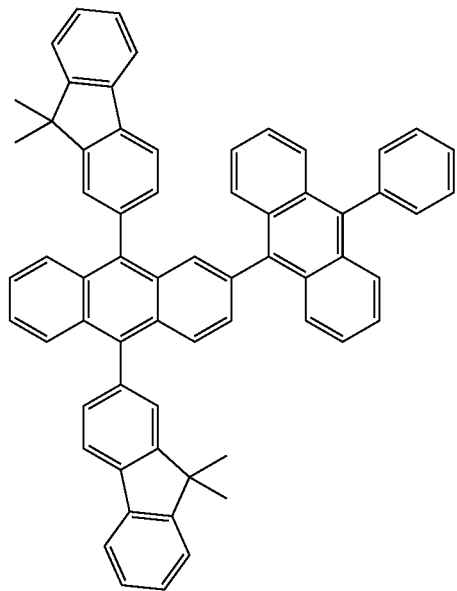
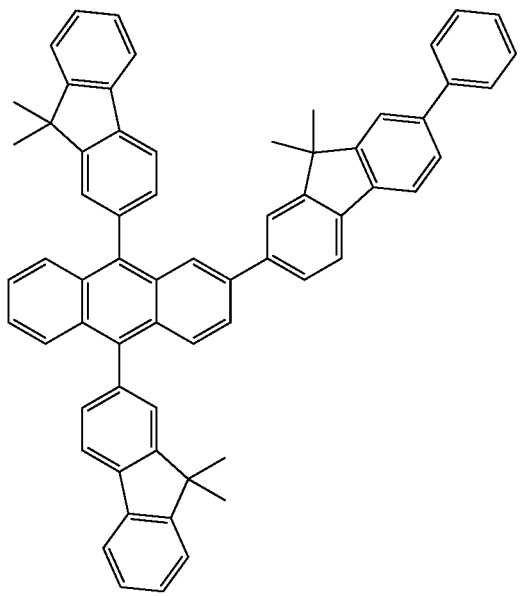
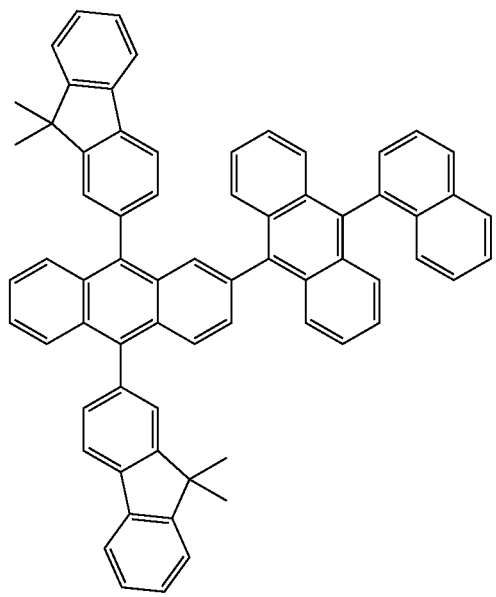

263
-continued
264
-continued
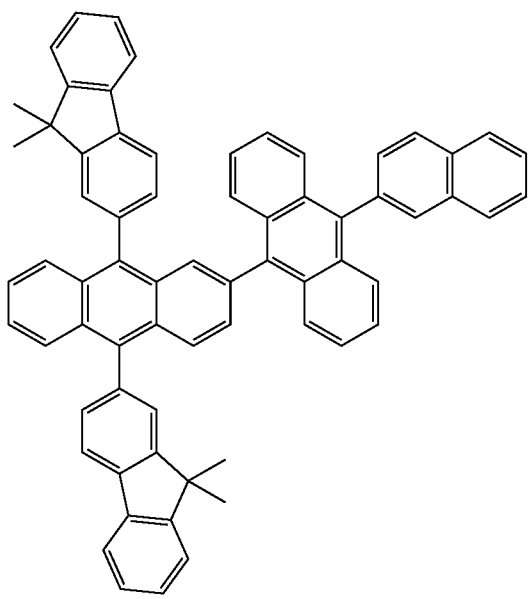
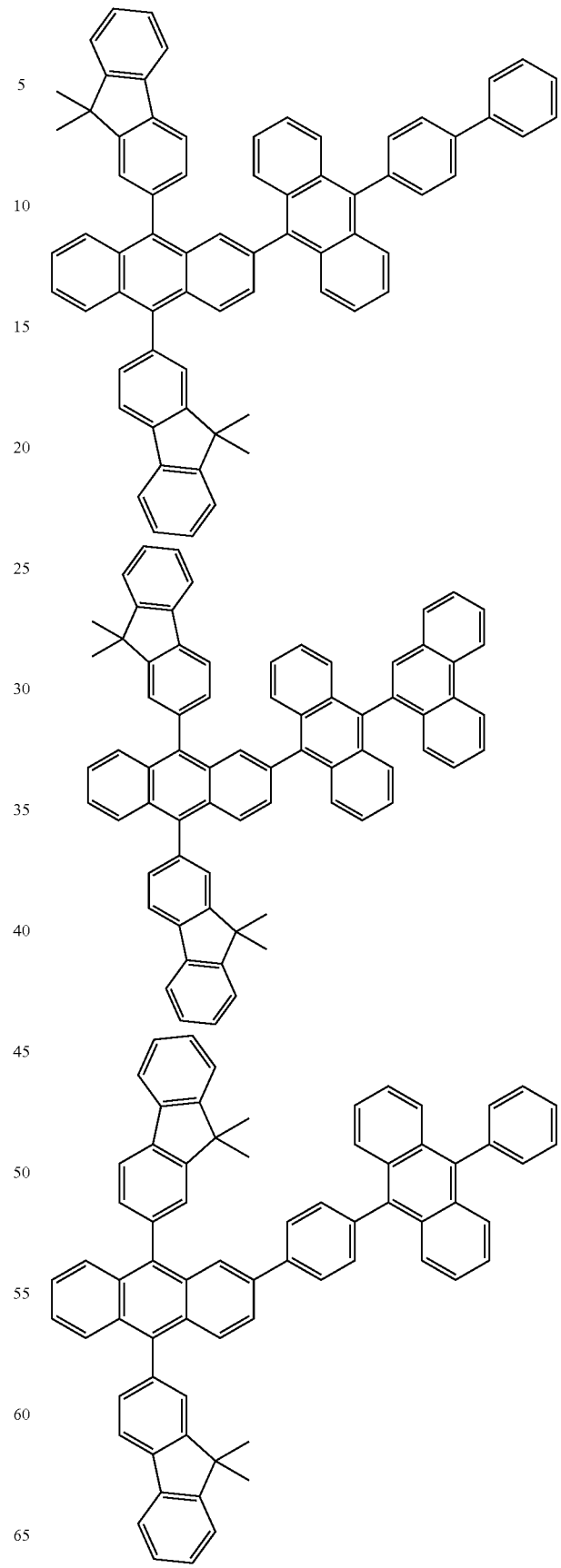

265
-continued
266
-continued
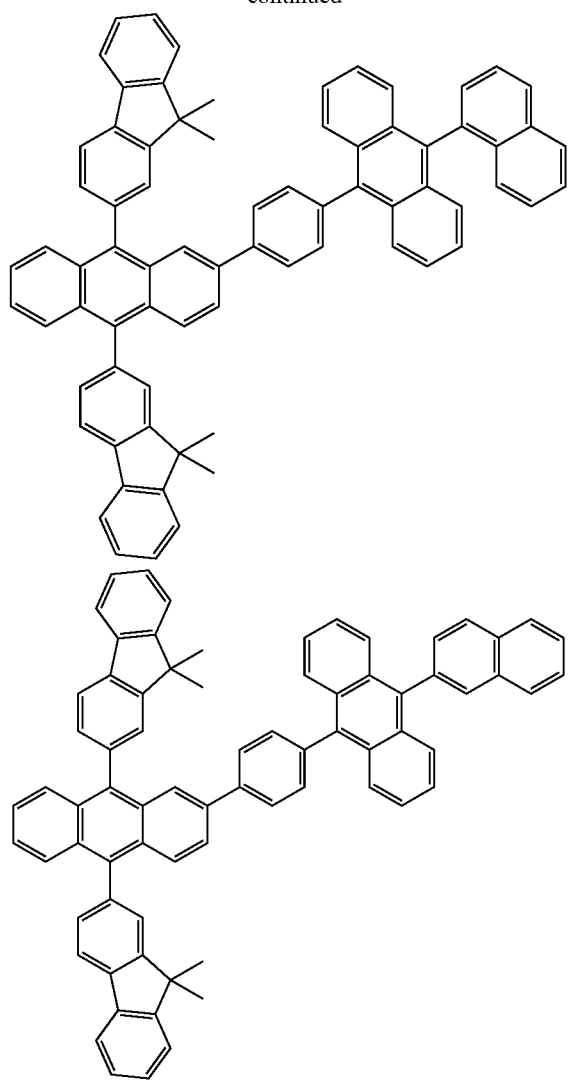
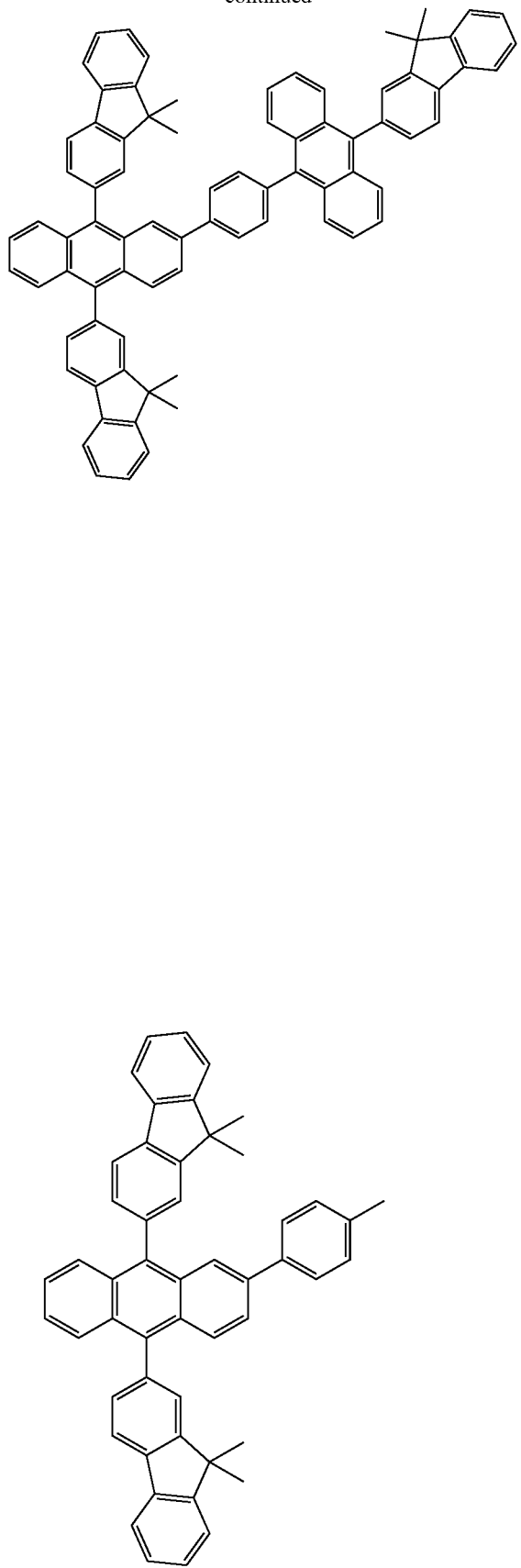

[Formula 159]
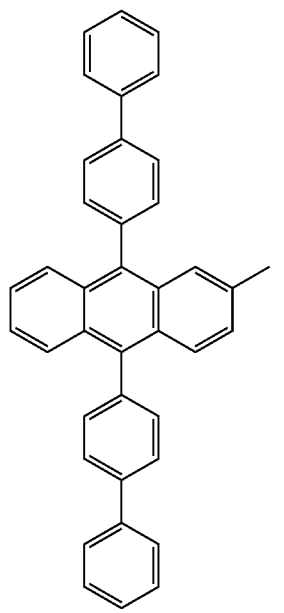
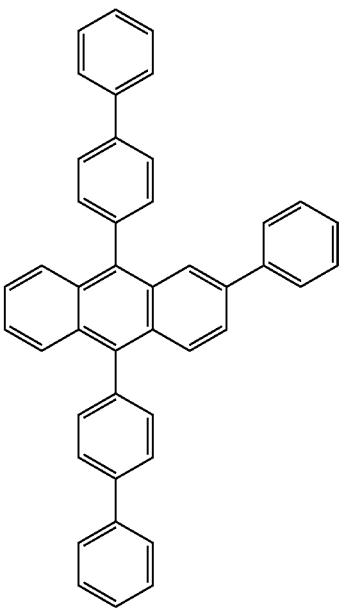
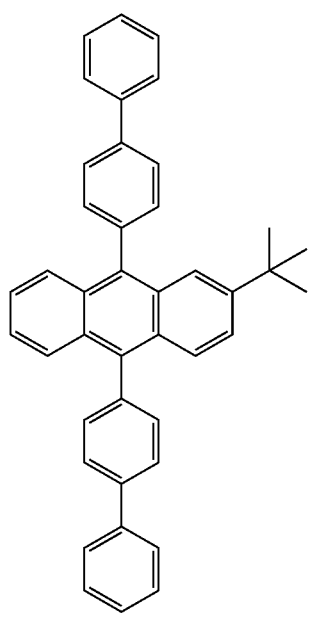
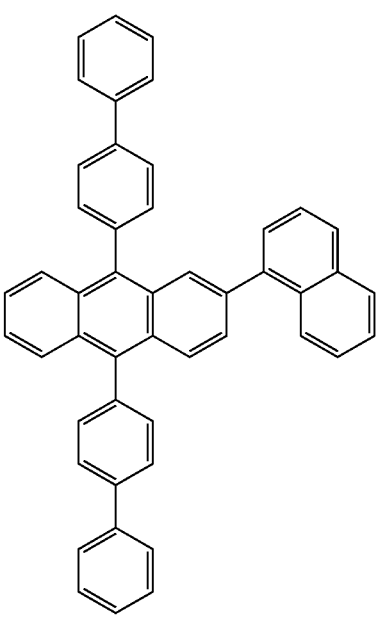

269
-continued
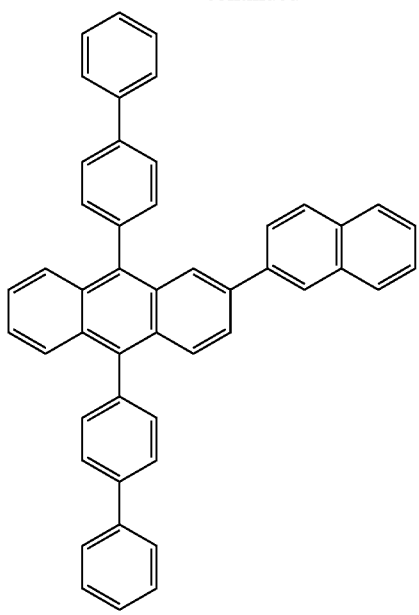
270
-continued
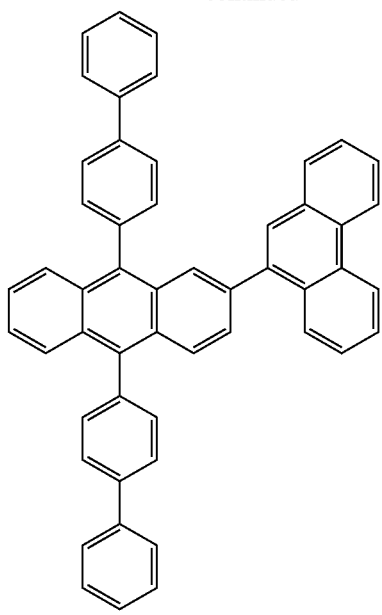
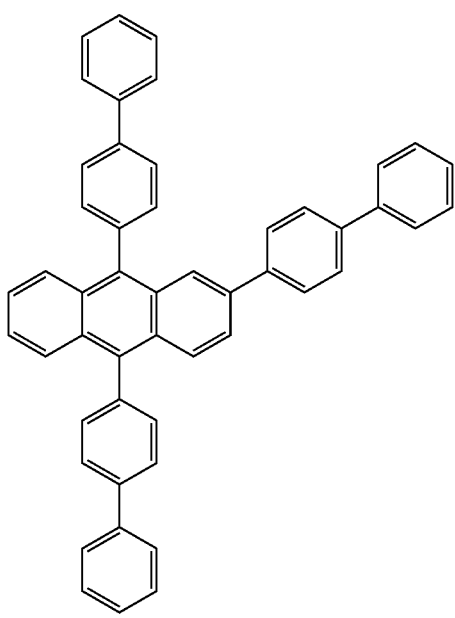
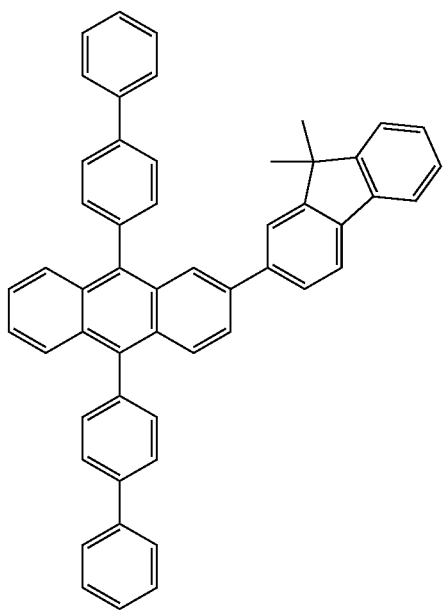

271
-continued
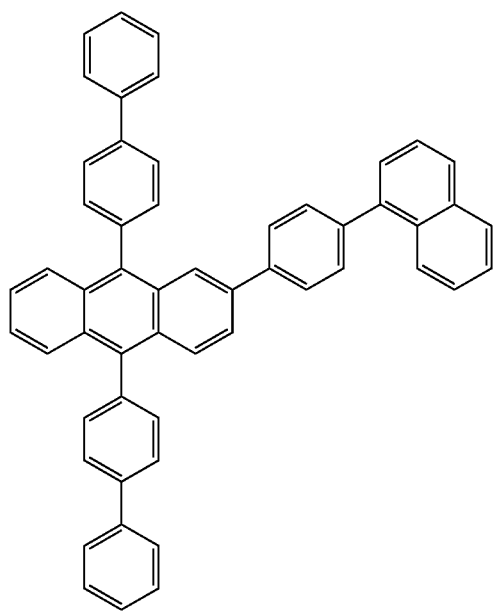
272
-continued
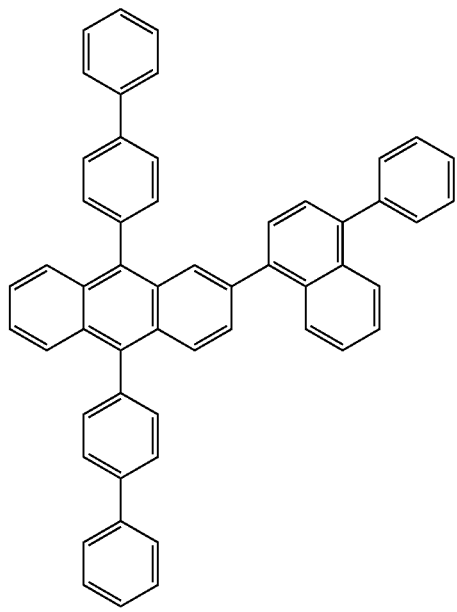
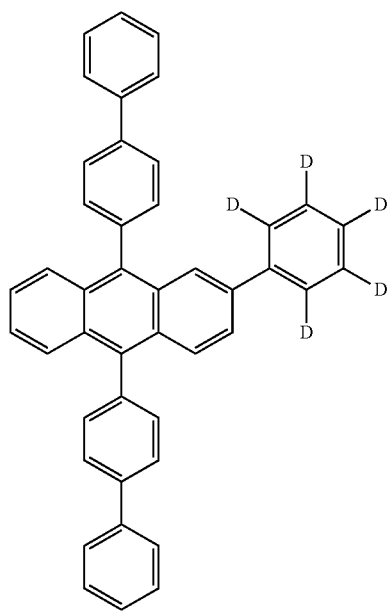
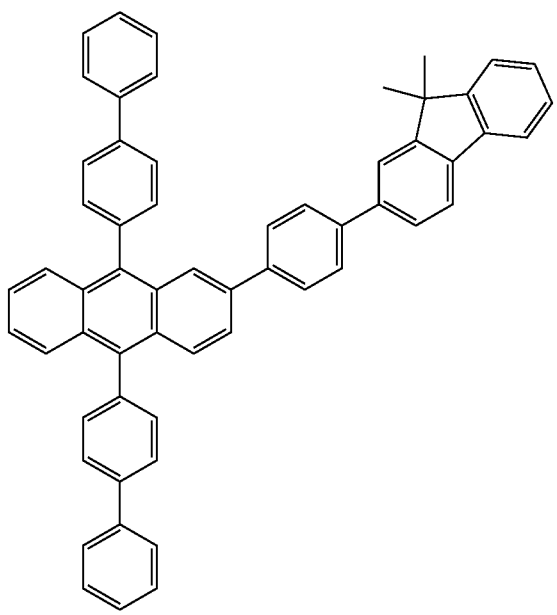

273
-continued
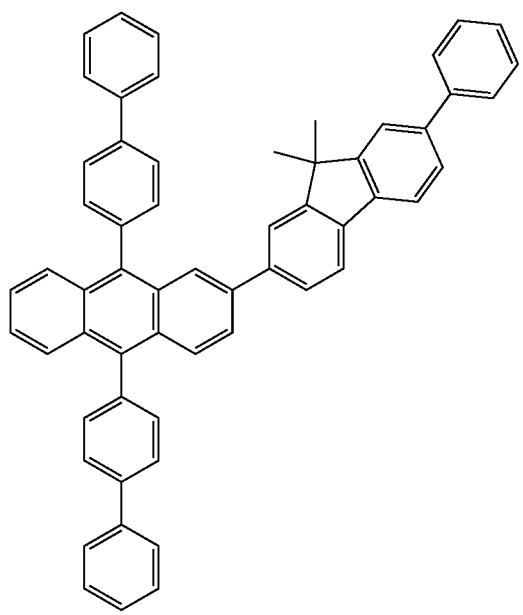
274
-continued
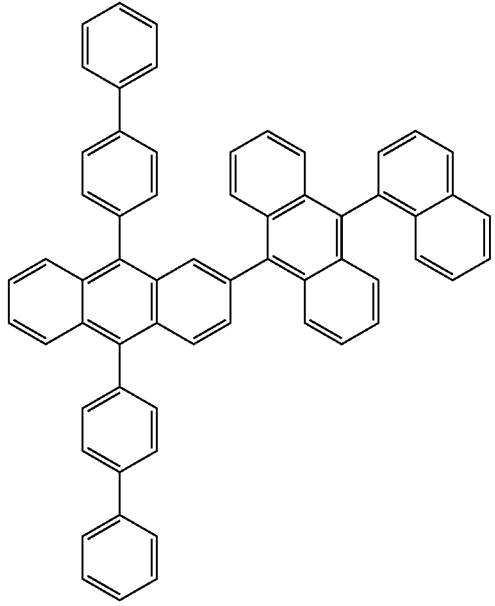
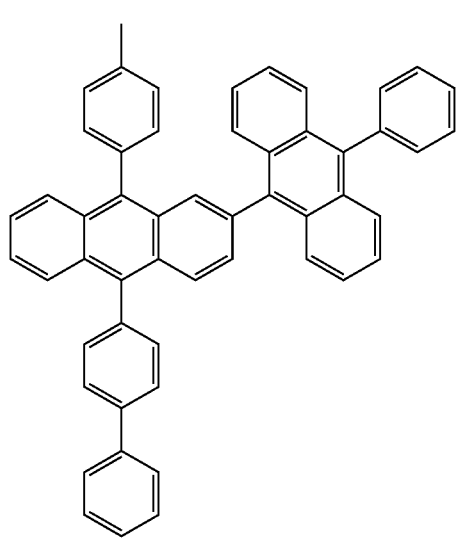
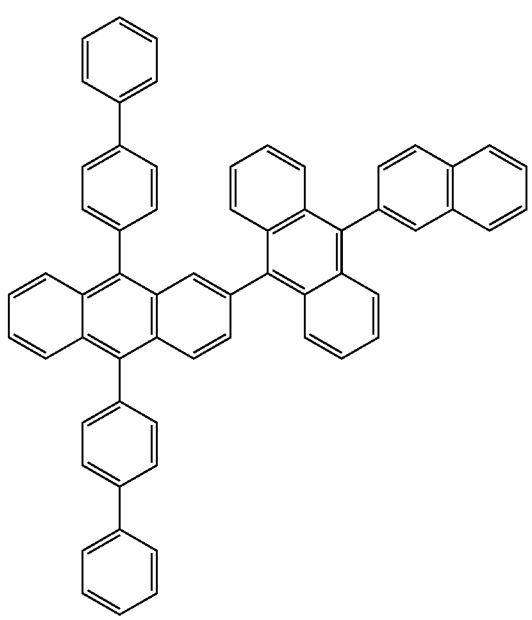

275
-continued
276
-continued
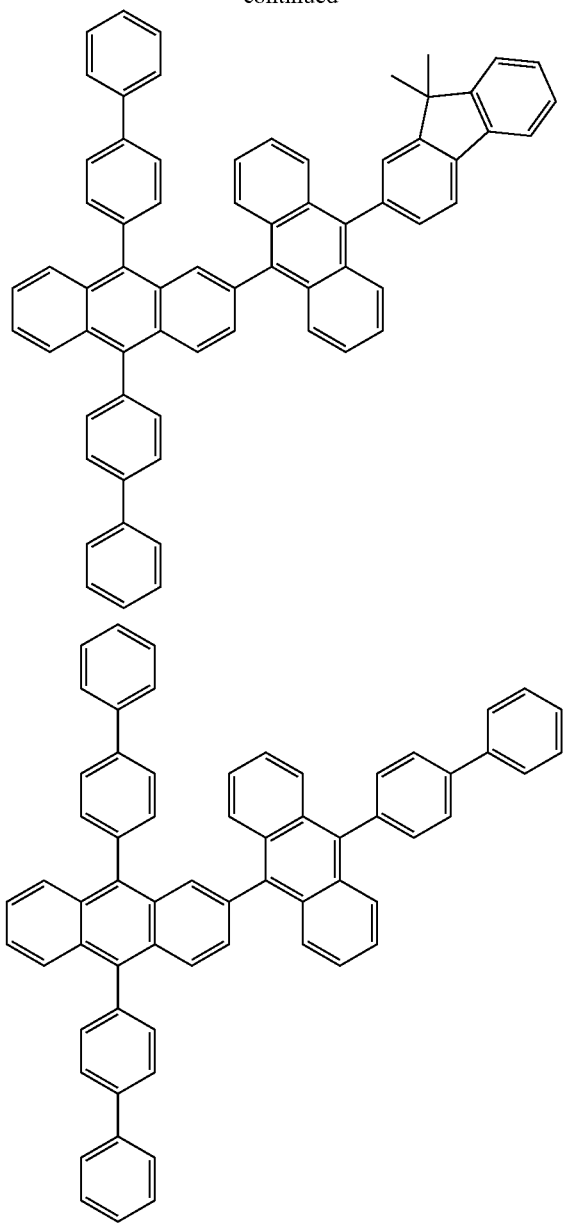
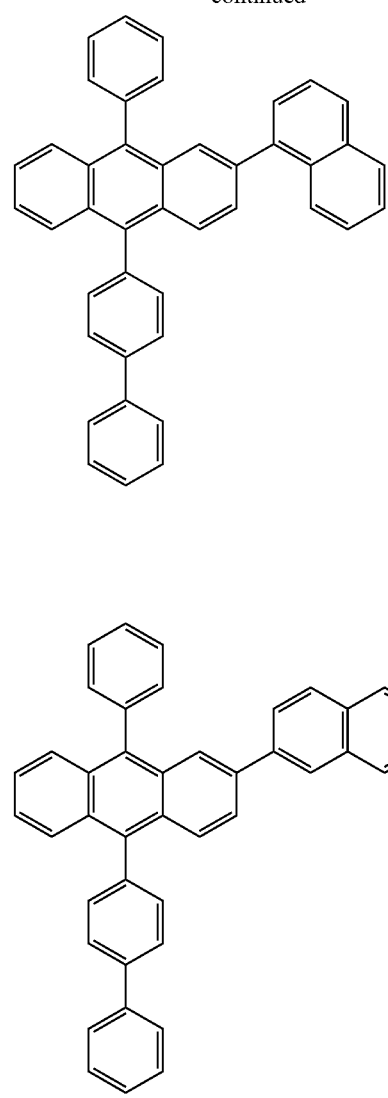
[Formula 160]
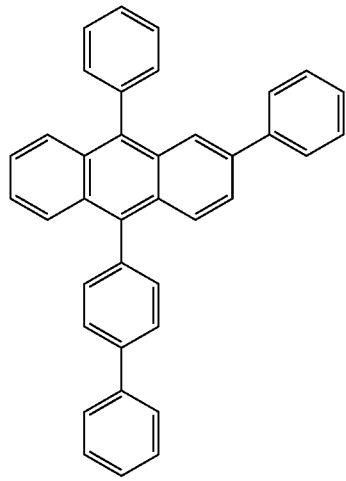
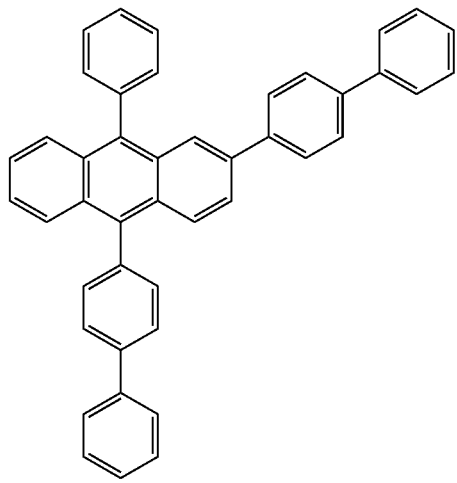

277
-continued
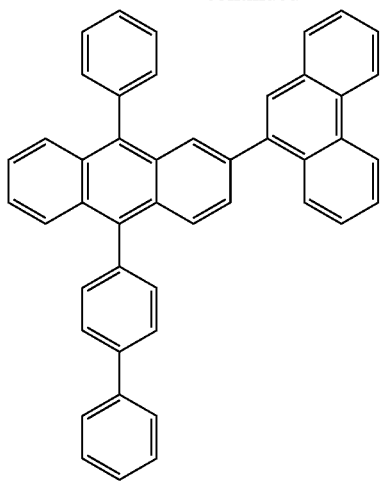
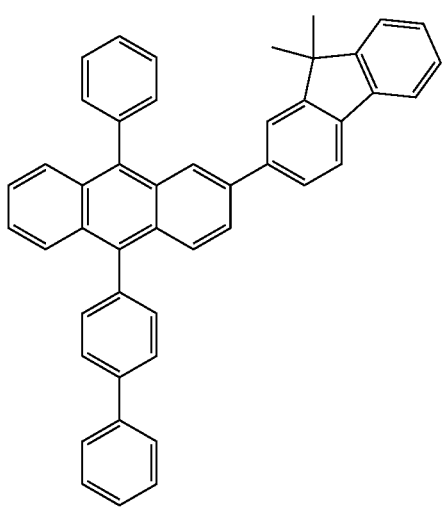
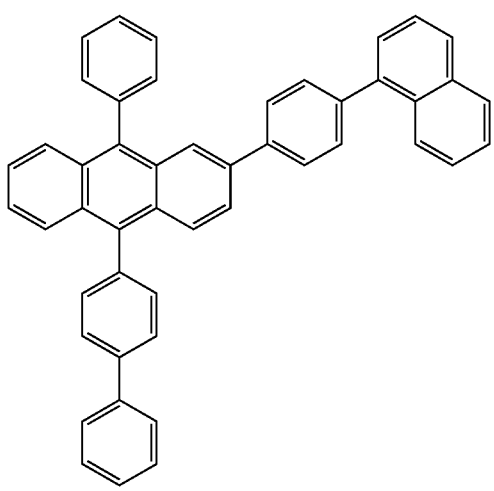
278
-continued
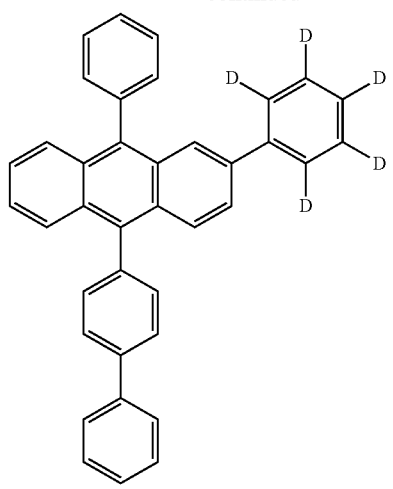
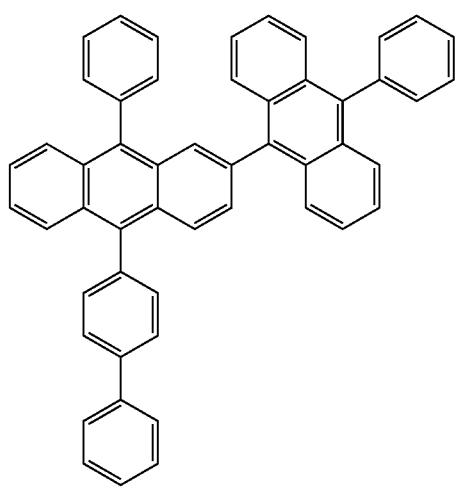
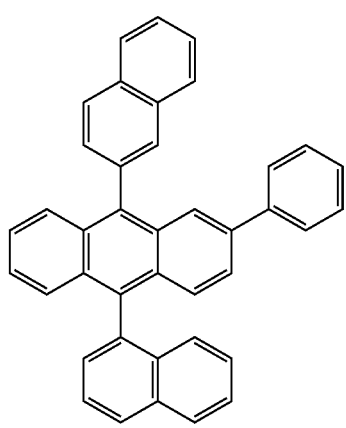

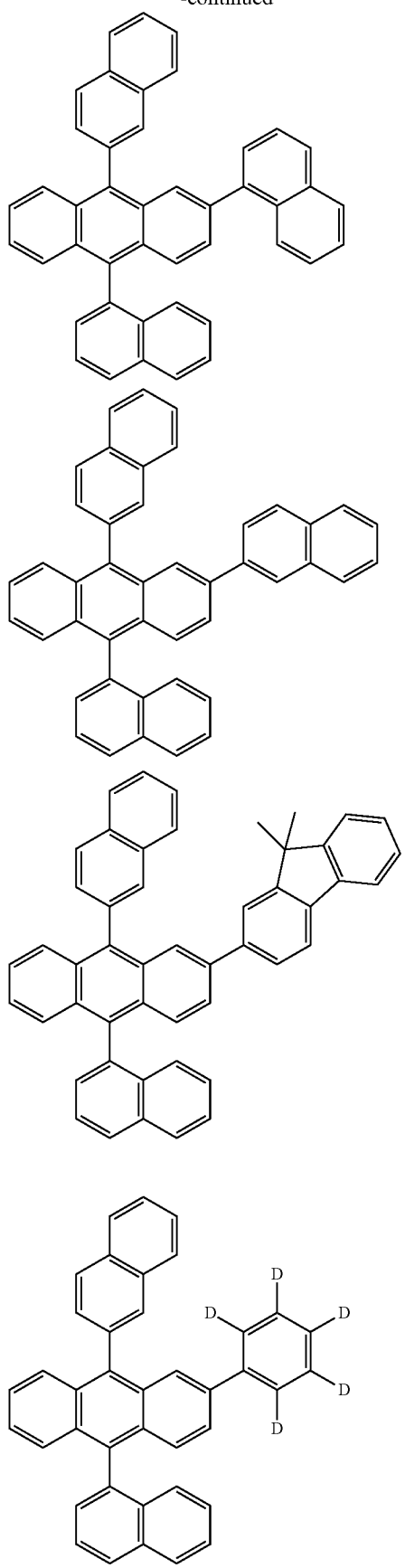
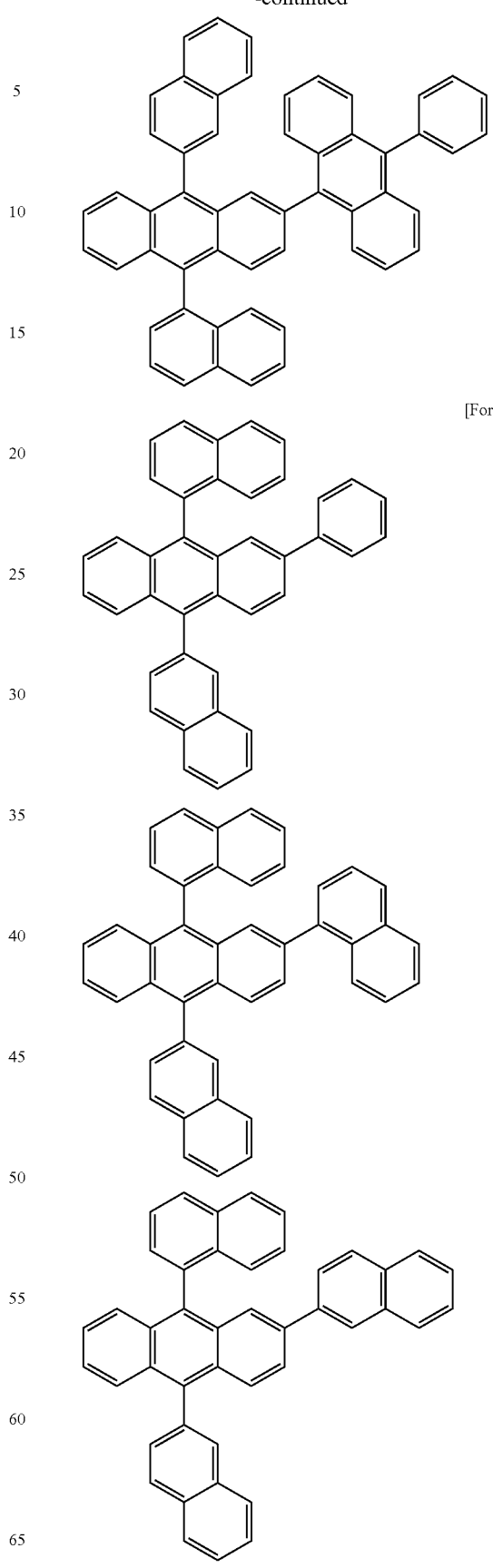
[Formula 161]

281
-continued
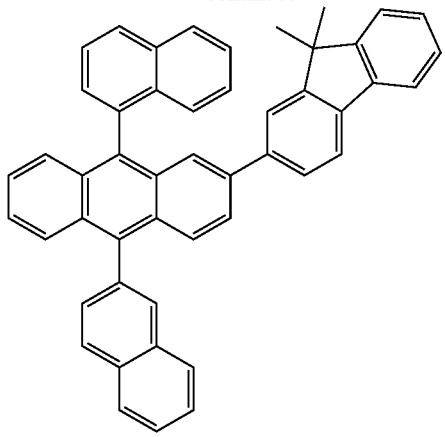
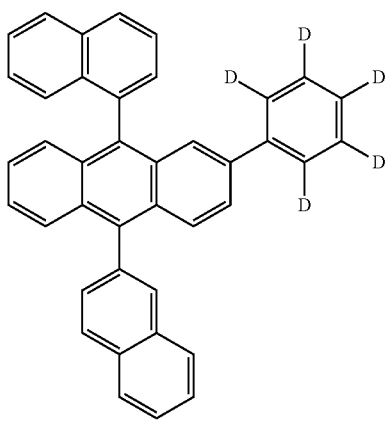
[Formula 162]
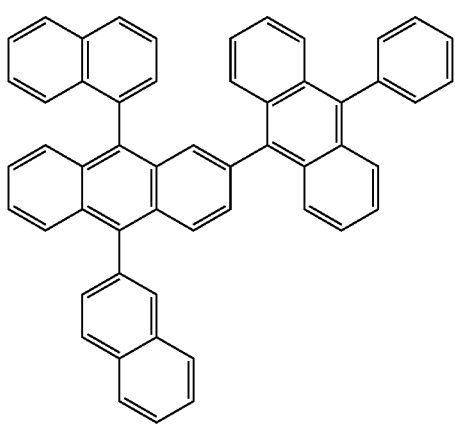
282
-continued
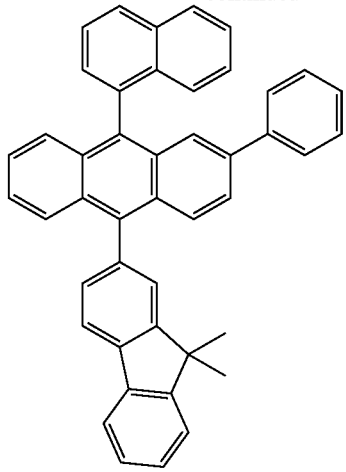
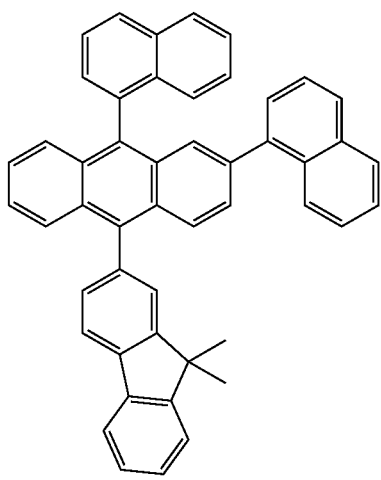
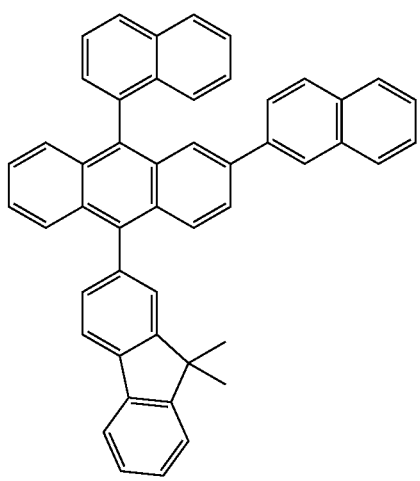

283
-continued
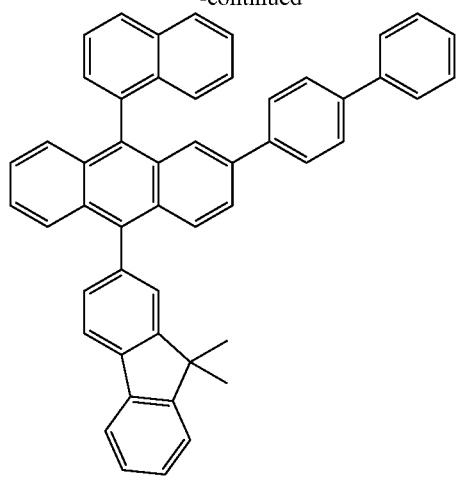
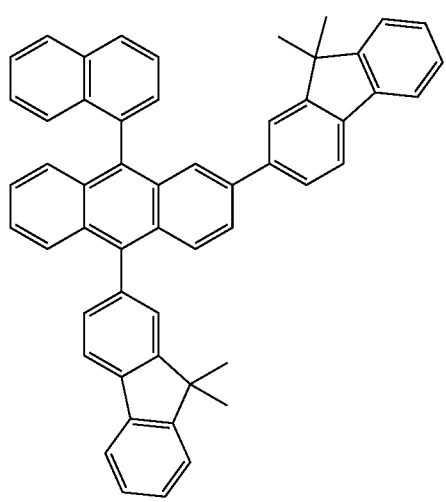
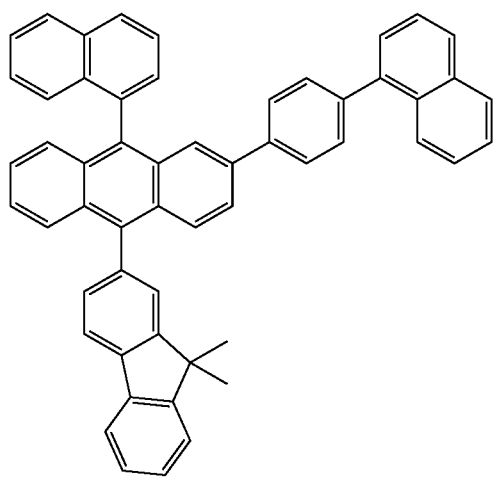
284
-continued
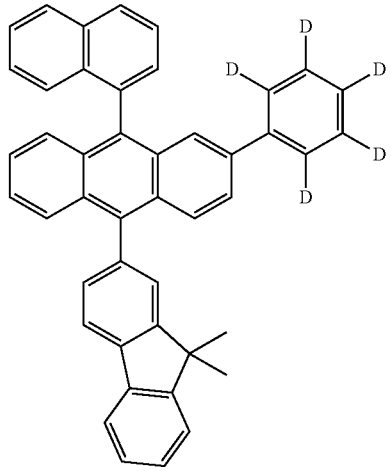
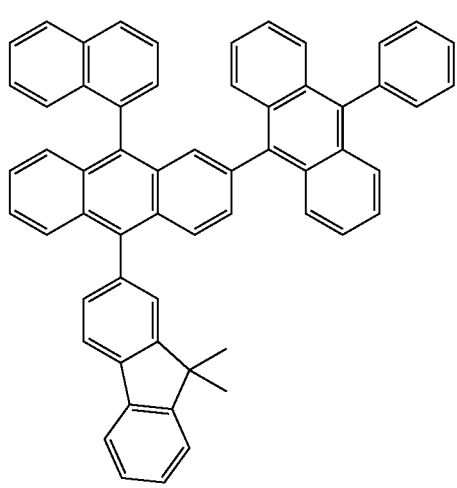
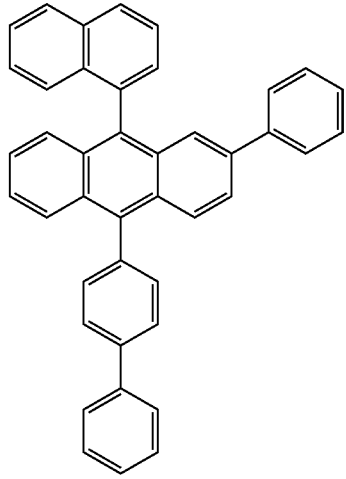

285
-continued
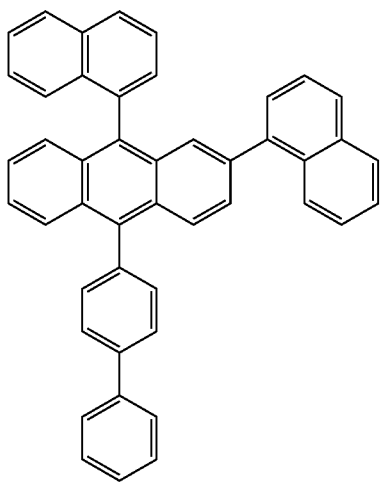
286
-continued
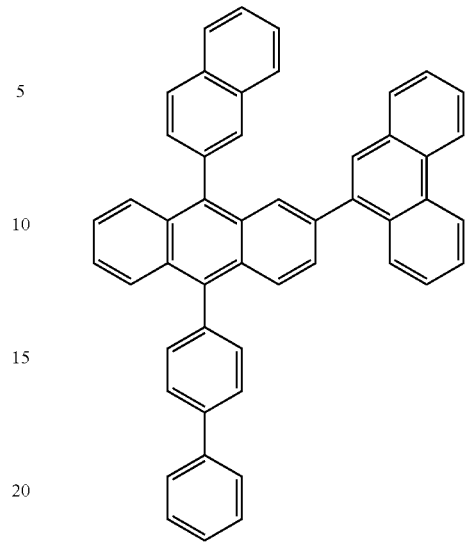
[Formula 163]
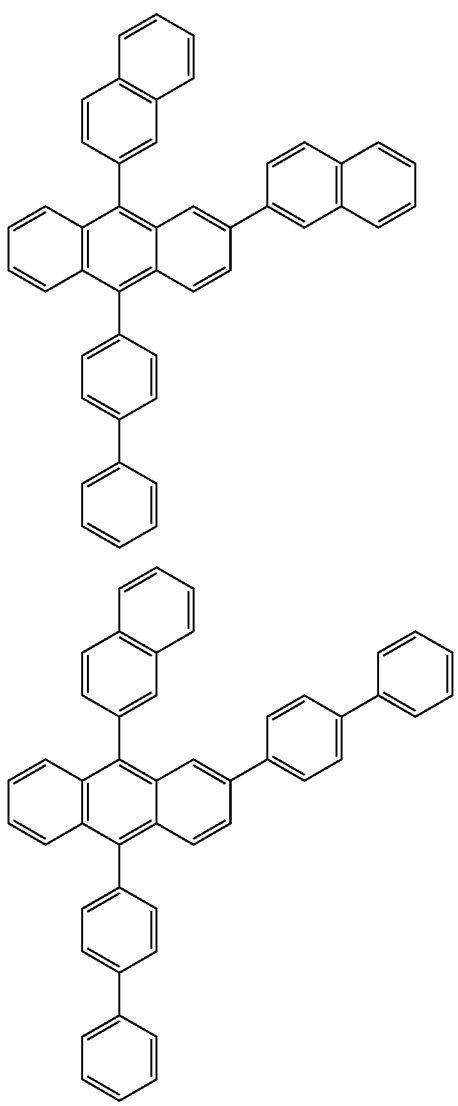
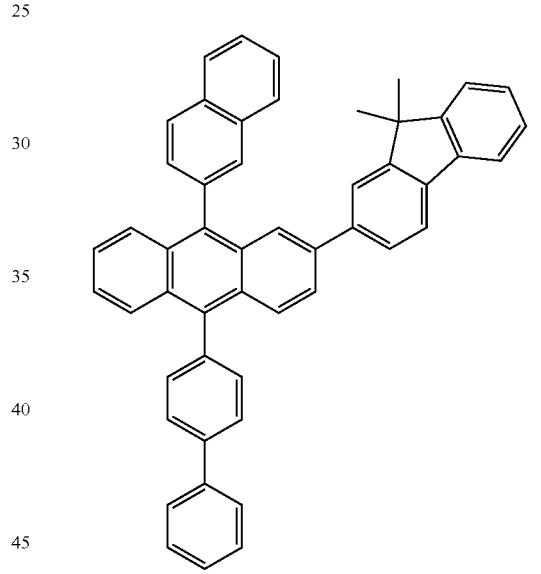
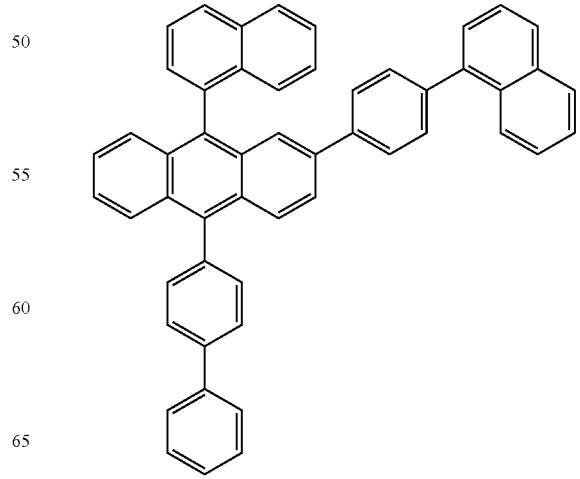

287
-continued
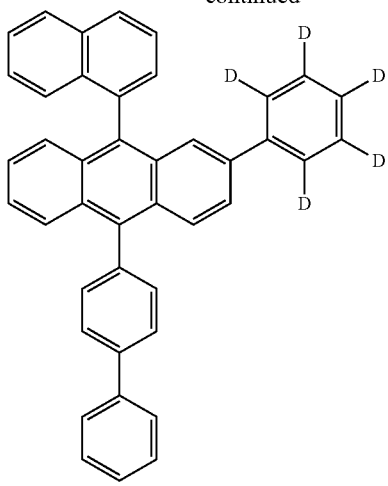
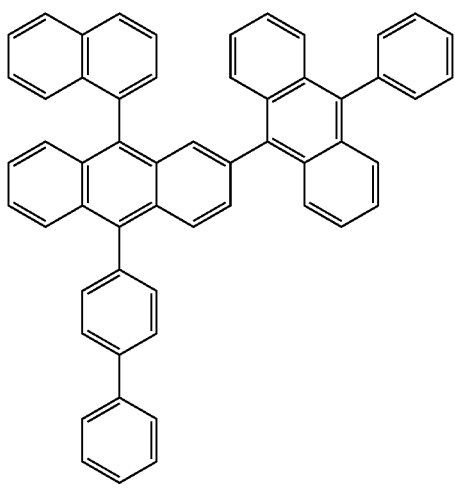
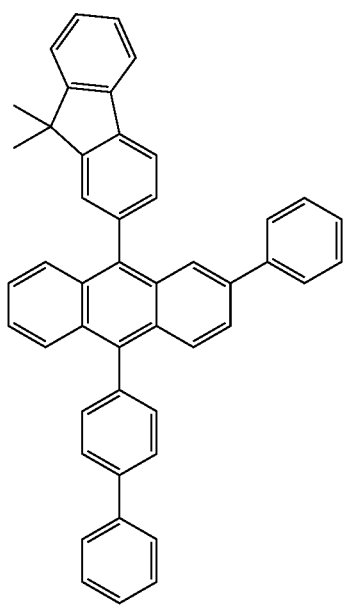
288
-continued
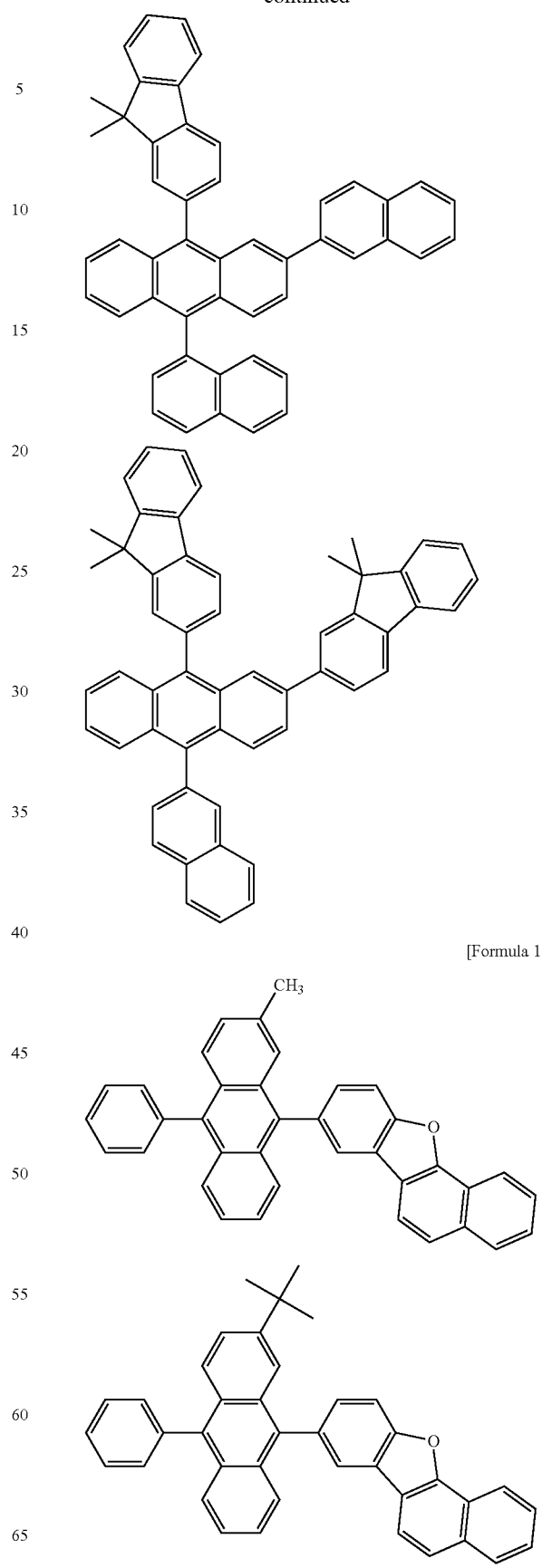
[Formula 164]

289
-continued
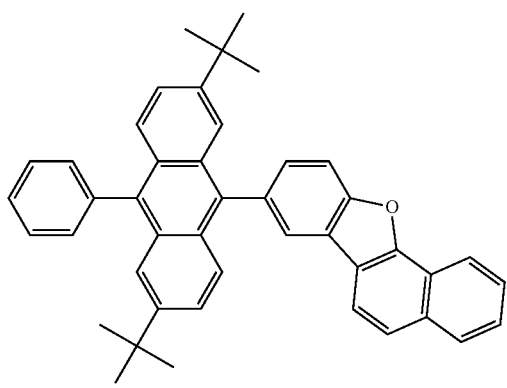
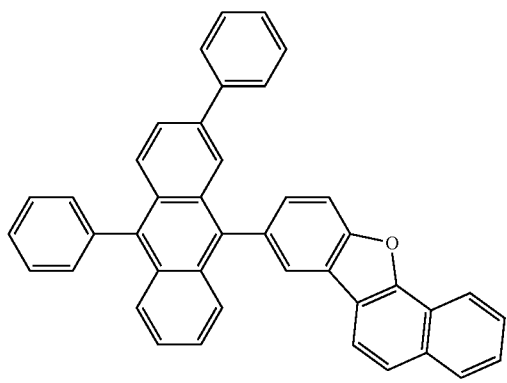
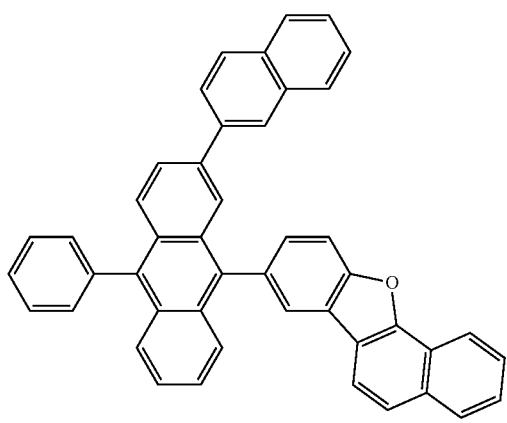
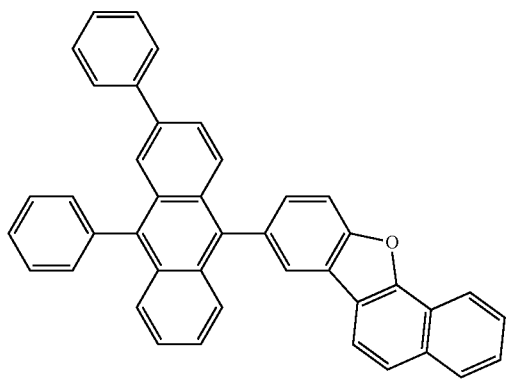
290
-continued
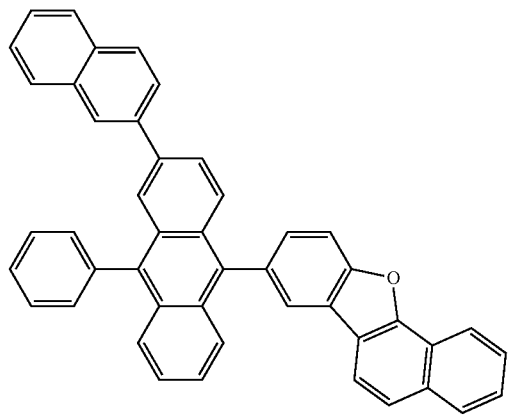
[Formula 165]
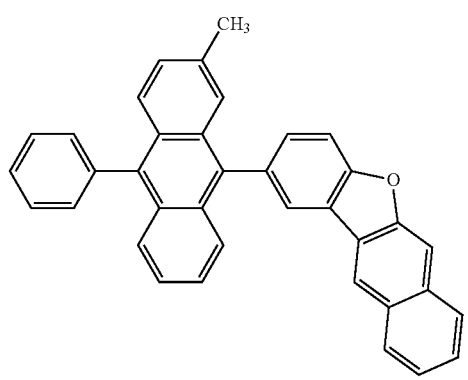
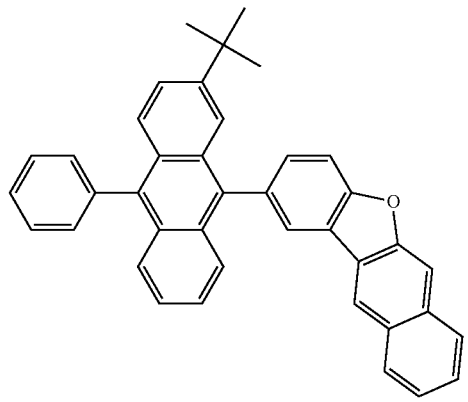
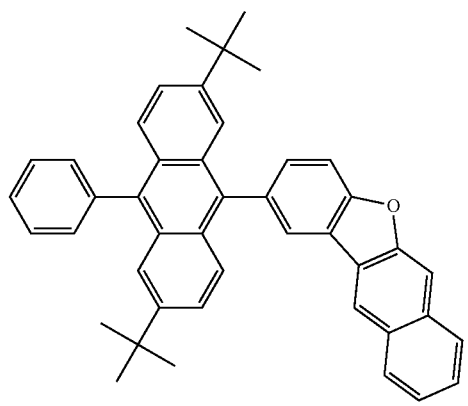

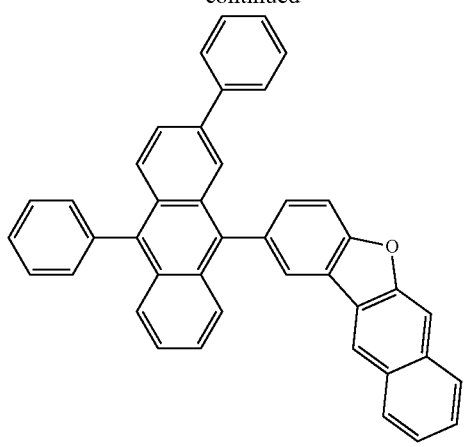
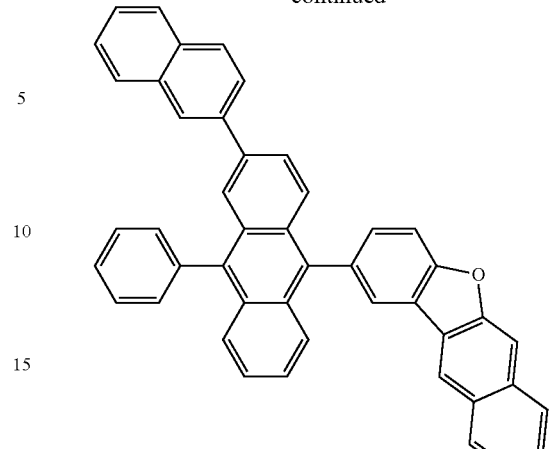
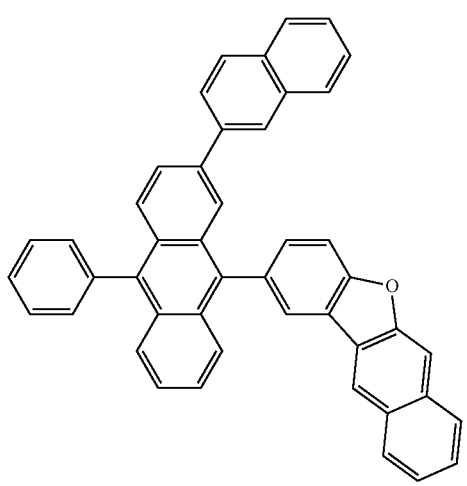
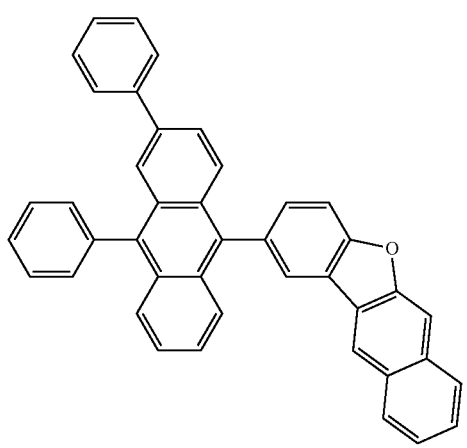

Second Compound

The second compound is the compound represented by the formula (2).

The second compound preferably has a main peak wavelength in a range from 430 nm to 480 nm, more preferably in a range from 445 nm to 480 nm.

Herein, the main peak wavelength means a peak wavelength of an emission spectrum exhibiting a maximum luminous intensity among emission spectra measured in a toluene solution in which a measurement target compound is dissolved at a concentration ranging from $10^{-6}$ mol/l to $10^{-5}$ mol/l.

The second compound preferably fluoresces blue.

The second compound is preferably a material having a high emission quantum efficiency.

Molar Absorbance Coefficient

A molar absorbance coefficient of the second compound at an absorption peak located closest to the long-wavelength region preferably ranges from 29,000 L/(mol·cm) to 1,000,000 L/(mol·cm), more preferably from 30,000 L/(mol·cm) to 250,000 L/(mol·cm), further preferably from 40,000 L/(mol·cm) to 150,000 L/(mol·cm).

Stokes Shift

The second compound preferably has Stokes shift in a range from 4 nm to 18 nm, more preferably in a range from 5 nm to 17 nm.

Relationship Between First Compound and Second Compound in Emitting Layer

When the first compound is a delayed fluorescent compound, a singlet energy $S_1(M1)$ of the first compound and a singlet energy $S_1(M2)$ of the second compound preferably satisfy a relationship of the following numerical formula (Numerical Formula 1).

$$S_1(M1) > S_1(M2) \qquad \text{(Numerical Formula 1)}.$$

An energy gap $T_{77K}(M1)$ at 77 [K] of the first compound is preferably larger than an energy gap $T_{77K}(M2)$ at 77 [K] of the second compound. In other words, a relationship of the following numerical formula (Numerical Formula 4) is preferably satisfied.

$$T_{77K}(M1) > T_{77K}(M2) \qquad \text{(Numerical Formula 4)}.$$

When the organic EL device 1 of the exemplary embodiment emits light, it is preferable that the second compound in the emitting layer 5 mainly emits light.

Relationship Between Triplet Energy and Energy Gap at 77K

Here, a relationship between a triplet energy and an energy gap at 77K will be described. In the exemplary embodiment, the energy gap at 77 [K] is different from a typical triplet energy in some aspects.

Triplet energy is measured as follows. Firstly, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. The triplet energy is calculated by a predetermined conversion equation based on a wavelength value at an intersection of the tangent and the abscissa axis.

Here, the delayed fluorescent compound used in the exemplary embodiment is preferably a compound having a small $\Delta ST$. When $\Delta ST$ is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. An energy amount is calculated as the energy gap $T_{77K}$ at 77K according to a conversion equation (F1) below based on a wavelength value $\lambda_{edge}$ (nm) at an intersection of the tangent and the abscissa axis.

$$T_{77K} [eV] = 1239.85/\lambda_{edge} \qquad \text{Conversion Equation (F1):}$$

The tangent to the rise of the phosphorescence spectrum close to the short-wavelength region is drawn as follows. While moving on a curve of the phosphorescence spectrum from the short-wavelength region to the maximum spectral value closest to the short-wavelength region among the maximum spectral values, a tangent is checked at each point on the curve toward the long-wavelength of the phosphorescence spectrum. An inclination of the tangent is increased along the rise of the curve (i.e., a value of the ordinate axis is increased). A tangent drawn at a point of the maximum inclination (i.e., a tangent at an inflection point) is defined as the tangent to the rise of the phosphorescence spectrum close to the short-wavelength region.

The maximum with peak intensity being 15% or less of the maximum peak intensity of the spectrum is not included in the above-mentioned maximum closest to the short-wavelength region. The tangent drawn at a point of the maximum spectral value being closest to the short-wavelength region and having the maximum inclination is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy $S_1$

A method of measuring a singlet energy $S_1$ with use of a solution (occasionally referred to as a solution method) is exemplified by a method below.

A 10-μmol/L toluene solution of a compound (measurement target) is prepared and put in a quartz cell to prepare a sample. An absorption spectrum (ordinate axis: luminous intensity, abscissa axis: wavelength) of the sample is measured at a normal temperature (300K). A tangent is drawn to the fall of the absorption spectrum close to the long-wavelength region, and a wavelength value $\lambda_{edge}$ (nm) at an intersection of the tangent and the abscissa axis is obtained. The wavelength value $\lambda_{edge}$ (nm) is substituted in a conversion equation (F2) below to calculate a singlent energy.

$$S_1 [eV] = 1239.85/\lambda_{edge} \qquad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the maximum spectral value closest to the long-wavelength region in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength region (except when absorbance is 0.1 or less) is defined as the tangent to the fall of the absorption spectrum close to the long-wavelength region.

The maximum absorbance of 0.2 or less is not included in the above-mentioned maximum absorbance close to the long-wavelength region.

Content Ratios of Compounds in Emitting Layer

Content ratios of the respective first and second compounds in the emitting layer 5 preferably range as follows.

The content ratio of the first compound preferably ranges from 90 mass % to 99.9 mass %, more preferably from 95 mass % to 99.9 mass %, further preferably from 99 mass % to 99.9 mass %.

The content ratio of the second compound preferably ranges from 0.01 mass % to 10 mass %, more preferably from 0.01 mass % to 5 mass %, further preferably from 0.01 mass % to 1 mass %.

It should be noted that the emitting layer 5 of the exemplary embodiment may contain a material other than the first compound and the second compound.

Thickness of Emitting Layer

A thickness of the emitting layer 5 preferably ranges from 5 nm to 50 nm, more preferably from 7 nm to 50 nm, further preferably from 10 nm to 50 nm. The emitting layer 5 having the thickness of 5 nm or more is easily formable and easily adjustable in chromaticity. The emitting layer 5 having the thickness of 50 nm or less can restrain a rise in the drive voltage.

TADF Mechanism

Figure 4:
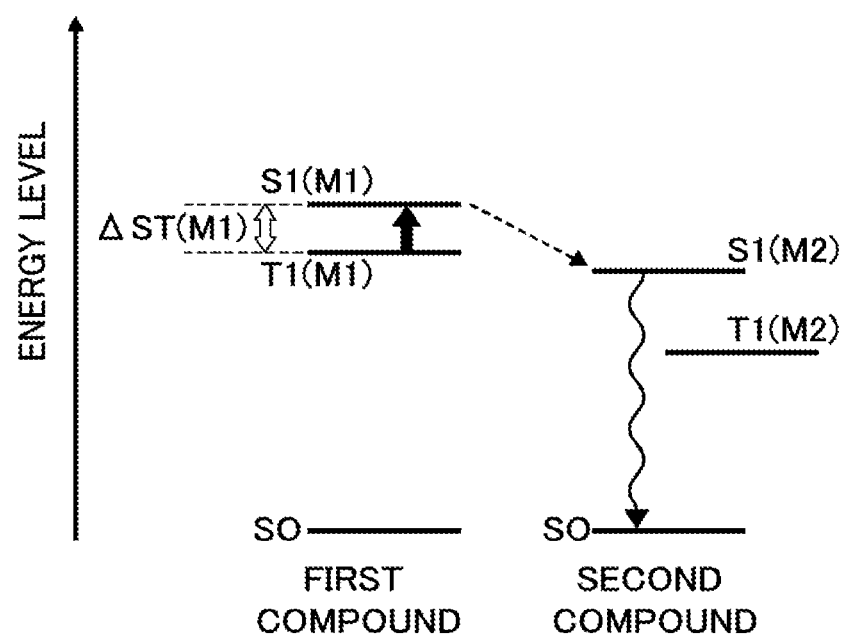
FIG. 4 shows a relationship between energy levels of a first compound and a second compound and an energy transfer between the first compound and the second compound in an emitting layer of an exemplary organic electroluminescence device of the first exemplary embodiment of the invention.

FIG. 4 shows an example of a relationship between energy levels of the first compound and the second compound in the emitting layer. In FIG. 4, S0 represents a ground state. S1(M1) represents the lowest singlet state of the first compound. T1(M1) represents the lowest triplet state of the first compound. S1(M2) represents the lowest singlet state of the second compound. T1(M2) represents the lowest triplet state of the second compound.

A dashed arrow directed from S1(M1) to S1(M2) in FIG. 4 represents Forster energy transfer from the lowest singlet state of the first compound to the lowest singlet state of the second compound.

As shown in FIG. 4, when a compound having a small $\Delta ST(M1)$ is used as the first compound, inverse intersystem crossing from the lowest triplet state T1(M1) to the lowest singlet state S1(M1) can be caused by a heat energy. Subsequently, Forster energy transfer from the lowest singlet state S1(M1) of the first compound the second compound occurs to generate the lowest singlet state S1(M2). Consequently, fluorescence from the lowest singlet state S1(M2) of the second compound can be observed. It is inferred that the internal quantum efficiency can be theoretically raised up to 100% also by using delayed fluorescence by the TADF mechanism.

Substrate

The substrate 2 is used as a support for the organic EL device 1. For instance, glass, quartz, plastics and the like are usable as the substrate 2. A flexible substrate is also usable. The flexible substrate is a bendable substrate, which is exemplified by a plastic substrate. Examples of a material for forming the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), alloy, an electrically conductive compound and a mixture thereof are preferably usable as the anode 3 formed on the substrate 2. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), nitrides of these metal materials (e.g., titanium nitride) and the like are usable.

The above materials are typically formed into a film by sputtering. For instance, a target of the indium zinc oxide which is prepared by adding zinc oxide in a range from 1 mass % to 10 mass % relative to indium oxide is used for forming a film by sputtering. Moreover, for instance, as for the indium oxide containing tungsten oxide and zinc oxide, a target thereof prepared by adding tungsten oxide in a range from 0.5 mass % to 5 mass % and zinc oxide in a range from 0.1 mass % to 1 mass % relative to indium oxide is usable for forming a film by sputtering. In addition, vapor deposition, coating, ink jet printing, spin coating and the like may be used for forming a film.

Among the organic layers formed on the anode 3, the hole injecting layer 6 formed adjacent to the anode 3 is formed of a composite material in which holes are easily injectable irrespective of the work function of the anode 3. Accordingly, other materials usable as an electrode material (e.g., a metal, alloy, electrically conductive compound, mixture thereof, and elements belonging to Group 1 or 2 in the periodic table of the elements) are also usable for the anode 3.

A material having a small work function such as elements belonging to Groups 1 and 2 in the periodic table of the elements, a rare earth metal and an alloy including the elements and/or the rare earth metal are also usable for the anode 3. Examples of the elements belonging to Group 1 in the periodic table of the elements include an alkali metal. Examples of the elements belonging to Group 2 in the periodic table of the elements include an alkaline earth metal. Examples of the alkali metal include lithium (Li) and cesium (Cs). Examples of the alkaline earth metal include magnesium (Mg), calcium (Ca) and strontium (Sr). Examples of the rare earth metal include europium (Eu) and ytterbium (Yb). Examples of the alloy include MgAg and AlLi.

When the cathode 3 is formed of the alkali metal, alkaline earth metal and alloys thereof, vapor deposition and sputtering are usable. Moreover, when the cathode 4 is formed of silver paste and the like, coating, ink jet printing and the like are usable.

Hole Injecting Layer

The hole injecting layer 6 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

Moreover, a macromolecular compound is also usable as the highly hole-injectable substance. Examples of the macromolecular compound include an oligomer, dendrimer and polymer. Specific examples of the macromolecular compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido](abbreviation: PTPDMA), and poly[N,N'-bis(4-butylphenyl)-N,N'-bis(phenyl)benzidine] (abbreviation: Poly-TPD). Moreover, the examples of the macromolecular compound include a macromolecular compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

The hole transporting layer 7 is a layer containing a highly hole-transporting substance. For instance, an aromatic amine compound, carbazole derivative, anthracene derivative and the like are usable for the hole transporting layer 7.

Specifically, for instance, an aromatic amine compound is usable for the hole transporting layer. Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(Vs) or more. A carbazole derivative (e.g., CBP, 9-[4-(N-carbazolyl)]phenyl-10-phenylanthracene (CzPA), and 9-phenyl-3-[4-(10-phenyl-9-anthryl)phenyl]-9H-carbazole (PCzPA)) and an anthracene derivative (e.g., t-BuDNA, DNA, and DPAnth) may be used for the hole transporting layer 7. Moreover, a macromolecular compound such as poly(N-vinylcarbazole) (abbreviation: PVK) and poly(4-vinyltriphenylamine) (abbreviation: PVTPA) is also usable for the hole transporting layer 6.

However, any substance having a hole transporting performance higher than an electron transporting performance may be used in addition to the above substances. A layer including the highly hole-transporting substance may be provided in the form of a single layer or a laminate of two or more layers.

When the hole transporting layer includes two or more layers, one of the layers with a larger energy gap is preferably provided closer to the emitting layer 5.

Electron Transporting Layer

The electron transporting layer 8 is a layer containing a highly electron-transporting substance. For the electron transporting layer 8, (1) a metal complex such as an aluminum complex, beryllium complex and zinc complex, (2) heteroaromatic compound such as an imidazole derivative, benzimidazole derivative, azine derivative, carbazole derivative, and phenanthroline derivative, and (3) a macromolecular compound are usable. Specifically, as a low-molecule organic compound, a metal complex such as Alq, tris(4-methyl-8-quinolinolato)aluminum (abbreviation: Almq$_3$), bis(10-hydroxybenzo[h]quinolinato)beryllium (abbreviation: BeBq$_2$), BAlq, Znq, ZnPBO and ZnBTZ are usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. In the exemplary embodiments, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer 8 in addition to the above substances. The electron transporting layer 8 may be provided in the form of a single layer or a laminate of two or more layers made of the above substance(s).

Moreover, a macromolecular compound is also usable for the electron transporting layer 8. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer 9 is a layer containing a highly electron-injectable substance. Examples of a material for the electron injecting layer 9 include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a substance containing an alkali metal, alkaline earth metal and a compound thereof in the electron-transporting substance, specifically, a substance containing magnesium (Mg) in Alq may be used. In this case, electrons can be more efficiently injected from the cathode 4.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable. The electron donor may be any substance exhibiting an electron donating performance to the organic compound. Specifically, an alkali metal, an alkaline earth metal or a rare earth metal is preferable, examples of which include lithium, cesium, magnesium, calcium, erbium and ytterbium. Moreover, an alkali metal oxide and alkaline earth metal oxide are preferably used as the electron donor, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function, specifically, of 3.8 eV or less, is preferably usable as a material for the cathode 4. Specific examples of the material for the cathode include the elements belonging to Groups 1 and 2 in the periodic table of the elements, a rare-earth metal and an alloy including the elements and/or the rare-earth metal. Examples of the elements belonging to Group 1 in the periodic table of the elements include an alkali metal. Examples of the elements belonging to Group 2 in the periodic table of the elements include an alkaline earth metal. Examples of the alkali metal include lithium (Li) and cesium (Cs). Examples of the alkaline earth metal include magnesium (Mg), calcium (Ca) and strontium (Sr). Examples of the rare earth metal include europium (Eu) and ytterbium (Yb). Examples of the alloy include MgAg and AlLi.

When the cathode 4 is formed of the alkali metal, alkaline earth metal and alloy thereof, vapor deposition and sputtering are usable. Moreover, when the cathode 4 is formed of silver paste and the like, coating, ink jet printing and the like are usable.

By providing the electron injecting layer 9, various conductive materials such as Al, Ag, ITO, graphene and indium oxide-tin oxide containing silicon or silicon oxide are usable for forming the cathode 4 irrespective of the magnitude of the work function. The conductive materials can be deposited as a film by sputtering, ink jet printing, spin coating and the like.

Layer Formation Method(s)

A method for forming each layer of the organic EL device in the first exemplary embodiment is not limited except for the above particular description. Known methods of dry film-forming and wet film-forming are usable. Examples of the dry film-forming include vacuum deposition, sputtering, plasma deposition method and ion plating. Examples of the wet film-forming include spin coating, dipping, flow coating and ink-jet.

Thickness

A thickness of each of the organic layers in the organic EL device 1 according to the first exemplary embodiment is not limited except for the above particular description. In general, the thickness preferably ranges from several nanometers to 1 μm in order to avoid defects such as a pin hole and to prevent efficiency from being deteriorated since a high voltage needs to be applied.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., a hydrogen atom for terminating the atoms forming the ring) and atoms included in a substituent substituting the ring are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Hydrogen atoms respectively bonded to carbon atoms of the pyridine ring and the quinazoline ring and atoms forming the substituents are not counted in the number of the ring atoms. When a fluorene ring is substituted by, for instance, a fluorene ring (inclusive of a spirofluorene ring), the number of atoms of the fluorene ring as a substituent is not included in the number of the ring atoms for the fluorene ring.

Next, each of substituents described in the above formulae will be described.

Examples of the aryl group (occasionally, referred to as aromatic hydrocarbon group) having 6 to 30 ring carbon atoms or the aryl group having 6 to 50 ring carbon atoms include a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Herein, the aryl group preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. A carbon atom in a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms described later herein.

Herein, the heteroaryl group (occasionally, referred to as a heterocyclic group, heteroaromatic ring group or aromatic heterocyclic group) having 5 to 30 ring atoms or the heterocyclic group having 5 to 50 ring atoms preferably contains as a hetero atom at least one atom selected from the group consisting of nitrogen, sulfur, oxygen, silicon, selenium atom and germanium atom, and more preferably contains at least one atom selected from the group consisting of nitrogen, sulfur and oxygen.

Herein, examples of the heterocyclic group having 5 to 30 ring atoms or the heterocyclic group having 5 to 50 ring atoms are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

Herein, the heterocyclic group preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are further preferable. A nitrogen atom in position 9 of 1-carbazolyl group, 2-carbazolyl group, 3-carbazolyl group and 4-carbazolyl group is preferably substituted by the substituted or unsubstituted aryl group having 6 to 30 ring carbon atoms or the substituted or unsubstituted heterocyclic group having 5 to 30 ring atoms described herein.

Herein, the heterocyclic group may be a group derived from any one of partial structures represented by formulae (XY-1) to (XY-18).

[Formula 166]
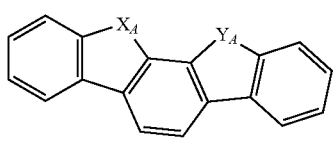 (XY-1)
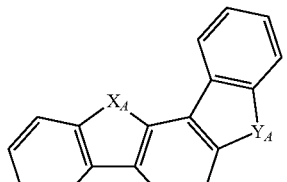 (XY-2)
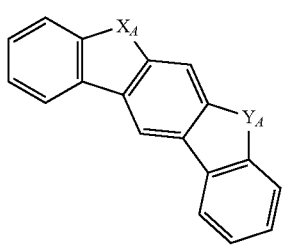 (XY-3)
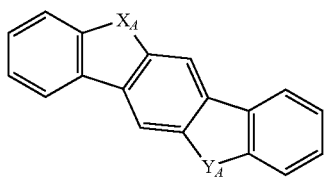 (XY-4)
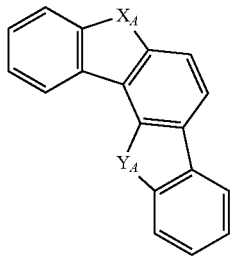 (XY-5)
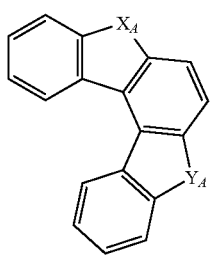 (XY-6)
[Formula 167]
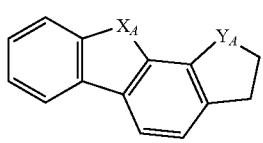 (XY-7)
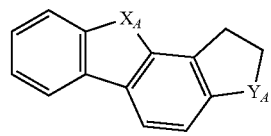 (XY-8)
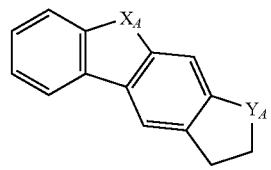 (XY-9)
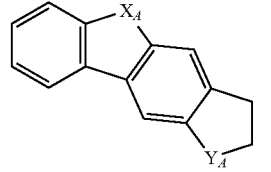 (XY-10)
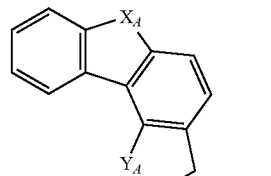 (XY-11)
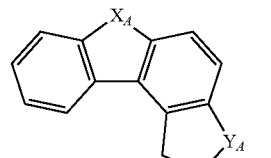 (XY-12)
[Formula 168]
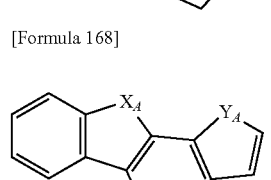 (XY-13)
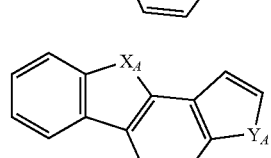 (XY-14)
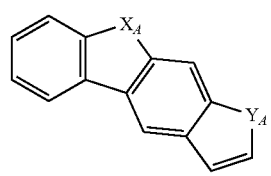 (XY-15)
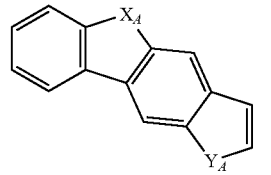 (XY-16)

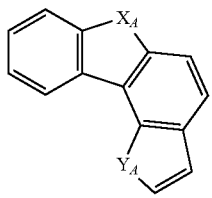
(XY-17)

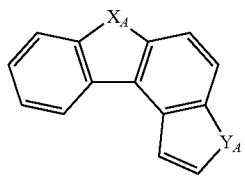
(XY-18)

In the formulae (XY-1) to (XY-18), $X_A$ and $Y_A$ each independently represent a hetero atom, and preferably represent an oxygen atom, sulfur atom, selenium atom, silicon atom or germanium atom. The partial structures represented by the formulae (XY-1) to (XY-18) may each be bonded in any position to be a heterocyclic group, which may be substituted.

Herein, examples of the substituted or unsubstituted carbazolyl group may include a group as represented by formulae below in which a carbazole ring is further fused with a ring(s). Such a group also may be substituted. A bonding position is alterable as desired.

[Formula 169]

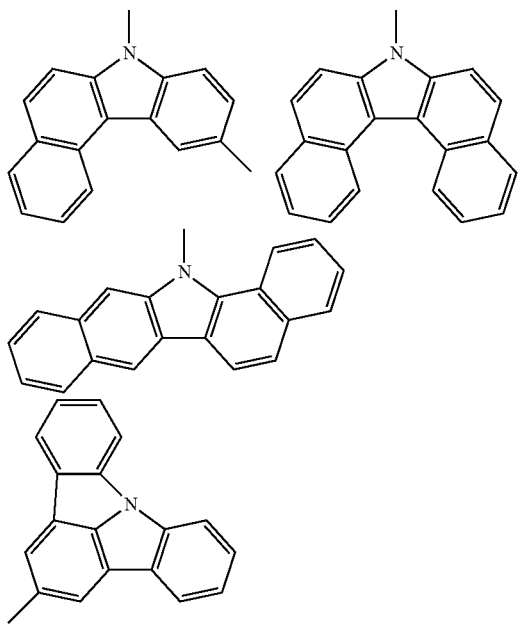

The alkyl group having 1 to 30 carbon atoms or the alkyl group having 1 to 50 carbon atoms may be linear, branched or cyclic. Also, the alkyl group may be an alkyl halide group.

Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

Herein, the linear or branched alkyl group preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are preferable.

Herein, examples of the cyclic alkyl group include a cycloalkyl group having 3 to 30 ring carbon atoms or a cycloalkyl group having 3 to 50 ring carbon atoms.

Herein, examples of the cycloalkyl group having 3 to 30 ring carbon atoms or the cycloalkyl group having 3 to 50 ring carbon atoms include a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are further preferable.

Herein, the alkyl halide group provided by substituting the alkyl group with a halogen atom is exemplified by an alkyl halide group provided by substituting the alkyl group having 1 to 30 carbon atoms with at least one halogen atom, preferably at least one fluorine atom.

Herein, examples of the alkyl halide group having 1 to 30 carbon atoms include a fluoromethyl group, difluoromethyl group, trifluoromethyl group, fluoroethyl group, trifluoromethylmethyl group, trifluoroethyl group, and pentafluoroethyl group.

Herein, examples of a substituted silyl group include an alkylsilyl group having 3 to 30 carbon atoms and an arylsilyl group having 6 to 30 ring carbon atoms.

Herein, the alkylsilyl group having 3 to 30 carbon atoms is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be mutually the same or different.

Herein, examples of the arylsilyl group having 6 to 30 ring carbon atoms include a dialkylarylsilyl group, alkyldiarylsilyl group and triarylsilyl group.

The dialkylarylsilyl group is exemplified by a dialkylarylsilyl group including two of the examples of the alkyl group having 1 to 30 carbon atoms and one of the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the examples of the alkyl group having 1 to 30 carbon atoms and two of the examples of the aryl group having 6 to 30 ring carbon atoms. The alkyldiarylsilyl group preferably has 13 to 30 carbon atoms.

The triarylsilyl group is exemplified by a triarylsilyl group including three of the examples of the aryl group having 6 to 30 ring carbon atoms. The triarylsilyl group preferably has 18 to 30 carbon atoms.

Herein, an aryl group in an aralkyl group (occasionally referred to as an arylalkyl group) is an aromatic hydrocarbon group or a heterocyclic group.

Herein, the aralkyl group having 7 to 30 carbon atoms is preferably a group having an aryl group having 6 to 30 ring carbon atoms, and the aralkyl group having 7 to 50 carbon atoms is preferably a group having an aryl group having 6 to 50 ring carbon atoms. Each of the aralkyl groups is represented by —$Z_3$-$Z_4$. $Z_3$ is exemplified by an alkylene group derived from the above alkyl group having 1 to 30 carbon atoms or alkyl group having 1 to 50 carbon atoms. $Z_4$ is exemplified by the above aryl group having 6 to 30 ring carbon atoms or aryl group having 6 to 50 ring carbon atoms. In this aralkyl group, an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Herein, the substituted phosphoryl group is represented by a formula (P) below.

[Formula 170]

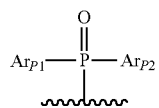

(P)

In the formula (P), $Ar_{P1}$ and $Ar_{P2}$ are each independently a substituent, preferably a substituent selected from the group consisting of an alkyl group having 1 to 30 carbon atoms and an aryl group having 6 to 30 ring carbon atoms, more preferably a substituent selected from the group consisting of an alkyl group having 1 to 10 carbon atoms and an aryl group having 6 to 20 ring carbon atoms, further preferably a substituent selected from the group consisting of an alkyl group having 1 to 6 carbon atoms and an aryl group having 6 to 14 ring carbon atoms.

Herein, the alkoxy group having 1 to 30 carbon atoms or the alkoxy group having 1 to 50 carbon atoms is represented by —$OZ_1$. $Z_1$ is exemplified by an alkyl group having 1 to 30 carbon atoms or an alkyl group having 1 to 50 carbon atoms. Examples of the alkoxy group include a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a halogenated alkoxy group provided by substituting the alkoxy group having 1 to 30 carbon atoms with one or more fluorine groups.

Herein, examples of an aryl group in an aryloxy group (occasionally referred to as an arylalkoxy group) include a heteroaryl group.

Herein, the aryloxy group of the arylalkoxy group having 6 to 30 ring carbon atoms or the arylalkoxy group having 6 to 50 ring carbon atoms is represented by —$OZ_2$. $Z_2$ is exemplified by the above aryl group having 6 to 30 ring carbon atoms or aryl group having 6 to 50 ring carbon atoms. The arylalkoxy group preferably has 6 to 20 ring carbon atoms. The arylalkoxy group is exemplified by a phenoxy group.

Herein, the substituted amino group is represented by —$NHR_V$ or —$N(R_V)_2$. $R_V$ is exemplified by the above alkyl group having 1 to 30 carbon atoms or aryl group having 6 to 30 ring carbon atoms.

Herein, the alkenyl group having 2 to 30 carbon atoms or the alkenyl group having 2 to 50 carbon atoms is linear or branched. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

Herein, the alkynyl group having 2 to 30 carbon atoms or the alkynyl group having 2 to 50 carbon atoms may be linear or branched. Examples of the alkynyl group include ethynyl, propynyl and 2-phenylethynyl.

Herein, the substituted phosphanyl group is exemplified by a phenyl phosphanyl group.

Herein, the arylcarbonyl group having 6 to 30 ring carbon atoms is represented by —COOY'. Y' is exemplified by the above aryl group.

Herein, examples of the arylcarbonyl group having 6 to 30 ring carbon atoms include a phenyl carbonyl group, diphenyl carbonyl group, naphthyl carbonyl group, and triphenyl carbonyl group.

Herein, the alkylthio group having 1 to 30 carbon atoms, the alkylthio group having 1 to 50 carbon atoms, the arylthio group having 6 to 30 ring carbon atoms, and the arylthio group having 6 to 50 ring carbon atoms are each represented by —$SR_V$. Examples of $R_V$ include the above alkyl group having 1 to 30 carbon atoms, the above alkyl group having 1 to 50 carbon atoms, the above aryl group having 6 to 30 ring carbon atoms, and the above aryl group having 6 to 50 ring carbon atoms. The alkylthio group preferably has 1 to 20 carbon atoms. The arylthio group preferably has 6 to 20 ring carbon atoms.

Herein, examples of the halogen atom include a fluorine atom, a chlorine atom, a bromine atom and an iodine atom, among which a fluorine atom is preferable.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

Herein, the substituent meant by "substituted or unsubstituted" is at least one group selected from the group consisting of an alkynyl group having 2 to 30 carbon atoms, cyano group, hydroxyl group, nitro group, and carboxy group in addition to an aryl group having 6 to 30 ring carbon atoms, heteroaryl group having to 30 ring atoms, alkyl group (linear or branched alkyl group) having 1 to 30 carbon atoms, cycloalkyl group having 3 to 30 ring carbon atoms, alkyl halide group having 1 to 30 carbon atoms, alkylsilyl group having 3 to 30 carbon atoms, arylsilyl group having 6 to 30 ring carbon atoms, alkoxy group having 1 to 30 carbon atoms, aryloxy group having 6 to 30 carbon atoms, substituted amino group, alkylthio group having 1 to 30 carbon atoms, arylthio group having 6 to 30 ring carbon atoms, aralkyl group having 7 to 30 carbon atoms, alkenyl group having 2 to 30 carbon atoms, and halogen atom.

Herein, the substituent meant by "substituted or unsubstituted" is preferably at least one group selected from the group consisting of an aryl group having 6 to ring carbon atoms, heteroaryl group having 5 to 30 ring atoms, alkyl group (linear or branched alkyl group) having 1 to 30 carbon atoms, halogen atom, and cyano group, further preferably the specific preferable examples described in each of the substituents.

Herein, the substituent meant by "substituted or unsubstituted" may be further substituted by at least one group selected from the group consisting of an aryl group having 6 to 30 ring carbon atoms, heteroaryl group having 5 to 30 ring atoms, alkyl group (linear or branched alkyl group) having 1 to 30 carbon atoms, cycloalkyl group having 3 to 30 ring carbon atoms, alkyl halide group having 1 to 30 carbon atoms, alkylsilyl group having 3 to 30 carbon atoms, arylsilyl group having 6 to 30 ring carbon atoms, alkoxy group having 1 to 30 carbon atoms, aryloxy group having 6 to 30 carbon atoms, substituted amino group, alkylthio group having 1 to carbon atoms, arylthio group having 6 to 30 ring carbon atoms, aralkyl group having 7 to 30 carbon atoms, alkenyl group having 2 to 30 carbon atoms, an alkynyl group having 2 to 30 carbon atoms, halogen atom. cyano group, hydroxyl group, nitro group, and carboxy group. In addition, a plurality of ones of the substituent may be mutually bonded to form a ring.

Herein, the substituent further substituting for the substituent meant by "substituted or unsubstituted" is preferably at least one group selected from the group consisting of an aryl group having 6 to 30 ring carbon atoms, heteroaryl group having 5 to 30 ring atoms, alkyl group (linear or branched alkyl group) having 1 to 30 carbon atoms, halogen atom, and cyano group, and is further preferably at least one group selected from the specific preferable examples described in each of the substituents.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX." "XX" and "YY" each mean an integer of 1 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX." "XX" and "YY" each mean an integer of 1 or more.

The same description as the above applies to "substituted or unsubstituted" in compounds or partial structures thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group and the heterocyclic group in the linking group include a divalent or multivalent group obtained by eliminating one or more atoms from the above monovalent groups.

The organic EL device according to the exemplary embodiment emits light at a high efficiency.

Moreover, the organic EL device according to the exemplary embodiment can improve the luminous efficiency of the organic EL device particularly in the blue wavelength region.

Electronic Device

The organic EL device 1 according to the exemplary embodiments is applicable to an electronic device such as a display device and a light-emitting device. Examples of the display device include a display component (e.g., en organic EL panel module), TV, mobile phone, tablet and personal computer. Examples of the light-emitting device include an illuminator and a vehicle light.

Second Exemplary Embodiment

An arrangement of an organic EL device according to a second exemplary embodiment will be described. In the description of the second exemplary embodiment, the same components as those in the first exemplary embodiment are denoted by the same reference signs and names to simplify or omit an explanation of the components. In the second exemplary embodiment, any materials and compounds that are not specified may be the same as those in the first exemplary embodiment.

The organic EL device according to the second exemplary embodiment is different from the organic EL device according to the first exemplary embodiment in that the emitting layer further includes a third compound. The rest of the arrangement of the organic EL device according to the second exemplary embodiment is the same as as in the first exemplary embodiment.

Third Compound

It is preferable that a singlet energy $S_1(M3)$ of the third compound and a singlet energy $S_1(M1)$ of the first compound satisfy a relationship of Numerical Formula 2 below.

$$S_1(M3)>S_1(M1) \qquad \text{(Numerical Formula 2)}.$$

The third compound may be a delayed fluorescent compound or a compound exhibiting no delayed fluorescence.

The third compound is also preferably a host material (occasionally referred to as a matrix material). When the first compound and the third compound are the host materials, for instance, one of the compounds may be referred to as a first host material and the other may be referred to as a second host material.

Although the third compound is not particularly limited, the third compound is preferably a compound other than an amine compound. Moreover, the third compound may be a carbazole derivative, dibenzofuran derivative, dibenzothiophene derivative, however, the third compound is not limited thereto.

It is also preferable that the third compound has at least one of a partial structure represented by a formula (31) and a partial structure represented by a formula (32) in one molecule.

[Formula 171]

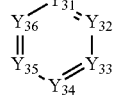

(31)

(32)

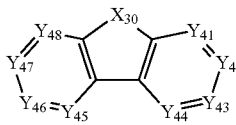

In the formula (31), $Y_{31}$ to $Y_{36}$ each independently represent a nitrogen atom or a carbon atom bonded to another atom in the molecule of the third compound.

At least one of $Y_{31}$ to $Y_{36}$ is a carbon atom bonded to another atom in the molecule of the third compound.

In the formula (32), $Y_{41}$ to $Y_{48}$ each independently represent a nitrogen atom or a carbon atom bonded to another atom in the molecule of the third compound.

At least one of $Y_{41}$ to $Y_{48}$ is a carbon atom bonded to another atom in the molecule of the third compound.

$X_{30}$ represents a nitrogen atom, an oxygen atom or a sulfur atom.

In the formula (32), it is also preferable that at least two of $Y_{41}$ to $Y_{48}$ are carbon atoms bonded to other atoms in the molecule of the third compound to form a cyclic structure including the carbon atoms.

For instance, the partial structure represented by the formula (32) is preferably any one selected from the group consisting of partial structures represented by formulae (321), (322), (323), (324), (325) and (326).

[Formula 172]

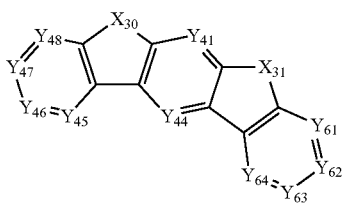
(321)

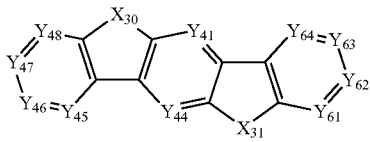
(322)

[Formula 173]

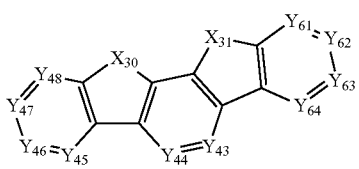
(323)

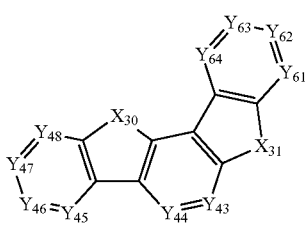
(324)

[Formula 174]

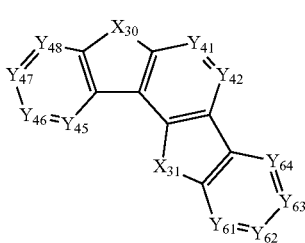
(325)

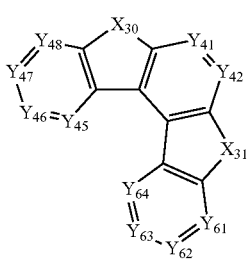
(326)

In the formulae (321) to (326), $X_{30}$ each independently represents a nitrogen atom, an oxygen atom, or a sulfur atom.

$Y_{41}$ to $Y_{48}$ each independently represent a nitrogen atom or a carbon atom bonded to another atom in the molecule of the third compound.

$X_{31}$ each independently represents a nitrogen atom, an oxygen atom, a sulfur atom, or a carbon atom.

$Y_{61}$ to $Y_{64}$ each independently represent a nitrogen atom or a carbon atom bonded to another atom in the molecule of the third compound.

In the exemplary embodiments, the third compound preferably has the partial structure represented by the formula (323) among those represented by the formulae (321) to (326).

The partial structure represented by the formula (31) is preferably included in the third compound as at least one group selected from the group consisting of a group represented by a formula (33) and a group represented by a formula (34).

It is also preferable that the third compound has at least one of the partial structures represented by the formulae (33) and (34). Since bonding positions are situated in meta positions as shown in the partial structures represented by the formulae (33) and (34), an energy gap $T_{77K}(M3)$ at 77 [K] of the third compound can be kept high.

[Formula 175]

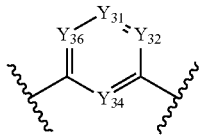
(33)

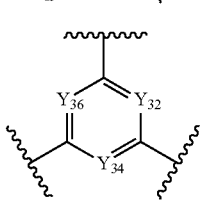
(34)

In the formula (33), $Y_{31}$, $Y_{32}$, $Y_{34}$ and $Y_{36}$ each independently represent a nitrogen atom or $CR_{31}$.

In the formula (34), $Y_{32}$, $Y_{34}$ and $Y_{36}$ each independently represent a nitrogen atom or $CR_{31}$.

In the formulae (33) and (34), $R_{31}$ each independently represents a hydrogen atom or a substituent.

$R_{31}$ as the substituent is each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

The substituted or unsubstituted aryl group having 6 to 30 ring carbon atoms in $R_{31}$ is preferably a non-fused ring.

Wavy lines in the formulae (33) and (34) each show a bonding position with another atom or another structure in the molecule of the third compound.

In the formula (33), $Y_{31}$, $Y_{32}$, $Y_{34}$ and $Y_{36}$ are each independently preferably $CR_{31}$, in which a plurality of $R_{31}$ are the same or different.

In the formula (34), $Y_{32}$, $Y_{34}$ and $Y_{36}$ are each independently preferably $CR_{31}$, in which a plurality of $R_{31}$ are the same or different.

The substituted germanium group is preferably represented by $-Ge(R_{301})_3$. $R_{301}$ is each independently a substituent. The substituent $R_{301}$ is preferably a substituted or unsubstituted alkyl group having 1 to 30 carbon atoms or a substituted or unsubstituted aryl group having 6 to 30 ring carbon atoms. A plurality of $R_{301}$ are mutually the same or different.

The partial structure represented by the formula (32) is preferably included in the third compound as at least one group selected from the group consisting of groups represented by formulae (35) to (39) and a group represented by a formula (30a).

[Formula 176]

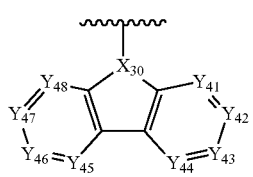
(35)

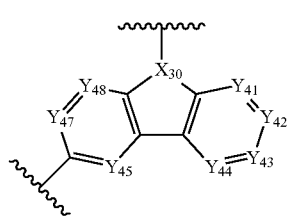
(30a)

-continued

[Formula 177]

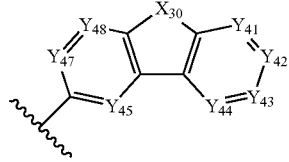
(37)

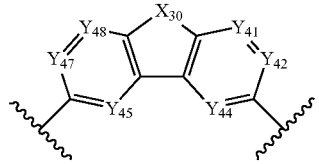
(38)

[Formula 178]

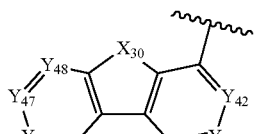
(39)

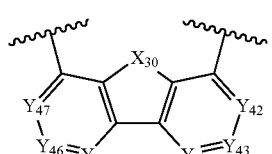
(40)

In the formula (35), $Y_{41}$ to $Y_{48}$ each independently represent a nitrogen atom or $CR_{32}$.

In the formulae (36) and (37), $Y_{41}$ to $Y_{45}$, $Y_{47}$ and $Y_{48}$ each independently represent a nitrogen atom or $CR_{32}$.

In the formula (38), $Y_{41}$, $Y_{42}$, $Y_{44}$, $Y_{45}$, $Y_{47}$, and $Y_{48}$ each independently represent a nitrogen atom or $CR_{32}$.

In the formula (39), $Y_{42}$ to $Y_{48}$ each independently represent a nitrogen atom or $CR_{32}$.

In the formula (30a), $Y_{42}$ to $Y_{48}$ each independently represent a nitrogen atom or $CR_{32}$.

In the formulae (35) to (39) and (30a), $R_{32}$ each independently represents a hydrogen atom or a substituent.

$R_{32}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

A plurality of $R_{32}$ are mutually the same or different.

In the formulae (35) and (36), $X_{30}$ represents a nitrogen atom.

In the formulae (37) to (39) and (30a), $X_{30}$ represents $NR_{33}$, an oxygen atom or a sulfur atom.

$R_{33}$ is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to carbon atoms, a substituted or unsubstituted silyl group, a substituted germanium group, a substituted phosphine oxide group, a fluorine atom, a cyano group, a nitro group, and a substituted or unsubstituted carboxy group.

A plurality of $R_{33}$ are mutually the same or different.

The substituted or unsubstituted aryl group having 6 to 30 ring carbon atoms in $R_{33}$ is preferably a non-fused ring.

Wavy lines in the formulae (35) to (39) and (30a) each show a bonding position with another atom or another structure in the molecule of the third compound.

In the formula (35), $Y_{41}$ to $Y_{48}$ are preferably each independently $CR_{32}$. In the formulae (36) and (37), $Y_{41}$ to $Y_{45}$, $Y_{47}$ and $Y_{48}$ are preferably each independently $CR_{32}$.

In the formula (38), $Y_{41}$, $Y_{42}$, $Y_{44}$, $Y_{45}$, $Y_{47}$ and $Y_{48}$ are preferably each independently $CR_{32}$.

In the formula (39), $Y_{42}$ to $Y_{48}$ are preferably each independently $CR_{32}$.

In the formula (30a), $Y_{42}$ to $Y_{47}$ are preferably each independently $CR_{32}$.

A plurality of $R_{32}$ are mutually the same or different.

In the third compound, $X_{30}$ is preferably an oxygen atom or a sulfur atom, more preferably an oxygen atom.

In the third compound, $R_{31}$ and $R_{32}$ each independently represent a hydrogen atom or a substituent. $R_{31}$ and $R_{32}$ as the substituents are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubstituted heteroaryl group having 5 to 30 ring atoms. When $R_{31}$ and $R_{32}$ as the substituents are each a substituted or unsubstituted aryl group having 6 to 30 ring carbon atoms, the aryl group is preferably a non-fused ring.

It is also preferable that the third compound is an aromatic hydrocarbon compound or an aromatic heterocyclic compound. Moreover, it is preferable that the third compound does not have a fused aromatic hydrocarbon ring in a molecule.

Method of Manufacturing Third Compound

The third compound can be manufactured by methods disclosed in International Publication No. WO2012/153780, International Publication No. WO2013/038650, and the like. Furthermore, the third compound can be manufactured, for instance, by application of known substitution reactions and/or materials depending on a target compound.

Examples of the substituent in the third compound are shown below, but the substituent according to the invention is not limited to the examples.

Specific examples of the aryl group (occasionally referred to as an aromatic hydrocarbonl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothiophenyl group, dibenzothiophenyl group, azadibenzothiophenyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothiophenyl group, carbazolyl group, pyridyl group, pyrimidinyl group, triazinyl group, azadibenzofuranyl group and azadibenzothiophenyl group may be preferable.

The heteroaryl group is preferably a dibenzofuranyl group, dibenzothiophenyl group, carbazolyl group, pyridyl group, pyrimidinyl group, triazinyl group, azadibenzofuranyl group or azadibenzothiophenyl group, and further preferably a dibenzofuranyl group, dibenzothiophenyl group, azadibenzofuranyl group and azadibenzothiophenyl group.

In the third compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound, it is also preferable that the substituted phosphine oxide group is a substituted or unsubstituted diaryl phosphine oxide group.

Specific examples of the substituted or unsubstituted diaryl phosphine oxide group include a diphenyl phosphine oxide group and ditolyl phosphine oxide group.

In the third compound, examples of the substituted carboxy group include benzoyloxy group.

Relationship Between First Compound, Second Compound and Third Compound in Emitting Layer The first compound, the second compound, and the third compound in the emitting layer preferably satisfy the relationship of Numerical Formula 1 and the relationship of Numerical Formula 2. In other words, a relationship of the following numerical formula (Numerical Formula 3) is preferably satisfied.

$$S_1(M3) > S_1(M1) > S_1(M2) \quad \text{(Numerical Formula 3).}$$

An energy gap $T_{77K}(M3)$ at 77 [K] of the third compound is preferably larger than the energy gap $T_{77K}(M1)$ at 77 [K] of the first compound. In other words, a relationship of the following numerical formula (Numerical Formula 5) is preferably satisfied.

$$T_{77K}(M3) > T_{77K}(M1) \quad \text{(Numerical Formula 5).}$$

The energy gap $T_{77K}(M3)$ at 77 [K] of the third compound is preferably larger than the energy gap $T_{77K}(M2)$ at 77 [K] of the second compound. In other words, a relationship of the following numerical formula (Numerical Formula 6) is preferably satisfied.

$$T_{77K}(M3) > T_{77K}(M2) \quad \text{(Numerical Formula 6).}$$

The first compound, the second compound, and the third compound in the emitting layer preferably satisfy the relationship of Numerical Formula 4 and the relationship of Numerical Formula 5. In other words, a relationship of the following numerical formula (Numerical Formula 7) is preferably satisfied.

$$T_{77K}(M3) > T_{77K}(M1) > T_{77K}(M2) \quad \text{(Numerical Formula 7).}$$

When the organic EL device of the exemplary embodiment emits light, it is preferable that the second compound in the emitting layer mainly emits light.

Content Ratio of Compounds in Emitting Layer

Content ratios of the respective first, second and third compounds in the emitting layer preferably range as follows.

The content ratio of the first compound preferably ranges from 10 mass % to 80 mass %, more preferably from 10 mass % to 60 mass %, further preferably from mass % to 60 mass %.

The content ratio of the second compound preferably ranges from 0.01 mass % to 10 mass %, more preferably from 0.01 mass % to 5 mass %, further preferably from 0.01 mass % to 1 mass %.

The content ratio of the third compound preferably ranges from 10 mass % to 80 mass %.

An upper limit of the total of the respective content ratios of the first, second and third compounds in the emitting layer is 100 mass %. It should be noted that the emitting layer of the exemplary embodiment may further contain another material in addition to the first, second and third compounds.

Figure 5:
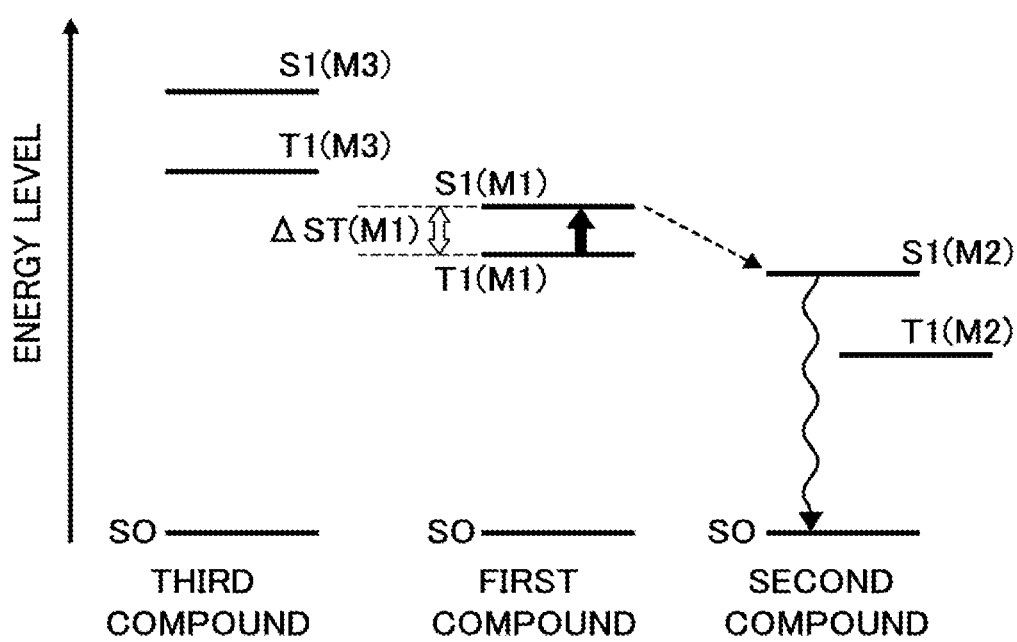
FIG. 5 shows a relationship between energy levels of a first compound, a second compound and a third compound and an energy transfer between the first compound, the second compound and the third compound in an emitting layer of an exemplary organic electroluminescence device of a second exemplary embodiment of the invention.

FIG. 5 shows an example of a relationship among energy levels of the first compound, the second compound and the third compound in the emitting layer. In FIG. 5, S0 represents a ground state. S1(M1) represents the lowest singlet state of the first compound.

T1(M1) represents the lowest triplet state of the first compound. S1(M2) represents the lowest singlet state of the second compound.

T1(M2) represents the lowest triplet state of the second compound. S1(M3) represents the lowest singlet state of the third compound.

T1(M3) represents the lowest triplet state of the third compound. A dashed arrow directed from S1(M1) to S1(M2) in FIG. 5 represents Forster energy transfer from the lowest singlet state of the first compound to the lowest singlet state of the second compound.

As shown in FIG. 5, when a compound having a small $\Delta ST(M1)$ is used as the first compound, inverse intersystem crossing from the lowest triplet state T1(M1) to the lowest singlet state S1(M1) can be caused by a heat energy. Subsequently, Förster energy transfer from the lowest singlet state S1(M1) of the first compound the second compound occurs to generate the lowest singlet state S1(M2). Consequently, fluorescence from the lowest singlet state S1(M2) of the second compound can be observed. It is inferred that the internal quantum efficiency can be theoretically raised up to 100% also by using delayed fluorescence by the TADF mechanism.

The organic EL device according to the second exemplary embodiment emits light at a high efficiency.

Moreover, the organic EL device according to the second exemplary embodiment can improve the luminous efficiency of the organic EL device particularly in the blue wavelength region.

The organic EL device of the second exemplary embodiment, in which the emitting layer includes the delayed fluorescent first compound, the fluorescent second compound, and the third compound having the singlet energy larger than that of the first compound, improves the luminous efficiency. It is presumed that an improvement in the luminous efficiency is caused by an improvement in a carrier balance of the emitting layer since the emitting layer contains the third compound.

The organic EL device according to the second exemplary embodiment is applicable to an electronic device such as a display device and a light-emitting device in the same manner as the organic EL device according to the first exemplary embodiment.

Modification of Exemplary Embodiments

It should be noted that the invention is not limited to the above exemplary embodiments but may include any modification and improvement as long as such modification and improvement are compatible with the invention.

For instance, the emitting layer is not limited to a single layer, but is multi-layered emitting layers in some embodiments. When the organic EL device has a plurality of emitting layers, it is only required that at least one of the emitting layers satisfies the conditions described in the above exemplary embodiments. For instance, in some embodiments, the rest of the emitting layers is a fluorescent emitting layer or a phosphorescent emitting layer using emission by electronic transition from the triplet state directly to the ground state.

Moreover, when the organic EL device has the plurality of emitting layers, in some embodiments, the plurality of emitting layers are adjacent to each other, or provide a so-called tandem-type organic EL device in which a plurality of emitting units are layered through an intermediate layer.

Moreover, for instance, in some embodiments, a blocking layer is adjacent to at least one side of the emitting layer among a side close to the anode and a side close to the cathode. The blocking layer is preferably provided in contact with the emitting layer to block at least one of holes, electrons and excitons.

For instance, when the blocking layer is provided in contact with the side close to the cathode of the emitting layer, the blocking layer permits transport of electrons, but blocks holes from reaching a layer provided close to the cathode (e.g., the electron transporting layer) beyond the blocking layer. When the organic EL device includes an electron transporting layer, the blocking layer is preferably interposed between the emitting layer and the electron transporting layer.

When the blocking layer is provided in contact with the side close to the anode of the emitting layer, the blocking layer permits transport of holes, but blocks electrons from reaching a layer provided close to the anode (e.g., the hole transporting layer) beyond the blocking layer. When the organic EL device includes the hole transporting layer, the blocking layer is preferably interposed between the emitting layer and the hole transporting layer.

Further, the blocking layer may be provided in contact with the emitting layer to prevent an excitation energy from leaking from the emitting layer into neighboring layers. The blocking layer blocks excitons generated in the emitting layer from moving into a layer provided close to the electrode (e.g., the electron transporting layer and the hole transporting layer) beyond the blocking layer.

The emitting layer is preferably bonded to the blocking layer.

Specific structure and shape of the components for implementing the invention may be designed in any manner as long as the object of the invention can be achieved.

EXAMPLES

Examples of the invention will be described below. However, the invention is by no means limited to Examples.
Compounds
Compounds used for manufacturing the organic EL device will be shown below.

[Formula 179]

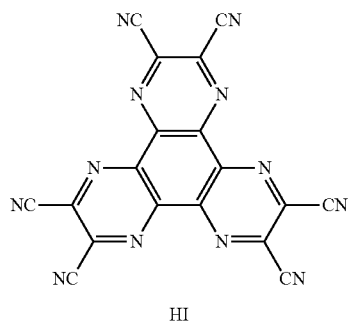

HI

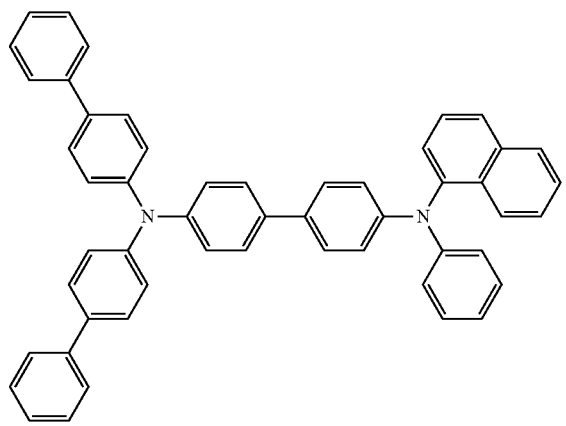

HT1

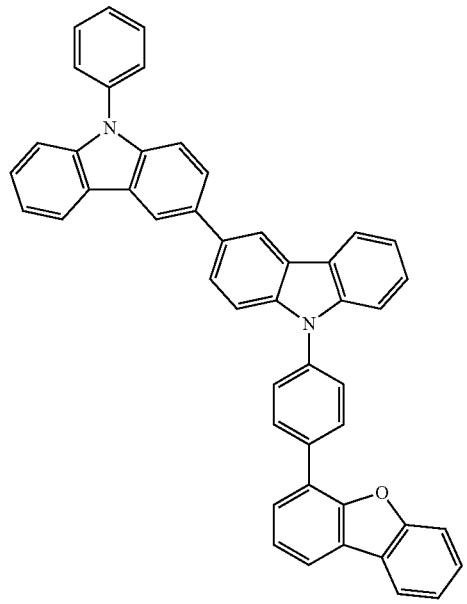

HT2

-continued
[Formula 180]
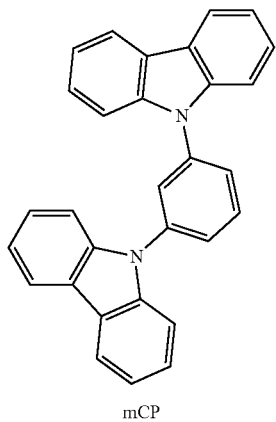
mCP
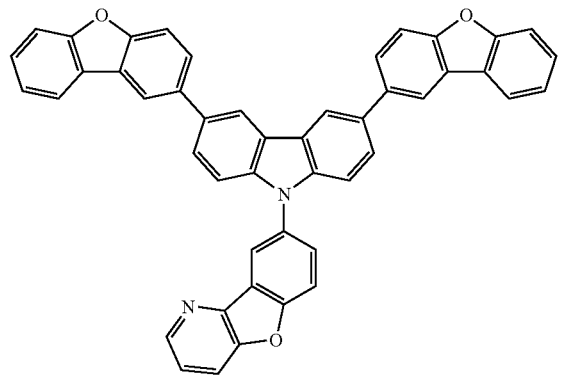
ET-1
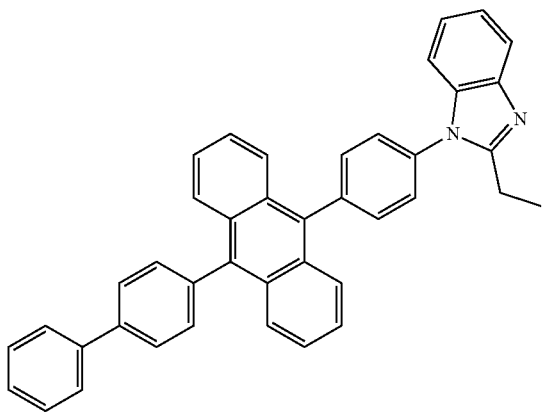
ET-2
[Formula 181]
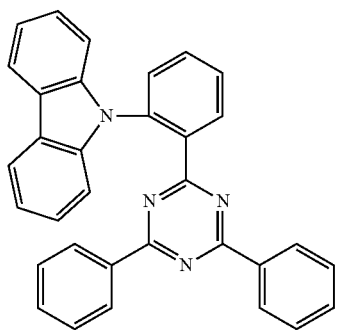
TADF-1
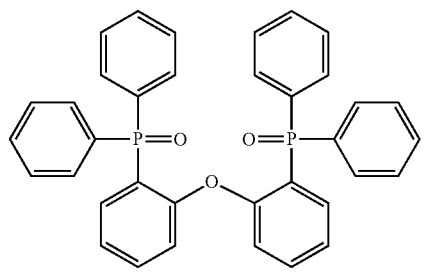
DPEPO

[Formula 182]
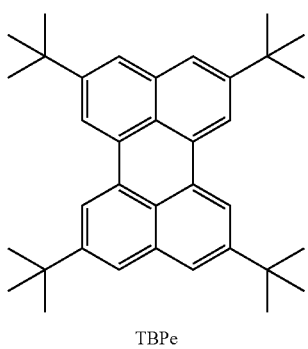
TBPe
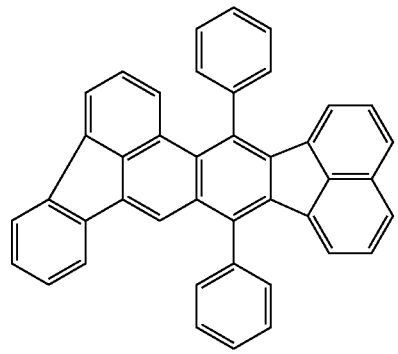
ref-1
[Formula 183]
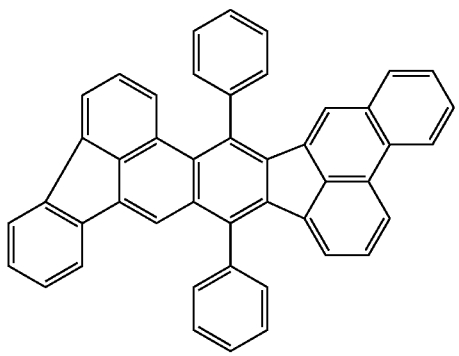
Ref-2
[Formula 184]
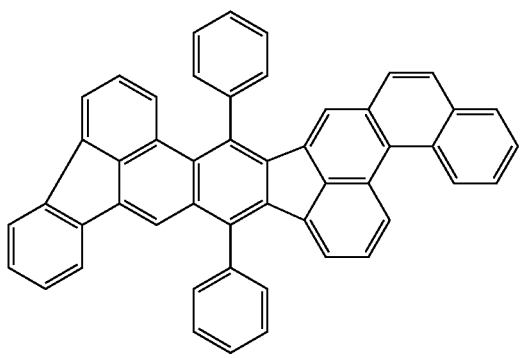
BD-1a
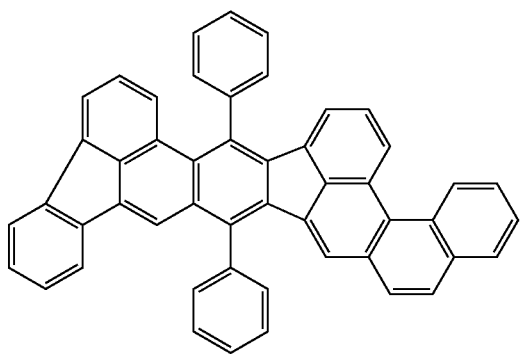
BD-1b -continued
[Formula 185]
BD-2a
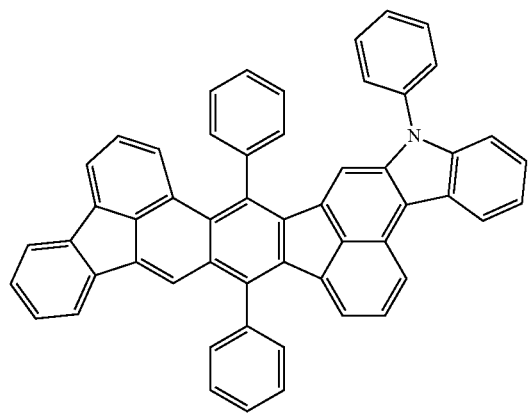
BD-2b
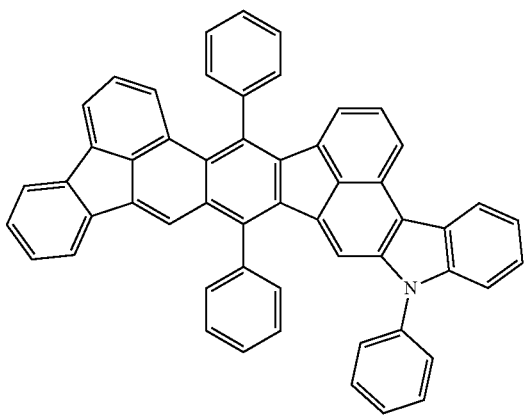
[Formula 186]
BD-3a
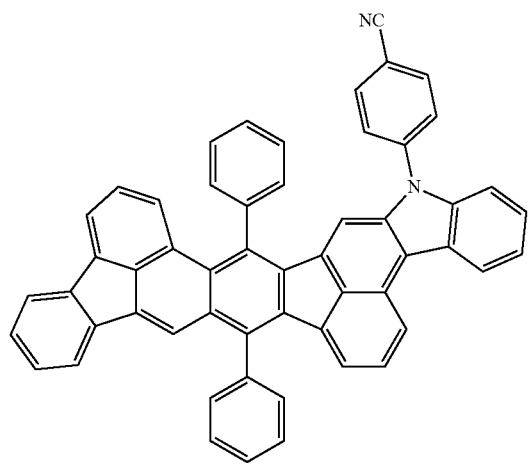
BD-3b
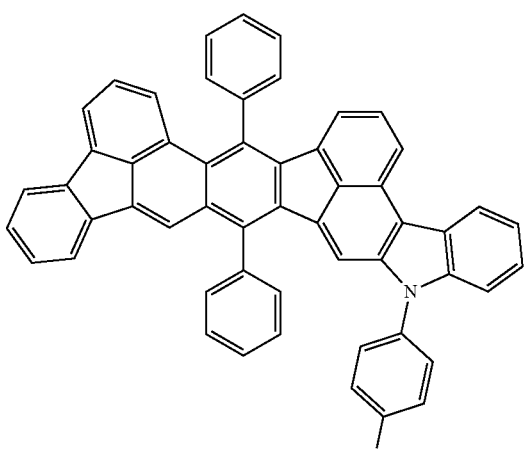
[Formula 187]
BD-4a
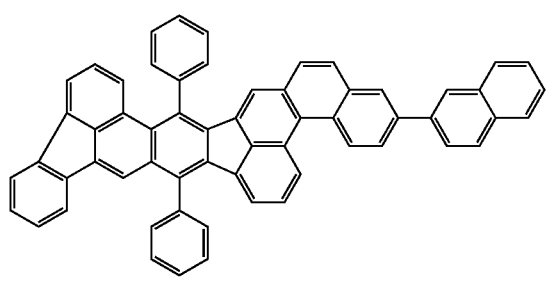
BD-4b
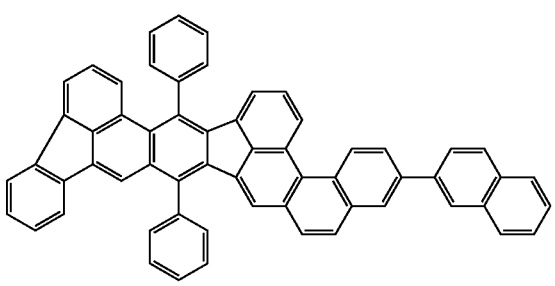

-continued
[Formula 188]
BD-5a
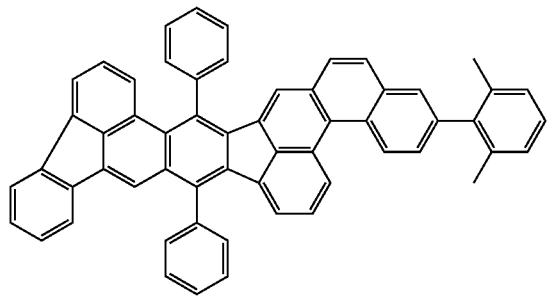
BD-5b
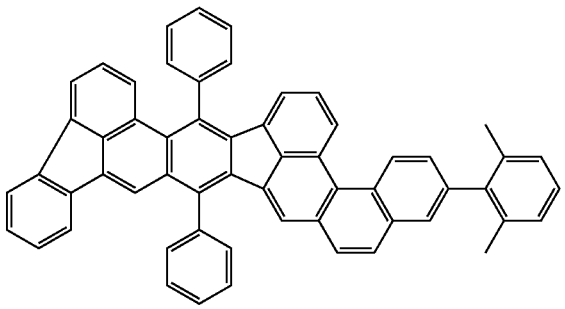
[Formula 189]
BD-6a
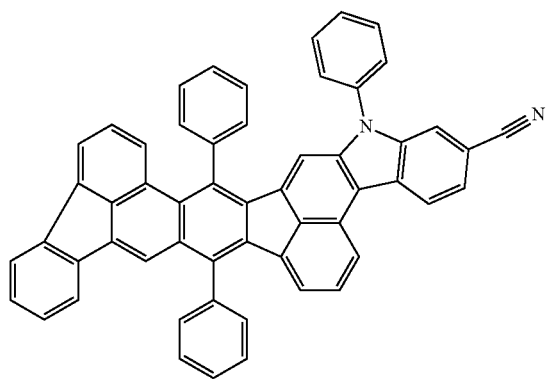
BD-6b
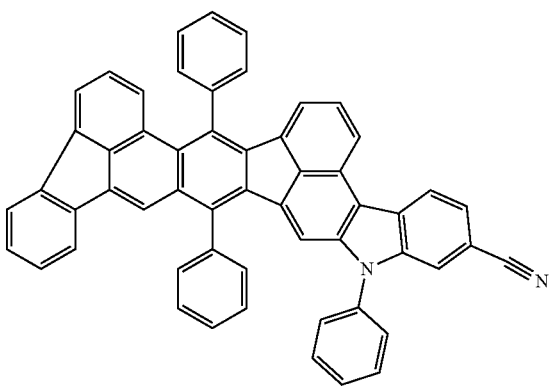
[Formula 190]
BD-7a
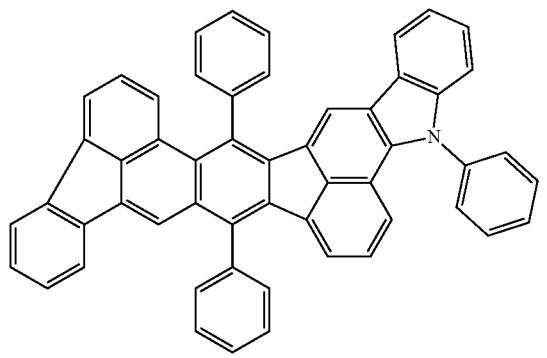
BD-7b
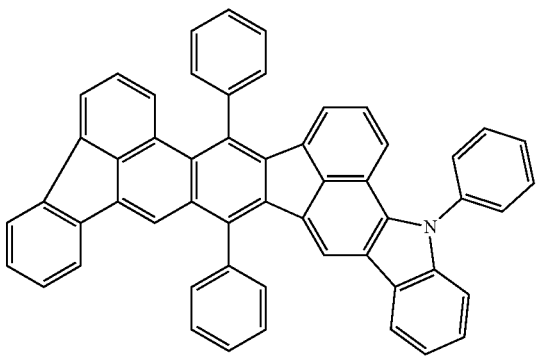

-continued
[Formula 191]
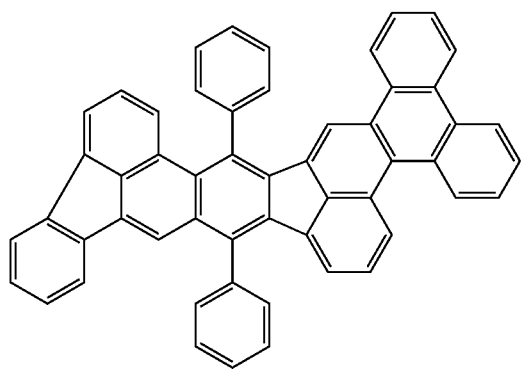
BD-8a
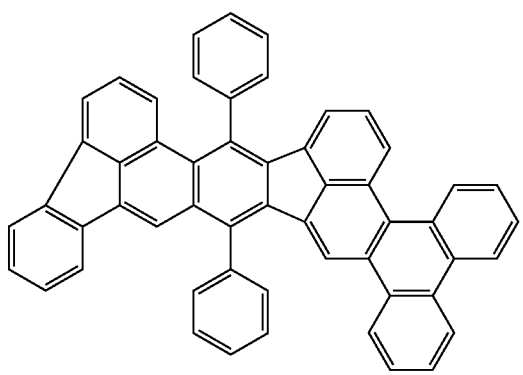
BD-8b
[Formula 192]
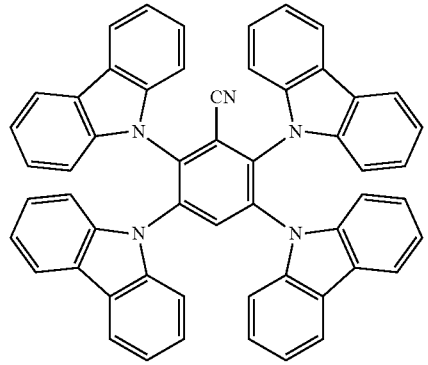
TADF-2
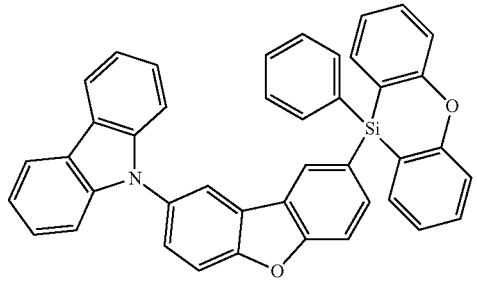
A-1
[Formula 193]
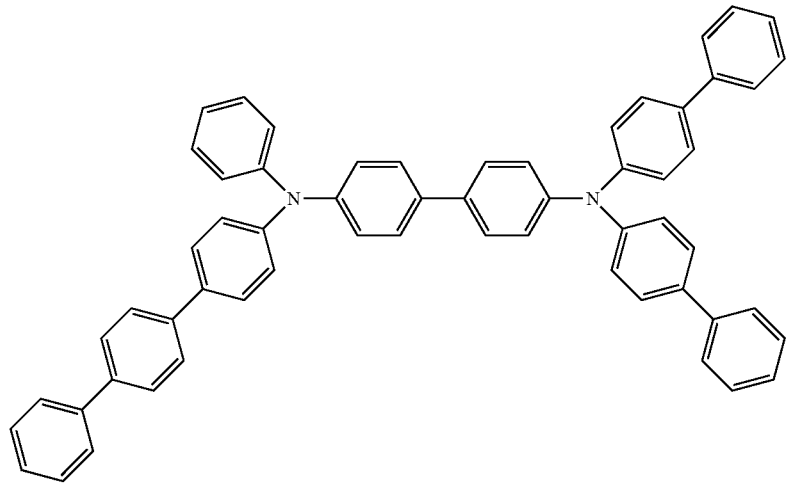
HT3

HT4
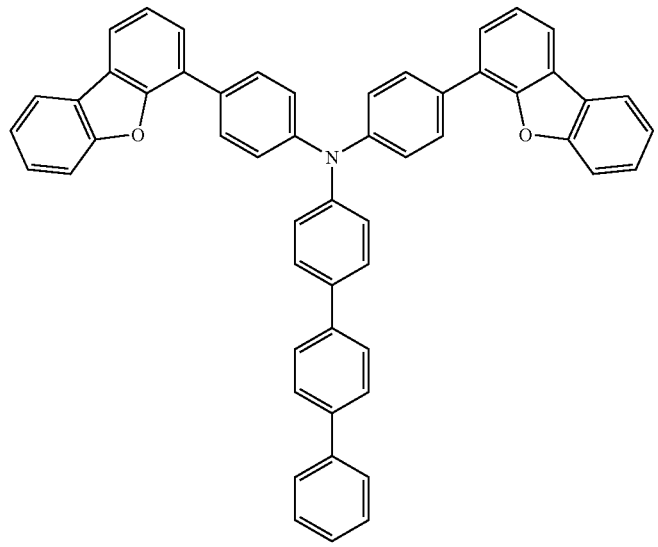
[Formula 194]
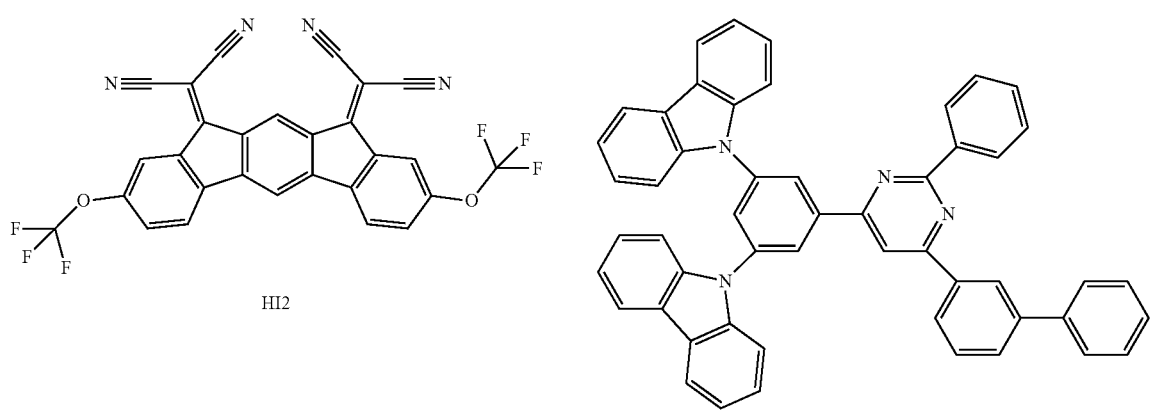
HI2
ET-3
[Formula 195]
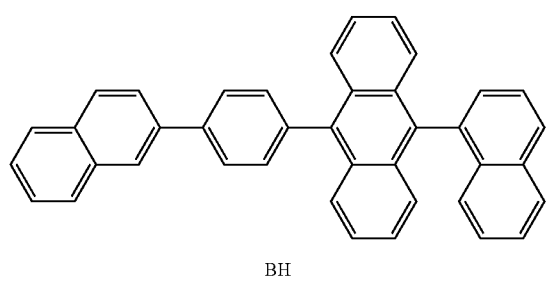
BH

Synthesis of Compound(s)

Synthesis Example 1: Synthesis of Compound BD-1

(1-1) Synthesis of Intermediate (Int-1)

[Formula 196]

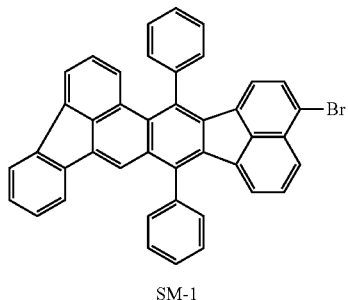

SM-1

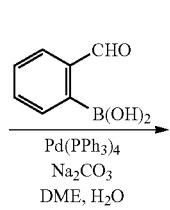

Pd(PPh$_3$)$_4$
Na$_2$CO$_3$
DME, H$_2$O

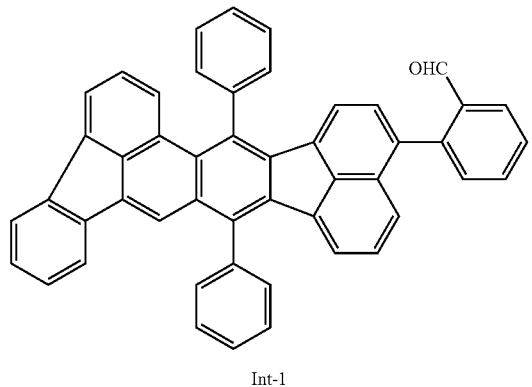

Int-1

To a three-necked flask, 2.0 g (3.29 mmol) of a starting material (SM-1: isomer mixture), 0.59 g (3.95 mmol) of 2-formylphenyl boronic acid, 0.87 g (8.23 mmol) of sodium carbonate, 10 mL of 1,2-dimethoxyethane (DME), and 10 mL of water were added. Subsequently, 0.19 g (0.17 mmol) of tetrakis(triphenylphosphine)palladium was further added to the flask to provide a mixture solution. The mixture solution was heated for reflux with stirring for eight hours under an argon gas atmosphere. After the mixture solution was heated for reflux with stirring, an organic layer was separated from the mixture solution. The separated organic layer was condensed under reduced pressure. The obtained residue was refined by silica-gel column chromatography. A mixture solvent of dichloromethane and n-hexane was used as an eluent. After the refinement, the obtained solid was suspended in and washed with methanol to obtain an intermediate (Int-1). A yield of the intermediate (Int-1) was 2.1 g and a yield rate thereof was 100%.

(1-2) Synthesis of Intermediate (Int-2)

[Formula 197]

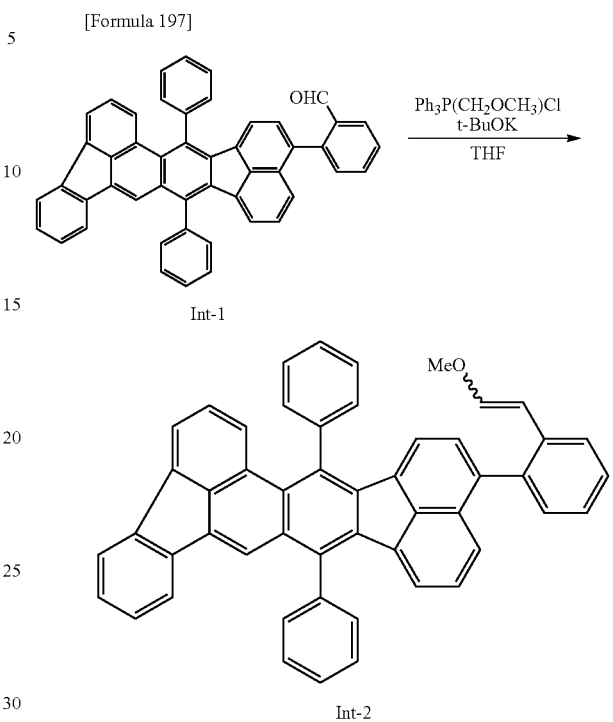

Int-2

To a three-necked flask, 1.7 g (4.98 mmol) of (methoxymethyl)triphenyl phosphonium chloride and 3.5 mL of tetrahydrofuran (THF) were added. Subsequently, 0.61 g (5.48 mmol) of potassium t-butoxide was added to the flask to prepare a ylide solution in red. Further, a THF solution (5 mL) of the intermediate (Int-1) (2.1 g (3.29 mmol)) was added to the flask and stirred for two hours under argon atmosphere. After water was added to the flask to stop a reaction, dichloromethane was used for extraction. The extracted organic layer was condensed under reduced pressure. The obtained residue was refined by silica-gel column chromatography. A mixture solvent of dichloromethane and n-hexane was used as an eluent. After the refinement, the obtained solid was suspended in and washed with methanol to obtain an intermediate (Int-2). A yield of the intermediate (Int-2) was 1.8 g and a yield rate thereof was 82%.

(1-3) Synthesis of Compound BD-1

[Formula 198]

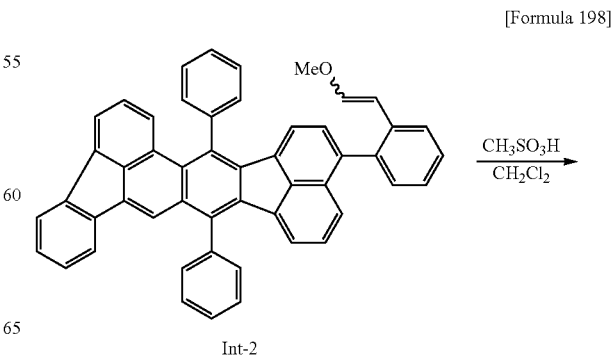

Int-2

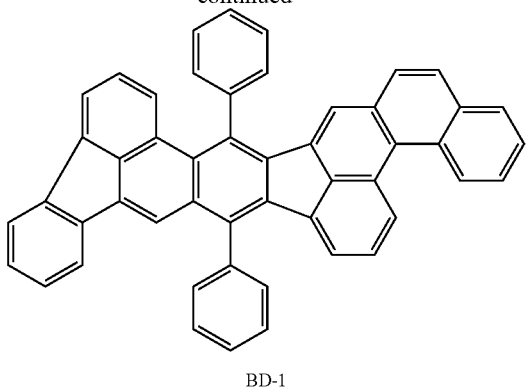

BD-1

To a three-necked flask, 1.8 g (2.72 mmol) of the intermediate (Int-2) and 25 mL of dichloromethane were added. Subsequently, 0.26 g (2.72 mmol) of methane sulfonic acid was dropped in the flask and was stirred for 0.5 hour. After sodium hydrogen carbonate aqueous solution was added to the flask to stop a reaction, dichloromethane was used for extraction. The extracted organic layer was condensed under reduced pressure. The obtained residue was refined by silica-gel column chromatography. A mixture solvent of dichloromethane and n-hexane was used as an eluent. After the refinement, the obtained solid was suspended in and washed with methanol to obtain a target substance (compound BD-1) in a form of a yellow solid. A yield of the compound was 0.84 g and a yield rate thereof was 49%. A result of FD-MS (Field Desorption Mass Spectrometry) analysis showed m/e=628 relative to a molecular weight of 628. It should be noted that BD-1 was a mixture of BD-1a and BD-1b, which was derived from that the starting material (SM-1) was the isomer mixture (mixture of SM-1a and SM-1b). In a reaction formula of Synthesis Example 1, a representative structure of "SM-1" was shown only by a structure of SM-1a and a representative structure of "BD-1" was shown only by a structure of BD-1a. Structures of the intermediates Int-1 and Int-2 were also shown only by the intermediate obtained from SM-1a.

[Formula 199]

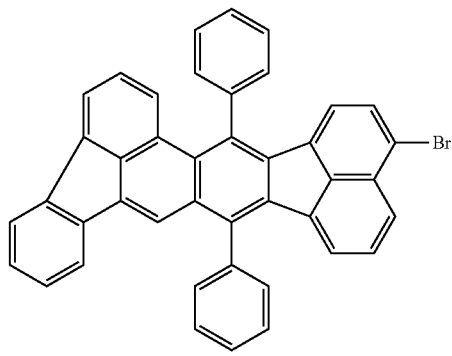

SM-1a

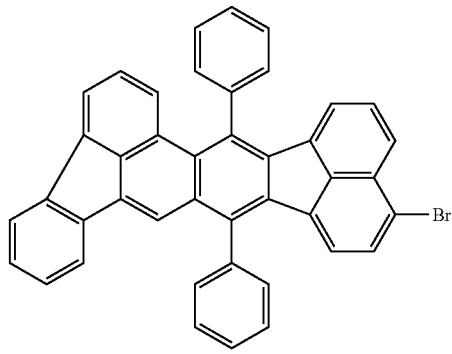

SM-1b

Synthesis Example 2: Synthesis of Compound BD-2

(2-1) Synthesis of Intermediate 2A

[Formula 200]

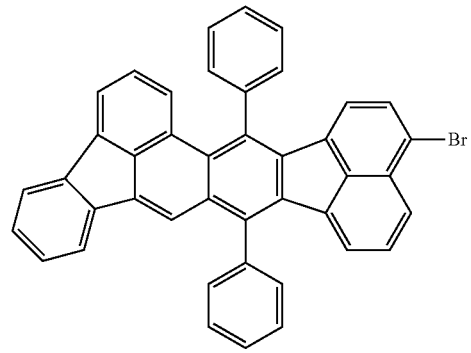

SM-1

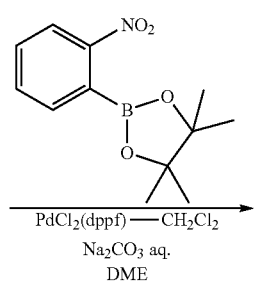

PdCl$_2$(dppf)—CH$_2$Cl$_2$
Na$_2$CO$_3$ aq.
DME

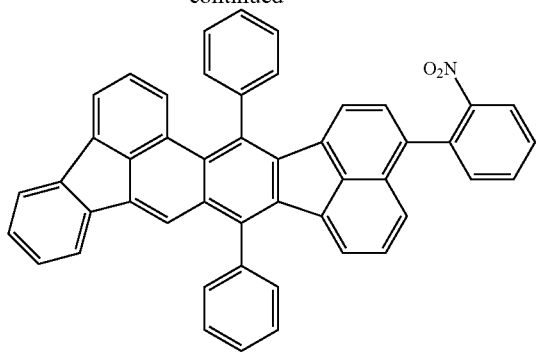

Intermediate 2A

To a three-necked flask, under argon atmosphere, 3.0 g (4.94 mmol) of the starting material (SM-1: isomer mixture), 2.5 g (9.88 mmol) of 2-nitrophenyl boronic acid pinacol ester, and 30 mL of 1,2-dimethoxyethane (DME) were added. Subsequently, 0.16 g (0.2 mmol) of PdCl₂(dppf)/ CH₂Cl₂ was added to the flask and then 7.4 mL of an aqueous solution of 2M sodium carbonate was added thereto. The obtained mixture solution was heated with stirring at 80 degrees C. for six hours. After heated with stirring, the mixture solution was returned to a room temperature and a deposited solid was filtrated. After the obtained solid was dissolved in toluene, added with silica gel and stirred, the obtained solution was filtrated and condensed to obtain an intermediate 2A. A yield of the intermediate 2A was 2.74 g and a yield rate thereof was 85%.

(2-2) Synthesis of Intermediate 2B

To a three-necked flask, 2.1 g (3.23 mmol) of the intermediate 2A, 2.12 g (8.08 mmol) of triphenylphosphine (PPh₃), and 20 mL of ortho dichlorobenzene (o-DCB) were added, and heated with stirring at 140 degrees C. for 24 hours under argon atmosphere. During the reaction, 2.11 g of triphenylphosphine was additionally put in the flask. After the solvent was distilled away under reduced pressure, the obtained residue was refined by silica-gel column chromatography (a mobile phase; hexane:toluene=2:1 (volume ratio)), so that an intermediate 2B was obtained. A yield of the intermediate 2B was 1.59 g and a yield rate thereof was 75%.

(2-3) Synthesis of Compound BD-2

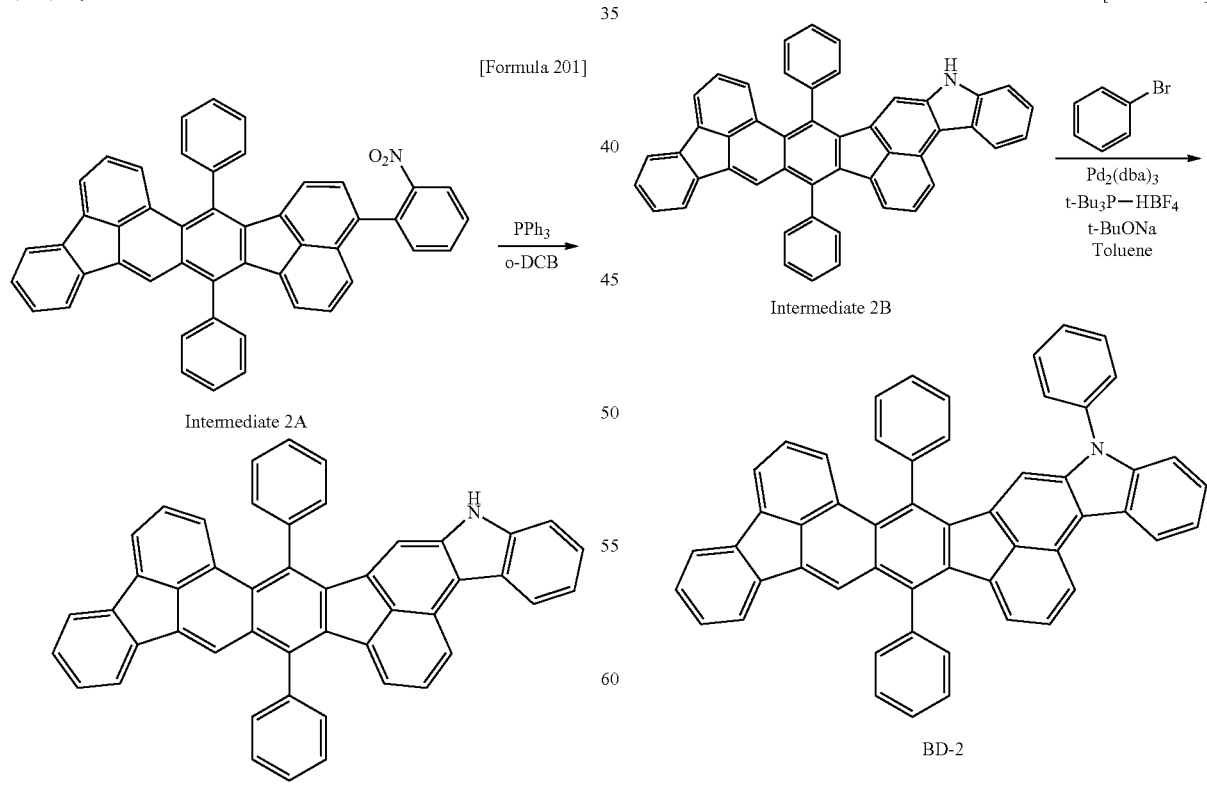

To a three-necked flask, under argon atmosphere, 1.57 g (2.54 mmol) of the intermediate 2B, 0.6 g (3.81 mmol) of bromobenzene, 47 mg (0.051 mmol) of Pd₂(dba)₃, 0.13 g (0.20 mmol) of t-Bu₃P—HBF₄, and 0.34 g (3.56 mmol) of t-BuONa were added and subsequently 20 mL of toluene was added. The obtained mixture solution was heated with stirring at 105 degrees C. for seven hours. After heated with stirring, the mixture solution was returned to the room temperature and a deposited solid was filtrated. After the obtained solid was dissolved in chlorobenzene, added with silica gel and stirred, the obtained solution was filtrated and condensed. The obtained residue was refined by silica-gel column chromatography (a mobile phase; hexane:toluene=2:1 (volume ratio)). Further, the obtained solid was suspended in and washed with ethyl acetate to obtain a compound BD-2. A yield of the compound was 0.78 g and a yield rate thereof was 44%. A result of FD-MS analysis showed m/e=693 relative to a molecular weight of 693. It should be noted that BD-2 was a mixture of BD-2a and BD-2b, which was derived from that the starting material (SM-1) was the isomer mixture (mixture of SM-1a and SM-1b) In a reaction formula of Synthetic Example 2, the representative structure of "SM-1" was shown only by the structure of SM-1a and a representative structure of "BD-2" was shown only by a structure of BD-2a. Both structures of the intermediate 2A and the intermediate 2B were shown only by a structure of an intermediate obtained from SM-1a.

Synthesis Example 3: Synthesis of Compound BD-3

[Formula 203]

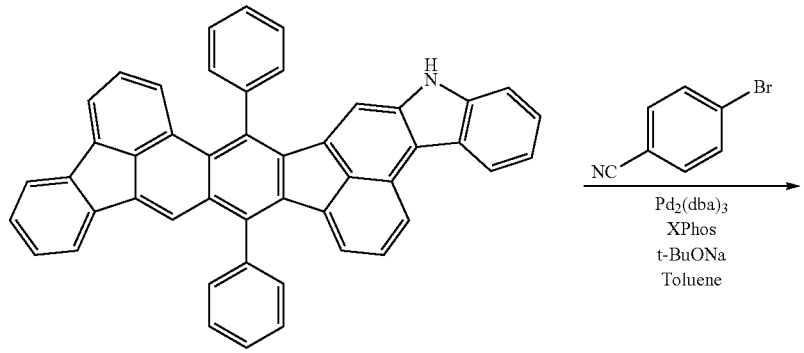

Intermediate 2B

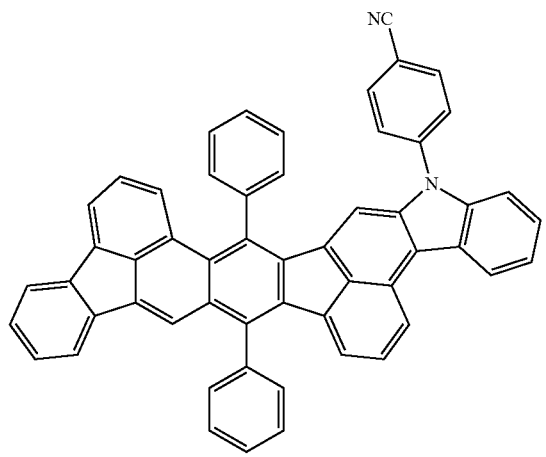

BD-3

To a three-necked flask, under argon atmosphere, 2.33 g (3.77 mmol) of the intermediate 2B, 1.37 g (7.53 mmol) of 4-bromobenzonitrile, 0.14 g (0.15 mmol) of $Pd_2(dba)_3$, 0.29 g (0.61 mmol) of XPhos, and 0.51 g (5.27 mmol) of t-BuONa were added and subsequently 20 mL of toluene was added. The obtained mixture solution was heated with stirring at 100 degrees C. for 15 hours. After heated with stirring, the mixture solution was returned to the room temperature and a deposited solid was filtrated. After the obtained solid was dissolved in chlorobenzene, added with silica gel and stirred, the obtained solution was filtrated and condensed. The obtained solid was suspended in and washed with methanol to obtain a compound BD-3. A yield of the compound was 2.19 g and a yield rate thereof was 81%. A result of FD-MS analysis showed that m/e=718 relative to a molecular weight of 718. It should be noted that BD-3 was a mixture of BD-3a and BD-3b, which was derived from that the starting material (SM-1) was the isomer mixture (mixture of SM-1a and SM-1b). In a reaction formula of Synthetic Example 3, a representative structure of "BD-3" was shown only by a structure of BD-3a. The representative structure of the intermediate 2B was also shown only by the structure of the intermediate obtained from SM-1a.

Synthesis Example 4: Synthesis of Compound BD-4

(4-1) Synthesis of Intermediate 4A

[Formula 204]

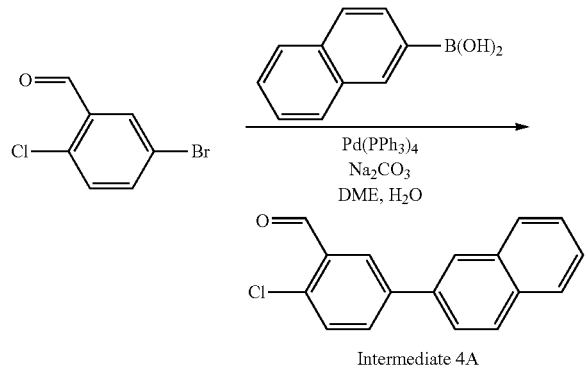

To a three-necked flask, 41.5 g (189 mmol) of 5-bromo-2-chlorobenzaldehyde, 39.0 g (227 mmol) of naphthalene-2-ylboronic acid, 189 mL (378 mmol) of 2M sodium carbonate aqueous solution, and 378 mL of 1,2-dimethoxyethane (DME) were added. Subsequently, 4.37 g (3.78 mmol) of tetrakis(triphenylphosphine)palladium was further added to the flask to provide a mixture solution. The mixture solution was heated for reflux with stirring for eight hours under an argon gas atmosphere. After the mixture solution was heated for reflux with stirring, an organic layer was separated with toluene. The separated organic layer was condensed under reduced pressure. The obtained residue was suspended in and washed with methanol to obtain an intermediate 4A. A yield of the intermediate was 49.4 g and a yield rate thereof was 98%.

(4-2) Synthesis of Intermediate 4B

[Formula 205]

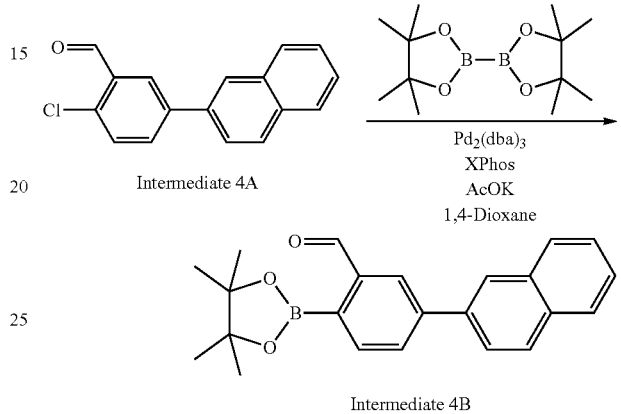

To a three-necked flask, under argon atmosphere, 30.0 g (112 mmol) of the intermediate 4A, 34.3 g (135 mmol) of bis(pinacolato)diboron, 2.06 g (2.25 mmol) of $Pd_2(dba)_3$, 4.29 g (9.00 mmol) of XPhos, and 22.1 g (225 mmol) of potassium acetate were added and subsequently 375 mL of 1,4-dioxane was added. The obtained mixture solution was heated with stirring at 80 degrees C. for four hours. After the mixture solution was returned to the room temperature, water was added to the three-necked flask and an organic layer was extracted with ethyl acetate. After the solvent was distilled away from the extracted organic layer under reduced pressure, the obtained residue was refined by silica-gel column chromatography (a mobile phase; hexane:dichloromethane), so that an intermediate 4B was obtained. A yield of the intermediate was 40.3 g and a yield rate thereof was 100%.

(4-3) Synthesis of Intermediate 4C

[Formula 206]

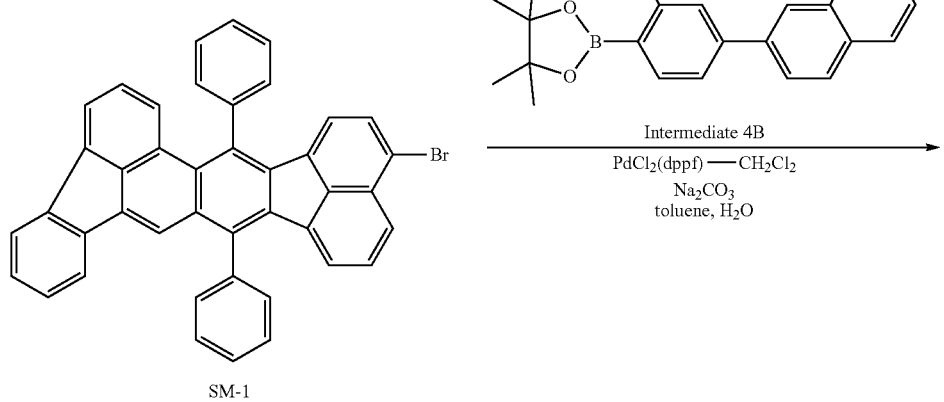

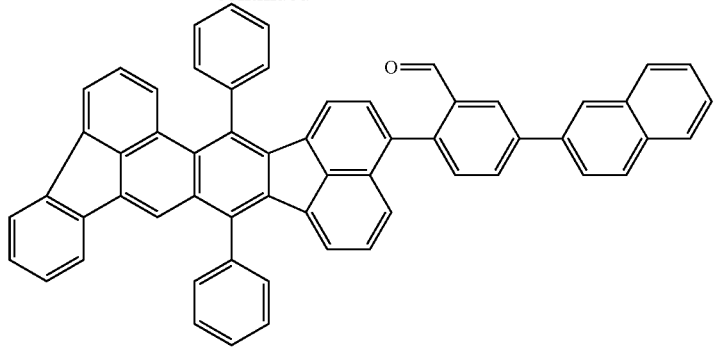

Intermediate 4C

To a three-necked flask, under argon atmosphere, 5.0 g (8.23 mmol) of the starting material (SM-1: isomer mixture), 4.42 g (12.3 mmol) of the intermediate 4B, and 82 mL of toluene were added. Subsequently, 0.13 g (0.16 mmol) of $PdCl_2(dppf)/CH_2Cl_2$ was added to the flask and then 8.2 mL of 2M sodium carbonate aqueous solution was added thereto. The obtained mixture solution was heated with stirring at 90 degrees C. for 22 hours. After heated with stirring, the mixture solution was returned to the room temperature. An aqueous layer was removed from the mixture solution. An organic layer was added with silica gel and stirred. Subsequently, the obtained solution was filtrated and condensed. The obtained residue was washed with ethyl acetate and filtrated to obtain an intermediate 4C. A yield of the intermediate was 4.71 g and a yield rate thereof was 75%.

(4-4) Synthesis of Intermediate 4D

[Formula 207]

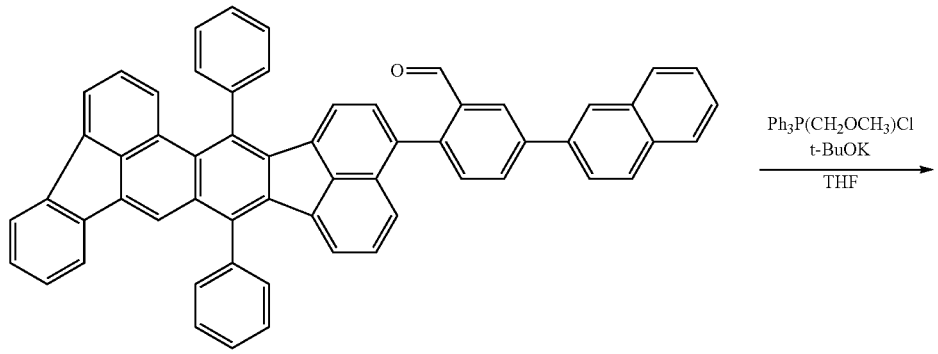

Intermediate 4C

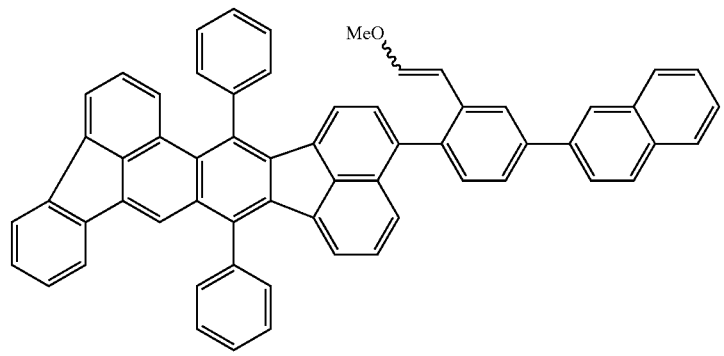

Intermediate 4D

To a three-necked flask, 6.03 g (17.6 mmol) of (methoxymethyl)triphenyl phosphonium chloride and 60 mL of tetrahydrofuran (THF) were added. Subsequently, 2.17 g (19.4 mmol) of t-BuOK was added to the flask to prepare a ylide solution in red. Further, a THE solution (60 mL) of the intermediate 4C (8.90 g (11.7 mmol)) was added to the flask and stirred for two hours under argon atmosphere. After water was added to the flask to stop a reaction, dichloromethane was used for extraction. The extracted organic layer was condensed under reduced pressure. The obtained residue was refined by silica-gel column chromatography. A mixture solvent of dichloromethane and n-hexane was used as an eluent. After the refinement, the obtained solid was suspended in and washed with methanol to obtain an intermediate 4D. A yield of the intermediate was 7.98 g and a yield rate thereof was 86%.

(4-5) Synthesis of Compound BD-4

[Formula 208]

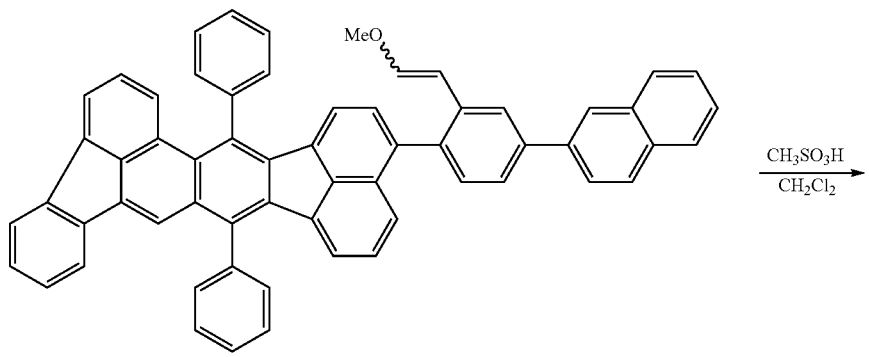

Intermediate 4D

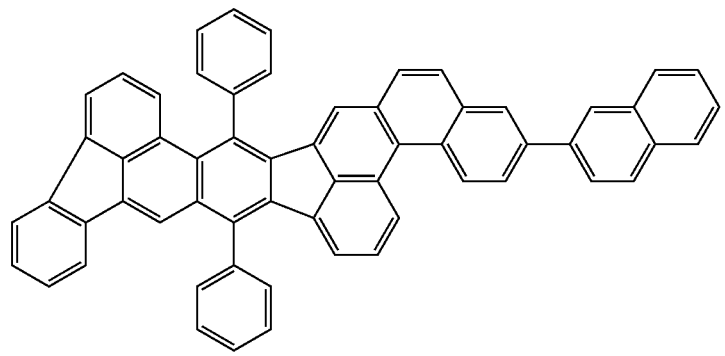

BD-4

To a three-necked flask, 7.98 g (10.1 mmol) of the intermediate 4D and 100 mL of dichloromethane were added. Subsequently, 0.97 g (10.1 mmol) of methane sulfonic acid was dropped in the flask and was stirred for 0.5 hour. After sodium hydrogen carbonate aqueous solution was added to the flask to stop a reaction, dichloromethane was used for extraction. The extracted organic layer was condensed under reduced pressure. The obtained residue was refined by silica-gel column chromatography. After the refinement, the obtained solid was suspended in and washed with methanol to obtain a target substance (compound BD-4) in a form of a yellow solid. A yield of the compound was 4.0 g and a yield rate thereof was 52%. A result of FD-MS (Field Desorption Mass Spectrometry) analysis showed m/e=754 relative to a molecular weight of 754. It should be noted that BD-4 was a mixture of BD-4a and BD-4b, which was derived from that the starting material (SM-1) was the isomer mixture (mixture of SM-1a and SM-1b). In a reaction formula of Synthetic Example 4, the representative structure of "SM-1" was shown only by the structure of SM-1a and a representative structure of "BD-4" was shown only by a structure of BD-4a. A representative structure of each of the intermediates 4A, 4B, 4C and 4D was also shown only by the structure of the intermediate obtained from SM-1a.

Synthesis Example 5: Synthesis of Compound BD-5

A compound BD-5 was obtained in the same manner as in Synthesis Example 4 except that 2,6-dimethylphenylboronic acid was used in place of naphthalene-2-ylboronic acid used at (4-1) Synthesis of Intermediate 4A in Synthesis Example 4: Synthesis of Compound BD-4. A result of FD-MS (Field Desorption Mass Spectrometry) analysis showed m/e=732 relative to a molecular weight of 732. It should be noted that BD-5 was a mixture of BD-5a and BD-5b, which was derived from that the starting material (SM-1) was the isomer mixture (mixture of SM-1a and SM-1b).

[Formula 209]

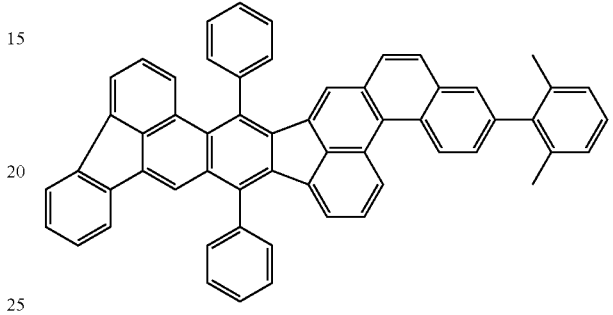

BD-5

Synthesis Example 6: Synthesis of Compound BD-6

(6-1) Synthesis of Intermediate 6A

[Formula 210]

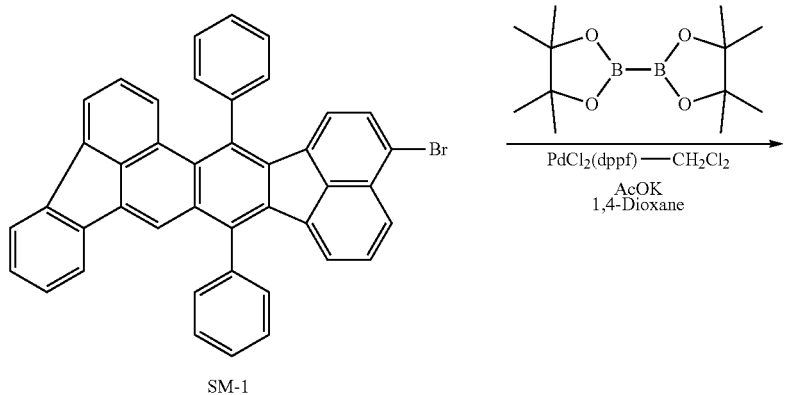

SM-1

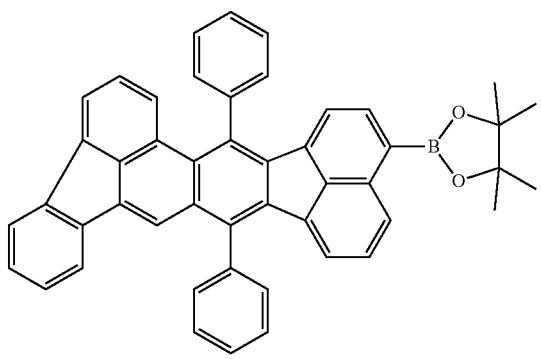

Intermediate 6A

To a three-necked flask, under argon atmosphere, 5.00 g (8.23 mmol) of the starting material (SM-1: isomer mixture), 4.18 g (16.5 mmol) of bis(pinacolato)diboron, 0.20 g (0.247 mmol) of PdCl$_2$(dppf)/CH$_2$Cl$_2$, and 1.62 g (16.5 mmol) of potassium acetate were added and subsequently 50 mL of 1,4-dioxane was added. The obtained mixture solution was heated with stirring at 100 degrees C. for four hours. After the mixture solution was returned to the room temperature, the mixture solution was added with silica gel, filtrated, and washed with toluene. After the solvent was distilled away under reduced pressure, the obtained residue was refined by silica-gel column chromatography (the mobile phase; hexane:toluene), so that an intermediate 6A was obtained. A yield of the intermediate was 3.66 g and a yield rate thereof was 63%.

(6-2) Synthesis of Intermediate 6B ture solution was heated with stirring at 80 degrees C. for 14 hours. After the mixture solution was returned to the room temperature, the mixture solution was filtrated and washed with toluene. After the solvent was distilled away under reduced pressure, the obtained residue was refined by silica-gel column chromatography (the mobile phase; hexane: toluene), so that an intermediate 6B was obtained. A yield of the intermediate was 1.64 g and a yield rate thereof was 44%.

(6-3) Synthesis of Compound BD-6

A compound BD-6 was obtained in the same manner as in Synthesis Example 2 except that the intermediate 6B was used in place of the intermediate 2A used at (2-2) Synthesis of Intermediate 2B in Synthesis Example 2: Synthesis of

[Formula 211]

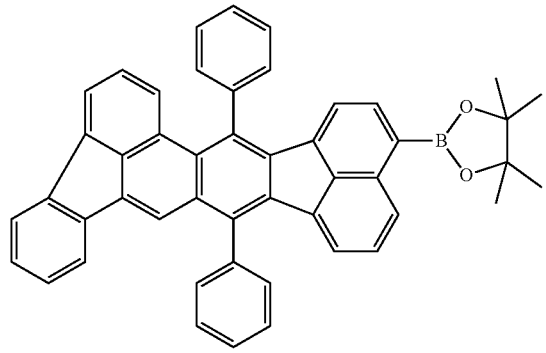

Intermediate 6A

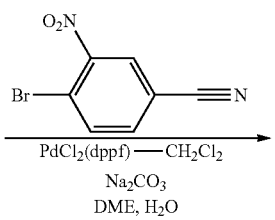

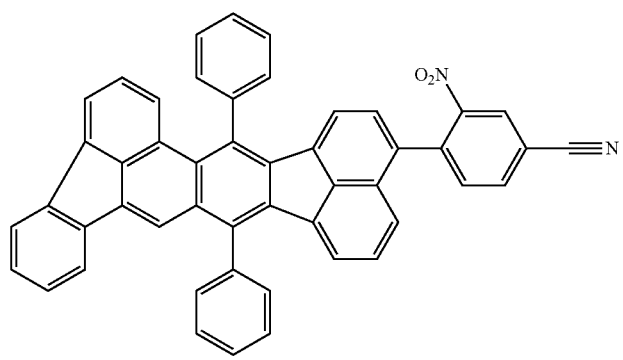

Intermediate 6B

To a three-necked flask, under argon atmosphere, 1.37 g (6.05 mmol) of 4-bromo-3-nitrobenzonitrile, 3.60 g (5.50 mmol) of the intermediate 6A, and 40 mL of DME were added, subsequently 0.090 g (0.11 mmol) of PdCl$_2$(dppf)/CH$_2$Cl$_2$ was added, and subsequently 3.85 mL of 2M sodium carbonate aqueous solution was added. The obtained mix- Compound BD-2. A result of FD-MS (Field Desorption Mass Spectrometry) analysis showed m/e=718 relative to a molecular weight of 718. It should be noted that BD-6 was a mixture of BD-6a and BD-6b, which was derived from that the starting material (SM-1) was the isomer mixture (mixture of SM-1a and SM-1b).

[Formula 212]

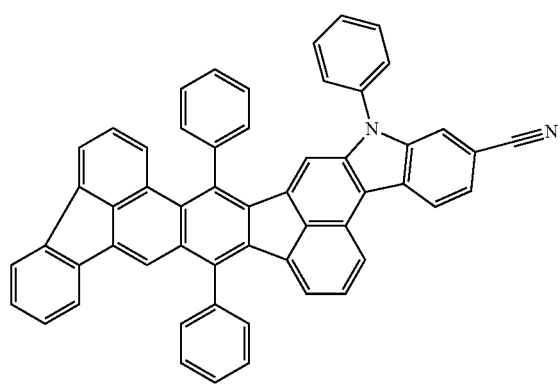

BD-6

Synthesis Example 7: Synthesis of Compound BD-7

(7-1) Synthesis of Intermediate 7A

[Formula 213]

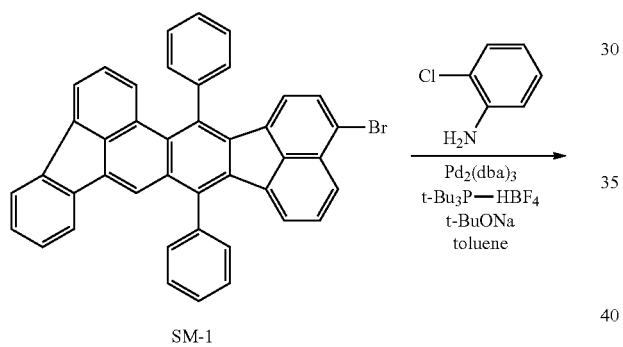

To a three-necked flask, under argon atmosphere, 3.00 g (4.94 mmol) of the starting material (SM-1: isomer mixture), 0.63 g (4.94 mmol) of 2-chloroaniline, 0.090 g (0.099 mmol) of $Pd_2(dba)_3$, 0.12 g (0.395 mmol) of t-$Bu_3$P—$HBF_4$, and 0.66 g (0.41 mmol) of t-BuONa were added, and subsequently 30 mL of toluene was added. The obtained mixture solution was heated with stirring at 110 degrees C. for six hours. After the mixture solution was returned to the room temperature, the mixture solution was added with silica gel, filtrated, and washed with toluene. After the solvent was distilled away under reduced pressure, the obtained residue was refined by silica-gel column chromatography (the mobile phase; hexane:toluene), so that an intermediate 7A was obtained. A yield of the intermediate was 1.34 g and a yield rate thereof was 97%.

(7-2) Synthesis of Intermediate 7B

[Formula 214]

To a three-necked flask, under argon atmosphere, 0.30 g (0.46 mmol) of the intermediate 7A, 10 mg (0.046 mmol) of palladium acetate, 0.034 mg (0.14 mmol) of $PCH_3(t$-$Bu)_2$-$HBF_4$, and 0.095 g (0.69 mmol) of potassium carbonate were added and subsequently 10 mL of dimethylacetamide (DMA) was added. The obtained mixture solution was heated with stirring at 160 degrees C. for 11 hours. After the mixture solution was returned to the room temperature, water was added to the mixture solution. The obtained mixture solution was subjected to extraction with a mixture solution of toluene and hexane. After the solvent was distilled away under reduced pressure, the obtained residue was refined by silica-gel column chromatography (the mobile phase; hexane:toluene), so that an intermediate 7B was obtained. A yield of the intermediate was 0.18 g and a yield rate thereof was 64%.

(7-3) Synthesis of Compound BD-7

Synthesis Example 8: Synthesis of Compound BD-8

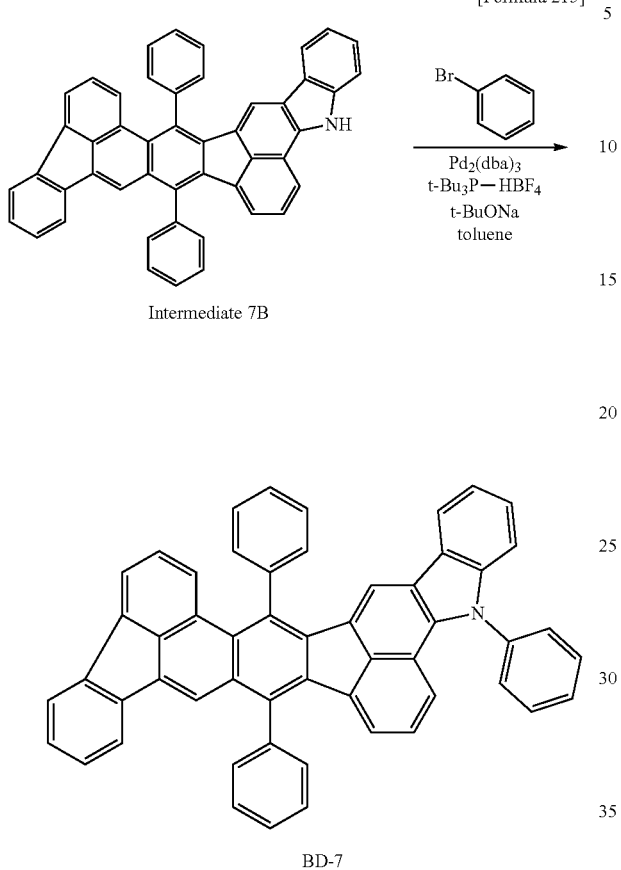

To a three-necked flask, under argon atmosphere, 0.18 g (0.29 mmol) of the intermediate 7B, 0.091 g (0.58 mmol) of bromobenzene, 5.3 mg (5.8 μmol) of Pd$_2$(dba)$_5$, 6.8 mg (0.023 mmol) of t-Bu$_3$P—HBF$_4$, and 0.039 g (0.41 mmol) of t-BuONa were added and subsequently 30 mL of toluene was added. The obtained mixture solution was heated with stirring at 110 degrees C. for 15 hours. After the mixture solution was returned to the room temperature, the mixture solution was added with silica gel, filtrated, and washed with toluene. After the solvent was distilled away under reduced pressure, the obtained residue was refined by silica-gel column chromatography (the mobile phase; hexane:toluene), so that a target substance (a compound BD-7) was obtained in a form of a yellow solid. A yield of the compound was 0.18 g and a yield rate thereof was 86%. A result of FD-MS (Field Desorption Mass Spectrometry) analysis showed m/e=693 relative to a molecular weight of 693. It should be noted that BD-7 was a mixture of BD-7a and BD-7b, which was derived from that the starting material (SM-1) was the isomer mixture (mixture of SM-1a and SM-1b). In a reaction formula of Synthetic Example 7, the representative structure of "SM-1" was shown only by the structure of SM-1a and a representative structure of "BD-7" was shown only by a structure of BD-7a. A representative structure of each of the intermediates 7A and 7B was also shown only by the structure of the intermediate obtained from SM-1a.

To a three-necked flask, under argon atmosphere, 1.00 g (1.65 mmol) of the starting material (SM-1: isomer mixture), 0.46 g (1.65 mmol) of 2-(2-bromophenyl)phenylboronic acid, 30 mg (0.033 mmol) of Pd$_2$(dba)$_3$, 49 mg (0.13 mmol) of tricyclohexylphosphine tetrafluoroborate, and 0.70 g (3.30 mmol) of potassium phosphate were added, and subsequently 15 mL of dimethylacetamide (DMA) was added. The obtained mixture solution was heated with stirring at 150 degrees C. for three hours. After the mixture solution was returned to the room temperature, the mixture solution was added with silica gel, filtrated, and washed with toluene. After the solvent was distilled away under reduced pressure, the obtained residue was refined by silica-gel column chromatography (the mobile phase, hexane:toluene), so that a target substance (a compound BD-8) was obtained in a form of a yellow solid. A yield of the compound was 0.22 g and a yield rate thereof was 20%. A result of FD-MS (Field Desorption Mass Spectrometry) analysis showed m/e=678 relative to a molecular weight of 678. It should be noted that BD-8 was a mixture of BD-8a and BD-8b, which was derived from that the starting material (SM-1) was the isomer mixture (mixture of SM-1a and SM-1b). In a reaction formula of Synthetic Example 8, the representative structure of "SM-1" was shown only by the structure of SM-1a and a representative structure of "BD-8" was shown only by a structure of BD-8a.

Synthesis Example 9: Synthesis of Compound TADF-1

(9-1) Synthesis of Intermediate A

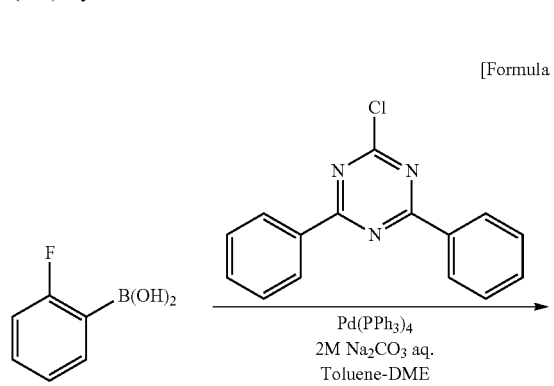

[Formula 217]

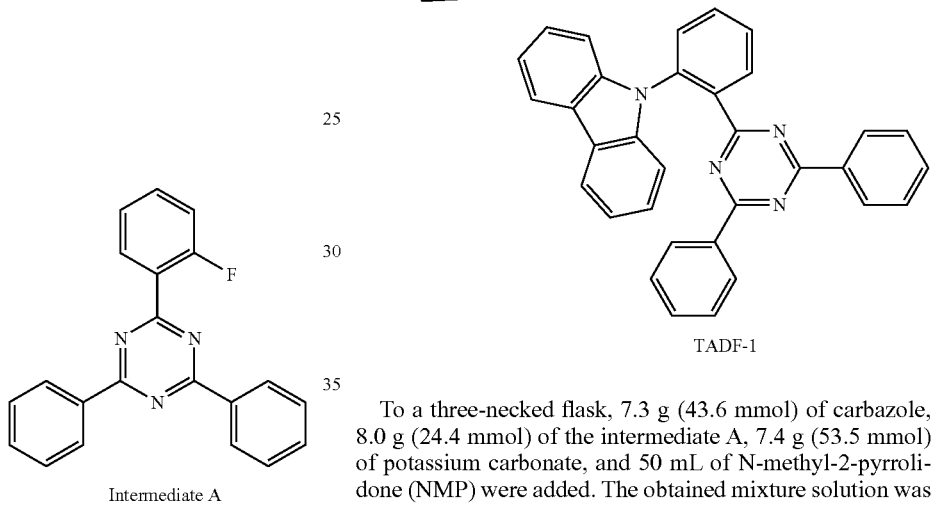

To a three-necked flask, 7.0 g (50 mmol) of 2-fluorophenylboronic acid, 13.4 g (50 mmol) of 2-chloro-4,6-diphenyltriazine, 62.5 mL of 2M sodium carbonate aqueous solution, 100 mL of 1,2-dimethoxyethane (DME) and 100 mL of toluene were added. Subsequently, 1.73 g (1.5 mmol) of tetrakis(triphenylphosphine)palladium was further added to the flask. The obtained mixture solution was heated for reflux with stirring for eight hours under an argon gas atmosphere. After the mixture solution was heated for reflux with stirring, an organic layer was separated from the mixture solution. The separated organic layer was condensed under reduced pressure. The obtained residue was refined by silica-gel column chromatography. A toluene solvent was used as an eluent solvent. After the refinement, the obtained solid was suspended in and washed with methanol to obtain an intermediate A in a form of a white solid. A yield of the intermediate was 11.6 g and a yield rate thereof was 71%.

(9-2) Synthesis of Compound TADF-1

[Formula 218]

To a three-necked flask, 7.3 g (43.6 mmol) of carbazole, 8.0 g (24.4 mmol) of the intermediate A, 7.4 g (53.5 mmol) of potassium carbonate, and 50 mL of N-methyl-2-pyrrolidone (NMP) were added. The obtained mixture solution was heated with stirring at 150 degrees C. for 20 hours under argon atmosphere. After heated with stirring, the obtained reaction solution was poured into 200 mL of water. The deposited solid was filtrated. Subsequently, the solid was repeatedly suspended in and washed with ethanol to obtain a target substance (compound TADF-1) in a form of a white solid. A yield of the compound was 6.3 g and a yield rate thereof was 54%. A result of FD-MS analysis showed m/e=474 relative to a molecular weight of 474.

Evaluation of Compounds

A method of measuring characteristics of the compounds is shown below.

Delayed Fluorescence

Delayed fluorescence characteristics were checked by measuring transient photoluminescence (PL) using a device shown in FIG. 2. A sample was prepared by co-depositing the compounds TADF-1 and TH-2 on a quartz substrate at a ratio of the compound TADF-1 being 12 mass % to form a 100-nm-thick thin film. There are two types of emission: Prompt emission observed promptly when the excited state is achieved by exciting the compound TADF-1 with a pulse beam (i.e., a beam emitted from a pulse laser) having a wavelength absorbable by the compound TADF-1, and Delay emission observed not promptly when but after the excited state is achieved. The delayed fluorescence in Examples means that the amount of Delay emission is 5% or more relative to the amount of Prompt emission. Specifically, provided that the amount of Prompt emission is denoted by $X_P$ and the amount of Delay emission is denoted by $X_D$, a value of $X_D/X_P$ is 0.05 or more.

It was found that the amount of Delay Emission was 5% or more relative to the amount of Prompt Emission in the compound TADF-1. Specifically, it was found that the value of $X_D/X_P$ was 0.05 or more in the compound TADF-1.

It was also found that the value of $X_D/X_P$ was 0.05 or more in a compound TADF-2.

The amount of Prompt emission and the amount of Delay emission can be obtained according to the method as described in "Nature 492, 234-238, 2012." A device used for calculating the amount of Prompt emission and the amount of Delay emission is not limited to the device described in FIG. 2 and Cited Literatures.

Singlet Energy $S_1$

A singlet energy $S_1$ of each of the compound TADF-1, compound TADF-2, compound A-1, compound BD-1, compound BD-2, compound BD-3, compound BD-4, compound BD-5, compound BD-6, compound BD-7, and compound BD-8 was measured according to the above-described solution method.

The singlet energy $S_1$ of the compound TADF-1 was 2.90 eV.

The singlet energy $S_1$ of the compound TADF-2 was 2.90 eV.

The singlet energy $S_1$ of the compound A-1 was 3.53 eV.
The singlet energy $S_1$ of the compound BD-1 was 2.75 eV.
The singlet energy $S_1$ of the compound BD-2 was 2.64 eV.
The singlet energy $S_1$ of the compound BD-3 was 2.64 eV.
The singlet energy $S_1$ of the compound BD-4 was 2.70 eV.
The singlet energy $S_1$ of the compound BD-5 was 2.74 eV.
The singlet energy $S_1$ of the compound BD-6 was 2.66 eV.
The singlet energy $S_1$ of the compound BD-7 was 2.59 eV.
The singlet energy $S_1$ of the compound BD-8 was 2.74 eV.

A singlet energy of a compound DPEPO is 4.0 eV as described in a literature (APPLIED PHYSICS LETTERS 101, 093306 (2012)).

Main Peak Wavelength of Compounds

Each of the measurement target compounds was dissolved in toluene at a concentration ranging from $10^{-6}$ mol/liter to $10^{-5}$ mol/liter to prepare a toluene solution. An emission spectrum of each of the measurement target compounds in the respective toluene solutions was measured. A peak wavelength of the emission spectrum exhibiting the maximum luminous intensity was defined as a main peak wavelength.

The main peak wavelength of the compound BD-1 was 448 nm.
The main peak wavelength of the compound BD-2 was 462 nm.
The main peak wavelength of the compound BD-3 was 460 nm.
The main peak wavelength of the compound BD-4 was 457 nm.
The main peak wavelength of the compound BD-5 was 451 nm.
The main peak wavelength of the compound BD-6 was 461 nm.
The main peak wavelength of the compound BD-7 was 475 nm.
The main peak wavelength of the compound BD-8 was 450 nm.

An absorption spectrum was measured. Based on the measurement result of the absorption spectrum, a molar absorbance coefficient E and Stokes shift ss were calculated.

Molar Absorbance Coefficient ε

The molar absorbance coefficient ε was calculated by dividing an absorption intensity of an absorption peak located closest to the long-wavelength region in the absorption spectrum by a solution concentration. A unit of the molar absorbance coefficient ε was defined as L/(mol·cm). The absorption peak located closest to the long-wavelength region is defined as a peak appearing at a position closest to the long-wavelength region among peaks appearing in a wavelength range from 350 nm to 500 nm and having an absorption intensity that is at least one tenth of an absorption intensity of the maximum absorption peak.

Absorption Spectrum

An absorption spectrum was measured according to a method described below.

A 20-μmol/L toluene solution of each of the compounds (measurement target) was prepared and put in a quartz cell. An absorption spectrum (ordinate axis: absorption intensity, abscissa axis: wavelength) of each of the samples was measured at a normal temperature (300K). In Examples, the absorption spectrum was measured using a spectrophotometer manufactured by Hitachi, Ltd. (device name: U3310). It should be noted that the absorption spectrum measuring device may be different from the above device.

Stokes Shift ss

The Stokes shift ss was calculated by subtracting the absorption peak wavelength, which was used for calculating the molar absorbance coefficient of the absorption spectrum, from the main peak wavelength of the emission spectrum. A unit of the Stokes shift ss was defined as nm.

Table 2 shows the molar absorbance coefficient, the main peak wavelength of the emission spectrum, the absorption peak wavelength, and the stokes shift of each of the compounds.

TABLE 2

| Compound | Molar Absorbance Coefficient [L/(mol·cm)] | Main Peak Wavelength of Emission Spectrum [nm] | Absorption Peak Wavelength [nm] | Stokes Shift [nm] |
|---|---|---|---|---|
| BD-1 | 69400 | 448 | 442 | 6 |
| BD-2 | 53500 | 462 | 454 | 8 |
| BD-3 | 59600 | 460 | 454 | 6 |
| BD-4 | 88600 | 457 | 448 | 9 |
| BD-5 | 69500 | 451 | 444 | 7 |
| BD-6 | 71600 | 461 | 455 | 6 |
| BD-7 | 69500 | 475 | 462 | 13 |
| BD-8 | 42500 | 450 | 441 | 9 |

Manufacturing 1 of Organic EL Device

Organic EL devices were manufactured and evaluated as follows.

Example 1-1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, a compound HI was vapor-deposited on a surface of the glass substrate where the transparent electrode line was provided in a manner to cover the transparent electrode, thereby forming a 5-nm-thick hole injecting layer.

Next, the compound HT1 was vapor-deposited on the hole injecting layer to form an 80-nm-thick first hole transporting layer on the HI film.

Next, a compound HT2 was vapor-deposited on the first hole transporting layer to form a 10-nm-thick second hole transporting layer.

Further, a compound mCP was vapor-deposited on the second hole transporting layer to form a 5-nm-thick third hole transporting layer.

Further, the compound TADF-1 (the first compound), the compound BD-1 (the second compound) and a compound DPEPO (the third compound) were co-deposited to form a 25-nm-thick emitting layer. A concentration of the compound TADF-1 was defined as 24 mass %, a concentration of the compound BD-1 was defined as 1 mass %, and a concentration of the compound DPEPO was defined as 75 mass % in the emitting layer.

Next, a compound ET-1 was vapor-deposited on the emitting layer to form a 5-nm-thick first electron transporting layer.

A compound ET-2 was then vapor-deposited on the first electron transporting layer to form a 20-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 1-1 is roughly shown as follows.

ITO(130)/HI(5)/HT1(80)/HT2(10)/mCP(5)/DPEPO:TADF-1:BD-1(25, 75%:24%:1%)/ET-1(5)/ET-2 (20)/LiF(1)/Al(80)

Numerals in parentheses represent a film thickness (unit: nm). The numerals represented by percentage in the same parentheses indicate a ratio (mass %) of the first compound, the second compound and the third compound in the emitting layer.

Example 1-2

An organic EL device of Example 1-2 was prepared in the same manner as the organic EL device of Example 1-1 except that a compound BD-2 was used in place of the compound BD-1 in the emitting layer of Example 1-1.

A device arrangement of the organic EL device of Example 1-2 is roughly shown as follows.

ITO(130)/HI(5)/HT1(80)/HT2(10)/mCP(5)/DPEPO:TADF-1:BD-2(25, 75%:24%:1%)/ET-1(5)/ET-2(20)/LiF(1)/Al(80)

Example 1-3

An organic EL device of Example 1-3 was prepared in the same manner as the organic EL device of Example 1-1 except that a compound BD-3 was used in place of the compound BD-1 in the emitting layer of Example 1-1.

A device arrangement of the organic EL device of Example 1-3 is roughly shown as follows.

ITO(130)/HI(5)/HT1(80)/HT2(10)/mCP(5)/DPEPO:TADF-1:BD-3(25, 75%:24%:1%)/ET-1(5)/ET-2(20)/LiF(1)/Al(80)

Example 1-4

An organic EL device of Example 1-4 was prepared in the same manner as the organic EL device of Example 1-1 except that a compound BD-4 was used in place of the compound BD-1 in the emitting layer of Example 1-1.

A device arrangement of the organic EL device of Example 1-4 is roughly shown as follows.

ITO(130)/HI(5)/HT1(80)/HT2(10)/mCP(5)/DPEPO:TADF-1:BD-4(25, 75%:24%:1%)/ET-1(5)/ET-2(20)/LiF(1)/Al(80)

Example 1-5

An organic EL device of Example 1-5 was prepared in the same manner as the organic EL device of Example 1-1 except that a compound BD-6 was used in place of the compound BD-1 in the emitting layer of Example 1-1.

A device arrangement of the organic EL device of Example 1-5 is roughly shown as follows.

ITO(130)/HI(5)/HT1(80)/HT2(10)/mCP(5)/DPEPO:TADF-1:BD-6(25, 75%:24%:1%)/ET-1(5)/ET-2(20)/LiF(1)/Al(80)

Comparative 1-1

An organic EL device of Comparative 1-1 was prepared in the same manner as the organic EL device of Example 1-1 except that a compound TBPe was used in place of the compound BD-1 in the emitting layer of Example 1-1.

A device arrangement of the organic EL device of Comparative 1-1 is roughly shown as follows.

ITO(130)/HI(5)/HT1(80)/HT2(10)/mCP(5)/DPEPO:TADF-1:TBPe(25, 75%:24%:1%)/ET-1(5)/ET-2(20)/LiF(1)/Al(80)

Comparative 1-2

An organic EL device of Comparative 1-2 was prepared in the same manner as the organic EL device of Example 1-1 except that a compound ref-1 was used in place of the compound BD-1 in the emitting layer of Example 1-1. A device arrangement of the organic EL device of Comparative 1-2 is roughly shown as follows.

ITO(130)/HI(5)/HT1(80)/HT2(10)/mCP(5)/DPEPO:TADF-1:ref-1(25, 75%:24%:1%)/ET-1(5)/ET-2(20)/LiF(1)/Al(80)

Comparative 1-3

An organic EL device of Comparative 1-3 was prepared in the same manner as the organic EL device of Example 1-1 except that a compound ref-2 was used in place of the compound BD-1 in the emitting layer of Example 1-1.

A device arrangement of the organic EL device of Comparative 1-3 is roughly shown as follows.

ITO(130)/HI(5)/HT1(80)/HT2(10)/mCP(5)/DPEPO:TADF-1:ref-2(25, 75%:24%:1%)/ET-1(5)/ET-2(20)/LiF(1)/Al(80)

Evaluation 1 of Organic EL Devices

The prepared organic EL devices of Examples 1-1 to 1-5 and Comparatives 1-1 to 1-3 were evaluated as follows. The evaluation results are shown in Table 3.

External Quantum Efficiency EQE and Main Peak Wavelength $\lambda_p$

Voltage was applied on each of the organic EL devices such that the current density was 0.1 mA/cm$^2$, where spectral radiance spectrum was measured by a spectroradiometer (CS-1000 manufactured by Konica Minolta, Inc.).

The external quantum efficiency EQE (unit: %) was calculated based on the obtained spectral-radiance spectra, assuming that the spectra were provided under a Lambertian radiation.

The main peak wavelength $\lambda_p$ (unit: nm) was calculated based on the obtained spectral-radiance spectra.

TABLE 3

|  | Second Compound Compound Name | EQE [%] | $\lambda p$ [nm] |
|---|---|---|---|
| Example 1-1 | BD-1 | 12.9 | 454 |
| Example 1-2 | BD-2 | 11.6 | 474 |
| Example 1-3 | BD-3 | 11.1 | 472 |
| Example 1-4 | BD-4 | 13.7 | 463 |
| Example 1-5 | BD-6 | 12.2 | 468 |
| Comparative 1-1 | TBPe | 8.7 | 464 |
| Comparative 1-2 | ref-1 | 9.5 | 446 |
| Comparative 1-3 | ref-2 | 9.5 | 446 |

The organic EL devices of Examples 1-1 to 1-5, in each of which the emitting layer contained the delayed fluorescent first compound and the second compound represented by the formula (2), emitted light in a blue wavelength region at a higher efficiency than the organic EL devices of Comparatives 1-1 to 1-3.

Manufacturing 2 of Organic EL Device

Organic EL devices were manufactured and evaluated as follows.

Example 2-1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, the compound HI was vapor-deposited on a surface of the glass substrate where the transparent electrode line was provided in a manner to cover the transparent electrode, thereby forming a 5-nm-thick hole injecting layer.

Next, the compound HT1 was vapor-deposited on the hole injecting layer to form an 80-nm-thick first hole transporting layer on the HI film.

Next, the compound HT2 was vapor-deposited on the first hole transporting layer to form a 10-nm-thick second hole transporting layer.

Further, the compound mCP was vapor-deposited on the second hole transporting layer to form a 5-nm-thick third hole transporting layer.

Further, the compound TADF-2 (the first compound), the compound BD-2 (the second compound) and a compound A-1 (the third compound) were co-deposited on the third hole transporting layer to form a 25-nm-thick emitting layer. A concentration of the compound TADF-2 was defined as 24 mass %, a concentration of the compound BD-2 was defined as 1 mass %, and a concentration of the compound A-1 was defined 75 mass % in the emitting layer.

Next, the compound ET-1 was vapor-deposited on the emitting layer to form a 5-nm-thick first electron transporting layer.

The compound ET-2 was then vapor-deposited on the first electron transporting layer to form a 20-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 2-1 is roughly shown as follows.

ITO(130)/HI(5)/HT1(80)/HT2(10)/mCP(5)/A-1:TADF-2:BD-2 (25, 75%:24%:1%)/ET-1(5)/ET-2(20)/LiF(1)/Al (80)

Numerals in parentheses represent a film thickness (unit: nm). The numerals represented by percentage in the same parentheses indicate a ratio (mass %) of the first compound, the second compound and the third compound in the emitting layer.

Example 2-2

An organic EL device of Example 2-2 was prepared in the same manner as the organic EL device of Example 2-1 except that the compound BD-3 was used in place of the compound BD-2 in the emitting layer of Example 2-1.

A device arrangement of the organic EL device of Example 2-2 is roughly shown as follows.

ITO(130)/HI(5)/HT1(80)/HT2(10)/mCP(5)/A-1:TADF-2:BD-3 (25, 75%:24%:1%)/ET-1(5)/ET-2(20)/LiF(1)/Al (80)

Example 2-3

An organic EL device of Example 2-3 was prepared in the same manner as the organic EL device of Example 2-1 except that the compound BD-4 was used in place of the compound BD-2 in the emitting layer of Example 2-1.

A device arrangement of the organic EL device of Example 2-3 is roughly shown as follows.

ITO(130)/HI(5)/HT1(80)/HT2(10)/mCP(5)/A-1:TADF-2:BD-4 (25, 75%:24%:1%)/ET-1(5)/ET-2(20)/LiF(1)/Al (80)

Example 2-4

An organic EL device of Example 2-4 was prepared in the same manner as the organic EL device of Example 2-1 except that the compound BD-6 was used in place of the compound BD-2 in the emitting layer of Example 2-1.

A device arrangement of the organic EL device of Example 2-4 is roughly shown as follows.

ITO(130)/HI(5)/HT1(80)/HT2(10)/mCP(5)/A-1:TADF-2:BD-6 (25, 75%:24%:1%)/ET-1(5)/ET-2(20)/LiF(1)/Al (80)

Evaluation 2 of Organic EL Devices

The prepared organic EL devices of Examples 2-1 to 2-4 were evaluated in the same manner as the organic EL device of Example 1-1. The evaluation results are shown in Table 4.

TABLE 4

|  | Second Compound Compound Name | EQE [%] | λp [nm] |
|---|---|---|---|
| Example 2-1 | BD-2 | 15.5 | 470 |
| Example 2-2 | BD-3 | 15.2 | 470 |
| Example 2-3 | BD-4 | 16.4 | 462 |
| Example 2-4 | BD-6 | 12.2 | 468 |

The organic EL devices of Examples 2-1 to 2-4, in each of which the emitting layer contained the delayed fluorescent first compound and the second compound represented by the formula (2), emitted light in a blue wavelength region at a high efficiency in the same manner as in the organic EL devices of Examples 1-1 to 1-5.

Manufacturing 3 of Organic EL Device

Organic EL devices were manufactured and evaluated as follows.

Example 3-1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, a compound HI2 was vapor-deposited on a surface of the glass substrate where the transparent electrode line was provided in a manner to cover the transparent electrode, thereby forming a 5-nm-thick hole injecting layer.

Next, a compound HT3 was vapor-deposited on the hole injecting layer to form an 80-nm-thick first hole transporting layer on the HI2 film.

Next, a compound HT4 was vapor-deposited on the first hole transporting layer to form a 10-nm-thick second hole transporting layer.

Further, on the second hole transporting layer, a compound BH and the compound BD-4 (dopant material) obtained in Synthesis Example 4 were co-deposited to form a 25-nm-thick emitting layer. A concentration of the compound BD-4 (dopant material) in the emitting layer was set at 1 mass % and a concentration of the compound BH in the emitting layer was set at 99 mass %.

Next, a compound ET-3 was vapor-deposited on the emitting layer to form a 10-nm-thick first electron transporting layer.

The compound ET-2 was then vapor-deposited on the first electron transporting layer to form a 15-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 3-1 is roughly shown as follows.

ITO(130)/HI2(5)/HT3(80)/HT4(10)/BH:BD-4 (25, 99%: 1%)/ET-3(10)/ET-2(15)/LiF(1)/Al(80)

Numerals in parentheses represent a film thickness (unit: nm). The numerals in the form of percentage in parentheses indicate ratios (mass %) of the compounds BH and BD-4 in the emitting layer.

Comparative 3-1

The organic EL device of Comparative 3-1 was prepared in the same manner as the organic EL device of Example 3-1 except that the compound TBPe was used in place of the compound BD-4 in the emitting layer of Example 3-1. A device arrangement of the organic EL device of Comparative 3-1 is roughly shown as follows.

ITO(130)/HI2(5)/HT3(80)/HT4(10)/BH:TBPe (25, 99%: 1%)/ET-3(10)/ET-2(15)/LiF(1)/Al(80)

Evaluation 3 of Organic EL Devices

The prepared organic EL devices of Example 3-1 and Comparative 3-1 were evaluated in the same manner as the organic EL device of Example 1-1. The evaluation results are shown in Table 5.

TABLE 5

|  | Second Compound Compound Name | EQE [%] | λp [nm] |
|---|---|---|---|
| Example 3-1 | BD-4 | 6.9 | 463 |
| Comparative 3-1 | TBPe | 5.4 | 463 |

The organic EL device of Example 3-1, in which the emitting layer contained the compound BH represented by the formula (15) and the compound BD-4 represented by the formula (2), emitted light in a blue wavelength region at a higher efficiency than the organic EL device of Comparative 3-1.

The invention claimed is:
1. A compound represented by a formula (2) below,

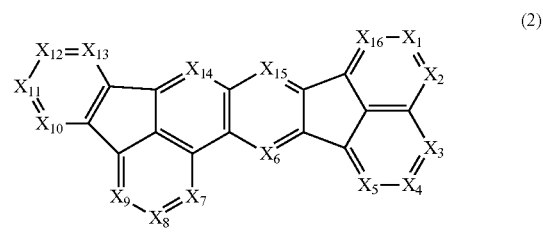

where: $X_1$ to $X_5$, $X_7$ to $X_{13}$, and $X_{16}$ each independently represent $CR_x$ or a carbon atom to be bonded to a structure represented by a formula (2a) or (2b) below;
$X_6$, $X_{14}$, and $X_{15}$ each independently represent $CR_x$;
$R_x$ each independently represents a hydrogen atom or a substituent;
$R_x$ as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom;

a plurality of $R_x$ are mutually the same or different;

when a plurality of ones of $X_1$ to $X_{16}$ are $CR_x$ and $R_x$ is a substituent, a plurality of $R_x$ as the substituents are not bonded to each other; and at least one pair of a pair of $X_1$ and $X_2$, a pair of $X_2$ and $X_3$, a pair of $X_3$ and $X_4$, a pair of $X_4$ and $X_5$, a pair of $X_7$ and $X_8$, a pair of $X_8$ and $X_9$, a pair of $X_{10}$ and $X_{11}$, a pair of $X_{11}$ and $X_{12}$, a pair of $X_{12}$ and $X_{13}$, and a pair of $X_{16}$ and $X_1$ are carbon atoms to be bonded to the structure represented by the formula (2a) or (2b) below,

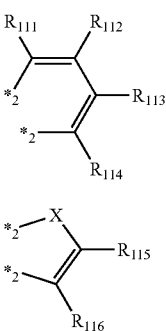

in the formula (2a):
  *2 represent bonding positions to carbon atoms at one pair of the pair of $X_1$ and $X_2$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2);
  $R_{111}$ to $R_{114}$ each independently represent a hydrogen atom or a substituent;
  $R_{111}$ to $R_{114}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and at least one pair of a pair of $R_{111}$ and $R_{112}$, a pair of $R_{112}$ and $R_{113}$, and a pair of $R_{113}$ and $R_{114}$ are substituents, and the substituents are bonded to each other to form a ring, in the formula (2b):
  *2 represent bonding positions to carbon atoms at one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2);
  $R_{115}$ and $R_{116}$ each independently represent a hydrogen atom or a substituent;
  $R_{115}$ and $R_{116}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom;
  $R_{115}$ and $R_{116}$ as the substituents are bonded to each other to further form a ring, or are not bonded to each other;
  X is selected from the group consisting of an oxygen atom, a sulfur atom, $CR_{117}R_{118}$, $SiR_{119}R_{120}$ and $NR_{121}$;
  $R_{117}$ to $R_{121}$ each independently represent a hydrogen atom or a substituent;
  $R_{117}$ to $R_{121}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom;
  $R_{117}$ and $R_{118}$ as the substituents are bonded to each other to further form a ring, or are not bonded to each other; and R$_{119}$ and R$_{120}$ as the substituents are bonded to each other to further form a ring, or are not bonded to each other.

2. The compound according to claim 1, wherein at least one pair of the pair of X$_1$ and X$_2$ and the pair of X$_3$ and X$_4$ in the formula (2) are carbon atoms to be bonded to the structure represented by the formula (2a).

3. The compound according to claim 1, wherein the structure represented by the formula (2a) is a structure represented by a formula (2a-1),

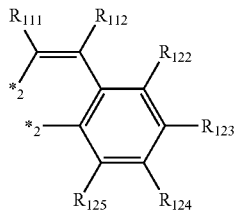

(2a-1)

where: *2 represents the same as *2 in the formula (2a); R$_{111}$, R$_{112}$ and R$_{122}$ to R$_{125}$ each independently represent a hydrogen atom or a substituent;

R$_{111}$, R$_{112}$ and R$_{122}$ to R$_{125}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of R$_{111}$, R$_{112}$ and R$_{122}$ to R$_{125}$ as the substituents are bonded to each other to further form a ring, or are not bonded to each other.

4. The compound according to claim 3, wherein the compound represented by the formula (2) is represented by a formula (21 A) below,

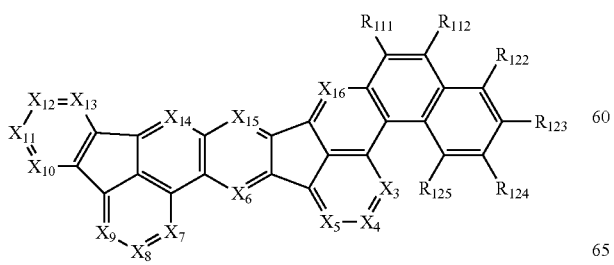

(21A)

where: X$_3$ to X$_{16}$ and R$_x$ respectively represent the same as X$_3$ to X$_{16}$ and R$_x$ in the formula (2), and R$_{111}$, R$_{112}$ and R$_{122}$ to R$_{125}$ respectively represent the same as R$_{111}$, R$_{112}$ and R$_{122}$ to R$_{125}$ in the formula (2a-1).

5. The compound according to claim 3, wherein the compound represented by the formula (2) is represented by a formula (21B) below,

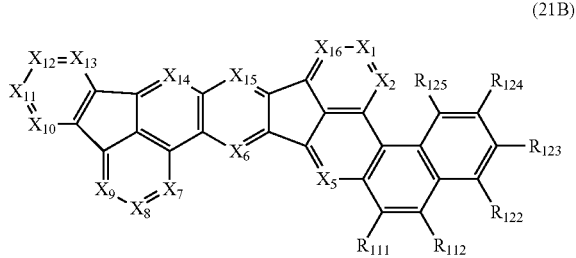

(21B)

where: X$_b$, X$_2$, X$_5$ to X$_{16}$ and R$_x$ respectively represent the same as X$_1$, X$_2$, X$_5$ to X$_{16}$ and R$_x$ in the formula (2), and R$_{111}$, R$_{112}$ and R$_{122}$ to R$_{125}$ respectively represent the same as R$_{111}$, R$_{112}$ and R$_{122}$ to R$_{125}$ in the formula (2a-1).

6. The compound according to claim 1, wherein at least one pair of the pair of X$_1$ and X$_2$, the pair of X$_2$ and X$_3$ and the pair of X$_3$ and X$_4$ in the formula (2) are carbon atoms to be bonded to the structure represented by the formula (2b).

7. The compound according to claim 6, wherein the compound represented by the formula (2) is represented by a formula (25 A) below,

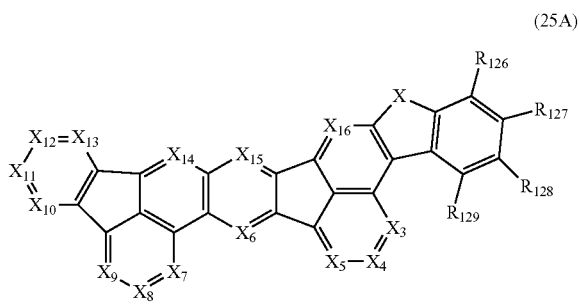

(25A)

where: X$_3$ to X$_{16}$ and R$_x$ respectively represent the same as X$_3$ to X$_{16}$ and R$_x$ in the formula (2);
X represents the same as X in the formula (2b);
R$_{126}$ to R$_{129}$ each independently represent a hydrogen atom or a substituent;
R$_{126}$ to R$_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of $R_{126}$ to $R_{129}$ as the substituents are bonded to each other to further form a ring, or are not bonded to each other.

8. The compound according to claim 6, wherein the compound represented by the formula (2) is represented by a formula (25B) below,

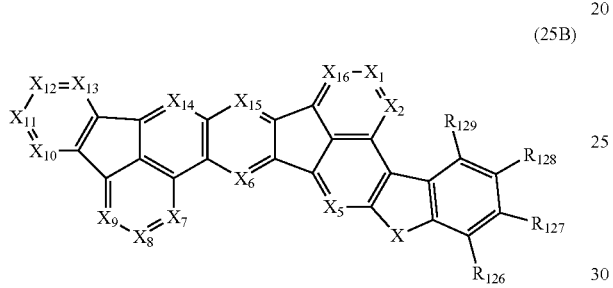

(25B)

where: $X_1$, $X_2$, $X_5$ to $X_{16}$ and $R_x$ respectively represent the same as $X_1$, $X_2$, $X_5$ to $X_{16}$ and $R_x$ in the formula (2);

X represents the same as X in the formula (2b);

$R_{126}$ to $R_{129}$ each independently represent a hydrogen atom or a substituent;

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of $R_{126}$ to $R_{129}$ as the substituents are bonded to each other to further form a ring, or are not bonded to each other.

9. The compound according to claim 6, wherein the compound represented by the formula (2) is represented by a formula (26A) below,

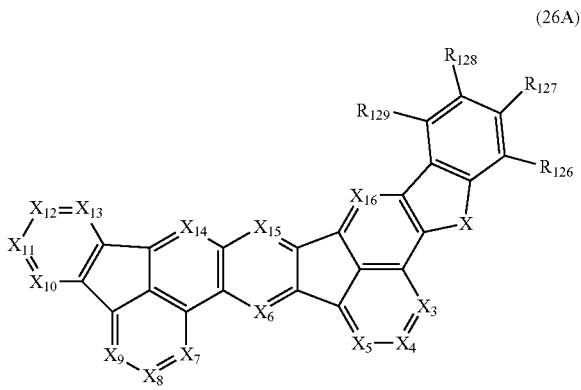

(26A)

where: $X_3$ to $X_{16}$ and $R_x$ respectively represent the same as $X_3$ to $X_{16}$ and $R_x$ in the formula (2);

X represents the same as X of the formula (2b);

$R_{126}$ to $R_{129}$ each independently represent a hydrogen atom or a substituent;

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of $R_{126}$ to $R_{129}$ as the substituents are bonded to each other to further form a ring, or are not bonded to each other.

10. The compound according to claim 6, wherein the compound represented by the formula (2) is represented by a formula (26B) below,

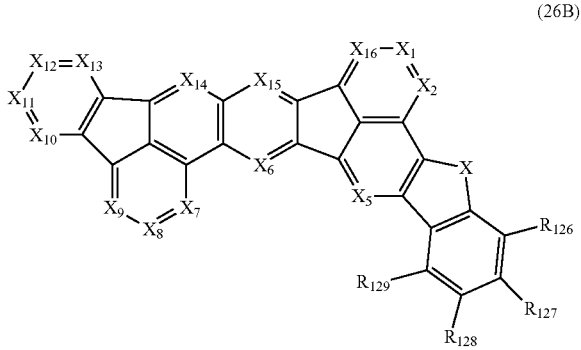

(26B)

where: $X_1$, $X_2$, $X_5$ to $X_{16}$ and $R_x$ respectively represent the same as $X_1$, $X_2$, $X_5$ to $X_{16}$ and $R_x$ in the formula (2);
X represents the same as X in the formula (2b);
$R_{126}$ to $R_{129}$ each independently represent a hydrogen atom or a substituent;
$R_{126}$ to $R_{129}$ as the substituents are each independently selected from the group consisting of a substituted or unsubstituted alley 1 group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and
adjacent ones of $R_{126}$ to $R_{129}$ as the substituents are bonded to each other to further form a ring, or are not bonded to each other.

11. The compound according to claim 1, wherein in the formula (2): $X_6$ is $CR_6$; $X_{15}$ is $CR_{15}$; and $R_6$ and $R_{15}$ are each independently a substituted or unsubstituted aryl group having 6 to 30 ring carbon atoms.

12. The compound according to claim 1, wherein in the formula (2), $X_6$ is $CR_6$, $X_{15}$ is $CR_{15}$, and $R_6$ and $R_{15}$ are each independently a substituted or unsubstituted phenyl group.

13. The compound according to claim 1, wherein in the formula (2): $X_5$ is $CR_5$; $X_6$ is $CR_6$; $X_7$ is $CR_7$; $X_8$ is $CR_8$; $X_9$ is $CR_9$; $X_{10}$ is $CR_{10}$; Xu is $CR_{11}$; $X_{12}$ is $CR_{12}$; $X_{13}$ is $CR_{13}$; $X_{14}$ is $CR_{14}$; $X_{15}$ is $CR_{15}$; $X_{16}$ is $CR_{16}$; $R_6$, and $R_{15}$ are each independently a substituted or unsubstituted phenyl group; and $R_5$, $R_7$ to $R_{14}$, and $R_{16}$ are hydrogen atoms.

14. A composition comprising a plurality of compounds each represented by a formula (2) below,

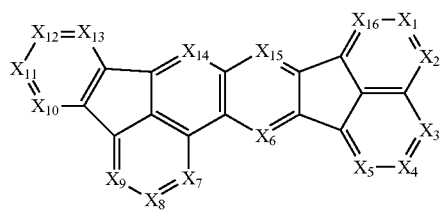

(2)

where: $X_1$ to $X_5$, $X_7$ to $X_{13}$, and $X_{16}$ each independently represent $CR_x$ or a carbon atom to be bonded to a structure represented by a formula (2a) or (2b) below; $X_6$, $X_{14}$, and $X_{15}$ each independently represent $CR_x$;
$R_x$ each independently represents a hydrogen atom or a substituent;
$R_x$ as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and
a plurality of $R_x$ are mutually the same or different;
when a plurality of ones of $X_1$ to $X_{16}$ are $CR_x$ and $R_x$ is a substituent, a plurality of $R_x$ as the substituents are not bonded to each other; and
at least one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ are carbon atoms to be bonded to a structure represented by the formula (2a) or (2b) below,

(2a)

(2b)

in the formula (2a);
*2 represent bonding positions to carbon atoms at one pair of the pair of $X_1$ and $X_2$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_H$ and $X_{12}$, the pair of $X_{12}$ and $X_{13}$, and the pair of $X_{16}$ and $X_1$ in the formula (2);
$R_{111}$ to $R_{114}$ each independently represent a hydrogen atom or a substituent;
$R_{111}$ to $R_{114}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and at least one pair of a pair of $R_{111}$ and $R_{112}$, a pair of $R_{112}$ and $R_{113}$, and a pair of $R_{113}$ and $R_{114}$ are substituents, and the substituents are bonded to each other to form a ring, in the formula (2b):

*2 represent bonding positions to carbon atoms at one pair of the pair of $X_1$ and $X_2$, the pair of $X_2$ and $X_3$, the pair of $X_3$ and $X_4$, the pair of $X_4$ and $X_5$, the pair of $X_7$ and $X_8$, the pair of $X_8$ and $X_9$, the pair of $X_{10}$ and $X_{11}$, the pair of $X_{11}$ and $X_{12}$, the pair of $X_{12}$ and $X_{13}$, and the pair of $X_{16}$ and $X_1$ in the formula (2);

$R_{115}$ and $R_{116}$ each independently represent a hydrogen atom or a substituent;

$R_{115}$ and $R_{116}$ as the substituent are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and $R_{115}$ and $R_{116}$ as the substituents are bonded to each other to further form a ring, or are not bonded to each other;

X is selected from the group consisting of an oxygen atom, a sulfur atom, $CR_{117}R_{118}$, $SiR_{119}R_{120}$ and $NR_{121}$;

$R_{117}$ to $R_{121}$ each independently represent a hydrogen atom or a substituent;

$R_{117}$ to $R_{121}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and $R_{117}$ and $R_{118}$ as the substituents are bonded to each other to further form a ring, or are not bonded to each other; and $R_{119}$ and $R_{120}$ as the substituents are bonded to each other to further form a ring, or are not bonded to each other.

15. The composition according to claim 14, wherein at least one pair of the pair of $X_1$ and $X_2$ and the pair of $X_3$ and $X_4$ in the formula (2) are carbon atoms to be bonded to the structure represented by the formula (2a).

16. The composition according to claim 14, wherein the structure represented by the formula (2a) is a structure represented by a formula (2a-1),

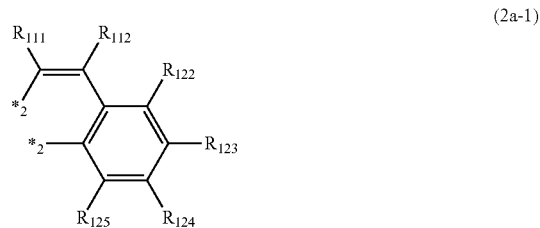

(2a-1)

where: *2 represents the same as *2 in the formula (2a);

$R_{111}$, $R_{112}$ and $R_{122}$ to $R_{125}$ each independently represent a hydrogen atom or a substituent;

$R_{111}$, $R_{112}$ and $R_{122}$ to $R_{125}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of $R_{111}$, $R_{112}$ and $R_{122}$ to $R_{125}$ as the substituents are bonded to each other to further form a ring, or are not bonded to each other.

17. The composition according to claim 16, wherein the composition comprises a compound represented by a formula (21A) below and a compound represented by a formula (21B) below as the compounds each represented by the formula (2):

(21A)

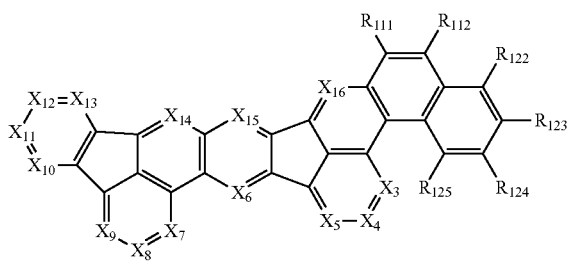

(21B)

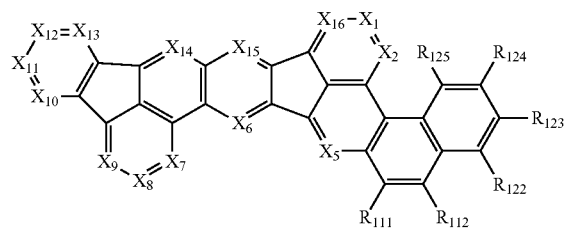

in the formula (21 A), $X_3$ to $X_{16}$ and $R_x$ respectively represent the same as $X_3$ to $X_{16}$ and $R_x$ of the formula (2);

in the formula (21B), $X_1$, $X_2$, $X_5$ to $X_{16}$ and $R_x$ respectively represent the same as $X_1$, $X_2$, $X_5$ to $X_{16}$ and $R_x$ of the formula (2); and in the formulae (21A) and (21B), $R_{111}$, $R_{112}$ and $R_{122}$ to $R_{125}$ respectively represent the same as $R_{111}$, $R_{112}$ and $R_{122}$ to $R_{125}$ of the formula (2a-1).

18. The composition according to claim 14, wherein at least one pair of the pair of $X_1$ and $X_2$, the pair of $X_2$ and $X_3$ and the pair of $X_3$ and $X_4$ in the formula (2) are carbon atoms to be bonded to the structure represented by the formula (2b).

19. The composition according to claim 18, wherein
the composition comprises a compound represented by a formula (25A) below and a compound represented by a formula (25B) below as the compounds each represented by the formula (2), (25A)

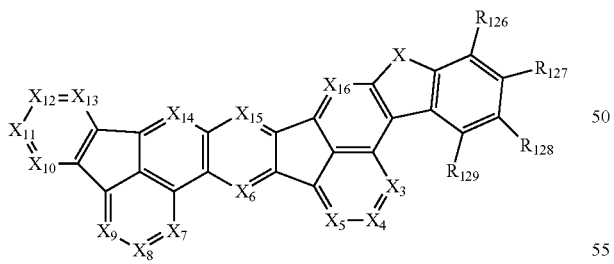

(25B)

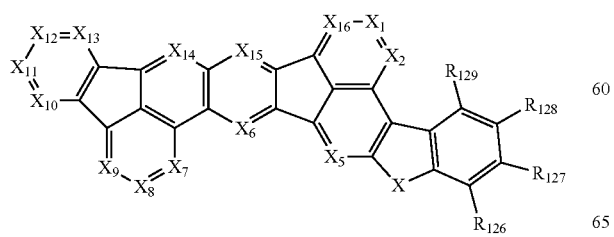

in the formula (25A), $X_3$ to $X_{16}$ and $R_x$ respectively represent the same as $X_3$ to $X_{16}$ and $R_x$ of the formula (2);

in the formula (25B), $X_1$, $X_2$, $X_5$ to $X_{16}$ and $R_x$ respectively represent the same as $X_1$, $X_2$, $X_5$ to $X_{16}$ and $R_x$ of the formula (2);

in the formulae (25A) and (25B), X represents the same as X of the formula (2b);

$R_{126}$ to $R_{129}$ each independently represent a hydrogen atom or a substituent;

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphonyl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of $R_{126}$ to $R_{129}$ as the substituents are bonded to each other to further form a ring, or are not bonded to each other.

20. The composition according to claim 18, wherein the composition comprises a compound represented by a formula (26A) below and a compound represented by a formula (26B) below as the compounds each represented by the formula (2), (26A)

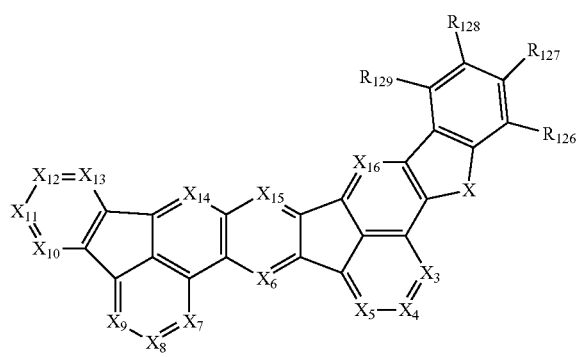

-continued (26B)

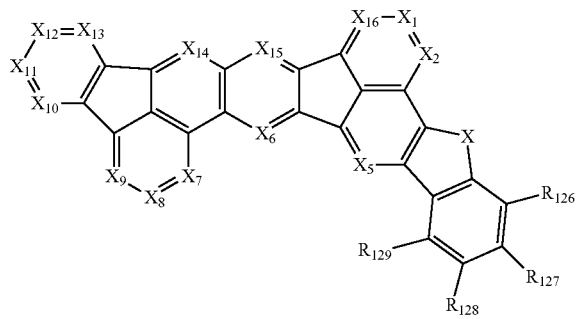

in the formula (26A), $X_3$ to $X_{16}$ and $R_x$ respectively represent the same as $X_3$ to $X_{16}$ and $R_x$ of the formula (2);

in the formula (26B), $X_1$, $X_2$, $X_5$ to $X_{16}$ and $R_x$ respectively represent the same as $X_1$, $X_2$, $X_5$ to $X_{16}$ and $R_x$ of the formula (2);

in the formulae (26A) and (26B), X represents the same as X of the formula (2b);

$R_{126}$ to $R_{129}$ each independently represent a hydrogen atom or a substituent;

$R_{126}$ to $R_{129}$ as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and adjacent ones of $R_{126}$ to $R_{129}$ as the substituents are bonded to each other to further form a ring, or are not bonded to each other.

21. An organic electroluminescence device comprising:
an anode;
an emitting layer; and
a cathode, wherein
the emitting layer comprises a first compound and a second compound, and
the second compound is the compound according to claim 1.

22. The organic electroluminescence device according to claim 21, wherein
the first compound is a delayed fluorescent compound, and
a singlet energy $S_1(M1)$ of the first compound and a singlet energy $S_1(M2)$ of the second compound satisfy a relationship of a numerical formula 1 below, $S_1(M1) > S_1(M2)$ (Numerical Formula 1).

23. The organic electroluminescence device according to claim 22, wherein the second compound has a main peak wavelength of an emission spectrum in a range from 430 nm to 480 nm.

24. The organic electroluminescence device according to claim 22, wherein the second compound has a main peak wavelength of an emission spectrum in a range from 445 nm to 480 nm.

25. The organic electroluminescence device according to claim 22, wherein
the first compound is a compound represented by a formula (1) below,

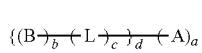

(1)

where: A is a group having a partial structure selected from the group consisting of partial structures represented by formulae (a-1) to (a-7) below;
a plurality of A are mutually the same or different;
the plurality of A are mutually bonded to form a saturated or unsaturated ring, or not bonded;
B is a group having a partial structure selected from the group consisting of partial structures represented by formulae (b-1) to (b-6) below;
a plurality of B are mutually the same or different;
the plurality of B are mutually bonded to form a saturated or unsaturated ring, or not bonded;
a, b and d are each independently an integer of 1 to 5;
c is an integer of 0 to 5;
when c is 0, A is bonded to B by a single bond or a spiro bond;
when c is an integer of 1 to 5, L is a linking group selected from the group consisting of a substituted or unsubstituted aryl group having 6 to 30 ring carbon atoms, and a substituted or unsubstituted heteroaryl group having 5 to 30 ring atoms;
when c is an integer of 2 to 5, a plurality of L are mutually the same or different; and
the plurality of L are mutually bonded to form a saturated or unsaturated ring, or not bonded,

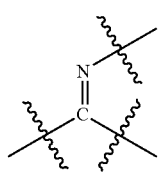
(a-1)

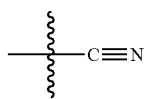
(a-2)

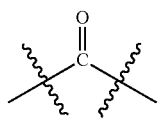
(a-3)

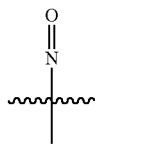
(a-4)

-continued

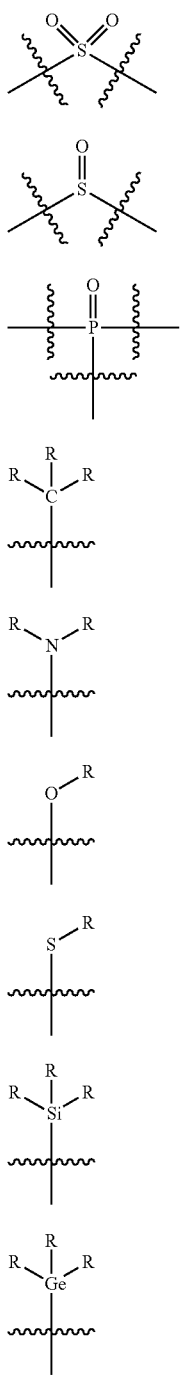

in the formulae (b-1) to (b-6):
R each independently represents a hydrogen atom or a substituent;
R as the substituent is each independently a group selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms;
a plurality of R are mutually the same or different; and
the plurality of R are mutually bonded to form a saturated or unsaturated ring, or not bonded.

26. The organic electroluminescence device according to claim 25, wherein A is a group having the partial structure selected from the group consisting of the partial structures represented by the respective formulae (a-1), (a-2), (a-3) and (a-5).

27. The organic electroluminescence device according to claim 25, wherein B is a group having the partial structure selected from the group consisting of the partial structures represented by the respective formulae (b-2), (b-3) and (b-4).

28. The organic electroluminescence device according to claim 22, wherein the first compound is a compound represented by a formula (11) below, $$Cz\text{---}(L)_c\text{---}Az \quad (11)$$

where: Az is a cyclic structure selected from the group consisting of a substituted or unsubstituted pyridine ring, a substituted or unsubstituted pyrimidine ring, a substituted or unsubstituted triazine ring, and a substituted or unsubstituted pyrazine ring;

c is an integer of 0 to 5;

when c is 0, Cz and Az are bonded by a single bond;

when c is an integer of 1 to 5, L is a linking group selected from the group consisting of a substituted or unsubstituted aryl group having 6 to 30 ring carbon atoms, and a substituted or unsubstituted heteroaryl group having 5 to 30 ring atoms;

when c is an integer of 2 to 5, a plurality of L are mutually the same or different;

the plurality of L are mutually bonded to form a ring, or not bonded; and

Cz is represented by a formula (12) below, $$\begin{array}{c}\text{(12)}\\ Y_{23}{=}Y_{24}\quad Y_{25}{=}Y_{26}\\ Y_{22}\diagdown\quad\diagup Y_{27}\\ Y_{21}\diagdown N\diagup Y_{28}\\ *_1\end{array}$$

where: $Y_{21}$ to $Y_{28}$ are each independently a nitrogen atom or $CR_y$;

$R_y$ each independently represents a hydrogen atom or a substituent;

$R_y$ as the substituent is each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of $R_y$ are mutually the same or different;

when a plurality of ones of $Y_{21}$ to $Y_{28}$ are $CR_y$ and $R_y$ is a substituent, a plurality of $R_y$ as the substituents are bonded to each other to form a ring, or are not bonded; and

*1 represents a bonding position with a carbon atom in a structure of the linking group represented by L or a bonding position with a carbon atom of the cyclic structure represented by Az.

29. The organic electroluminescence device according to claim 22, wherein the emitting layer further comprises a third compound, and a singlet energy $S_1(M1)$ of the first compound and a singlet energy $S_1(M3)$ of the third compound satisfy a relationship of a numerical formula 2 below, $$S_1(M3) > S_1(M1) \qquad \text{(Numerical Formula 2)}.$$

30. The organic electroluminescence device according to claim 29, wherein a content ratio of the first compound in the emitting layer ranges from 10 mass % to 80 mass %.

31. The organic electroluminescence device according to claim 21, wherein the emitting layer comprises a plurality of the second compounds.

32. The organic electroluminescence device according to claim 21, further comprising:

a hole transporting layer between the anode and the emitting layer.

33. The organic electroluminescence device according to claim 21, further comprising:

an electron transporting layer between the cathode and the emitting layer.

34. An electronic device comprising the organic electroluminescence device according to claim 21.

* * * * *